(12) United States Patent
Moghadam

(10) Patent No.: US 10,906,931 B2
(45) Date of Patent: Feb. 2, 2021

(54) METHODS FOR TREATING DISEASES RELATED TO MITOCHONDRIAL STRESS

(71) Applicant: 712 NORTH, INC., San Francisco, CA (US)

(72) Inventor: Marcel Victor Alavi Khorassani Moghadam, San Francisco, CA (US)

(73) Assignee: 712 NORTH INC., San Francisco, CA (US)

( * ) Notice: Subject to any disclaimer, the term of this patent is extended or adjusted under 35 U.S.C. 154(b) by 0 days.

(21) Appl. No.: 16/022,481

(22) Filed: Jun. 28, 2018

(65) Prior Publication Data

US 2018/0371007 A1    Dec. 27, 2018

Related U.S. Application Data

(63) Continuation of application No. PCT/US2017/064195, filed on Dec. 1, 2017.

(60) Provisional application No. 62/581,723, filed on Nov. 5, 2017, provisional application No. 62/481,392, filed on Apr. 4, 2017, provisional application No. 62/429,846, filed on Dec. 4, 2016.

(51) Int. Cl.
| | |
|---|---|
| *C07H 21/04* | (2006.01) |
| *A61K 38/02* | (2006.01) |
| *A61K 9/00* | (2006.01) |
| *A61K 31/7088* | (2006.01) |
| *C12N 15/00* | (2006.01) |
| *A61K 38/17* | (2006.01) |

(52) U.S. Cl.
CPC ............ *C07H 21/04* (2013.01); *A61K 9/0073* (2013.01); *A61K 31/7088* (2013.01); *A61K 38/02* (2013.01); *A61K 38/1793* (2013.01); *C12N 15/00* (2013.01); *C07K 2319/00* (2013.01)

(58) Field of Classification Search
CPC ...... C07H 21/04; A61K 38/02; A61K 9/0073; C07K 2319/00
USPC ......................................................... 514/44
See application file for complete search history.

(56) References Cited

U.S. PATENT DOCUMENTS

| | | |
|---|---|---|
| 2004/0101874 A1 | 5/2004 | Ghosh et al. |
| 2005/0142094 A1 | 6/2005 | Kumar |
| 2009/0209615 A1 | 8/2009 | Lipton et al. |
| 2010/0209436 A1 | 8/2010 | Reichert et al. |
| 2012/0157386 A1 | 6/2012 | Smith et al. |
| 2013/0052184 A1 | 2/2013 | Chang et al. |
| 2017/0101679 A1 | 4/2017 | Davezac et al. |

FOREIGN PATENT DOCUMENTS

| | | |
|---|---|---|
| KR | 20180047397 A | 5/2018 |
| WO | 2000/030656 A1 | 6/2000 |
| WO | 200030656 A1 | 6/2000 |
| WO | 2001/057190 A2 | 8/2001 |
| WO | 2005/103716 A2 | 11/2005 |
| WO | 2011053825 A2 | 5/2011 |
| WO | 2018/132662 A1 | 7/2018 |

OTHER PUBLICATIONS

Xiao et al. OMA1 mediates OPA1 proteolysis and mitochondrial fragmentation in experimental models of ischemic kidney injury. Am J Physiol Renal Physiol 306: F1318-F1326, 2014. (Year: 2014).*
Nagaj et al. Acid—base characterization, coordination properties towards copper(II) ions and DNA interaction studies of ribavirin, an antiviral drug. Journal of Inorganic Biochemistry 142 (2015) 68-74. (Year: 2015).*
Product Monograph. Virazole® (Ribavirin for Inhalation Solution, USP). Jul. 22, 2014. (Year: 2014).*
Akhtar, M. et al., "Elevated glucose and oligomeric β-amyloid disrupt synapses via a common pathway of aberrant protein S-nitrosylation," Nature Communications, vol. 7, 10242, 11 pages,(2016).
Alavi et al., "A splice site mutation in the purine Opa1 gene features pathology of autosomal dominant optic atrophy," Brain, 2007, vol. 130, p. 1029-1042.
Alavi et al., "Dominant optic atrophy, OPA1, and mitochondrial quality control: understanding mitochondrial networks dynamics," Molecular Neurodegeneration, 2013, vol. 8, No. 32, 12 pages.
Alexander, C. et al., "OPA1, encoding a dynamin-related GTPase, is mutated in autosomal dominant optic atrophy linked to chromosome 3q28," Nature Genetics, 2000, vol. 26, p. 211-215.
Alirol, E. et al., "Mitochondria and cancer: is there a morphological connection?" Oncogene, 2006, vol. 25, p. 4706-4716.
Ameri, K. et al., "Nuclear localization of the mitochondrial factor HIGD1A during metabolic stress," PLOS One, Apr. 2013, vol. 8, Issue 4, e62758, 11 pages.
Ameri, K. et al., "HIGD1A-mediated dormancy and tumor survival," Molecular & Cellular Oncology, Dec. 2015, vol. 2, Issue 4, 3 pages.

(Continued)

*Primary Examiner* — Yih-Horng Shiao
(74) *Attorney, Agent, or Firm* — Nevrivy Patent Law Group P.L.L.C.

(57) ABSTRACT

Means and methods for therapeutic intervention of mitochondrial disorders or diseases, and in particular to a method for the treatment, prevention and/or amelioration of a disorder or disease correlated with mitochondrial stress or dysfunction, a mitochondrial disorder or disease, or a disorder or disease characterized by OPA1 alterations are disclosed. Thereby, a pharmaceutically active amount of a compound capable of modulating the activity of OMA1 and/or an oligomeric complex comprising OMA1 is administered to a patient in need of medical intervention. Methods of screening for a compound capable of modulating the activity of OMA1 and/or an oligomeric complex comprising OMA1 are disclosed. Methods for determining the susceptibility for, predisposition for, or the presence of such a disorder or disease and whether a person in need will benefit from the therapeutic intervention, i.e. personalized medicine are also disclosed.

17 Claims, 26 Drawing Sheets

Specification includes a Sequence Listing.

(56) References Cited

OTHER PUBLICATIONS

Ameri, K. et al., "HIGD1A regulates oxygen consumption, ROS production and AMPK activity during glucose deprivation to modulate cell survival and tumor growth," Cell Reports, 2016, 20 pages.
An, H. et al., "Higd-1a interacts with Opa1 and is required for the morphological and functional integrity of mitochondria," Proceedings of the National Academy of Sciences, Aug. 2013, vol. 110, Issue 32, p. 13014-13019.
An, H., et al., "The survival effect of mitochondrial Higd-1a is associated with suppression of cytochrome C release and prevention of caspase activation," Biochimica et Biophysica Acta, Molecular Cell Research, Dec. 2011, vol. 1813, Issue 12, p. 2088-2098.
Arnoult, D., et al., "Release of OPA1 during Apoptosis Participates in the Rapid and Complete Release of Cytochrome c and Subsequent Mitochondrial Fragmentation," The Journal of Biological Chemistry, Oct. 2005, vol. 280, No. 42, p. 35742-35750.
Atorino, et al., "Loss of m-AAA protease in mitochondria causes complex I deficiencies and increased sensitivity to oxidative stress in hereditary spastic paraplegia," The Journal of Cell Biology, 2003, vol. 163, No. 4, p. 777-787.
Baek, S. et al., "Inhibition of Drp1 Ameliorates Synaptic Depression, Aβ Deposition, and Cognitive Impairment in an Alzheimer's Disease Model," Journal of Neuroscience, May 2017, vol. 37, No. 20, p. 5099-5110.
Barrera, M. et al., "OPA1 functionally interacts with MIC60 but is dispensable for crista junction formation," FEBS Letters, Oct. 2016, vol. 590, No. 19, p. 3309-3322.
Bohovych, I. et al., "Oma1 Links Mitochondrial Protein Quality Control and TOR Signaling to Modulate Physiological Plasticity and Cellular Stress Responses," Molecular and Cellular Biology, Sep. 2016, vol. 36, No. 17, p. 2300-2312.
Bond, M. et al., "A little sugar goes a long way: The cell biology of O-GlcNAc," The Journal of Cell Biology, Mar. 2015, vol. 208, No. 7, p. 869-880.
Bose, A. et al., "Mitochondrial dysfunction in Parkinson's disease," Journal of Neurochemistry, 2016, vol. 139, p. 216-231.
Burke, N. e al., "OPA1 in Cardiovascular Health and Disease," Current Drug Targets, 2015, vol. 16, Issue 8, p. 912-920.
Cardoso, S.M. et al., "Mitochondrial dysfunction of Alzheimer's disease cybrids enhances Abeta toxicity," Journal of Neurochemistry, Jun. 2004, vol. 89, No. 6, p. 1417-1426.
Carelli, V. et al., "Optic nerve degeneration and mitochondrial dysfunction: genetic and acquired optic neuropathies," Neurochemistry International, May 2002, vol. 40, Issue 6, p. 573-584.
Carvalho, A.S. et al., "Global mass spectrometry and transcriptomics array based drug profiling provides novel insight into glucosamine induced endoplasmic reticulum stress," Molecular & Cellular Proteomics, Dec. 2014, vol. 13, No. 12, p. 3294-3307.
Casari, G. et al., "Spastic paraplegia and OXPHOS impairment caused by mutations in paraplegin, a nuclear-encoded mitochondrial metalloprotease," Cell, Jun. 1998, vol. 93, No. 6, p. 973-983.
Chen et al., "Mitochondrial OPA1, apoptosis, and heart failure," Cardiovascular Research, 2009, vol. 84, p. 91-99.
Chen et al., "OPA1 mutation and late-onset cardiomyopathy: mitochondrial dysfunction and mtDNA instability," Journal of the American Heart Association, Oct. 2012, vol. 1, e003012, 12 pages.
Chen et al., "Disruption of fusion results in mitochondrial heterogeneity and dysfunction," The Journal of Biological Chemistry, Jul. 2005, vol. 280, No. 28, p. 26185-26192.
Choubey, V. et al., "Mutant A53T α-Synuclein Induces Neuronal Death by Increasing Mitochondrial Autophagy," The Journal of Biological Chemistry, Mar. 2011, vol. 286, No. 12, p. 10814-10824.
Cipolat, S. et al., "Mitochondrial rhomboid PARL regulates cytochrome c release during apoptosis via OPA1-dependent cristae remodeling," Cell, Jul. 2006, vol. 126, p. 163-175.
Cipolat, S. et al., "OPA1 requires mitofusin 1 to promote mitochondrial fusion," Proceedings of the National Academy of Sciences, Nov. 2004, vol. 101, No. 45, p. 15927-15932.

Cogliati, S. et al., "Mitochondrial cristae shape determines respiratory chain supercomplexes assembly and respiratory efficiency," Cell, Sep. 2013, vol. 155, p. 160-171.
Coughlin, L. et al., "Mitochondrial Morphology Differences in Mitophagy Deficit in Murine Glaucomatous Optic Nerve," Investigative Opthalmology & Visual Science, Mar. 2015, vol. 56, No. 3, p. 1437-1446.
Delettre, C. et al., "Nuclear gene OPA1, encoding a mitochondrial dynamin-related protein, is mutated in dominant optic atrophy," Nature Genetics, Oct. 2000, vol. 26, p. 207-210.
Devi, L. et al., Accumulation of amyloid precursor protein in the Mitochondrial Import Channels of Human Alzheimer's Disease Brain Is Associated with Mitochondrial Dysfunction, The Journal of Neuroscience, Aug. 2006, vol. 26, p. 9057-9068.
Diana, A. et al., "Mitochondria morphology and DNA content upon sublethal exposure to beta-amyloid(1-42) peptide," Coll Anthropol, Jan. 2008, vol. 32, p. 51-58.
Dolle, C. et al., "Defective mitochondrial DNA homeostasis in the substantia nigra in Parkinson disease," Nature Communications, Apr. 2016, vol. 7, 13548, 11 pages.
Dorn, G.W., "Mitochondrial Dynamics in Heart Disease," Biochimica et Biophysica Acta, Jan. 2013, vol. 1833(1), 20 pages.
Duvezin-Caubet, S. et al., "Proteolytic processing of OPA1 links mitochondrial dysfunction to alterations in mitochondrial morphology," The Journal of Biological Chemistry, Dec. 2006, vol. 281, No. 49, p. 37972-37979.
Eberlin, M. et al., "A comprehensive review of the pharmacodynamics, pharmacokinetics, and clinical effects of the neutral endopeptidase inhibitor racecadotril," Frontiers in Pharmacology, Gastrointestinal Pharmacology, May 2012, vol. 3, Article 93, 16 pages.
Edgar, R. et al., "Gene Expression Omnibus: NCBI gene expression and hybridization array data repository," Nucleic Acids Research, 2002, vol. 30, No. 1, p. 207-210.
Ehses, S. et al., "Regulation of OAP1 processing and mitochondrial fusion by m-AAA protease isoenzymes and OMA1," The Journal of Cell Biology, 2009, vol. 187, No. 7, p. 1023-1036.
Faccenda, D. et al., "Control of Mitochondrial Remodeling by the ATPase Inhibitory Factor 1 Unveils a Pro-survival Relay via OPA1," Cell Reports, Feb. 2017, vol. 18, p. 1869-1883.
Ferreirinha, F. et al., "Axonal degeneration in paraplegin-deficient mice is associated with abnormal mitochondria and impairment of axonal transport," The Journal of Clinical Investigation, Jan. 2004, vol. 113, No. 2, p. 231-242.
Frank, S. et al., "The role of dynamin-related protein 1, a mediator of mitochondrial fission, in apoptosis," Developmental Cell, Oct. 2001, vol. 1, No. 4, p. 515-525.
Frezza, C. et al., "OPA1 controls apoptotic cristae remodeling independently from mitochondrial fusion," Cell, Jul. 2006, vol. 126, p. 177-189.
Frezza, C. et al., "Mitochondria in cancer: Not just innocent bystanders," Seminars in Cancer Biology, Feb. 2009, vol. 19, Issue 1, p. 4-11.
Fuhrmann, N. et al., "Solving a 50 year mystery of a missing OPA1 mutation: more insights from the first family diagnosed with autosomal dominant optic atrophy," Molecular Neurodegeneration, 2010, vol. 5, No. 25, 13 pages.
Gleissner, C.A. et al., "CXCL4 induces a unique transcriptome in monocyte-derived macrophages," Journal of Immunology, May 2010, vol. 184, No. 9, p. 4810-4818.
Glytsou, C. et al., "Optic Atrophy 1 us Epistatic to the Core MICOS Component MIC60 in Mitochondrial Cristae Shape Control," Cell Reports, Dec. 2016, vol. 17, No. 11, p. 3024-3034.
Griparic, L. et al., "Regulation of the mitochondrial dynamin-like protein Opa1 by proteolytic cleavage," The Journal of Cell Biology, Aug. 2007, vol. 178, No. 5, p. 757-764.
Griparic, L., et al., "Loss of the intermembrane space protein Mgm1/OPA1 induces swelling and localized constrictions along the lengths of mitochondria," The Journal of Biological Chemistry, 2004, vol. 279, No. 18, p. 18792-18798.
Guardia-Laguarta, C. et al., "α-synuclein is localized to mitochondria-associated ER membranes," The Journal of Neuroscience, Jan. 2014, vol. 34, p. 249-259.

(56) References Cited

OTHER PUBLICATIONS

Guo, Y. et al., "Association of OPA1 polymorphisms with NTG and HTG: a meta-analysis," PLOS One, 2012, vol. 7, No. 8, e42387, 12 pages.
Hackenbrock, C.R. "Ultrastructural bases for metabolically linked mechanical activity in mitochondria," The Journal of Cell Biology, Aug. 1966, vol. 30, No. 2, p. 269-297.
Hanahan, D. et al., "Hallmarks of cancer: the next generation," Cell, Mar. 2011, vol. 144, No. 5, p. 646-674.
Head, B. et al., "Inducible proteolytic inactivation of OPA1 mediated by the OMA1 protease in mammalian cells," The Journal of Cell Biology, Dec. 2009, vol. 187, No. 7, p. 959-966.
Herlan, M. et al., "Alternative topogenesis of Mgm1 and mitochondrial morphology depend on ATP and a functional import motor," The Journal of Cell Biology, 2004, vol. 165, No. 2, p. 167-173.
Hessenberger, M. et al., "Regulated membrane remodeling by Mic60 controls formation of mitochondrial crista junctions," Nature Communications, May 2017, vol. 8, No. 15258, 11 pages.
Hokama, M. et al., "Altered expression of diabetes-related genes in Alzheimer's disease brains: the Hisayama study," Cerebral Cortex, Sep. 2014, vol. 24, No. 9, p. 2476-2488.
Imaizumi, Y. et al., "Mitochondrial dysfunction associated with increased oxidative stress and α-synuclein accumulation in PARK2 iPSC-derived neurons and postmortem brain tissue," Molecular Brain, 2012, vol. 5, No. 35, 13 pages.
Ishihara, N. et al., "Regulation of mitochondrial morphology through proteolytic cleavage of OPA1," The EMBO Journal, Jul. 2006, vol. 25, No. 13, p. 2966-2977.
Jakobs, S. et al., "Spatial and temporal dynamics of budding yeast mitochondria lacking the division component Fis1," Journal of Cell Science, May 2003, vol. 116, p. 2005-2014.
Jiang, X. et al., "Activation of mitochondrial protease OMA1 by Bax and Bak promotes cytochrome c release during apoptosis," Proceedings of the National Academy of Sciences, Oct. 2014, vol. 111, No. 41, p. 14782-14787.
Ju, W.K. et al., "Intraocular Pressure Elevation Induces Mitochondrial Fission and Triggers OPA1 Release in Glaucomatous Optic Nerve," Investigative Ophthalmology and Visual Science, Nov. 2008, vol. 49, No. 11, p. 4903-4911.
Kandimalla, R. et al., "Reduced dynamin-related protein 1 protects against phosphorylated Tau-induced mitochondrial dysfunction and synaptic damage in Alzheimer's disease," Human Molecular Genetics, Nov. 2016, vol. 25, No. 22, p. 4881-4897.
Karbowski, M. et al., "Spatial and temporal association of Bax with mitochondrial fission sites, Drp1, and Mfn2 during apoptosis," The Journal of Cell Biology, Dec. 2002, vol. 159, No. 6, p. 931-938.
Kaser, M. et al., "OMA1, a novel membrane-bound metallopeptidase in mitochondria with activities overlapping with the m-AAA protease," The Journal of Biological Chemistry, Nov. 2003, vol. 278, No. 47, p. 46414-46423.
Keeney, P. et al., "Parkinson's Disease Brain Mitochondrial Complex I Has Oxidatively Damaged Subunits and Is Functionally Impaired and Misassembled," The Journal of Neuroscience, May 2006, vol. 26, No. 19, p. 5256-5264.
Kim, K.Y. et al., "DRP1 inhibition rescues retinal ganglion cells and their axons by preserving mitochondrial integrity in a mouse model of glaucoma," Cell Death and Disease, 2015, vol. 6, e1839, 15 pages.
Kong, B. et al., "p53 is required for cisplatin-induced processing of the mitochondrial fusion protein L-Opa1 that is mediated by the mitochondrial metallopeptidase Oma1 in gynecologic cancers," The Journal of Biological Chemistry, The American Society for Biochemistry and Molecular Biology, Sep. 2014, vol. 289, No. 39, p. 27134-27145.
Koob, S. et al., "The non-glycosylated isoform of MIC26 is a constituent of the mammalian MICOS complex and promotes formation of crista junctions," Biochimica et Biophysica Acta, Jul. 2015, vol. 1853, No. 7, p. 1551-1563.
Koppen et al., "Variable and Tissue-Specific Subunit Composition of Mitochondrial m-AAA Protease Complexes Linked to Hereditary Spastic Paraplegia," Molecular and Cellular Biology, Jan. 2007, vol. 27, No. 2, p. 758-767.
Korowitz, A. et al., "Loss of OMA1 delays neurodegeneration by preventing stress-induced OPA1 processing in mitochondria," The Journal of Cell Biology, Jan. 2016, vol. 212, No. 2, p. 157-166.
Landes, T. et al., "The BH3-only Bnip3 binds to the dynamin Opa1 to promote mitochondrial fragmentation and apoptosis by distinct mechanisms," EMBO Reports, Jun. 2010, vol. 11, No. 6, p. 459-465.
Le Page et al., "Increase in Cardiac Ischemia-Reperfusion Injuries in Opa1$^{+/-}$ Mouse Model," PLOS One, 2016, vol. 11, No. 10, e0164066, 19 pages.
Lee, Y. et al., "Roles of the mammalian mitochondrial fission and fusion mediators Fis1, Drp1, and Opa1 in apoptosis," Molecular Biology of the Cell, Nov. 2004, vol. 15, No. 11, p. 5001-5011.
Leonhard, K. et al., "Membrane protein degradation by AAA proteases in mitochondria: extraction of substrates from either membrane surface," Molecular Cell, 2000, vol. 5, No. 4, p. 629-638.
Lesnick, T.G. et al., "A Genomic Pathway Approach to a Complex Disease: Axon Guidance and Parkinson Disease," PLOS Genetics. Jun. 2007, vol. 3. Issue 6, e98, p. 984-995.
Li, F. et al., "Increased plaque burden in brains of APP mutant MnSOD heterozygous knockout mice," Journal of Neurochemistry, Jun. 2004, vol. 89, No. 5, p. 1308-1312.
Li, Z. et al., "The Importance of Dendric Mitochondria in the Morphogenesis and Plasticity of Spines and Synapses," Cell, Dec. 2004, vol. 119, p. 873-887.
Lustbader, J.W. et al., "ABAD directly links Abeta to mitochondrial toxicity in Alzheimer's disease," Science, Apr. 2004, vol. 304, p. 448-452.
Lutz, A.K. et al., "Loss of parkin or PINK1 function increases Drp1-dependent mitochondrial fragmentation," The Journal of Biological Chemistry, Aug. 2009, vol. 284, No. 34, p. 22938-22951.
Lyamzaev, K.G. et al., "Selective elimination of mitochondrial from living cells induced by inhibitors of bioenergetic functions," Biochemical Society Transactions, 2004, vol. 23, part 6, p. 1070-1071.
Manczak, M. et al., "Mitochondria are a direct site of Aβ accumulation in Alzheimer's disease neurons: implications for free radical generation and oxidative damage in disease progression," Human Molecular Genetics, May 2006, vol. 15, No. 9, p. 1437-1449.
Manczak, M. et al., "Impaired mitochondrial dynamics and abnormal interaction of amyloid beta with mitochondrial protein Drp1 in neurons from patients with Alzheimer's disease: implications for neuronal damage," Human Molecular Genetics, Jul. 2011, vol. 20, No. 13, p. 2495-2509.
Manczak, M. et al., "Protective effects of reduced dynamin-related protein 1 against amyloid beta-induced mitochondrial dysfunction and synaptic damage in Alzheimer's disease," Human Molecular Genetics, Dec. 2016, vol. 25, No. 23, p. 5148-5166.
Manczak, M. et al., "Abnormal interaction between the mitochondrial fission protein Drp1 and hyperphosphorylated tau in Alzheimer's disease neurons: implications for mitochondrial dysfunction and neuronal damage," Human Molecular Genetics, 2012, vol. 21, No. 11 p. 2538-2547.
Maraganore, D.M. et al., "High-resolution whole-genome association study of Parkinson disease," American Journal of Human genetics, Nov. 2005, vol. 77, No. 3, p. 685-693.
Maresca, A. et al., "The optic nerve: a "mito-window" on mitochondrial neurodegeneration," Molecular and Cell Neurosciences, Jul. 2013, vol. 55, p. 62-76.
Medja, F. et al., "Thiorphan, a neutral endopeptidase inhibitor used for diarrhoea, is neuroprotective in newborn mice," Brain, Dec. 2006, vol. 129, Part 12, p. 3209-3223.
Merkwirth, C.S. et al., "Prohibitins control cell proliferation and apoptosis by regulating OPA1-dependent cristae morphogenesis in mitochondria," Genes & Development, 2008, vol. 22, p. 476-488.
Merz, K.M. et al., "The Protein Folding Problem and Tertiary Structure Prediction," Birkhauser, Boston, 1994, p. 433-506.
Miller, J.A. et al., "Genes and pathways underlying regional and cell type changes in Alzheimer's disease," Genome Medicine, 2013, vol. 5, No. 48, 17 pages.

(56) References Cited

OTHER PUBLICATIONS

Mukherjee, U.A. et al., "Parkinson's disease proteins: Novel mitochondrial targets for cardioprotection," Pharmacology & Therapeutics, Dec. 2015, vol. 156, p. 34-43.

Nakamura, K. "α-Synuclein and Mitochondria: Partners in Crime?" Neurotherapeutics, Jul. 2013, vol. 10, No. 3, p. 391-399.

Nakamura, K. et al., "Direct membrane association drives mitochondrial fission by the Parkinson disease-associated protein alpha-synuclein," The Journal of Biological Chemistry, Jun. 2011, vol. 286, No. 23, p. 20710-20726.

Niemann, A. et al., "Ganglioside-induced differentiation associated protein 1 is a regulator of the mitochondrial network: New implications for Charcot-Marie-Tooth disease" The Journal of Cell Biology, Sep. 2005, vol. 170, No. 7, p. 1067-1078.

Nunnari, J. et al., "Mitochondrial transmission during mating in *Saccharomyces cerevisiae* is determined by mitochondrial fusion and fission and the intramitochondrial segregation of mitochondrial DNA," Molecular Biology of the Cell, Jul. 1997, vol. 8, No. 7, p. 1233-1242.

Olichon, A. et al., "Loss of OPA1 Perturbates the Mitochondrial Inner Membrane Structure and Integrity, Leading to Cytochrome c Release and Apoptosis," The Journal of Biological Chemistry, Mar. 2003, vol. 278, No. 10, p. 7743-7746.

Olichon, A. et al., "OPA1 alternate splicing uncouples an evolutionary conserved function in mitochondrial fusion from a vertebrate restricted function in apoptosis," Cell Death and Differentiation, Apr. 2007, vol. 14, No. 4, p. 682-692.

Ong et al., "Mitochondrial-Shaping Proteins in Cardiac Health and Disease—the Long and the Short of It?," Cardiovascular Drugs Therapy, 2017, vol. 31, p. 87-107.

Ott, C. et al., "Detailed Analysis of the Human Mitochondrial Contact Site Complex Indicate a Hierarchy of Subunits," PLOS One, Mar. 2015, vol. 10, e0120213, 15 pages.

Parker, W. D. et al., "Complex I Deficiency in Parkinson's Disease Frontal Cortex," Brain Res, 2008, vol. 1189, p. 215-218.

Piquereau, J. et al., "Down-regulation of OPA1 alters mouse mitochondrial morphology, PTP function, and cardiac adaptation to pressure overload," Cardiovascular Research, 2012, vol. 94, p. 408-417.

Piquereau, J. et al., "Mitochondrial dynamics in the adult cardiomyocytes: which roles for a highly specialized cell?," Frontiers in Physiology, May 2013, vol. 4, Article 102, 12 pages.

Priault, M. et al., "Impairing the bioenergetic status and the biogenesis of mitochondria triggers mitophagy in yeast," Cell Death and Differentiation, 2005, vol. 12, p. 1613-1621.

Quiros, P. et al., "New roles for OMA1 metalloprotease," Adipocyte, 2013, vol. 2, No. 1, p. 7-11.

Rainboldt, T. K. et al., "Reciprocal Degradation of YME1L and OMA1 Adapts Mitochondrial Proteolytic Activity during Stress," Cell Reports, 2016, vol. 14, p. 2041-2049.

Rappold, P.M. et al., "Drp1 inhibition attenuates neurotoxicity and dopamine release deficits in vivo," Nature Communications, Nov. 2014, vol. 5, 13 pages.

Reddy, P.H. et al., "Gene expression profiles of transcripts in amyloid precursor protein transgenic mice: up-regulation of mitochondrial metabolism and apoptotic genes is an early cellular change in Alzheimer's disease," Human Molecular Genetics, 2004, vol. 13, No. 12, p. 1225-1240.

Reddy, P.H. et al., "Mitochondria-Division Inhibitor 1 Protects Against Amyloid-β induced Mitochondrial Fragmentation and Synaptic Damage in Alzheimer's Disease," Journal of Alzheimers Disease, 2017, vol. 58, No. 1, p. 147-162.

Richter, U. et al., "Quality control of mitochondrial protein synthesis is required for membrane integrity and cell fitness," Journal of Cell Biology, Oct. 2015, vol. 211, No. 2, p. 373-389.

Sadun, A.A., "Mitochondrial optic neuropathies," The Journal of Neurology, Neurosurgery & Psychiatry, Apr. 2002, vol. 72, p. 423-425.

Schmidt, C. et al., "Amyloid precursor protein and amyloid b-peptide bind to ATP synthase and regulate its activity at the surface of neural cells," Molecular Psychiatry, 2008, vol. 13, p. 953-969.

Shields, L.Y. et al., "Dynamin-related protein 1 is required for normal mitochondrial bioenergetic and synaptic function in CA1 hippocampal neurons," Cell Death and Disease, 2015, vol. 6, e1725, 11 pages.

Song, Z. et al., "OPA1 processing controls mitochondrial fusion and is regulated by mRNA splicing, membrane potential, and Yme1L," The Journal of Cell Biology, Aug. 2007, vol. 178, No. 5, p. 749-755.

Stafa, K. et al., "Functional interaction of Parkinson's disease-associated LRRK2 with members of the dynamin GTPase superfamily," Human Molecular Genetics, 2014, vol. 23, No. 8, p. 2055-2077.

Takihara, Y. et al., "In vivo imaging of axonal transport of mitochondria in the diseased and aged mammalian CNS," Proceedings of the National Academy of Sciences, Aug. 2015, vol. 112, No. 33, p. 10515-10520.

Tan, E.P. et al., "Sustained O-GlcNAcylation reprograms mitochondrial function to regulate energy metabolism," Journal of Biology & Chemistry, 2017, vol. 292, No. 36, p. 14940-14962.

Tatsuta, T. et al., "m-AAA protease-driven membrane dislocation allows intramembrane cleavage by rhomboid in mitochondria," The EMBO Journal, Jan. 2007, vol. 26, p. 325-335.

Taube, J.H. et al., "Epigenetic silencing of microRNA-203 is required for EMT and cancer stem cell properties," Scientific Reports, Sep. 2013, 2687, 10 pages.

Thomas, E. et al., "Ribavirin potentiates interferon action by augmenting interferon-stimulated gene induction in hepatitis C virus cell culture models," Hepatology, Jan. 2011, vol. 53, No. 1, p. 32-41.

Tuccinardi, T. et al., "Amber force field implementation, molecular modelling study, synthesis and MMP-1/MMP-2 inhibition profile of (R)- and (S)-N-hydroxy-2-(N-isopropoxybiphenyl-4-ylsulfonamido)-3-methylbutanamides,"Bioorganic & Medicinal Chemistry, 2006, vol. 14, p. 4260-4276.

Verstreken, P. et al., "Synaptic Mitochondria Are Critical for Mobilization of Reserve Pool Vesicles at *Drosophila* Neuromuscular Junctions," Neuron, 2005, vol. 47, No. 3, p. 365-378.

Voigt, A. et al., "The mitochondrial kinase PINK1: functions beyond mitophagy," Journal of Neurochemistry, 2016, vol. 139, Suppl. 1, p. 232-239.

Vyas, S. et al., "Mitochondria and Cancer," Cell, Jul. 2016, vol. 166, No. 3, p. 555-566.

Wai, T. et al., "The membrane scaffold SLP2 anchors a proteolytic hub in mitochondria containing PARL and the i-AAA protease YME1L," Science, 2016, vol. 17, No. 12, p. 1844-1856.

Wallace, D.C. et al., "Mitochondria and cancer," National Review Cancer, Oct. 2012, vol. 12, No. 10, p. 685-698.

Wang, Z. et al., "Amyloid-beta overproduction causes abnormal mitochondrial dynamics via differential modulation of mitochondrial fission/fusion proteins," Proceedings of the National Academy of Sciences, Dec. 2008, vol. 105, No. 49, p. 19318-19323.

Wang, Z. et al., "GSK-3 promotes conditional association of CREB and its coactivators with MEIS1 to facilitate HOX-mediated transcription and oncogenesis," Cancer Cell, Jun. 2010, vol. 17, No. 6, p. 297-608.

Wang, Z., et al., "Parkin Ubiquitinates Drp1 for Proteasome-dependent Degradation," The Journal of Biological Chemistry, Apr. 2011, vol. 286, No. 13, p. 11649-11658.

Wang, C.W. et al., "Apg2 is a novel protein required for the cytoplasm to vacuole targeting, autophagy, and pexophagy pathways," The Journal of Biological Chemistry, Aug. 2001, vol. 276, No. 32, p. 30442-30451.

Warburg, O. et al., "On the Origin of Cancer Cells," Science, Feb. 1956, vol. 123, No. 3191, p. 309-314.

Xiao, X. et al., "OMA1 mediates OPA1 proteolysis and mitochondrial fragmentation in experimental models of ischemic kidney injury," American Journal of Physiology, Renal Physiology, Jun. 2014, vol. 306, No. 11, p. F1318-F1326.

(56) References Cited

OTHER PUBLICATIONS

Yang, Y. et al., "Pink1 regulates mitochondrial dynamics through interaction with the fission/fusion machinery," Proceedings of the National Academy of Sciences, May 2008, vol. 105, No. 19, p. 7070-7075.

Yao, J. et al., "Mitochondrial bioenergetic deficit precedes Alzheimer's pathology in female mouse model of Alzheimer's disease," Proceedings of the national Academy of Sciences, Aug. 2009, vol. 106, No. 34, p. 14670-14675.

Zhang, T. et al., "BNIP3 Protein Suppresses PINK1 Kinase Proteolytic Cleavage to Promote Mitophagy," The Journal of Biological Chemistry, Oct. 2016, vol. 291, No. 41, p. 21616-21629.

Zhao, X. et al., "OPA1 downregulation is involved in sorafenib-induced apoptosis in hepatocellular carcinoma," Lab Invest., Jan. 2013, vol. 93, No. 1, 19 pages.

Zuchner, S. et al., "Mutations in the mitochondrial GTPase mitofusin 2 cause Charcot-Marie-Tooth neuropathy type 2A," Nature Genetics, May 2004, vol. 36, No. 5, p. 449-451.

International Search Report and Written Opinion for Application No. PCT/EP2008/005400, dated Jan. 19, 2009, 15 pages.

Aliev, G. et al., "Mitochondrial and vascular lesion as a central target for the development of Alzheimer's disease and Alzheimer disease-like pathology in transgenic mice," Neurological Research, A Journal of Progress in Neurosurgery, Neurology and Neurosciences, 2003, vol. 25, Issue 6, p. 665-674.

Banfi, S. et al., "Identification and Characterization of AFG3L2, a Novel Paraplegin-Related Gene," Genomics, Jul. 1999, vol. 59, Issue 1, p. 52-58.

Bowie, J.U. et al., "Deciphering the message in protein sequences: tolerance to amino acid substitutions," Science, 1990, vol. 247, p. 1306-1610.

Burte, F. et al., "Disturbed mitochondrial dynamics and neurodegenerative disorders," Nature Reviews Neurology, Jan. 2015, vol. 11, No. 1, p. 11-24.

Butterfield, D.A. et al., "Evidence of oxidative damage in Alzheimer's disease brain: central role for amyloid β-peptide," Trends in Molecular Medicine, Dec. 2001, vol. 7, Issue 12, p. 548-554.

Carelli, V. et al., "Mitochondrial dysfunction as a cause of optic neuropathies," Progress in Retinal and Eye Research, Jan. 2004, vol. 23, Issue 1, p. 53-89.

Caspersen, C. et al., "Mitochondrial Aβ: a potential focal point for neuronal metabolic dysfunction in Alzheimer's disease," FASEB J., Dec. 2005, vol. 19, No. 14, p. 2040-2041.

Chrysostomou, V. et al., "Oxidative stress and mitochondrial dysfunction in glaucoma," Current Opinion in Pharmacology, Feb. 2013, vol. 13, Issue 1, p. 12-15.

Daoud, H., et al., "Resequencing of 29 Candidate Genes in Patients with Familial and Sporadic Amyotrophic Lateral Sclerosis," Archives of Neurology, May 2011, vol. 68, p. 587-593.

Delettre, C. et al., "Mutation spectrum and splicing variants in the OPA1 gene," Human Genetics, Dec. 2001, vol. 109, Issue 6, p. 584-591.

Del Dotto, V. et al., "OPA1: How much do we know to approach therapy?," Pharmacological Research, Feb. 2018, 12 pages.

Ekert, A., et al., "Soluble Beta-Amyloid Leads to Mitochondrial Defects in Amyloid Precursor Protein and Tau Transgenic Mice," Neuro-Degenerative Diseases, Mar. 2008, vol. 5, No. 3-4, p. 157-159.

Ghio, S. et al., "Interaction of α-synuclein with biomembranes in Parkinson's disease—role of cardiolipin," Progress in Lipid Research, Jan. 2016, vol. 61, p. 73-82.

Gibson, G.E. et al., "Abnormalities of mitochondrial enzymes in Alzheimer disease," Journal of Neural Transmission, Nov. 1998, vol. 105, Issue 8-9, p. 855-870.

Kong, B. et al., "Mitochondrial dynamics regulating chemoresistance in gynecological cancers," Annals of the New York Academy of Sciences, Sep. 2015, vol. 1350, Issue 1, p. 1-16.

Kong, G.Y. et al., "Mitochondrial dysfunction and glaucoma," Journal of Glaucoma, Feb. 2009, vol. 18, No. 2, p. 93-100.

Lenaers, G. et al., "OPA1 functions in mitochondria and dysfunctions in optic nerve," The International Journal of Biochemistry & Cell Biology, Oct. 2009, vol. 41, Issue 10, p. 1866-1874.

Lee, S. et al., "Mitochondrial dysfunction in glaucoma and emerging bioenergetic therapies," Experimental Eye Research, Aug. 2011, vol. 93, Issue 2, p. 204-212.

Martin-Garcia, J. et al., "Mitochondrial dynamics and cell death in heart failure," Heart Failure Reviews, Mar. 2016, vol. 21, Issue 2, p. 123-136.

Maurer, I. et al., "A selective defect of cytochrome c oxidase is present in brain of Alzheimer disease patients," Neurobiology of Aging, May-Jun. 2000, vol. 21, No. 3, p. 455-462.

McQuibban, G.A. et al., "Mitochondrial membrane remodelling regulated by a conserved rhomboid protease," Nature, May 2003, vol. 423, No. 6939, p. 537-541.

Nakada, K. et al., "Inter-mitochondrial complementation: Mitochondria-specific system preventing mice from expression of disease phenotypes by mutant mtDNA," Nature Medicine, Aug. 2001, vol. 7, p. 934-940.

Okamoto, K. et al., "Mitochondrial morphology and dynamics in yeast and multicellular eukaryotes," Annual Review of Genetics, 2005, vol. 39, p. 503-536.

Ono, T. et al., "Human cells are protected from mitochondrial dysfunction by complementation of DNA products in fused mitochondria," Nature Genetics, Jul. 2001, vol. 28, No. 3, p. 272-275.

Osborne, N.N. et al., "Mitochondria: Their role in ganglion cell death and survival in primary open angle glaucoma," Experimental Eye Research, 2010, vol. 90, No. 6, p. 750-757.

Pan et al., "Rat brain DNA transcript profile of halothane and isoflurane exposure." Pharmacogenet Genomics, 2006, vol. 16, No. 3, p. 171-182.

Parker, W. D. et al. "Cytochrome oxidase deficiency in Alzheimer's disease." Neurology, 1990, vol. 40, No. 8, p. 1302-1303.

Philibert, R. A., "Transcriptional profiling of subjects from the Iowa adoption studies," American Journal of Medical Genetics Part B, Neuropsychiatric Genetics, 2007, vol. 144B, p. 683-690.

Rossello, A.E. et al., "New N-arylsulfonyl-N-alkoxyaminoacetohydroxamic acids as selective inhibitors of gelatinase A (MMP-2)," Bioorganic & Medicianl Chemistry, 2004, vol. 12, p. 2441-2450.

Salminen, A.A. et al., "Impaired mitochondrial energy metabolism in Alzheimer's disease: Impact on pathogenesis via disturbed epigenetic regulation of chromatin landscape," Progress in Neurobiology, 2015, vol. 131, p. 1-20.

Santos, D. et al., "The Impact of Mitochondrial Fusion and Fission Modulation in Sporadic Parkinson's Disease," Mol Neurobiology, Sep. 2014, vol. 52, No. 1, p. 573-586.

Satoh, M. et al., "Differential sublocalization of the dynamin-related protein OPA1 isoforms in mitochondria," Biochemical and Biophysical Research Communications, Jan. 2003, vol. 300, Issue 2, p. 482-493.

Schapira, A.H. et al., "Mitochondrial complex I deficiency in Parkinson's disease," Journal of Neurochemistry, 1990, vol. 54, No. 3, p. 823-827.

Sesaki, H. et al., "Cells lacking Pcp1p/Ugo2p, a rhomboid-like protease required for Mgm1p processing, lose mtDNA and mitochondrial structure in a Dnm1p-dependent manner, but remain competent for mitochondrial fusion," Biochemical and Biophysical Research Communications, 2003, vol. 308, p. 276-283.

Sit, A.J. "Intraocular pressure variations: causes and clinical significance," Can J Ophthalmol, 2014, vol. 49, No. 6, p. 484-488.

Skulachev, V.P. et al., "Thread-grain transition of mitochondrial reticulum as a step of mitoptosis and apoptosis," Molecular and Cellular Biochemistry, 2004, vol. 256, p. 341-358.

Smith, M.A. et al., "Oxidative damage in Alzheimer's," Nature, Jul. 1996, vol. 382, Issue 6587, p. 120-121.

Taylor, J.P. et al., "Toxic proteins in neurodegenerative disease," Science, Jun. 2002, vol. 296, Issue 5575, p. 1991-1995.

Wai, T. et al., "Imbalanced OPA1 processing and mitochondrial fragmentation cause heart failure in mice," Science, Dec. 2015, vol. 350, Issue 6265, p. 1221, aad0116-1.

Wells, J.A. "Additivity of mutational effects in proteins," Biochemistry, 1990, vol. 29, No. 37, p. 8509-8517.

(56) References Cited

OTHER PUBLICATIONS

Yan, J. et al., "Blockage of GSK3beta-mediated Drp1 phosphorylation provides neuroprotection in neuronal and mouse models of Alzheimer's disease," Neurobiology of Aging, 2015, vol. 36, No. 1, p. 211-227.

Yang, X. et al., "Aberrant Alterations of Mitochondrial Factors Drp1 and Opa1 in the Brains of Scrapie Experiment Rodents," Journal of Molecular Neuroscience, 2017, vol. 61, No. 3, p. 368-378.

Zhang, Y. et al., "Transcriptional analysis of multiple brain regions in Parkinson's disease supports the involvement of specific protein processing, energy metabolism, and signaling pathways, and suggests novel disease mechanisms," American Journal of Medical Genetics Part B (Neuropsychiatric Genetics), 2005, vol. 137B, p. 5-16.

Supplementary Partial European Search Report from Appl. No. EP17877363, dated Jul. 6, 2020.

Zhang et al., Membrane depolarization activates the mitochondrial protease OMA1 by stimulating self-cleavage, EMBO reports, (2014), 15:576-585.

Ruchika et al., The i-AAA protease YME1L and OMA1 cleave OPA1 to balance mitochondrial fusion and fission, The Journal of Cell Biology, (2014), 204:919-929.

\* cited by examiner

FIG. 4
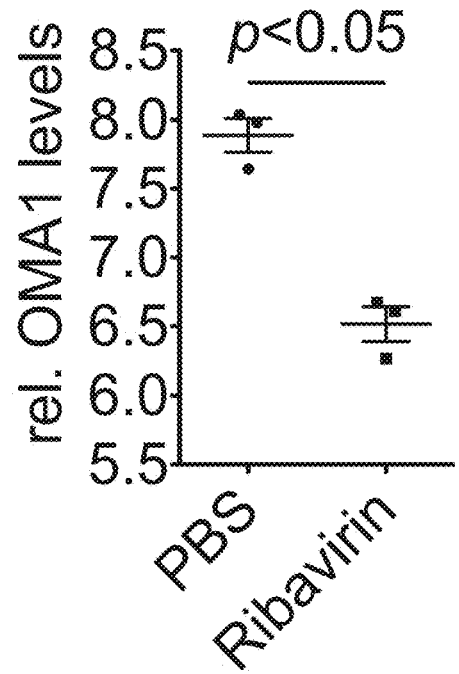
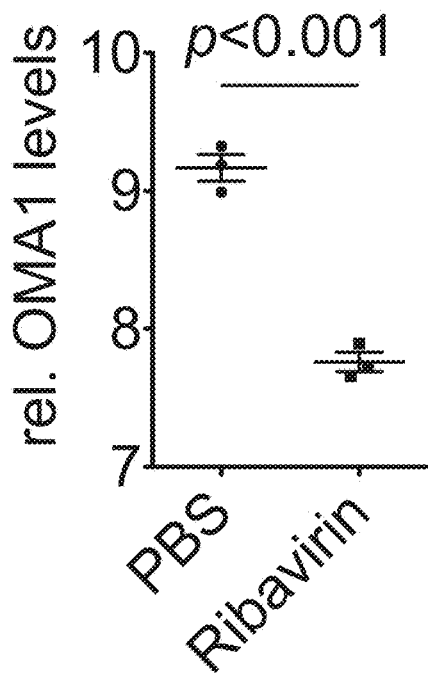

FIG. 8

Breast Cancer

| Gene | Gene ID | Min | Max | Median | Group "low" | Group "high" |
|---|---|---|---|---|---|---|
| OPA1 | 4976 | 6 | 1853 | 319 | 6-319 | 320-1853 |
| OMA1 | 115209 | 48 | 3238 | 807 | 48-807 | 808-3238 |
| HIGD1A | 25994 | 20 | 4949 | 284 | 20-284 | 285-4949 |
| BNIP3 | 664 | 121 | 17729 | 1325 | 121-1325 | 1326-17729 |
| YME1L1 | 10730 | 113 | 17733 | 3597 | 113-3597 | 3598-17733 |
| PHB | 5245 | 36 | 18120 | 617 | 36-617 | 618-18120 |
| PHB2 | 11331 | 730 | 25835 | 6605 | 730-6605 | 6606-25835 |
| SAMM50 | 25813 | 18 | 4437 | 825 | 18-825 | 826-4437 |
| IMMT | 10989 | 337 | 9324 | 1714 | 337-1714 | 1715-9324 |

Lung Cancer

| Gene | Gene ID | Min | Max | Median | Group "low" | Group "high" |
|---|---|---|---|---|---|---|
| OPA1 | 4976 | 18 | 6742 | 329 | 18-329 | 330-6742 |
| OMA1 | 115209 | 23 | 3181 | 577 | 23-577 | 578-3181 |
| HIGD1A | 25994 | 7 | 3573 | 249 | 7-249 | 250-3573 |
| BNIP3 | 664 | 126 | 16723 | 2193 | 126-2193 | 2194-16723 |
| YME1L1 | 10730 | 348 | 22613 | 3186 | 348-3186 | 3187-22613 |
| PHB | 5245 | 40 | 3328 | 575 | 40-575 | 576-3328 |
| PHB2 | 11331 | 298 | 28456 | 6737 | 298-6737 | 6738-28456 |
| SAMM50 | 25813 | 166 | 3378 | 800 | 166-800 | 801-3378 |
| IMMT | 10989 | 110 | 6432 | 1563 | 110-1563 | 1564-6432 |

FIG. 9

Gastric Cancer

| Gene | Gene ID | Min | Max | Median | Group "low" | Group "high" |
|---|---|---|---|---|---|---|
| OPA1 | 4976 | 68 | 1693 | 411 | 68-411 | 412-1693 |
| OMA1 | 115209 | 38 | 2403 | 1096 | 38-1096 | 1097-2403 |
| HIGD1A | 25994 | 78 | 3247 | 580 | 78-580 | 581-3247 |
| BNIP3 | 664 | 15 | 7614 | 319 | 15-319 | 320-7614 |
| YME1L1 | 10730 | 811 | 10704 | 3388 | 811-3388 | 3389-10704 |
| PHB | 5245 | 138 | 2014 | 622 | 138-622 | 623-2014 |
| PHB2 | 11331 | 2187 | 22306 | 5434 | 2187-5434 | 5435-22306 |
| SAMM50 | 25813 | 217 | 2532 | 1181 | 217-1181 | 1182-2532 |
| IMMT | 10989 | 459 | 5445 | 2017 | 459-2017 | 2018-5445 |

Ovarian Cancer

| Gene | Gene ID | Min | Max | Median | Group "low" | Group "high" |
|---|---|---|---|---|---|---|
| OPA1 | 4976 | 4 | 1872 | 378 | 4-378 | 379-1872 |
| OMA1 | 115209 | 12 | 2459 | 827 | 12-827 | 828-2459 |
| HIGD1A | 25994 | 2 | 2820 | 344 | 2-344 | 345-2820 |
| BNIP3 | 664 | 4 | 15905 | 2256 | 4-2256 | 2257-15905 |
| YME1L1 | 10730 | 63 | 16279 | 4363 | 63-4363 | 4364-16279 |
| PHB | 5245 | 42 | 2441 | 562 | 42-562 | 563-2441 |
| PHB2 | 11331 | 170 | 35557 | 10261 | 170-10261 | 10262-35557 |
| SAMM50 | 25813 | 20 | 35563 | 922 | 20-922 | 923-35563 |
| IMMT | 10989 | 32 | 6025 | 1798 | 32-1798 | 1799-6025 |

FIG. 20

| Name | Cas number | Name | Cas number |
|---|---|---|---|
| N-acetyl-L-Carnosine | 56353-15-2 | NSC319726 | 71555-25-4 |
| 1-Napthylisothiocyanate | 551-06-4 | ONO 4817 | 223472-31-9 |
| Actinonin | 13434-13-4 | Paclitaxel | 33069-62-4 |
| Afimoxifene | 68392-35-8 | Palbociclib | 827022-32-2 |
| ARP 100 | 704888-90-4 | PD166793 | 199850-67-4 |
| Ascorbic acid | 50-81-7 | PhIP | 105650-23-5 |
| Atazanavir | 198904-31-3 | Prinomastat | 192329-42-3 |
| Batimastat | 130370-60-4 | Racecadrotil | 81110-73-8 |
| Belinostat | 414864-00-9 | Ritonavir | 155213-67-5 |
| BIO | 667463-62-9 | Ro-28-2653 | 261956-22-3 |
| Brodalumab | 1174395-19-7 | SAHA | 149647-78-9 |
| CCCP | 555-60-2 | Saquinavir | 149845-06-7 |
| CGS 27023A | 161314-70-1 | SB-3CT | 292605-14-2 |
| Decitabin | 2353-33-5 | SCH 32615 | 83861-02-3 |
| Dexamethasone | 50-02-2 | SCH 34826 | 105262-04-2 |
| edelfosine | 70641-51-9 | Sodium valproate | 1069-66-5 |
| Elamipretide | 736992-21-5 | Sulforaphane | 4478-93-7 |
| GM6001 | 142880-36-2 | Tamoxifen | 10540-29-1 |
| Indinavir sulfate | 157810-81-6 | TAPI-0 | 143457-40-3 |
| Interleukin 2 | P60568 (Uniprot) | TAPI-1 | 171235-71-5 |
| JQ1 | 1268524-70-4 | TAPI-2 | 187034-31-7 |
| Lisinopril | 76547-98-3 | Tazemetostat | 1403254-99-8 |
| Lopinavir | 192725-17-0 | Thiorphan | 76721-89-6 |
| LY2811376 | 1194044-20-6 | Tipranavir | 174484-41-4 |
| Marimastat | 154039-60-8 | TPEN | 16858-02-9 |
| Metformin | 1115-70-4 | Trichostatin A | 58880-19-6 |
| MG132 | 133407-82-6 | Trovafloxacin | 147059-72-1 |
| MLN4924 | 905579-51-3 | UCF 101 | 313649-08-0 |
| MMP-3 Inhibitor VIII | 208663-26-7 | Valproic acid | 99-66-1 |
| Napthylisothiocyanate | 551-06-4 | Verubecestat | 1286770-55-5 |
| NNGH | 161314-17-6 | | |

FIG. 22
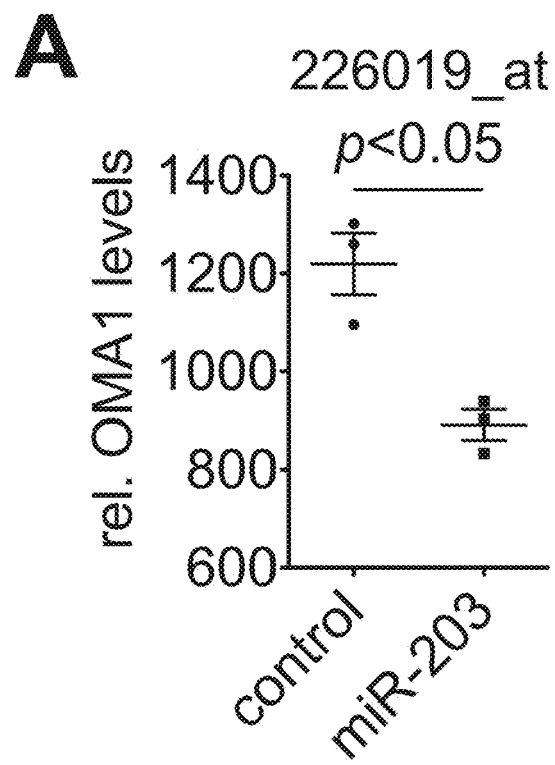
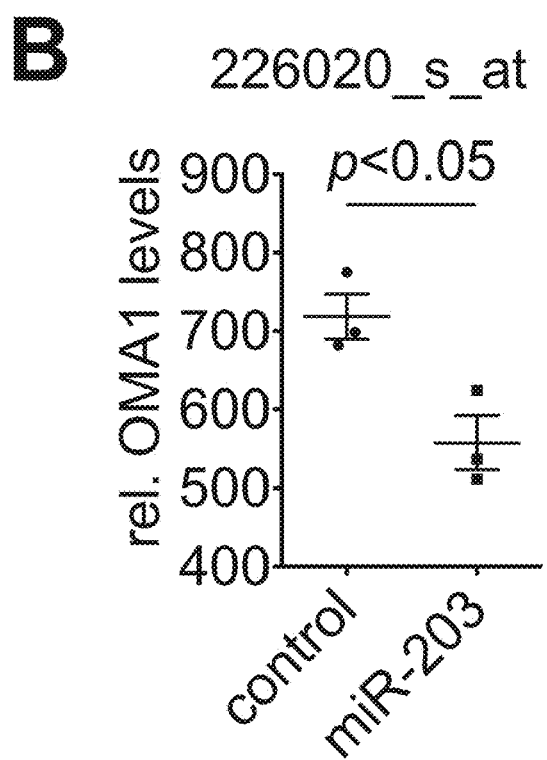

FIG. 24
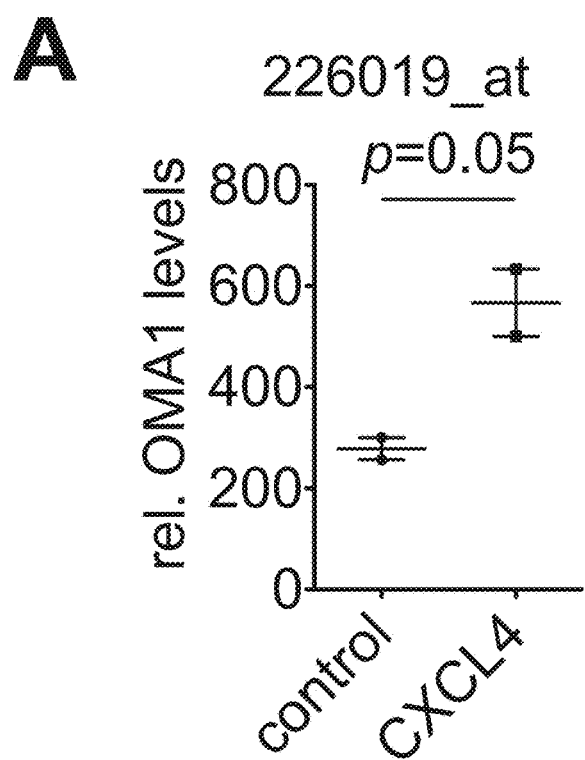
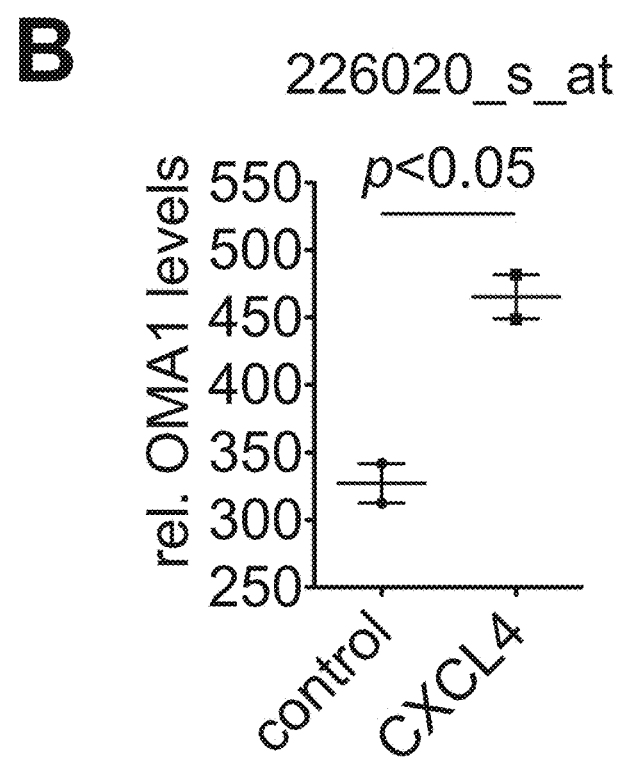

SEQUENCE LISTING

<160> NUMBER OF SEQ ID NOS: 63

<210> SEQ ID NO 1
<211> LENGTH: 6345
<212> TYPE: DNA
<213> ORGANISM: Homo sapiens

<400> SEQUENCE: 1

| | | | | | | |
|---|---|---|---|---|---|---|
| gtgctgcccg | cctagaaagg | gtgaagtggt | tgtttccgtg | acggactgag | tacgggtgcc | 60 |
| tgtcaggctc | ttgcggaagt | ccatgcgcca | ttgggagggc | ctcggccgcg | gctctgtgcc | 120 |
| cttgctgctg | agggccactt | cctgggtcat | tcctggaccg | ggagccgggc | tggggctcac | 180 |
| acggggggctc | ccgcgtggcc | gtctcggcgc | ctgcgtgacc | tccccgccgg | cgggatgtgg | 240 |
| cgactacgtc | gggccgctgt | ggcctgtgag | gtctgccagt | ctttagtgaa | acacagctct | 300 |
| ggaataaaag | gaagtttacc | actacaaaaa | ctacatctgg | tttcacgaag | catttatcat | 360 |
| tcacatcatc | ctaccttaaa | gcttcaacga | ccccaattaa | ggacatcctt | tcagcagttc | 420 |
| tcttctctga | caaaccttcc | tttacgtaaa | ctgaaattct | ctccaattaa | atatggctac | 480 |
| cagcctcgca | ggaattttg | gccagcaaga | ttagctacga | gactcttaaa | acttcgctat | 540 |
| ctcatactag | gatcggctgt | tgggggtggc | tacacagcca | aaaagacttt | tgatcagtgg | 600 |
| aaagatatga | taccggacct | tagtgaatat | aaatggattg | tgcctgacat | tgtgtgggaa | 660 |
| attgatgagt | atatcgattt | tgagaaaatt | agaaaagccc | ttcctagttc | agaagacctt | 720 |
| gtaaagttag | caccagactt | tgacaagatt | gttgaaagcc | ttagcttatt | gaaggacttt | 780 |
| tttacctcag | gttctccgga | agaaacggcg | tttagagcaa | cagatcgtgg | atctgaaagt | 840 |
| gacaagcatt | ttagaaaggt | gtcagacaaa | gagaaaattg | accaacttca | ggaagaactt | 900 |
| ctgcacactc | agttgaagta | tcagagaatc | ttggaacgat | tagaaaagga | gaacaaagaa | 960 |
| ttgagaaaat | tagtattgca | gaaagatgac | aaaggcattc | atcatagaaa | gcttaagaaa | 1020 |
| tctttgattg | acatgtattc | tgaagttctt | gatgttctct | ctgattatga | tgccagttat | 1080 |
| aatacgcaag | atcatctgcc | acgggttgtt | gtggttggag | atcagagtgc | tggaaagact | 1140 |
| agtgtgttgg | aaatgattgc | ccaagctcga | atattcccaa | gaggatctgg | ggagatgatg | 1200 |
| acacgttctc | cagttaaggt | gactctgagt | gaaggtcctc | accatgtggc | cctatttaaa | 1260 |
| gatagttctc | gggagtttga | tcttaccaaa | gaagaagatc | ttgcagcatt | aagacatgaa | 1320 |
| atagaacttc | gaatgaggaa | aaatgtgaaa | gaaggctgta | ccgttagccc | tgagaccata | 1380 |
| tccttaaatg | taaaaggccc | tggactacag | aggatggtgc | ttgttgactt | accaggtgtg | 1440 |
| attaatactg | tgacatcagg | catggctcct | gacacaaagg | aaactatttt | cagtatcagc | 1500 |
| aaagcttaca | tgcagaatcc | taatgccatc | atactgtgta | ttcaagatgg | atctgtggat | 1560 |
| gctgaacgca | gtattgttac | agacttggtc | agtcaaatgg | accctcatgg | aaggagaacc | 1620 |
| atattcgttt | tgaccaaagt | agacctggca | gagaaaaatg | tagccagtcc | aagcaggatt | 1680 |
| cagcagataa | ttgaaggaaa | gctcttccca | atgaaagctt | taggttattt | tgctgttgta | 1740 |
| acaggaaaag | ggaacagctc | tgaaagcatt | gaagctataa | gagaatatga | agaagagttt | 1800 |
| tttcagaatt | caaagctcct | aaagacaagc | atgctaaagg | cacaccaagt | gactacaaga | 1860 |
| aatttaagcc | ttgcagtatc | agactgcttt | tggaaaatgg | tacgagagtc | tgttgaacaa | 1920 |
| caggctgata | gtttcaaagc | aacacgtttt | aaccttgaaa | ctgaatggaa | gaataactat | 1980 |
| cctcgcctgc | gggaacttga | ccggaatgaa | ctatttgaaa | aagctaaaaa | tgaaatcctt | 2040 |
| gatgaagtta | tcagtctgag | ccaggttaca | ccaaaacatt | gggaggaaat | ccttcaacaa | 2100 |

```
tctttgtggg aaagagtatc aactcatgtg attgaaaaca tctaccttcc agctgcgcag    2160
accatgaatt caggaacttt taacaccaca gtggatatca agcttaaaca gtggactgat    2220
aaacaacttc ctaataaagc agtagaggtt gcttgggaga ccctacaaga agaattttcc    2280
cgctttatga cagaaccgaa agggaaagag catgatgaca tatttgataa acttaaagag    2340
gctgttaagg aagaaagtat taaacgacac aagtggaatg actttgcgga ggacagcttg    2400
agggttattc aacacaatgc tttggaagac cgatccatat ctgataaaca gcaatgggat    2460
gcagctattt attttatgga agaggctctg caggctcgtc tcaaggatac tgaaaatgca    2520
attgaaaaca tggtgggtcc agactggaaa aagaggtggt tatactgaa gaatcggacc     2580 caagaacagt gtgttcacaa tgaaaccaag aatgaattgg agaagatgtt gaaatgtaat    2640
gaggagcacc cagcttatct tgcaagtgat gaaataacca cagtccggaa gaaccttgaa    2700
tcccgaggag tagaagtaga tccaagcttg attaaggata cttggcatca agtttataga    2760
agacattttt taaaaacagc tctaaaccat tgtaacctt gtcgaagagg tttttattac      2820
taccaaaggc attttgtaga ttctgagttg gaatgcaatg atgtggtctt gttttggcgt    2880
atacagcgca tgcttgctat caccgcaaat actttaaggc aacaacttac aaatactgaa    2940
gttaggcgat tagagaaaaa tgttaaagag gtattggaag attttgctga agatggtgag    3000
aagaagatta aattgcttac tggtaaacgc gttcaactgg cggaagacct caagaaagtt    3060
agagaaattc aagaaaaact tgatgctttc attgaagctc ttcatcagga gaaataaatt    3120
aaaatcgtac tcataatcag ctctgcatac atctgaagaa caaaaacatc aacgtctttt    3180
gtccagcctc ttttctctt gctgttccac ctttctaaac atacaataaa gtcatgggat    3240
aaaaataatc gatgtatgtt acgggcgctt taaccatcag ctgcctctcg aatggaagaa    3300
cagtggtaat ggattaacat cctatttgt tgtactaaag tgacaaatcg gaataatata     3360
attggtatgg ccattaggtt cagtccttga agataagaaa cttgttctct gtttgttgtc    3420
ttatttgtgg tggcactcgt ttaatggatt aactgaggtt gctcaatgtt cagtttcttt    3480
tccagaaata caatgctagg tgttttgaaa taaaacttat atagcaattg tttaagtta     3540 tcaattgtat ataaaatcac agtagcctgc taaatcattg tatgtgtctg tagtattcta    3600
ttcccagaaa ctatttgacc atgataattc agtttatatt caccacatga agaaaaatg     3660 ggtaacagaa gaacccttaa aacaggttaa tttggattgt aacgttcagt gaaagaaatt    3720
tcaacccttc atagccagcg aagaaatttg ccttggaagc caagtcagta ccagcttacc    3780
tatttgattc agttgctgtt ttctcactct ctatatccat ttgaaattga tttattttag    3840
atgttgtata cttacgttag gctttctgtt aatagtggtt tttctcctgt tgacagagcc    3900
accggattat gacacaggat gaggaagatt aaggataatc aattgactaa tttcatttag    3960
aatattatca aacatttcaa ctaggtatca gaaaaaggct ttctttcata agactatttt    4020
aaatagaaat tatttcaaca attaaagtaa tgttgaccat cccctctca gctgaataaa      4080 gaaaaattta gttcaattta ttgcaattta attacaatac taccttcaca acattttcat    4140
gtgttttaaa taatatttt ttaattggct aaaggacatt caagcaaaga aatgcttct      4200 ttacttaaaa tgtctatctc atttgctgcc ttttcactaa gcctttactt tgttaataaa    4260
agtgtccatt gtgtgatgtt tttgatttta cagtttgcta aatcttattt tcttggagtt    4320 gcttttggt aacagcccca ttgctactcc ccatttt att gttttacatc aatgcatgct     4380
tcgttgtgat ccctcaagat gtaacacttg gtatgctcgg ttgaggatat gaaaaaatac    4440
```

-continued

```
ttccgaaacc aggaattcaa tgtatgtttg ttttatactg tttgataaga aaagtaggtc    4500
cagccttaag cagcacagat gcgctggtag atgcatagtc aggaactttt tttatttctt    4560
ttaggtctag ggacaggagt gaatagaaag ggaggagagc tctattatgt tctatacaca    4620
gattaggaga tgaccttact gggtacaccc ctctaaccag tgcttacagg ttaatgcatg    4680
ttaatgaata tttttgcagt tgtaaagcat aacaattaca actacacatc tatttctaaa    4740
gaataaaaca ggaccatatt tatttacttc tgtcaactat agaaagaaag accttcagct    4800
gtatttccac agatttctcc caaggaaaag gctaatatta gtcactactg ttatcacatc    4860
cctttgtata agttttaaaa agagatggag ggagatcttc atttctttga ggagatcagt    4920
attgtaacgt atgtgaatag atgataacaa ttaatattac taaaagtccc acatgagagt    4980
cctgacgccc tctccatgcc ccacagtaat gtggcttctt tcatgggttt ttttttcttc    5040
tttttagctg atctcatcct aagcatgctt tattttcct tgaaagctag gtattatca    5100 actgcagatg ttattgaaag aaaataaaat tcagtctcaa gagtaaaccc tgtgtcttgt    5160
gtctgtagtt caaaagtcag aaatgattct aatttaaaca aaaagatact aaatatacag    5220
aagttaaatt cgaactagcc acagaatcat ttgtttttat gtcagaattt gcaaagagtg    5280
gagtggacaa agctctgtat ggaagactga acaactgtaa atagatgata tccaaactta    5340
atttggctag gacttcaatt ttaaaaatca gtgtacctag gcagtgcaca gcacgaaata    5400
agtggcccct tgcagcttccc cgtttaaccc actgtgtcat agttgcgggt ggaacagtca    5460
acctttctag tagtttatga tattgccctc tttgtattcc catttctac agttttttcc    5520 gcagacttct ttctgcaaat tattcagcct ccaaatgcaa atgaatgata taaaaataag    5580
tagggaacat ggcagagagt ggtgcttccc agcctcacaa tgtgggaatt tgacatagga    5640
tgagagtcag agtataggtt taaaagataa aatctttagt taataatttt gtatttattt    5700
attctagatg tatgtatctg aggaaagaaa tctggtattt ttgctttcca ataaagggga    5760
tcaaagtaat ggttttttctc tcagttctct aagctggtct atgttatagc tctagcagta    5820
tggaaatgtg cttttaaaata tgcttacctt ttgaatgatc atggctatat gttgttgaga    5880
tatttgaaac ttaccttgtt ttcacttgtg cactgtgaat gaactttgta ttatttttt    5940 aaaaccttca cattacgtgt agatattatt gcaacttata ttttgcctga gcttgatcaa    6000
aggtcatttg tgtagatgag taattaaaaa atatttaaat cacattataa ttctattatt    6060
ggagagcatc ttttaaattt ttttctgttt taacgaggga aagagaaacc tgtataccta    6120
gggtcattat ttgaccccat agtataacca gattcatggt ctaacaagct tcagtgtgg    6180 cttttctctg aatgcttgaa tttcacatgc cttgcatttc acagttgtac tccatggtca    6240
accggtgctt ttttcacat cgtggtactt gtcaaaacat tttgttattt tccttggtaa    6300
aatatataaa aaaggttttc taatttcaaa aaaaaaaaa aaaaa                     6345
```

<210> SEQ ID NO 2
<211> LENGTH: 960
<212> TYPE: PRT
<213> ORGANISM: Homo sapiens

<400> SEQUENCE: 2

Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu

```
                35                  40                  45
Lys Leu Gln Arg Pro Gln Leu Arg Thr Ser Phe Gln Gln Phe Ser Ser
 50                  55                  60

Leu Thr Asn Leu Pro Leu Arg Lys Leu Lys Phe Ser Pro Ile Lys Tyr
 65                  70                  75                  80

Gly Tyr Gln Pro Arg Asn Phe Trp Pro Ala Arg Leu Ala Thr Arg
                 85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
            115                 120                 125

Leu Ser Glu Tyr Lys Trp Ile Val Pro Asp Ile Val Trp Glu Ile Asp
            130                 135                 140

Glu Tyr Ile Asp Phe Glu Lys Ile Arg Lys Ala Leu Pro Ser Ser Glu
145                 150                 155                 160

Asp Leu Val Lys Leu Ala Pro Asp Phe Asp Lys Ile Val Glu Ser Leu
            165                 170                 175

Ser Leu Leu Lys Asp Phe Phe Thr Ser Gly Ser Pro Glu Glu Thr Ala
            180                 185                 190

Phe Arg Ala Thr Asp Arg Gly Ser Glu Ser Asp Lys His Phe Arg Lys
            195                 200                 205

Val Ser Asp Lys Glu Lys Ile Asp Gln Leu Gln Glu Glu Leu Leu His
            210                 215                 220

Thr Gln Leu Lys Tyr Gln Arg Ile Leu Glu Arg Leu Glu Lys Glu Asn
225                 230                 235                 240

Lys Glu Leu Arg Lys Leu Val Leu Gln Lys Asp Asp Lys Gly Ile His
            245                 250                 255

His Arg Lys Leu Lys Ser Leu Ile Asp Met Tyr Ser Glu Val Leu
            260                 265                 270

Asp Val Leu Ser Asp Tyr Asp Ala Ser Tyr Asn Thr Gln Asp His Leu
            275                 280                 285

Pro Arg Val Val Val Gly Asp Gln Ser Ala Gly Lys Thr Ser Val
            290                 295                 300

Leu Glu Met Ile Ala Gln Ala Arg Ile Phe Pro Arg Gly Ser Gly Glu
305                 310                 315                 320

Met Met Thr Arg Ser Pro Val Lys Val Thr Leu Ser Glu Gly Pro His
            325                 330                 335

His Val Ala Leu Phe Lys Asp Ser Ser Arg Glu Phe Asp Leu Thr Lys
            340                 345                 350

Glu Glu Asp Leu Ala Ala Leu Arg His Glu Ile Glu Leu Arg Met Arg
            355                 360                 365

Lys Asn Val Lys Glu Gly Cys Thr Val Ser Pro Glu Thr Ile Ser Leu
            370                 375                 380

Asn Val Lys Gly Pro Gly Leu Gln Arg Met Val Leu Val Asp Leu Pro
385                 390                 395                 400

Gly Val Ile Asn Thr Val Thr Ser Gly Met Ala Pro Asp Thr Lys Glu
            405                 410                 415

Thr Ile Phe Ser Ile Ser Lys Ala Tyr Met Gln Asn Pro Asn Ala Ile
            420                 425                 430

Ile Leu Cys Ile Gln Asp Gly Ser Val Asp Ala Glu Arg Ser Ile Val
            435                 440                 445

Thr Asp Leu Val Ser Gln Met Asp Pro His Gly Arg Arg Thr Ile Phe
            450                 455                 460
```

```
Val Leu Thr Lys Val Asp Leu Ala Glu Lys Asn Val Ala Ser Pro Ser
465                 470                 475                 480

Arg Ile Gln Gln Ile Ile Glu Gly Lys Leu Phe Pro Met Lys Ala Leu
                485                 490                 495

Gly Tyr Phe Ala Val Val Thr Gly Lys Gly Asn Ser Ser Glu Ser Ile
                500                 505                 510

Glu Ala Ile Arg Glu Tyr Glu Glu Phe Phe Gln Asn Ser Lys Leu
                515                 520                 525

Leu Lys Thr Ser Met Leu Lys Ala His Gln Val Thr Thr Arg Asn Leu
    530                 535                 540

Ser Leu Ala Val Ser Asp Cys Phe Trp Lys Met Val Arg Glu Ser Val
545                 550                 555                 560

Glu Gln Gln Ala Asp Ser Phe Lys Ala Thr Arg Phe Asn Leu Glu Thr
                565                 570                 575

Glu Trp Lys Asn Asn Tyr Pro Arg Leu Arg Glu Leu Asp Arg Asn Glu
                580                 585                 590

Leu Phe Glu Lys Ala Lys Asn Glu Ile Leu Asp Glu Val Ile Ser Leu
            595                 600                 605

Ser Gln Val Thr Pro Lys His Trp Glu Ile Leu Gln Gln Ser Leu
    610                 615                 620

Trp Glu Arg Val Ser Thr His Val Ile Glu Asn Ile Tyr Leu Pro Ala
625                 630                 635                 640

Ala Gln Thr Met Asn Ser Gly Thr Phe Asn Thr Val Asp Ile Lys
                645                 650                 655

Leu Lys Gln Trp Thr Asp Lys Gln Leu Pro Asn Lys Ala Val Glu Val
                660                 665                 670

Ala Trp Glu Thr Leu Gln Glu Glu Phe Ser Arg Phe Met Thr Glu Pro
                675                 680                 685

Lys Gly Lys Glu His Asp Asp Ile Phe Asp Lys Leu Lys Glu Ala Val
            690                 695                 700

Lys Glu Glu Ser Ile Lys Arg His Lys Trp Asn Asp Phe Ala Glu Asp
705                 710                 715                 720

Ser Leu Arg Val Ile Gln His Asn Ala Leu Glu Asp Arg Ser Ile Ser
                725                 730                 735

Asp Lys Gln Gln Trp Asp Ala Ala Ile Tyr Phe Met Glu Glu Ala Leu
            740                 745                 750

Gln Ala Arg Leu Lys Asp Thr Glu Asn Ala Ile Glu Asn Met Val Gly
            755                 760                 765

Pro Asp Trp Lys Lys Arg Trp Leu Tyr Trp Lys Asn Arg Thr Gln Glu
    770                 775                 780

Gln Cys Val His Asn Glu Thr Lys Asn Glu Leu Glu Lys Met Leu Lys
785                 790                 795                 800

Cys Asn Glu Glu His Pro Ala Tyr Leu Ala Ser Asp Glu Ile Thr Thr
                805                 810                 815

Val Arg Lys Asn Leu Glu Ser Arg Gly Val Glu Val Asp Pro Ser Leu
            820                 825                 830

Ile Lys Asp Thr Trp His Gln Val Tyr Arg Arg His Phe Leu Lys Thr
            835                 840                 845

Ala Leu Asn His Cys Asn Leu Cys Arg Arg Gly Phe Tyr Tyr Gln
    850                 855                 860

Arg His Phe Val Asp Ser Glu Leu Glu Cys Asn Asp Val Val Leu Phe
865                 870                 875                 880
```

```
Trp Arg Ile Gln Arg Met Leu Ala Ile Thr Ala Asn Thr Leu Arg Gln
                885                 890                 895

Gln Leu Thr Asn Thr Glu Val Arg Arg Leu Glu Lys Asn Val Lys Glu
            900                 905                 910

Val Leu Glu Asp Phe Ala Glu Asp Gly Glu Lys Lys Ile Lys Leu Leu
        915                 920                 925

Thr Gly Lys Arg Val Gln Leu Ala Glu Asp Leu Lys Lys Val Arg Glu
    930                 935                 940

Ile Gln Glu Lys Leu Asp Ala Phe Ile Glu Ala Leu His Gln Glu Lys
945                 950                 955                 960

<210> SEQ ID NO 3
<211> LENGTH: 6237
<212> TYPE: DNA
<213> ORGANISM: Homo sapiens

<400> SEQUENCE: 3
```

| | | | | | |
|---|---|---|---|---|---|
| gtgctgcccg | cctagaaagg | gtgaagtggt | tgtttccgtg | acggactgag | tacgggtgcc | 60 |
| tgtcaggctc | ttgcggaagt | ccatgcgcca | ttgggagggc | ctcggccgcg | gctctgtgcc | 120 |
| cttgctgctg | agggccactt | cctgggtcat | tcctggaccg | ggagccgggc | tggggctcac | 180 |
| acggggctc | ccgcgtggcc | gtctcggcgc | ctgcgtgacc | tccccgccgg | cgggatgtgg | 240 |
| cgactacgtc | gggccgctgt | ggcctgtgag | gtctgccagt | ctttagtgaa | acacagctct | 300 |
| ggaataaaag | gaagtttacc | actacaaaaa | ctacatctgg | tttcacgaag | catttatcat | 360 |
| tcacatcatc | ctaccttaaa | gcttcaacga | ccccaattaa | ggacatcctt | tcagcagttc | 420 |
| tcttctctga | caaaccttcc | tttacgtaaa | ctgaaattct | ctccaattaa | atatggctac | 480 |
| cagcctcgca | ggaattttg | gccagcaaga | ttagctacga | gactcttaaa | acttcgctat | 540 |
| ctcatactag | gatcggctgt | tggggggtggc | tacacagcca | aaaagacttt | tgatcagtgg | 600 |
| aaagatatga | taccggacct | tagtgaatat | aaatggattg | tgcctgacat | tgtgtgggaa | 660 |
| attgatgagt | atatcgattt | tggttctccg | gaagaaacgg | cgtttagagc | aacagatcgt | 720 |
| ggatctgaaa | gtgacaagca | ttttagaaag | gtgtcagaca | agagaaaat | tgaccaactt | 780 |
| caggaagaac | ttctgcacac | tcagttgaag | tatcagagaa | tcttggaacg | attagaaaag | 840 |
| gagaacaaag | aattgagaaa | attagtattg | cagaaagatg | acaaaggcat | tcatcataga | 900 |
| aagcttaaga | aatctttgat | tgacatgtat | tctgaagttc | ttgatgttct | ctctgattat | 960 |
| gatgccagtt | ataatacgca | agatcatctg | ccacggggttg | ttgtggttgg | agatcagagt | 1020 |
| gctggaaaga | ctagtgtgtt | ggaaatgatt | gcccaagctc | gaatattccc | aagaggatct | 1080 |
| ggggagatga | tgacacgttc | tccagttaag | gtgactctga | gtgaaggtcc | tcaccatgtg | 1140 |
| gccctattta | agatagttc | tcgggagttt | gatcttacca | agaagaaga | tcttgcagca | 1200 |
| ttaagacatg | aaatagaact | tcgaatgagg | aaaaatgtga | agaaggctg | taccgttagc | 1260 |
| cctgagacca | tatccttaaa | tgtaaaaggc | cctggactac | agaggatggt | gcttgttgac | 1320 |
| ttaccaggtg | tgattaatac | tgtgacatca | ggcatggctc | ctgacacaaa | ggaaactatt | 1380 |
| ttcagtatca | gcaaagctta | catgcagaat | cctaatgcca | tcatactgtg | tattcaagat | 1440 |
| ggatctgtgg | atgctgaacg | cagtattgtt | acagacttgg | tcagtcaaat | ggaccctcat | 1500 |
| ggaaggagaa | ccatattcgt | tttgaccaaa | gtagacctgg | cagagaaaaa | tgtagccagt | 1560 |
| ccaagcagga | ttcagcagat | aattgaagga | aagctcttcc | caatgaaagc | tttaggttat | 1620 |
| tttgctgttg | taacaggaaa | agggaacagc | tctgaaagca | ttgaagctat | aagagaatat | 1680 |

-continued

```
gaagaagagt tttttcagaa ttcaaagctc ctaaagacaa gcatgctaaa ggcacaccaa    1740
gtgactacaa gaaatttaag ccttgcagta tcagactgct tttggaaaat ggtacgagag    1800
tctgttgaac aacaggctga tagtttcaaa gcaacacgtt ttaaccttga aactgaatgg    1860
aagaataact atcctcgcct gcgggaactt gaccggaatg aactatttga aaaagctaaa    1920
aatgaaatcc ttgatgaagt tatcagtctg agccaggtta caccaaaaca ttgggaggaa    1980
atccttcaac aatctttgtg ggaaagagta tcaactcatg tgattgaaaa catctacctt    2040
ccagctgcgc agaccatgaa ttcaggaact tttaacacca cagtggatat caagcttaaa    2100
cagtggactg ataaacaact tcctaataaa gcagtagagg ttgcttggga gaccctacaa    2160
gaagaatttt cccgctttat gacagaaccg aaagggaaag agcatgatga catatttgat    2220
aaacttaaag aggctgttaa ggaagaaagt attaaacgac acaagtggaa tgactttgcg    2280
gaggacagct tgagggttat tcaacacaat gctttggaag accgatccat atctgataaa    2340
cagcaatggg atgcagctat ttattttatg gaagaggctc tgcaggctcg tctcaaggat    2400
actgaaaatg caattgaaaa catggtgggt ccagactgga aaaagaggtg ttatactgg     2460 aagaatcgga cccaagaaca gtgtgttcac aatgaaacca agaatgaatt ggagaagatg    2520
ttgaaatgta atgaggagca cccagcttat cttgcaagtg atgaaataac cacagtccgg    2580
aagaaccttg aatcccgagg agtagaagta gatccaagct tgattaagga tacttggcat    2640
caagtttata gaagacattt tttaaaaaca gctctaaacc attgtaacct ttgtcgaaga    2700 ggttttttatt actaccaaag gcattttgta gattctgagt tggaatgcaa tgatgtggtc    2760
ttgttttggc gtatacagcg catgcttgct atcaccgcaa atactttaag gcaacaactt    2820
acaaatactg aagttaggcg attagagaaa aatgttaaag aggtattgga agattttgct    2880
gaagatggtg agaagaagat taaattgctt actggtaaac gcgttcaact ggcggaagac    2940
ctcaagaaag ttagagaaat tcaagaaaaa cttgatgctt tcattgaagc tcttcatcag    3000
gagaaataaa ttaaaatcgt actcataatc agctctgcat acatctgaag aacaaaaaca    3060
tcaacgtctt ttgtccagcc tcttttcctt ctgctgttcc accttttctaa acatacaata    3120 aagtcatggg ataaaaataa tcgatgtatg ttacgggcgc tttaaccatc agctgcctct    3180
cgaatggaag aacagtggta atggattaac atcctatttt gttgtactaa agtgacaaat    3240
cggaataata taattggtat ggccattagg ttcagtcctt gaagataaga aacttgttct    3300
ctgtttgttg tcttatttgt ggtggcactc gtttaatgga ttaactgagg ttgctcaatg    3360
ttcagtttct tttccagaaa tacaatgcta ggtgttttga aataaaactt atatagcaat    3420
tgtttaaagt tatcaattgt atataaaatc acagtagcct gctaaatcat tgtatgtgtc    3480
tgtagtattc tattcccaga aactatttga ccatgataat tcagtttata ttcaccacat    3540
gaaagaaaaa tgggtaacag aagaaccctt aaaacaggtt aatttggatt gtaacgttca    3600
gtgaaagaaa tttcaacccct tcatagccag cgaagaaatt tgccttggaa gccaagtcag    3660
taccagctta cctatttgat tcagttgctg ttttctcact ctctatatcc atttgaaatt    3720
gatttatttt agatgttgta tacttacgtt aggctttctg ttaatagtgg tttttctcct    3780
gttgacagag ccaccggatt atgacacagg atgaggaaga ttaaggataa tcaattgact    3840
aatttcattt agaatattat caaacatttc aactaggtat cagaaaaagg ctttctttca    3900
taagactatt ttaaatagaa attatttcaa caattaaagt aatgttgacc atcccctct    3960 cagctgaata aagaaaaatt tagttcaatt tattgcaatt taattacaat actaccttca    4020
caacattttc atgtgtttta aataaatatt ttttaattgg ctaaaggaca ttcaagcaaa    4080
```

```
gaaatgcttt ctttacttaa aatgtctatc tcatttgctg cctttcact aagcctttac    4140 tttgttaata aaagtgtcca ttgtgtgatg tttttgattt tacagtttgc taaatcttat    4200
tttcttggag ttgcttttg gtaacagccc cattgctact ccccatttta ttgttttaca    4260
tcaatgcatg cttcgttgtg atccctcaag atgtaacact tggtatgctc ggttgaggat    4320
atgaaaaaat acttccgaaa ccaggaattc aatgtatgtt tgttttatac tgtttgataa    4380
gaaaagtagg tccagcctta agcagcacag atgcgctggt agatgcatag tcaggaactt    4440
ttttattttc ttttaggtct agggacagga gtgaatagaa agggaggaga gctctattat    4500
gttctataca cagattagga gatgacctta ctgggtacac ccctctaacc agtgcttaca    4560
ggttaatgca tgttaatgaa tatttttgca gttgtaaagc ataacaatta caactacaca    4620
tctatttcta aagaataaaa caggaccata tttatttact tctgtcaact atagaaagaa    4680
agaccttcag ctgtatttcc acagatttct cccaaggaaa aggctaatat tagtcactac    4740
tgttatcaca tcccttttgta taagttttaa aaagagatgg agggagatct tcatttcttt    4800
gaggagatca gtattgtaac gtatgtgaat agatgataac aattaatatt actaaaagtc    4860
ccacatgaga gtcctgacgc cctctccatg ccccacagta atgtggcttc tttcatgggt    4920 tttttttct tcttttagc tgatctcatc ctaagcatgc tttatttttc cttgaaagct    4980
aggtatttat caactgcaga tgttattgaa agaaaataaa attcagtctc aagagtaaac    5040
cctgtgtctt gtgtctgtag ttcaaaagtc agaaatgatt ctaatttaaa caaaaagata    5100
ctaaatatac agaagttaaa ttcgaactag ccacagaatc atttgttttt atgtcagaat    5160
ttgcaaagag tggagtggac aaagctctgt atggaagact gaacaactgt aaatagatga    5220
tatccaaact taatttggct aggacttcaa ttttaaaaat cagtgtacct aggcagtgca    5280
cagcacgaaa taagtggccc ttgcagcttc cccgtttaac ccactgtgct atagttgcgg    5340
gtggaacagt caacctttct agtagtttat gatattgccc tctttgtatt cccattttct    5400 acagttttt ccgcagactt ctttctgcaa attattcagc ctccaaatgc aaatgaatga    5460
tataaaaata agtagggaac atggcagaga gtggtgcttc ccagcctcac aatgtgggaa    5520
tttgacatag gatgagagtc agagtatagg tttaaaagat aaaatcttta gttaataatt    5580
ttgtatttat ttattctaga tgtatgtatc tgaggaaaga aatctggtat ttttgctttc    5640
caataaaggg gatcaaagta atggtttttc tctcagttct ctaagctggt ctatgttata    5700
gctctagcag tatggaaatg tgctttaaaa tatgcttacc ttttgaatga tcatggctat    5760
atgttgttga gatatttgaa acttaccttg ttttcacttg tgcactgtga atgaactttg    5820
tattattttt ttaaaacctt cacattacgt gtagatatta ttgcaactta tattttgcct    5880
gagcttgatc aaaggtcatt tgtgtagatg agtaattaaa aaatatttaa atcacattat    5940
aattctatta ttggagagca tcttttaaat ttttttctgt tttaacgagg gaaagagaaa    6000
cctgtatacc tagggtcatt atttgacccc atagtataac cagattcatg gtctaacaag    6060
ctctcagtgt ggcttttctc tgaatgcttg aatttcacat gccttgcatt tcacagttgt    6120
actccatggt caaccggtgc ttttttttcac atcgtggtac ttgtcaaaac attttgttat    6180
tttccttggt aaaatatata aaaaggtttt tctaatttca aaaaaaaaa aaaaaaa       6237
```

<210> SEQ ID NO 4
<211> LENGTH: 924
<212> TYPE: PRT
<213> ORGANISM: Homo sapiens

```
<400> SEQUENCE: 4

Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Gly Ser Pro Glu Glu Thr Ala Phe Arg Ala Thr
145                 150                 155                 160

Asp Arg Gly Ser Glu Ser Asp Lys His Phe Arg Lys Val Ser Asp Lys
                165                 170                 175

Glu Lys Ile Asp Gln Leu Gln Glu Glu Leu Leu His Thr Gln Leu Lys
            180                 185                 190

Tyr Gln Arg Ile Leu Glu Arg Leu Glu Lys Glu Asn Lys Glu Leu Arg
        195                 200                 205

Lys Leu Val Leu Gln Lys Asp Asp Lys Gly Ile His His Arg Lys Leu
    210                 215                 220

Lys Lys Ser Leu Ile Asp Met Tyr Ser Glu Val Leu Asp Val Leu Ser
225                 230                 235                 240

Asp Tyr Asp Ala Ser Tyr Asn Thr Gln Asp His Leu Pro Arg Val Val
                245                 250                 255

Val Val Gly Asp Gln Ser Ala Gly Lys Thr Ser Val Leu Glu Met Ile
            260                 265                 270

Ala Gln Ala Arg Ile Phe Pro Arg Gly Ser Gly Glu Met Met Thr Arg
        275                 280                 285

Ser Pro Val Lys Val Thr Leu Ser Glu Gly Pro His His Val Ala Leu
    290                 295                 300

Phe Lys Asp Ser Ser Arg Glu Phe Asp Leu Thr Lys Glu Glu Asp Leu
305                 310                 315                 320

Ala Ala Leu Arg His Glu Ile Glu Leu Arg Met Arg Lys Asn Val Lys
                325                 330                 335

Glu Gly Cys Thr Val Ser Pro Glu Thr Ile Ser Leu Asn Val Lys Gly
            340                 345                 350

Pro Gly Leu Gln Arg Met Val Leu Val Asp Leu Pro Gly Val Ile Asn
        355                 360                 365

Thr Val Thr Ser Gly Met Ala Pro Asp Thr Lys Glu Thr Ile Phe Ser
    370                 375                 380

Ile Ser Lys Ala Tyr Met Gln Asn Pro Asn Ala Ile Ile Leu Cys Ile
385                 390                 395                 400

Gln Asp Gly Ser Val Asp Ala Glu Arg Ser Ile Val Thr Asp Leu Val
                405                 410                 415
```

-continued

Ser Gln Met Asp Pro His Gly Arg Arg Thr Ile Phe Val Leu Thr Lys
            420                 425                 430

Val Asp Leu Ala Glu Lys Asn Val Ala Ser Pro Ser Arg Ile Gln Gln
            435                 440                 445

Ile Ile Glu Gly Lys Leu Phe Pro Met Lys Ala Leu Gly Tyr Phe Ala
        450                 455                 460

Val Val Thr Gly Lys Gly Asn Ser Ser Glu Ser Ile Glu Ala Ile Arg
465                 470                 475                 480

Glu Tyr Glu Glu Glu Phe Phe Gln Asn Ser Lys Leu Leu Lys Thr Ser
                485                 490                 495

Met Leu Lys Ala His Gln Val Thr Thr Arg Asn Leu Ser Leu Ala Val
            500                 505                 510

Ser Asp Cys Phe Trp Lys Met Val Arg Glu Ser Val Glu Gln Gln Ala
            515                 520                 525

Asp Ser Phe Lys Ala Thr Arg Phe Asn Leu Glu Thr Glu Trp Lys Asn
    530                 535                 540

Asn Tyr Pro Arg Leu Arg Glu Leu Asp Arg Asn Glu Leu Phe Glu Lys
545                 550                 555                 560

Ala Lys Asn Glu Ile Leu Asp Glu Val Ile Ser Leu Ser Gln Val Thr
                565                 570                 575

Pro Lys His Trp Glu Glu Ile Leu Gln Gln Ser Leu Trp Glu Arg Val
            580                 585                 590

Ser Thr His Val Ile Glu Asn Ile Tyr Leu Pro Ala Ala Gln Thr Met
        595                 600                 605

Asn Ser Gly Thr Phe Asn Thr Thr Val Asp Ile Lys Leu Lys Gln Trp
    610                 615                 620

Thr Asp Lys Gln Leu Pro Asn Lys Ala Val Glu Val Ala Trp Glu Thr
625                 630                 635                 640

Leu Gln Glu Glu Phe Ser Arg Phe Met Thr Glu Pro Lys Gly Lys Glu
                645                 650                 655

His Asp Asp Ile Phe Asp Lys Leu Lys Glu Ala Val Lys Glu Glu Ser
            660                 665                 670

Ile Lys Arg His Lys Trp Asn Asp Phe Ala Glu Asp Ser Leu Arg Val
        675                 680                 685

Ile Gln His Asn Ala Leu Glu Asp Arg Ser Ile Ser Asp Lys Gln Gln
    690                 695                 700

Trp Asp Ala Ala Ile Tyr Phe Met Glu Glu Ala Leu Gln Ala Arg Leu
705                 710                 715                 720

Lys Asp Thr Glu Asn Ala Ile Glu Asn Met Val Gly Pro Asp Trp Lys
                725                 730                 735

Lys Arg Trp Leu Tyr Trp Lys Asn Arg Thr Gln Glu Gln Cys Val His
            740                 745                 750

Asn Glu Thr Lys Asn Glu Leu Glu Lys Met Leu Lys Cys Asn Glu Glu
        755                 760                 765

His Pro Ala Tyr Leu Ala Ser Asp Glu Ile Thr Thr Val Arg Lys Asn
    770                 775                 780

Leu Glu Ser Arg Gly Val Glu Val Asp Pro Ser Leu Ile Lys Asp Thr
785                 790                 795                 800

Trp His Gln Val Tyr Arg Arg His Phe Leu Lys Thr Ala Leu Asn His
                805                 810                 815

Cys Asn Leu Cys Arg Arg Gly Phe Tyr Tyr Gln Arg His Phe Val
            820                 825                 830

-continued

```
Asp Ser Glu Leu Glu Cys Asn Asp Val Val Leu Phe Trp Arg Ile Gln
            835                 840                 845

Arg Met Leu Ala Ile Thr Ala Asn Thr Leu Arg Gln Gln Leu Thr Asn
850                 855                 860

Thr Glu Val Arg Arg Leu Glu Lys Asn Val Lys Glu Val Leu Glu Asp
865                 870                 875                 880

Phe Ala Glu Asp Gly Glu Lys Lys Ile Lys Leu Leu Thr Gly Lys Arg
                885                 890                 895

Val Gln Leu Ala Glu Asp Leu Lys Lys Val Arg Glu Ile Gln Glu Lys
            900                 905                 910

Leu Asp Ala Phe Ile Glu Ala Leu His Gln Glu Lys
            915                 920

<210> SEQ ID NO 5
<211> LENGTH: 6291
<212> TYPE: DNA
<213> ORGANISM: Homo sapiens

<400> SEQUENCE: 5
```

| | | | | | |
|---|---|---|---|---|---|
| gtgctgcccg | cctagaaagg | gtgaagtggt | tgtttccgtg | acggactgag | tacgggtgcc         60 |
| tgtcaggctc | ttgcggaagt | ccatgcgcca | ttgggagggc | ctcggccgcg | gctctgtgcc        120 |
| cttgctgctg | agggccactt | cctgggtcat | tcctggaccg | ggagccgggc | tggggctcac        180 |
| acggggctc  | ccgcgtggcc | gtctcggcgc | ctgcgtgacc | tccccgccgg | cgggatgtgg        240 |
| cgactacgtc | gggccgctgt | ggcctgtgag | gtctgccagt | ctttagtgaa | acacagctct        300 |
| ggaataaaag | gaagtttacc | actacaaaaa | ctacatctgg | tttcacgaag | catttatcat        360 |
| tcacatcatc | ctaccttaaa | gcttcaacga | ccccaattaa | ggacatcctt | tcagcagttc        420 |
| tcttctctga | caaaccttcc | tttacgtaaa | ctgaaattct | ctccaattaa | atatggctac        480 |
| cagcctcgca | ggaattttg  | gccagcaaga | ttagctacga | gactcttaaa | acttcgctat        540 |
| ctcatactag | gatcggctgt | tgggggtggc | tacacagcca | aaaagacttt | tgatcagtgg        600 |
| aaagatatga | taccggacct | tagtgaatat | aaatggattg | tgcctgacat | tgtgtgggaa        660 |
| attgatgagt | atatcgattt | tggtcacaaa | ttggttagtg | aagtcatagg | agcttctgac        720 |
| ctacttctct | tgttaggttc | tccggaagaa | acggcgttta | gagcaacaga | tcgtggatct        780 |
| gaaagtgaca | agcattttag | aaaggtgtca | gacaaagaga | aaattgacca | acttcaggaa        840 |
| gaacttctgc | acactcagtt | gaagtatcag | agaatcttgg | aacgattaga | aaaggagaac        900 |
| aaagaattga | gaaattagt  | attgcagaaa | gatgacaaag | gcattcatca | tagaaagctt        960 |
| aagaaatctt | tgattgacat | gtattctgaa | gttcttgatg | ttctctctga | ttatgatgcc       1020 |
| agttataata | cgcaagatca | tctgccacgg | gttgttgtgg | ttggagatca | gagtgctgga       1080 |
| aagactagtg | tgttggaaat | gattgcccaa | gctcgaatat | tcccaagagg | atctggggag       1140 |
| atgatgacac | gttctccagt | taaggtgact | ctgagtgaag | gtcctcacca | tgtggcccta       1200 |
| tttaaagata | gttctcggga | gtttgatctt | accaaagaag | aagatcttgc | agcattaaga       1260 |
| catgaaatag | aacttcgaat | gaggaaaaat | gtgaagaag  | gctgtaccgt | tagccctgag       1320 |
| accatatcct | aaatgtaaa  | aggccctgga | ctacagagga | tggtgcttgt | tgacttacca       1380 |
| ggtgtgatta | atactgtgac | atcaggcatg | gctcctgaca | caaggaaac  | tattttcagt       1440 |
| atcagcaaag | cttacatgca | gaatcctaat | gccatcatac | tgtgtattca | agatggatct       1500 |
| gtggatgctg | aacgcagtat | tgttacagac | ttggtcagtc | aaatggaccc | tcatggaagg       1560 |
| agaaccatat | tcgttttgac | caaagtagac | ctggcagaga | aaaatgtagc | cagtccaagc       1620 |

```
aggattcagc agataattga aggaaagctc ttcccaatga aagctttagg ttattttgct   1680
gttgtaacag gaaaagggaa cagctctgaa agcattgaag ctataagaga atatgaagaa   1740
gagttttttc agaattcaaa gctcctaaag acaagcatgc taaaggcaca ccaagtgact   1800
acaagaaatt taagccttgc agtatcgagac tgcttttgga aatggtacg agagtctgtt   1860 gaacaacagg ctgatagttt caaagcaaca cgttttaacc ttgaaactga atggaagaat   1920
aactatcctc gcctgcggga acttgaccgg aatgaactat ttgaaaaagc taaaaatgaa   1980
atccttgatg aagttatcag tctgagccag gttacaccaa acattggga ggaaatccct   2040 caacaatctt tgtgggaaag agtatcaact catgtgattg aaaacatcta ccttccagct   2100
gcgcagacca tgaattcagg aacttttaac accacagtgg atatcaagct taaacagtgg   2160
actgataaac aacttcctaa taaagcagta gaggttgctt gggagaccct acaagaagaa   2220
ttttcccgct ttatgacaga accgaaaggg aaagagcatg atgacatatt tgataaactt   2280
aaagaggctg ttaaggaaga aagtattaaa cgacacaagt ggaatgactt tgcggaggac   2340
agcttgaggg ttattcaaca caatgctttg gaagaccgat ccatatctga taaacagcaa   2400
tgggatgcag ctatttattt tatggaagag gctctgcagg ctcgtctcaa ggatactgaa   2460
aatgcaattg aaaacatggt gggtccagac tggaaaaaga ggtggttata ctggaagaat   2520
cggacccaag aacagtgtgt tcacaatgaa accaagaatg aattggagaa gatgttgaaa   2580
tgtaatgagg agcacccagc ttatcttgca agtgatgaaa taaccacagt ccggaagaac   2640
cttgaatccc gaggagtaga agtagatcca agcttgatta aggatacttg gcatcaagtt   2700
tatagaagac attttttaaa aacagctcta aaccattgta acctttgtcg aagaggtttt   2760
tattactacc aaaggcattt tgtagattct gagttggaat gcaatgatgt ggtcttgttt   2820
tggcgtatac agcgcatgct tgctatcacc gcaaatactt taaggcaaca acttacaaat   2880
actgaagtta ggcgattaga gaaaaatgtt aaagaggtat tggaagattt tgctgaagat   2940
ggtgagaaga agattaaatt gcttactggt aaacgcgttc aactggcgga agacctcaag   3000
aaagttagag aaattcaaga aaacttgat gctttcattg aagctcttca tcaggagaaa   3060
taaattaaaa tcgtactcat aatcagctct gcatacatct gaagaacaaa acatcaacg   3120 tcttttgtcc agcctctttt tcttctgctg ttccacctt ctaaacatac aataaagtca   3180
tgggataaaa ataatcgatg tatgttacgg gcgctttaac catcagctgc ctctcgaatg   3240
gaagaacagt ggtaatggat taacatccta ttttgttgta ctaaagtgac aaatcggaat   3300
aatataattg gtatggccat taggttcagt ccttgaagat aagaaacttg ttctctgttt   3360
gttgtcttat ttgtggtggc actcgtttaa tggattaact gaggttgctc aatgttcagt   3420
ttcttttcca gaaatacaat gctaggtgtt ttgaaataaa acttatatag caattgttta   3480
aagttatcaa ttgtatataa aatcacagta gcctgctaaa tcattgtatg tgtctgtagt   3540
attctattcc cagaaactat ttgaccatga taattcagtt tatattcacc acatgaaaga   3600
aaaatgggta acagaagaac ccttaaaaca ggttaatttg gattgtaacg ttcagtgaaa   3660
gaaatttcaa cccttcatag ccagcgaaga aatttgcctt ggaagccaag tcagtaccag   3720
cttacctatt tgattcagtt gctgtttctt cactctctat atccatttga aattgattta   3780
ttttagatgt tgtatactta cgttaggctt tctgttaata gtggttttc tcctgttgac   3840 agagccaccg gattatgaca caggatgagg aagattaagg ataatcaatt gactaatttc   3900
atttagaata ttatcaaaca tttcaactag gtatcagaaa aaggctttct ttcataagac   3960
```

```
tattttaaat agaaattatt tcaacaatta aagtaatgtt gaccatcccc ctctcagctg    4020
aataaagaaa aatttagttc aatttattgc aatttaatta caatactacc ttcacaacat    4080
tttcatgtgt tttaaataaa tatttttta ttggctaaag gacattcaag caaagaaatg    4140
ctttctttac ttaaaatgtc tatctcattt gctgccttt cactaagcct ttactttgtt    4200
aataaaagtg tccattgtgt gatgttttg attttacagt ttgctaaatc ttattttctt    4260
ggagttgctt tttggtaaca gccccattgc tactccccat tttattgttt tacatcaatg    4320
catgcttcgt tgtgatccct caagatgtaa cacttggtat gctcggttga ggatatgaaa    4380
aaatacttcc gaaaccagga attcaatgta tgtttgtttt atactgtttg ataagaaaag    4440
taggtccagc cttaagcagc acagatgcgc tggtagatgc atagtcagga acttttttta    4500 tttctttag gtctagggac aggagtgaat agaaagggag gagagctcta ttatgttcta    4560
tacacagatt aggagatgac cttactgggt acacccctct aaccagtgct tacaggttaa    4620
tgcatgttaa tgaatatttt tgcagttgta aagcataaca attacaacta cacatctatt    4680
tctaaagaat aaaacaggac catatttatt tacttctgtc aactatagaa agaaagacct    4740
tcagctgtat ttccacagat ttctcccaag gaaaaggcta atattagtca ctactgttat    4800
cacatccctt tgtataagtt ttaaaaagag atggagggag atcttcattt ctttgaggag    4860
atcagtattg taacgtatgt gaatagatga taacaattaa tattactaaa agtcccacat    4920
gagagtcctg acgccctctc catgccccac agtaatgtgg cttctttcat gggttttttt    4980
ttcttctttt tagctgatct catcctaagc atgctttatt tttccttgaa agctaggtat    5040
ttatcaactg cagatgttat tgaaagaaaa taaaattcag tctcaagagt aaaccctgtg    5100
tcttgtgtct gtagttcaaa agtcagaaat gattctaatt taaacaaaaa gatactaaat    5160
atacagaagt taaattcgaa ctagccacag aatcatttgt ttttatgtca gaatttgcaa    5220
agagtggagt ggacaaagct ctgtatggaa gactgaacaa ctgtaaatag atgatatcca    5280
aacttaattt ggctaggact tcaattttaa aaatcagtgt acctaggcag tgcacagcac    5340
gaaataagtg gcccttgcag cttccccgtt taacccactg tgctatagtt gcgggtggaa    5400
cagtcaacct ttctagtagt ttatgatatt gccctctttg tattcccatt ttctacagtt    5460
ttttccgcag acttctttct gcaaattatt cagcctccaa atgcaaatga atgatataaa    5520
aataagtagg gaacatggca gagagtggtg cttcccagcc tcacaatgtg ggaatttgac    5580
ataggatgag agtcagagta taggtttaaa agataaaatc tttagttaat aattttgtat    5640
ttatttattc tagatgtatg tatctgagga aagaaatctg gtattttgc tttccaataa    5700 agggatcaa agtaatggtt tttctctcag ttctctaagc tggtctatgt tatagctcta    5760
gcagtatgga aatgtgcttt aaaatatgct tacctttga atgatcatgg ctatatgttg    5820
ttgagatatt tgaaacttac cttgttttca cttgtgcact gtgaatgaac tttgtattat    5880
ttttttaaaa ccttcacatt acgtgtagat attattgcaa cttatatttt gcctgagctt    5940
gatcaaaggt catttgtgta gatgagtaat taaaaatat ttaaatcaca ttataattct    6000
attattggag agcatctttt aaatttttt ctgttttaac gagggaaaga gaaacctgta    6060
tacctagggt cattatttga ccccatagta taaccagatt catggtctaa caagctctca    6120
gtgtggcttt tctctgaatg cttgaatttc acatgccttg catttcacag ttgtactcca    6180
tggtcaaccg gtgctttttt tcacatcgtg gtacttgtca aaacattttg ttattttcct    6240
tggtaaaata tataaaaaag gttttctaat ttcaaaaaaa aaaaaaaaaa a            6291
```

<210> SEQ ID NO 6
<211> LENGTH: 942
<212> TYPE: PRT
<213> ORGANISM: Homo sapiens

<400> SEQUENCE: 6

Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Gly His Lys Leu Val Ser Val Ile Gly Ala
145                 150                 155                 160

Ser Asp Leu Leu Leu Leu Gly Ser Pro Glu Glu Thr Ala Phe Arg
                165                 170                 175

Ala Thr Asp Arg Gly Ser Glu Ser Asp Lys His Phe Arg Lys Val Ser
            180                 185                 190

Asp Lys Glu Lys Ile Asp Gln Leu Gln Glu Glu Leu Leu His Thr Gln
        195                 200                 205

Leu Lys Tyr Gln Arg Ile Leu Glu Arg Leu Glu Lys Glu Asn Lys Glu
    210                 215                 220

Leu Arg Lys Leu Val Leu Gln Lys Asp Asp Lys Gly Ile His His Arg
225                 230                 235                 240

Lys Leu Lys Lys Ser Leu Ile Asp Met Tyr Ser Glu Val Leu Asp Val
                245                 250                 255

Leu Ser Asp Tyr Asp Ala Ser Tyr Asn Thr Gln Asp His Leu Pro Arg
            260                 265                 270

Val Val Val Val Gly Asp Gln Ser Ala Gly Lys Thr Ser Val Leu Glu
        275                 280                 285

Met Ile Ala Gln Ala Arg Ile Phe Pro Arg Gly Ser Gly Glu Met Met
    290                 295                 300

Thr Arg Ser Pro Val Lys Val Thr Leu Ser Glu Gly Pro His His Val
305                 310                 315                 320

Ala Leu Phe Lys Asp Ser Ser Arg Glu Phe Asp Leu Thr Lys Glu Glu
                325                 330                 335

Asp Leu Ala Ala Leu Arg His Glu Ile Glu Leu Arg Met Arg Lys Asn
            340                 345                 350

Val Lys Glu Gly Cys Thr Val Ser Pro Glu Thr Ile Ser Leu Asn Val
        355                 360                 365

Lys Gly Pro Gly Leu Gln Arg Met Val Leu Val Asp Leu Pro Gly Val
    370                 375                 380

```
Ile Asn Thr Val Thr Ser Gly Met Ala Pro Asp Thr Lys Glu Thr Ile
385                 390                 395                 400

Phe Ser Ile Ser Lys Ala Tyr Met Gln Asn Pro Asn Ala Ile Ile Leu
            405                 410                 415

Cys Ile Gln Asp Gly Ser Val Asp Ala Glu Arg Ser Ile Val Thr Asp
        420                 425                 430

Leu Val Ser Gln Met Asp Pro His Gly Arg Arg Thr Ile Phe Val Leu
            435                 440                 445

Thr Lys Val Asp Leu Ala Glu Lys Asn Val Ala Ser Pro Ser Arg Ile
    450                 455                 460

Gln Gln Ile Ile Glu Gly Lys Leu Phe Pro Met Lys Ala Leu Gly Tyr
465                 470                 475                 480

Phe Ala Val Val Thr Gly Lys Gly Asn Ser Ser Glu Ser Ile Glu Ala
                485                 490                 495

Ile Arg Glu Tyr Glu Glu Phe Phe Gln Asn Ser Lys Leu Leu Lys
            500                 505                 510

Thr Ser Met Leu Lys Ala His Gln Val Thr Thr Arg Asn Leu Ser Leu
    515                 520                 525

Ala Val Ser Asp Cys Phe Trp Lys Met Val Arg Glu Ser Val Glu Gln
    530                 535                 540

Gln Ala Asp Ser Phe Lys Ala Thr Arg Phe Asn Leu Glu Thr Glu Trp
545                 550                 555                 560

Lys Asn Asn Tyr Pro Arg Leu Arg Glu Leu Asp Arg Asn Glu Leu Phe
                565                 570                 575

Glu Lys Ala Lys Asn Glu Ile Leu Asp Glu Val Ile Ser Leu Ser Gln
            580                 585                 590

Val Thr Pro Lys His Trp Glu Glu Ile Leu Gln Gln Ser Leu Trp Glu
            595                 600                 605

Arg Val Ser Thr His Val Ile Glu Asn Ile Tyr Leu Pro Ala Ala Gln
610                 615                 620

Thr Met Asn Ser Gly Thr Phe Asn Thr Thr Val Asp Ile Lys Leu Lys
625                 630                 635                 640

Gln Trp Thr Asp Lys Gln Leu Pro Asn Lys Ala Val Glu Val Ala Trp
            645                 650                 655

Glu Thr Leu Gln Glu Glu Phe Ser Arg Phe Met Thr Glu Pro Lys Gly
            660                 665                 670

Lys Glu His Asp Asp Ile Phe Asp Lys Leu Lys Glu Ala Val Lys Glu
        675                 680                 685

Glu Ser Ile Lys Arg His Lys Trp Asn Asp Phe Ala Glu Asp Ser Leu
    690                 695                 700

Arg Val Ile Gln His Asn Ala Leu Glu Asp Arg Ser Ile Ser Asp Lys
705                 710                 715                 720

Gln Gln Trp Asp Ala Ala Ile Tyr Phe Met Glu Ala Leu Gln Ala
            725                 730                 735

Arg Leu Lys Asp Thr Glu Asn Ala Ile Glu Asn Met Val Gly Pro Asp
            740                 745                 750

Trp Lys Lys Arg Trp Leu Tyr Trp Lys Asn Arg Thr Gln Glu Gln Cys
    755                 760                 765

Val His Asn Glu Thr Lys Asn Glu Leu Glu Lys Met Leu Lys Cys Asn
    770                 775                 780

Glu Glu His Pro Ala Tyr Leu Ala Ser Asp Glu Ile Thr Thr Val Arg
785                 790                 795                 800

Lys Asn Leu Glu Ser Arg Gly Val Glu Val Asp Pro Ser Leu Ile Lys
```

```
                 805                 810                 815
Asp Thr Trp His Gln Val Tyr Arg Arg His Phe Leu Lys Thr Ala Leu
            820                 825                 830

Asn His Cys Asn Leu Cys Arg Arg Gly Phe Tyr Tyr Gln Arg His
            835                 840                 845

Phe Val Asp Ser Glu Leu Glu Cys Asn Asp Val Val Leu Phe Trp Arg
        850                 855                 860

Ile Gln Arg Met Leu Ala Ile Thr Ala Asn Thr Leu Arg Gln Gln Leu
865                 870                 875                 880

Thr Asn Thr Glu Val Arg Arg Leu Glu Lys Asn Val Lys Glu Val Leu
            885                 890                 895

Glu Asp Phe Ala Glu Asp Gly Glu Lys Lys Ile Lys Leu Leu Thr Gly
        900                 905                 910

Lys Arg Val Gln Leu Ala Glu Asp Leu Lys Lys Val Arg Glu Ile Gln
            915                 920                 925

Glu Lys Leu Asp Ala Phe Ile Glu Ala Leu His Gln Glu Lys
        930                 935                 940

<210> SEQ ID NO 7
<211> LENGTH: 6348
<212> TYPE: DNA
<213> ORGANISM: Homo sapiens

<400> SEQUENCE: 7
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180
acggggctc ccgcgtggcc gtctcggcgc ctgcgtgacc tccccgccgg cgggatgtgg     240
cgactacgtc gggccgctgt ggcctgtgag gtctgccagt ctttagtgaa acacagctct     300
ggaataaaag gaagtttacc actacaaaaa ctacatctgg tttcacgaag catttatcat     360
tcacatcatc ctaccttaaa gcttcaacga ccccaattaa ggacatcctt tcagcagttc     420
tcttctctga caaaccttcc tttacgtaaa ctgaaattct ctccaattaa atatggctac     480
cagcctcgca ggaattttg ccagcaagaa ttagctacga gactcttaaa acttcgctat      540
ctcatactag gatcggctgt ggggggtggc tacacagcca aaaagacttt tgatcagtgg     600
aaagatatga taccggacct tagtgaatat aaatggattg tgcctgacat tgtgtgggaa     660
attgatgagt atatcgattt tggttctccg gaagaaacgg cgtttagagc aacagatcgt     720
ggatctgaaa gtgacaagca ttttagaaag ggtctgcttg gtgagctcat tctcttacaa     780
caacaaattc aagagcatga agaggaagcg cgcagccgg ctggccaata tagcacgagc       840
tatgcccaac agaagcgcaa ggtgtcagac aaagagaaaa ttgaccaact tcaggaagaa     900
cttctgcaca ctcagttgaa gtatcagaga atcttggaac gattagaaaa ggagaacaaa     960
gaattgagaa aattagtatt gcagaaagat gacaaaggca ttcatcatag aaagcttaag    1020
aaatctttga ttgacatgta ttctgaagtt cttgatgttc tctctgatta tgatgccagt    1080
tataatacgc aagatcatct gccacggggt gttgtggttg gagatcagag tgctggaaag    1140
actagtgtgt tggaaatgat tgcccaagct cgaatattcc aagaggatc tggggagatg     1200
atgacacgtt ctccagttaa ggtgactctg agtgaaggtc ctcaccatgt ggccctattt    1260
aaagatagtt ctcgggagtt tgatcttacc aagaagaag atcttgcagc attaagacat    1320
gaaatagaac ttcgaatgag gaaaaatgtg aagaaggct gtaccgttag ccctgagacc    1380
```

-continued

```
atatccttaa atgtaaaagg ccctggacta cagaggatgg tgcttgttga cttaccaggt    1440
gtgattaata ctgtgacatc aggcatggct cctgacacaa aggaaactat tttcagtatc    1500
agcaaagctt acatgcagaa tcctaatgcc atcatactgt gtattcaaga tggatctgtg    1560
gatgctgaac gcagtattgt tacagacttg gtcagtcaaa tggaccctca tggaaggaga    1620
accatattcg ttttgaccaa agtagacctg gcagagaaaa atgtagccag tccaagcagg    1680
attcagcaga taattgaagg aaagctcttc ccaatgaaag ctttaggtta ttttgctgtt    1740
gtaacaggaa aagggaacag ctctgaaagc attgaagcta aagagaata tgaagaagag    1800 ttttttcaga attcaaagct cctaaagaca agcatgctaa aggcacacca agtgactaca    1860
agaaatttaa gccttgcagt atcagactgc ttttggaaaa tggtacgaga gtctgttgaa    1920
caacaggctg atagtttcaa agcaacacgt tttaaccttg aaactgaatg gaagaataac    1980
tatcctcgcc tgcgggaact tgaccggaat gaactatttg aaaaagctaa aaatgaaatc    2040
cttgatgaag ttatcagtct gagccaggtt acaccaaaac attgggagga aatccttcaa    2100
caatctttgt gggaaagagt atcaactcat gtgattgaaa acatctacct tccagctgcg    2160
cagaccatga attcaggaac ttttaacacc acagtggata tcaagcttaa acagtggact    2220
gataaacaac ttcctaataa agcagtagag gttgcttggg agaccctaca agaagaattt    2280
tcccgcttta tgacagaacc gaagggaaa gagcatgatg acatatttga taaacttaaa    2340
gaggctgtta aggaagaaag tattaaacga cacaagtgga atgactttgc ggaggacagc    2400
ttgagggtta ttcaacacaa tgctttggaa gaccgatcca tatctgataa acagcaatgg    2460
gatgcagcta tttattttat ggaagaggct ctgcaggctc gtctcaagga tactgaaaat    2520
gcaattgaaa acatggtggg tccagactgg aaaaagaggt ggttatactg gaagaatcgg    2580
acccaagaac agtgtgttca caatgaaacc aagaatgaat tggagaagat gttgaaatgt    2640
aatgaggagc acccagctta tcttgcaagt gatgaaataa ccacagtccg gaagaacctt    2700
gaatcccgag gagtagaagt agatccaagc ttgattaagg atacttggca tcaagtttat    2760
agaagacatt tttaaaaaac agctctaaac cattgtaacc tttgtcgaag aggtttttat    2820
tactaccaaa ggcattttgt agattctgag ttggaatgca atgatgtggt cttgttttgg    2880
cgtatacagc gcatgcttgc tatcaccgca atactttaa ggcaacaact tacaaatact    2940
gaagttaggc gattagagaa aaatgttaaa gaggtattgg aagattttgc tgaagatggt    3000
gagaagaaga ttaaattgct tactggtaaa cgcgttcaac tggcggaaga cctcaagaaa    3060
gttagagaaa ttcaagaaaa acttgatgct ttcattgaag ctcttcatca ggagaaataa    3120
attaaaatcg tactcataat cagctctgca tacatctgaa gaacaaaaac atcaacgtct    3180
tttgtccagc ctcttttct tctgctgttc cacctttcta aacatacaat aaagtcatgg    3240
gataaaaata atcgatgtat gttacgggcg ctttaaccat cagctgcctc tcgaatggaa    3300
gaacagtggt aatggattaa catcctattt tgttgtacta aagtgacaaa tcggaataat    3360
ataattggta tggccattag gttcagtcct tgaagataag aaacttgttc tctgtttgtt    3420
gtcttatttg tggtggcact cgtttaatgg attaactgag gttgctcaat gttcagtttc    3480
ttttccagaa atacaatgct aggtgttttg aaataaaact tatatagcaa ttgtttaaag    3540
ttatcaattg tatataaaat cacagtagcc tgctaaatca ttgtatgtgt ctgtagtatt    3600
ctattcccag aaactatttg accatgataa ttcagtttat attcaccaca tgaaagaaaa    3660
atgggtaaca gaagaaccct taaaacaggt taatttggat tgtaacgttc agtgaaagaa    3720
```

```
atttcaaccc ttcatagcca gcgaagaaat ttgccttgga agccaagtca gtaccagctt    3780
acctatttga ttcagttgct gttttctcac tctctatatc catttgaaat tgatttattt    3840
tagatgttgt atacttacgt taggctttct gttaatagtg gttttctcc tgttgacaga     3900 gccaccggat tatgacacag gatgaggaag attaaggata atcaattgac taatttcatt    3960
tagaatatta tcaaacattt caactaggta tcagaaaaag gctttctttc ataagactat    4020
tttaaataga aattatttca acaattaaag taatgttgac catcccctc tcagctgaat     4080 aaagaaaaat ttagttcaat ttattgcaat ttaattacaa tactaccttc acaacatttt    4140
catgtgtttt aaataaatat ttttttaattg gctaaaggac attcaagcaa agaaatgctt   4200
tctttactta aaatgtctat ctcatttgct gcctttcac taagccttta ctttgttaat     4260
aaaagtgtcc attgtgtgat gttttttgatt ttacagtttg ctaaatctta ttttcttgga   4320
gttgcttttt ggtaacagcc ccattgctac tccccatttt attgttttac atcaatgcat    4380
gcttcgttgt gatccctcaa gatgtaacac ttggtatgct cggttgagga tatgaaaaaa    4440
tacttccgaa accaggaatt caatgtatgt ttgttttata ctgtttgata agaaaagtag    4500
gtccagcctt aagcagcaca gatgcgctgg tagatgcata gtcaggaact ttttttattt    4560
cttttaggtc tagggacagg agtgaataga aagggaggag agctctatta tgttctatac    4620
acagattagg agatgacctt actgggtaca cccctctaac cagtgcttac aggttaatgc    4680
atgttaatga atatttttgc agttgtaaag cataacaatt acaactacac atctatttct    4740
aaagaataaa acaggaccat atttatttac ttctgtcaac tatagaaaga aagaccttca    4800
gctgtatttc cacagatttc tcccaaggaa aaggctaata ttagtcacta ctgttatcac    4860 atcccttttgt ataagtttta aaaagagatg gagggagatc ttcatttctt tgaggagatc    4920
agtattgtaa cgtatgtgaa tagatgataa caattaatat tactaaaagt cccacatgag    4980
agtcctgacg ccctctccat gccccacagt aatgtggctt ctttcatggg tttttttttc     5040 ttcttttag ctgatctcat cctaagcatg ctttattttt ccttgaaagc taggtatta     5100 tcaactgcag atgttattga agaaaataa aattcagtct caagagtaaa ccctgtgtct    5160
tgtgtctgta gttcaaaagt cagaaatgat tctaatttaa acaaaagat actaaatata     5220 cagaagttaa attcgaacta gccacagaat catttgtttt tatgtcagaa tttgcaaaga    5280
gtggagtgga caaagctctg tatggaagac tgaacaactg taaatagatg atatccaaac    5340
ttaatttggc taggacttca attttaaaaa tcagtgtacc taggcagtgc acagcacgaa    5400
ataagtggcc cttgcagctt ccccgtttaa cccactgtgc tatagttgcg ggtggaacag    5460 tcaaccttc tagtagttta tgatattgcc ctctttgtat tcccatttc tacagttttt      5520 tccgcagact tctttctgca aattattcag cctccaaatg caaatgaatg atataaaaat    5580
aagtagggaa catggcagag agtggtgctt cccagcctca caatgtggga atttgacata    5640
ggatgagagt cagagtatag gtttaaaaga taaaatcttt agttaataat tttgtattta    5700
tttattctag atgtatgtat ctgaggaaag aaatctggta ttttttgcttt ccaataaagg   5760 ggatcaaagt aatggttttt ctctcagttc tctaagctgg tctatgttat agctctagca    5820
gtatggaaat gtgcttttaaa atatgcttac cttttgaatg atcatggcta tatgttgttg    5880
agatatttga aacttacctt gttttcactt gtgcactgtg aatgaacttt gtattatttt    5940
tttaaaacct tcacattacg tgtagatatt attgcaactt atattttgcc tgagcttgat    6000
caaaggtcat ttgtgtagat gagtaattaa aaaatatta aatcacatta taattctatt    6060
attggagagc atctttttaaa ttttttttctg ttttaacgag ggaaagagaa acctgtatac   6120
```

```
ctagggtcat tatttgaccc catagtataa ccagattcat ggtctaacaa gctctcagtg    6180
tggcttttct ctgaatgctt gaatttcaca tgccttgcat ttcacagttg tactccatgg    6240
tcaaccggtg ctttttttca catcgtggta cttgtcaaaa cattttgtta ttttccttgg    6300
taaaatatat aaaaaaggtt ttctaatttc aaaaaaaaaa aaaaaaaa               6348
```

<210> SEQ ID NO 8
<211> LENGTH: 961
<212> TYPE: PRT
<213> ORGANISM: Homo sapiens

<400> SEQUENCE: 8

```
Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Gly Ser Pro Glu Glu Thr Ala Phe Arg Ala Thr
145                 150                 155                 160

Asp Arg Gly Ser Glu Ser Asp Lys His Phe Arg Lys Gly Leu Leu Gly
                165                 170                 175

Glu Leu Ile Leu Leu Gln Gln Gln Ile Gln Glu His Glu Glu Glu Ala
            180                 185                 190

Arg Arg Ala Ala Gly Gln Tyr Ser Thr Ser Tyr Ala Gln Gln Lys Arg
        195                 200                 205

Lys Val Ser Asp Lys Glu Lys Ile Asp Gln Leu Gln Glu Glu Leu Leu
    210                 215                 220

His Thr Gln Leu Lys Tyr Gln Arg Ile Leu Glu Arg Leu Lys Glu
225                 230                 235                 240

Asn Lys Glu Leu Arg Lys Leu Val Leu Gln Lys Asp Asp Lys Gly Ile
                245                 250                 255

His His Arg Lys Leu Lys Lys Ser Leu Ile Asp Met Tyr Ser Glu Val
            260                 265                 270

Leu Asp Val Leu Ser Asp Tyr Asp Ala Ser Tyr Asn Thr Gln Asp His
        275                 280                 285

Leu Pro Arg Val Val Val Gly Asp Gln Ser Ala Gly Lys Thr Ser
    290                 295                 300

Val Leu Glu Met Ile Ala Gln Ala Arg Ile Phe Pro Arg Gly Ser Gly
305                 310                 315                 320

Glu Met Met Thr Arg Ser Pro Val Lys Val Thr Leu Ser Glu Gly Pro
                325                 330                 335
```

```
His His Val Ala Leu Phe Lys Asp Ser Ser Arg Glu Phe Asp Leu Thr
            340                 345                 350
Lys Glu Glu Asp Leu Ala Ala Leu Arg His Glu Ile Glu Leu Arg Met
            355                 360                 365
Arg Lys Asn Val Lys Glu Gly Cys Thr Val Ser Pro Glu Thr Ile Ser
370                 375                 380
Leu Asn Val Lys Gly Pro Gly Leu Gln Arg Met Val Leu Val Asp Leu
385                 390                 395                 400
Pro Gly Val Ile Asn Thr Val Thr Ser Gly Met Ala Pro Asp Thr Lys
            405                 410                 415
Glu Thr Ile Phe Ser Ile Ser Lys Ala Tyr Met Gln Asn Pro Asn Ala
            420                 425                 430
Ile Ile Leu Cys Ile Gln Asp Gly Ser Val Asp Ala Glu Arg Ser Ile
            435                 440                 445
Val Thr Asp Leu Val Ser Gln Met Asp Pro His Gly Arg Arg Thr Ile
            450                 455                 460
Phe Val Leu Thr Lys Val Asp Leu Ala Glu Lys Asn Val Ala Ser Pro
465                 470                 475                 480
Ser Arg Ile Gln Gln Ile Ile Glu Gly Lys Leu Phe Pro Met Lys Ala
            485                 490                 495
Leu Gly Tyr Phe Ala Val Val Thr Gly Lys Gly Asn Ser Ser Glu Ser
            500                 505                 510
Ile Glu Ala Ile Arg Glu Tyr Glu Glu Glu Phe Phe Gln Asn Ser Lys
            515                 520                 525
Leu Leu Lys Thr Ser Met Leu Lys Ala His Gln Val Thr Thr Arg Asn
            530                 535                 540
Leu Ser Leu Ala Val Ser Asp Cys Phe Trp Lys Met Val Arg Glu Ser
545                 550                 555                 560
Val Glu Gln Gln Ala Asp Ser Phe Lys Ala Thr Arg Phe Asn Leu Glu
            565                 570                 575
Thr Glu Trp Lys Asn Asn Tyr Pro Arg Leu Arg Glu Leu Asp Arg Asn
            580                 585                 590
Glu Leu Phe Glu Lys Ala Lys Asn Glu Ile Leu Asp Glu Val Ile Ser
            595                 600                 605
Leu Ser Gln Val Thr Pro Lys His Trp Glu Glu Ile Leu Gln Gln Ser
            610                 615                 620
Leu Trp Glu Arg Val Ser Thr His Val Ile Glu Asn Ile Tyr Leu Pro
625                 630                 635                 640
Ala Ala Gln Thr Met Asn Ser Gly Thr Phe Asn Thr Thr Val Asp Ile
            645                 650                 655
Lys Leu Lys Gln Trp Thr Asp Lys Gln Leu Pro Asn Lys Ala Val Glu
            660                 665                 670
Val Ala Trp Glu Thr Leu Gln Glu Glu Phe Ser Arg Phe Met Thr Glu
            675                 680                 685
Pro Lys Gly Lys Glu His Asp Asp Ile Phe Asp Lys Leu Lys Glu Ala
            690                 695                 700
Val Lys Glu Glu Ser Ile Lys Arg His Lys Trp Asn Asp Phe Ala Glu
705                 710                 715                 720
Asp Ser Leu Arg Val Ile Gln His Asn Ala Leu Glu Asp Arg Ser Ile
            725                 730                 735
Ser Asp Lys Gln Gln Trp Asp Ala Ala Ile Tyr Phe Met Glu Glu Ala
            740                 745                 750
```

```
Leu Gln Ala Arg Leu Lys Asp Thr Glu Asn Ala Ile Glu Asn Met Val
            755                 760                 765
Gly Pro Asp Trp Lys Lys Arg Trp Leu Tyr Trp Lys Asn Arg Thr Gln
770                 775                 780
Glu Gln Cys Val His Asn Glu Thr Lys Asn Glu Leu Glu Lys Met Leu
785                 790                 795                 800
Lys Cys Asn Glu Glu His Pro Ala Tyr Leu Ala Ser Asp Glu Ile Thr
                805                 810                 815
Thr Val Arg Lys Asn Leu Glu Ser Arg Gly Val Glu Val Asp Pro Ser
            820                 825                 830
Leu Ile Lys Asp Thr Trp His Gln Val Tyr Arg Arg His Phe Leu Lys
            835                 840                 845
Thr Ala Leu Asn His Cys Asn Leu Cys Arg Arg Gly Phe Tyr Tyr Tyr
850                 855                 860
Gln Arg His Phe Val Asp Ser Glu Leu Glu Cys Asn Asp Val Val Leu
865                 870                 875                 880
Phe Trp Arg Ile Gln Arg Met Leu Ala Ile Thr Ala Asn Thr Leu Arg
                885                 890                 895
Gln Gln Leu Thr Asn Thr Glu Val Arg Arg Leu Glu Lys Asn Val Lys
            900                 905                 910
Glu Val Leu Glu Asp Phe Ala Glu Asp Gly Glu Lys Lys Ile Lys Leu
            915                 920                 925
Leu Thr Gly Lys Arg Val Gln Leu Ala Glu Asp Leu Lys Lys Val Arg
            930                 935                 940
Glu Ile Gln Glu Lys Leu Asp Ala Phe Ile Glu Ala Leu His Gln Glu
945                 950                 955                 960
Lys
```

<210> SEQ ID NO 9
<211> LENGTH: 6399
<212> TYPE: DNA
<213> ORGANISM: Homo sapiens

<400> SEQUENCE: 9

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180
acggggggctc ccgcgtggcc gtctcggcgc ctgcgtgacc tccccgccgg cgggatgtgg    240
cgactacgtc gggccgctgt ggcctgtgag gtctgccagt ctttagtgaa acacagctct     300
ggaataaaag gaagtttacc actacaaaaa ctacatctgg tttcacgaag catttatcat     360
tcacatcatc ctaccttaaa gcttcaacga ccccaattaa ggacatcctt tcagcagttc     420
tcttctctga caaaccttcc tttacgtaaa ctgaaattct ctccaattaa atatggctac     480
cagcctcgca ggaattttttg gccagcaaga ttagctacga gactcttaaa acttcgctat     540
ctcatactag gatcggctgt tgggggtggc tacacagcca aaaagacttt tgatcagtgg     600
aaagatatga taccggacct tagtgaatat aaatggattg tgcctgacat tgtgtgggaa     660
attgatgagt atatcgattt tgagaaaatt agaaaagccc ttcctagttc agaagacctt     720
gtaaagttag caccagactt tgacaagatt gttgaaagcc ttagcttatt gaaggacttt     780
tttacctcag gtcacaaatt ggttagtgaa gtcataggag cttctgacct acttctcttg     840
ttaggttctc cggaagaaac ggcgtttaga gcaacagatc gtggatctga aagtgacaag     900
```

```
cattttagaa aggtgtcaga caaagagaaa attgaccaac ttcaggaaga acttctgcac      960
actcagttga agtatcagag aatcttggaa cgattagaaa aggagaacaa agaattgaga     1020
aaattagtat tgcagaaaga tgacaaaggc attcatcata gaaagcttaa gaaatctttg     1080
attgacatgt attctgaagt tcttgatgtt ctctctgatt atgatgccag ttataatacg     1140
caagatcatc tgccacgggt tgttgtggtt ggagatcaga gtgctggaaa gactagtgtg     1200
ttggaaatga ttgcccaagc tcgaatattc ccaagaggat ctggggagat gatgacacgt     1260
tctccagtta aggtgactct gagtgaaggt cctcaccatg tggccctatt taaagatagt     1320
tctcgggagt ttgatcttac caaagaagaa gatcttgcag cattaagaca tgaaatagaa     1380
cttcgaatga ggaaaaatgt gaaagaaggc tgtaccgtta gccctgagac catatcctta     1440
aatgtaaaag gccctggact acagaggatg gtgcttgttg acttaccagg tgtgattaat     1500
actgtgacat caggcatggc tcctgacaca aaggaaacta ttttcagtat cagcaaagct     1560
tacatgcaga atcctaatgc catcatactg tgtattcaag atggatctgt ggatgctgaa     1620
cgcagtattg ttacagactt ggtcagtcaa atggacccte atggaaggag aaccatattc     1680
gttttgacca agtagacct ggcagagaaa aatgtagcca gtccaagcag gattcagcag     1740
ataattgaag gaaagctctt cccaatgaaa gctttaggtt attttgctgt tgtaacagga     1800
aaagggaaca gctctgaaag cattgaagct ataagagaat atgaagaaga gttttttcag     1860
aattcaaagc tcctaaagac aagcatgcta aaggcacacc aagtgactac aagaaattta     1920
agccttgcag tatcagactg cttttggaaa atggtacgag agtctgttga caacaggct      1980 gatagtttca aagcaacacg ttttaacctt gaaactgaat ggaagaataa ctatcctcgc     2040
ctgcgggaac ttgaccggaa tgaactattt gaaaaagcta aaaatgaaat ccttgatgaa     2100
gttatcagtc tgagccaggt tacaccaaaa cattgggagg aaatccttca acaatctttg     2160
tgggaaagag tatcaactca tgtgattgaa acatctacc ttccagctgc gcagaccatg      2220
aattcaggaa cttttaacac cacagtggat atcaagctta acagtggac tgataaacaa      2280 cttcctaata aagcagtaga ggttgcttgg gagaccctac aagaagaatt ttcccgcttt     2340
atgacagaac cgaaagggaa agagcatgat gacatatttg ataaacttaa agaggctgtt     2400
aaggaagaaa gtattaaacg acacaagtgg aatgactttg cggaggacag cttgagggtt     2460
attcaacaca atgctttgga agaccgatcc atatctgata aacagcaatg ggatgcagct     2520
atttatttta tggaagaggc tctgcaggct cgtctcaagg atactgaaaa tgcaattgaa     2580
aacatggtgg gtccagactg gaaaaagagg tggttatact ggaagaatcg gacccaagaa     2640
cagtgtgttc acaatgaaac caagaatgaa ttggagaaga tgttgaaatg taatgaggag     2700
cacccagctt atcttgcaag tgatgaaata accacagtcc ggaagaacct tgaatcccga     2760
ggagtagaag tagatccaag cttgattaag gatacttggc atcaagttta tagaagacat     2820
tttttaaaaa cagctctaaa ccattgtaac ctttgtcgaa gaggttttta ttactaccaa     2880
aggcattttg tagattctga gttggaatgc aatgatgtg tcttgttttg gcgtatacag      2940
cgcatgcttg ctatcaccgc aaatactttta aggcaacaac ttacaaatac tgaagttagg    3000
cgattagaga aaaatgttaa agaggtattg gaagatttg ctgaagatgg tgagaagaag      3060
attaaattgc ttactggtaa acgcgttcaa ctggcggaag acctcaagaa agttagagaa     3120
attcaagaaa aacttgatgc tttcattgaa gctcttcatc aggagaaata aattaaaatc     3180
gtactcataa tcagctctgc atacatctga agaacaaaaa catcaacgtc ttttgtccag     3240 cctcttttc ttctgctgtt ccaccttct aaacatacaa taaagtcatg ggataaaaat        3300
```

```
aatcgatgta tgttacgggc gctttaacca tcagctgcct ctcgaatgga agaacagtgg   3360
taatggatta acatcctatt ttgttgtact aaagtgacaa atcggaataa tataattggt   3420
atggccatta ggttcagtcc ttgaagataa gaaacttgtt ctctgtttgt tgtcttattt   3480
gtggtggcac tcgtttaatg gattaactga ggttgctcaa tgttcagttt cttttccaga   3540
aatacaatgc taggtgtttt gaaataaaac ttatatagca attgtttaaa gttatcaatt   3600
gtatataaaa tcacagtagc ctgctaaatc attgtatgtg tctgtagtat tctattccca   3660
gaaactattt gaccatgata attcagttta tattcaccac atgaaagaaa aatgggtaac   3720
agaagaaccc ttaaaacagg ttaatttgga ttgtaacgtt cagtgaaaga aatttcaacc   3780
cttcatagcc agcgaagaaa tttgccttgg aagccaagtc agtaccagct tacctatttg   3840
attcagttgc tgttttctca ctctctatat ccatttgaaa ttgatttatt ttagatgttg   3900
tatacttacg ttaggctttc tgttaatagt ggttttctc ctgttgacag agccaccgga    3960
ttatgacaca ggatgaggaa gattaaggat aatcaattga ctaatttcat ttagaatatt   4020
atcaaacatt tcaactaggt atcagaaaaa ggctttcttt cataagacta ttttaaatag   4080
aaattatttc aacaattaaa gtaatgttga ccatccccct ctcagctgaa taagaaaaa    4140 tttagttcaa tttattgcaa tttaattaca atactaccct cacaacattt tcatgtgttt   4200
taaataaata ttttttaatt ggctaaagga cattcaagca aagaaatgct ttctttactt   4260
aaaatgtcta tctcatttgc tgccttttca ctaagccttt actttgttaa taaaagtgtc   4320
cattgtgtga tgttttttgat tttacagttt gctaaatctt attttcttgg agttgctttt  4380
tggtaacagc cccattgcta ctccccattt tattgtttta catcaatgca tgcttcgttg   4440
tgatccctca agatgtaaca cttggtatgc tcggttgagg atatgaaaaa atacttccga   4500
aaccaggaat tcaatgtatg tttgttttat actgtttgat aagaaaagta ggtccagcct   4560
taagcagcac agatgcgctg gtagatgcat agtcaggaac ttttttttatt tcttttaggt   4620 ctagggacag gagtgaatag aaagggagga gagctctatt atgttctata cacagattag   4680
gagatgacct tactgggtac accccctctaa ccagtgctta caggttaatg catgttaatg   4740 aatattttg cagttgtaaa gcataacaat tacaactaca catctatttc taagaataa     4800 aacaggacca tatttattta cttctgtcaa ctatagaaag aaagaccttc agctgtattt   4860
ccacagattt ctcccaagga aaaggctaat attagtcact actgttatca catcccttg    4920 tataagtttt aaaagagat ggagggagat cttcatttct ttgaggagat cagtattgta    4980
acgtatgtga atagatgata acaattaata ttactaaaag tcccacatga gagtcctgac   5040
gccctctcca tgccccacag taatgtggct tctttcatgg gttttttttt cttcttttta   5100
gctgatctca tcctaagcat gctttatttt tccttgaaag ctaggtattt atcaactgca   5160
gatgttattg aaagaaaata aaattcagtc tcaagagtaa accctgtgtc ttgtgtctgt   5220
agttcaaaag tcagaaatga ttctaattta acaaaaaga tactaaatat acagaagtta   5280
aattcgaact agccacagaa tcatttgttt ttatgtcaga atttgcaaag agtggagtgg   5340
acaaagctct gtatggaaga ctgaacaact gtaaatagat gatatccaaa cttaatttgg   5400
ctaggacttc aattttaaaa atcagtgtac ctaggcagtg cacagcacga ataagtggc    5460 ccttgcagct tccccgttta acccactgtg ctatagttgc gggtggaaca gtcaacctt    5520 ctagtagttt atgatattgc cctctttgta ttcccatttt ctacagtttt ttccgcagac   5580
ttctttctgc aaattattca gcctccaaat gcaaatgaat gatataaaaa taagtaggga   5640
```

-continued

```
acatggcaga gagtggtgct tcccagcctc acaatgtggg aatttgacat aggatgagag    5700
tcagagtata ggtttaaaag ataaaatctt tagttaataa ttttgtattt atttattcta    5760
gatgtatgta tctgaggaaa gaaatctggt attttttgctt tccaataaag gggatcaaag   5820
taatggtttt tctctcagtt ctctaagctg gtctatgtta tagctctagc agtatggaaa    5880
tgtgctttaa aatatgctta cctttttgaat gatcatggct atatgttgtt gagatatttg   5940
aaacttacct tgttttcact tgtgcactgt gaatgaactt tgtattattt ttttaaaacc    6000
ttcacattac gtgtagatat tattgcaact tatattttgc ctgagcttga tcaaaggtca    6060
tttgtgtaga tgagtaatta aaaaatattt aaatcacatt ataattctat tattggagag    6120
catcttttaa attttttttct gttttaacga gggaaagaga aacctgtata cctagggtca   6180
ttatttgacc ccatagtata accagattca tggtctaaca agctctcagt gtggcttttc    6240
tctgaatgct tgaatttcac atgccttgca tttcacagtt gtactccatg gtcaaccggt    6300 gcttttttttc acatcgtggt acttgtcaaa acattttgtt attttccttg gtaaaatata   6360
taaaaaaggt tttctaattt caaaaaaaaa aaaaaaaa                            6399
```

<210> SEQ ID NO 10
<211> LENGTH: 978
<212> TYPE: PRT
<213> ORGANISM: Homo sapiens

<400> SEQUENCE: 10

```
Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Glu Lys Ile Arg Lys Ala Leu Pro Ser Ser Glu
145                 150                 155                 160

Asp Leu Val Lys Leu Ala Pro Asp Phe Asp Lys Ile Val Glu Ser Leu
                165                 170                 175

Ser Leu Leu Lys Asp Phe Phe Thr Ser Gly His Lys Leu Val Ser Glu
            180                 185                 190

Val Ile Gly Ala Ser Asp Leu Leu Leu Leu Gly Ser Pro Glu Glu
        195                 200                 205

Thr Ala Phe Arg Ala Thr Asp Arg Gly Ser Glu Ser Asp Lys His Phe
    210                 215                 220

Arg Lys Val Ser Asp Lys Glu Lys Ile Asp Gln Leu Gln Glu Glu Leu
225                 230                 235                 240
```

```
Leu His Thr Gln Leu Lys Tyr Gln Arg Ile Leu Glu Arg Leu Glu Lys
                245                 250                 255

Glu Asn Lys Glu Leu Arg Lys Leu Val Leu Gln Lys Asp Asp Lys Gly
            260                 265                 270

Ile His His Arg Lys Leu Lys Lys Ser Leu Ile Asp Met Tyr Ser Glu
        275                 280                 285

Val Leu Asp Val Leu Ser Asp Tyr Asp Ala Ser Tyr Asn Thr Gln Asp
    290                 295                 300

His Leu Pro Arg Val Val Val Gly Asp Gln Ser Ala Gly Lys Thr
305                 310                 315                 320

Ser Val Leu Glu Met Ile Ala Gln Ala Arg Ile Phe Pro Arg Gly Ser
                325                 330                 335

Gly Glu Met Met Thr Arg Ser Pro Val Lys Val Thr Leu Ser Glu Gly
            340                 345                 350

Pro His His Val Ala Leu Phe Lys Asp Ser Ser Arg Glu Phe Asp Leu
        355                 360                 365

Thr Lys Glu Glu Asp Leu Ala Ala Leu Arg His Glu Ile Glu Leu Arg
    370                 375                 380

Met Arg Lys Asn Val Lys Glu Gly Cys Thr Val Ser Pro Glu Thr Ile
385                 390                 395                 400

Ser Leu Asn Val Lys Gly Pro Gly Leu Gln Arg Met Val Leu Val Asp
                405                 410                 415

Leu Pro Gly Val Ile Asn Thr Val Thr Ser Gly Met Ala Pro Asp Thr
            420                 425                 430

Lys Glu Thr Ile Phe Ser Ile Ser Lys Ala Tyr Met Gln Asn Pro Asn
        435                 440                 445

Ala Ile Ile Leu Cys Ile Gln Asp Gly Ser Val Asp Ala Glu Arg Ser
    450                 455                 460

Ile Val Thr Asp Leu Val Ser Gln Met Asp Pro His Gly Arg Arg Thr
465                 470                 475                 480

Ile Phe Val Leu Thr Lys Val Asp Leu Ala Glu Lys Asn Val Ala Ser
                485                 490                 495

Pro Ser Arg Ile Gln Gln Ile Ile Glu Gly Lys Leu Phe Pro Met Lys
            500                 505                 510

Ala Leu Gly Tyr Phe Ala Val Val Thr Gly Lys Gly Asn Ser Ser Glu
        515                 520                 525

Ser Ile Glu Ala Ile Arg Glu Tyr Glu Glu Glu Phe Phe Gln Asn Ser
    530                 535                 540

Lys Leu Leu Lys Thr Ser Met Leu Lys Ala His Gln Val Thr Thr Arg
545                 550                 555                 560

Asn Leu Ser Leu Ala Val Ser Asp Cys Phe Trp Lys Met Val Arg Glu
                565                 570                 575

Ser Val Glu Gln Gln Ala Asp Ser Phe Lys Ala Thr Arg Phe Asn Leu
            580                 585                 590

Glu Thr Glu Trp Lys Asn Asn Tyr Pro Arg Leu Arg Glu Leu Asp Arg
        595                 600                 605

Asn Glu Leu Phe Glu Lys Ala Lys Asn Glu Ile Leu Asp Glu Val Ile
    610                 615                 620

Ser Leu Ser Gln Val Thr Pro Lys His Trp Glu Glu Ile Leu Gln Gln
625                 630                 635                 640

Ser Leu Trp Glu Arg Val Ser Thr His Val Ile Glu Asn Ile Tyr Leu
                645                 650                 655

Pro Ala Ala Gln Thr Met Asn Ser Gly Thr Phe Asn Thr Thr Val Asp
```

|     |     |     |     |     |     |     |     |     |     |     |     |
| --- | --- | --- | --- | --- | --- | --- | --- | --- | --- | --- | --- |
|     |     |     | 660 |     |     | 665 |     |     | 670 |     |     |
| Ile | Lys | Leu | Lys | Gln | Trp | Thr | Asp | Lys | Gln | Leu | Pro | Asn | Lys | Ala | Val |
|     |     | 675 |     |     |     | 680 |     |     |     | 685 |     |
| Glu | Val | Ala | Trp | Glu | Thr | Leu | Gln | Glu | Glu | Phe | Ser | Arg | Phe | Met | Thr |
|     | 690 |     |     |     |     | 695 |     |     |     |     | 700 |
| Glu | Pro | Lys | Gly | Lys | Glu | His | Asp | Asp | Ile | Phe | Asp | Lys | Leu | Lys | Glu |
| 705 |     |     |     |     | 710 |     |     |     |     | 715 |     |     |     |     | 720 |
| Ala | Val | Lys | Glu | Glu | Ser | Ile | Lys | Arg | His | Lys | Trp | Asn | Asp | Phe | Ala |
|     |     |     |     | 725 |     |     |     |     | 730 |     |     |     |     | 735 |     |
| Glu | Asp | Ser | Leu | Arg | Val | Ile | Gln | His | Asn | Ala | Leu | Glu | Asp | Arg | Ser |
|     |     |     | 740 |     |     |     |     | 745 |     |     |     |     | 750 |     |     |
| Ile | Ser | Asp | Lys | Gln | Gln | Trp | Asp | Ala | Ala | Ile | Tyr | Phe | Met | Glu | Glu |
|     |     | 755 |     |     |     |     | 760 |     |     |     |     | 765 |     |     |     |
| Ala | Leu | Gln | Ala | Arg | Leu | Lys | Asp | Thr | Glu | Asn | Ala | Ile | Glu | Asn | Met |
|     | 770 |     |     |     |     | 775 |     |     |     |     | 780 |     |     |     |     |
| Val | Gly | Pro | Asp | Trp | Lys | Lys | Arg | Trp | Leu | Tyr | Trp | Lys | Asn | Arg | Thr |
| 785 |     |     |     |     | 790 |     |     |     |     | 795 |     |     |     |     | 800 |
| Gln | Glu | Gln | Cys | Val | His | Asn | Glu | Thr | Lys | Asn | Glu | Leu | Glu | Lys | Met |
|     |     |     |     | 805 |     |     |     |     | 810 |     |     |     |     | 815 |     |
| Leu | Lys | Cys | Asn | Glu | Glu | His | Pro | Ala | Tyr | Leu | Ala | Ser | Asp | Glu | Ile |
|     |     |     | 820 |     |     |     |     | 825 |     |     |     |     | 830 |     |     |
| Thr | Thr | Val | Arg | Lys | Asn | Leu | Glu | Ser | Arg | Gly | Val | Glu | Val | Asp | Pro |
|     |     | 835 |     |     |     |     | 840 |     |     |     |     | 845 |     |     |     |
| Ser | Leu | Ile | Lys | Asp | Thr | Trp | His | Gln | Val | Tyr | Arg | Arg | His | Phe | Leu |
|     | 850 |     |     |     |     | 855 |     |     |     |     | 860 |     |     |     |     |
| Lys | Thr | Ala | Leu | Asn | His | Cys | Asn | Leu | Cys | Arg | Arg | Gly | Phe | Tyr | Tyr |
| 865 |     |     |     |     | 870 |     |     |     |     | 875 |     |     |     |     | 880 |
| Tyr | Gln | Arg | His | Phe | Val | Asp | Ser | Glu | Leu | Glu | Cys | Asn | Asp | Val | Val |
|     |     |     |     | 885 |     |     |     |     | 890 |     |     |     |     | 895 |     |
| Leu | Phe | Trp | Arg | Ile | Gln | Arg | Met | Leu | Ala | Ile | Thr | Ala | Asn | Thr | Leu |
|     |     |     | 900 |     |     |     |     | 905 |     |     |     |     | 910 |     |     |
| Arg | Gln | Gln | Leu | Thr | Asn | Thr | Glu | Val | Arg | Arg | Leu | Glu | Lys | Asn | Val |
|     |     | 915 |     |     |     |     | 920 |     |     |     |     | 925 |     |     |     |
| Lys | Glu | Val | Leu | Glu | Asp | Phe | Ala | Glu | Asp | Gly | Glu | Lys | Lys | Ile | Lys |
|     | 930 |     |     |     |     | 935 |     |     |     |     | 940 |     |     |     |     |
| Leu | Leu | Thr | Gly | Lys | Arg | Val | Gln | Leu | Ala | Glu | Asp | Leu | Lys | Lys | Val |
| 945 |     |     |     |     | 950 |     |     |     |     | 955 |     |     |     |     | 960 |
| Arg | Glu | Ile | Gln | Glu | Lys | Leu | Asp | Ala | Phe | Ile | Glu | Ala | Leu | His | Gln |
|     |     |     |     | 965 |     |     |     |     | 970 |     |     |     |     | 975 |     |
| Glu | Lys |

<210> SEQ ID NO 11
<211> LENGTH: 6402
<212> TYPE: DNA
<213> ORGANISM: Homo sapiens

<400> SEQUENCE: 11

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180 acggggctc ccgcgtggcc gtctcggcgc ctgcgtgacc tccccgccgg cgggatgtgg     240
cgactacgtc gggccgctgt ggcctgtgag gtctgccagt ctttagtgaa acacagctct     300
```

```
ggaataaaag gaagtttacc actacaaaaa ctacatctgg tttcacgaag catttatcat    360
tcacatcatc ctaccttaaa gcttcaacga ccccaattaa ggacatcctt tcagcagttc    420
tcttctctga caaaccttcc tttacgtaaa ctgaaattct ctccaattaa atatggctac    480
cagcctcgca ggaattttg gccagcaaga ttagctacga gactcttaaa acttcgctat     540
ctcatactag gatcggctgt tggggtggc tacacagcca aaagacttt tgatcagtgg      600 aaagatatga taccggacct tagtgaatat aaatggattg tgcctgacat tgtgtgggaa    660
attgatgagt atatcgattt tggtcacaaa ttggttagtg aagtcatagg agcttctgac    720
ctacttctct tgttaggttc tccggaagaa acggcgttta gagcaacaga tcgtggatct    780
gaaagtgaca agcattttag aaagggtctg cttggtgagc tcattctctt acaacaacaa    840
attcaagagc atgaagagga agcgcgcaga gccgctggcc aatatagcac gagctatgcc    900
caacagaagc gcaaggtgtc agacaaagag aaaattgacc aacttcagga agaacttctg    960
cacactcagt tgaagtatca gagaatcttg gaacgattag aaaaggagaa caaagaattg   1020
agaaaattag tattgcagaa agatgacaaa ggcattcatc atagaaagct taagaaatct   1080
ttgattgaca tgtattctga agttcttgat gttctctctg attatgatgc cagttataat   1140
acgcaagatc atctgccacg ggttgttgtg gttggagatc agagtgctgg aaaagactagt  1200 gtgttggaaa tgattgccca agctcgaata ttcccaagag gatctgggga gatgatgaca   1260
cgttctccag ttaaggtgac tctgagtgaa ggtcctcacc atgtggccct atttaaagat   1320
agttctcggg agtttgatct taccaaagaa gaagatcttg cagcattaag acatgaaata   1380
gaacttcgaa tgaggaaaaa tgtgaaagaa ggctgtaccg ttagccctga gaccatatcc   1440
ttaaatgtaa aaggccctgg actacagagg atggtgcttg ttgacttacc aggtgtgatt   1500
aatactgtga catcaggcat ggctcctgac acaaaggaaa ctattttcag tatcagcaaa   1560
gcttacatgc agaatcctaa tgccatcata ctgtgtattc aagatggatc tgtggatgct   1620
gaacgcagta ttgttacaga cttggtcagt caaatggacc ctcatggaag gagaaccata   1680
ttcgttttga ccaaagtaga cctggcagag aaaaatgtag ccagtccaag caggattcag   1740
cagataattg aaggaaagct cttcccaatg aaagctttag gttattttgc tgttgtaaca   1800
ggaaaaggga acagctctga aagcattgaa gctataagag aatatgaaga agagttttt    1860 cagaattcaa agctcctaaa gacaagcatg ctaaaggcac accaagtgac tacaagaaat   1920
ttaagccttg cagtatcaga ctgcttttgg aaaatggtac gagagtctgt tgaacaacag   1980
gctgatagtt tcaaagcaac acgttttaac cttgaaactg aatggaagaa taactatcct   2040
cgcctgcggg aacttgaccg gaatgaacta tttgaaaaag ctaaaaatga aatccttgat   2100
gaagttatca gtctgagcca ggttacacca aaacattggg aggaaatcct tcaacaatct   2160
ttgtgggaaa gagtatcaac tcatgtgatt gaaaacatct accttccagc tgcgcagacc   2220
atgaattcag gaactttaa caccacagtg gatatcaagc ttaaacagtg gactgataaa   2280
caacttccta ataaagcagt agaggttgct tgggagaccc tacaagaaga attttcccgc   2340
tttatgacag aaccgaaagg gaaagagcat gatgacatat ttgataaact taagagggct   2400
gttaaggaag aaagtattaa acgacacaag tggaatgact ttgcggagga cagcttgagg   2460
gttattcaac acaatgcttt ggaagaccga tccatatctg ataaacagca atgggatgca   2520
gctatttatt ttatggaaga ggctctgcag gctcgtctca aggatactga aaatgcaatt   2580
gaaaacatgt gggtccagac tggaaaaag aggtggttat actggaagaa tcggacccaa   2640
gaacagtgtg ttcacaatga aaccaagaat gaattggaga agatgttgaa atgtaatgag   2700
```

```
gagcacccag cttatcttgc aagtgatgaa ataaccacag tccggaagaa ccttgaatcc    2760
cgaggagtag aagtagatcc aagcttgatt aaggatactt ggcatcaagt ttatagaaga    2820
cattttttaa aaacagctct aaaccattgt aacctttgtc gaagaggttt ttattactac    2880
caaaggcatt ttgtagattc tgagttggaa tgcaatgatg tggtcttgtt ttggcgtata    2940
cagcgcatgc ttgctatcac cgcaaatact ttaaggcaac aacttacaaa tactgaagtt    3000
aggcgattag agaaaaatgt taagaggta ttggaagatt ttgctgaaga tggtgagaag    3060
aagattaaat tgcttactgg taaacgcgtt caactggcgg aagacctcaa gaaagttaga    3120
gaaattcaag aaaaacttga tgctttcatt gaagctcttc atcaggagaa ataaattaaa    3180
atcgtactca taatcagctc tgcatacatc tgaagaacaa aaacatcaac gtcttttgtc    3240
cagcctcttt ttcttctgct gttccacctt tctaaacata caataaagtc atgggataaa    3300
aataatcgat gtatgttacg ggcgctttaa ccatcagctg cctctcgaat ggaagaacag    3360
tggtaatgga ttaacatcct attttgttgt actaaagtga caaatcggaa taatataatt    3420
ggtatggcca ttaggttcag tccttgaaga taagaaactt gttctctgtt tgttgtctta    3480
tttgtggtgg cactcgttta atggattaac tgaggttgct caatgttcag tttcttttcc    3540
agaaatacaa tgctaggtgt tttgaaataa aacttatata gcaattgttt aaagttatca    3600
attgtatata aaatcacagt agcctgctaa atcattgtat gtgtctgtag tattctattc    3660
ccagaaacta tttgaccatg ataattcagt ttatattcac cacatgaaag aaaaatgggt    3720
aacagaagaa cccttaaaac aggttaattt ggattgtaac gttcagtgaa agaaatttca    3780
acccttcata gccagcgaag aaatttgcct tggaagccaa gtcagtacca gcttacctat    3840
ttgattcagt tgctgttttc tcactctcta tatccatttg aaattgattt attttagatg    3900
ttgtatactt acgttaggct ttctgttaat agtggttttt ctcctgttga cagagccacc    3960
ggattatgac acaggatgag gaagattaag gataatcaat tgactaattt catttagaat    4020
attatcaaac atttcaacta ggtatcagaa aaaggctttc tttcataaga ctattttaaa    4080
tagaaattat ttcaacaatt aaagtaatgt tgaccatccc cctctcagct gaataaagaa    4140
aaatttagtt caatttattg caatttaatt acaaatactac cttcacaaca ttttcatgtg    4200
ttttaaataa atattttta attggctaaa ggacattcaa gcaaagaaat gctttcttta    4260
cttaaaatgt ctatctcatt tgctgccttt tcactaagcc tttactttgt taataaaagt    4320
gtccattgtg tgatgttttt gattttacag tttgctaaat cttattttct tggagttgct    4380
ttttggtaac agccccattg ctactcccca ttttattgtt ttacatcaat gcatgcttcg    4440
ttgtgatccc tcaagatgta acacttggta tgctcggttg aggatatgaa aaaatacttc    4500 cgaaccagg aattcaatgt atgtttgttt tatactgttt gataagaaaa gtaggtccag    4560
ccttaagcag cacagatgcg ctggtagatg catagtcagg aacttttttt atttctttta    4620
ggtctaggga caggagtgaa tagaaaggga ggagagctct attatgttct atacacagat    4680
taggagatga ccttactggg tacacccctc taaccagtgc ttacaggtta atgcatgtta    4740
atgaatattt ttgcagttgt aaagcataac aattacaact acacatctat ttctaaagaa    4800
taaaacagga ccatatttat ttacttctgt caactataga aagaaagacc ttcagctgta    4860
tttccacaga tttctcccaa ggaaaaggct aatattagtc actactgtta tcacatccct    4920
ttgtataagt tttaaaaaga gatggaggga gatcttcatt tctttgagga gatcagtatt    4980
gtaacgtatg tgaatagatg ataacaatta atattactaa aagtcccaca tgagagtcct    5040
```

-continued

| | |
|---|---|
| gacgccctct ccatgcccca cagtaatgtg gcttctttca tgggtttttt tttcttcttt | 5100 |
| ttagctgatc tcatcctaag catgctttat ttttccttga aagctaggta tttatcaact | 5160 |
| gcagatgtta ttgaaagaaa ataaaattca gtctcaagag taaaccctgt gtcttgtgtc | 5220 |
| tgtagttcaa aagtcagaaa tgattctaat ttaaacaaaa agatactaaa tatacagaag | 5280 |
| ttaaattcga actagccaca gaatcatttg tttttatgtc agaatttgca aagagtggag | 5340 |
| tggacaaagc tctgtatgga agactgaaca actgtaaata gatgatatcc aaacttaatt | 5400 |
| tggctaggac ttcaatttta aaaatcagtg tacctaggca gtgcacagca cgaaataagt | 5460 |
| ggcccttgca gcttccccgt ttaacccact gtgctatagt tgcgggtgga acagtcaacc | 5520 |
| tttctagtag tttatgatat tgccctcttt gtattcccat tttctacagt ttttccgca | 5580 |
| gacttctttc tgcaaattat tcagcctcca aatgcaaatg aatgatataa aaataagtag | 5640 |
| ggaacatggc agagagtggt gcttcccagc ctcacaatgt gggaatttga cataggatga | 5700 |
| gagtcagagt ataggtttaa aagataaaat ctttagttaa taattttgta tttatttatt | 5760 |
| ctagatgtat gtatctgagg aaagaaatct ggtatttttg ctttccaata aaggggatca | 5820 |
| aagtaatggt ttttctctca gttctctaag ctggtctatg ttatagctct agcagtatgg | 5880 |
| aaatgtgctt taaaatatgc ttaccttttg aatgatcatg gctatatgtt gttgagatat | 5940 |
| ttgaaactta ccttgttttc acttgtgcac tgtgaatgaa cttgtatta ttttttaaa | 6000 |
| accttcacat tacgtgtaga tattattgca acttatattt tgcctgagct tgatcaaagg | 6060 |
| tcatttgtgt agatgagtaa ttaaaaaata tttaaatcac attataattc tattattgga | 6120 |
| gagcatcttt taaatttttt tctgttttaa cgagggaaag agaaacctgt atacctaggg | 6180 |
| tcattatttg accccatagt ataaccagat tcatggtcta acaagctctc agtgtggctt | 6240 |
| ttctctgaat gcttgaattt cacatgcctt gcatttcaca gttgtactcc atggtcaacc | 6300 |
| ggtgcttttt ttcacatcgt ggtacttgtc aaaacatttt gttatttcc ttggtaaaat | 6360 |
| atataaaaaa ggttttctaa tttcaaaaaa aaaaaaaaaa aa | 6402 |

<210> SEQ ID NO 12
<211> LENGTH: 979
<212> TYPE: PRT
<213> ORGANISM: Homo sapiens

<400> SEQUENCE: 12

Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp

```
              130             135             140
Glu Tyr Ile Asp Phe Gly His Lys Leu Val Ser Glu Val Ile Gly Ala
145                 150                 155                 160

Ser Asp Leu Leu Leu Leu Gly Ser Pro Glu Thr Ala Phe Arg
                165                 170                 175

Ala Thr Asp Arg Gly Ser Glu Ser Asp Lys His Phe Arg Lys Gly Leu
                180                 185                 190

Leu Gly Glu Leu Ile Leu Leu Gln Gln Gln Ile Gln Glu His Glu Glu
                195                 200                 205

Glu Ala Arg Arg Ala Ala Gly Gln Tyr Ser Thr Ser Tyr Ala Gln Gln
                210                 215                 220

Lys Arg Lys Val Ser Asp Lys Glu Lys Ile Asp Gln Leu Gln Glu Glu
225                 230                 235                 240

Leu Leu His Thr Gln Leu Lys Tyr Gln Arg Ile Leu Glu Arg Leu Glu
                245                 250                 255

Lys Glu Asn Lys Glu Leu Arg Lys Leu Val Leu Gln Lys Asp Asp Lys
                260                 265                 270

Gly Ile His His Arg Lys Leu Lys Lys Ser Leu Ile Asp Met Tyr Ser
                275                 280                 285

Glu Val Leu Asp Val Leu Ser Asp Tyr Asp Ala Ser Tyr Asn Thr Gln
290                 295                 300

Asp His Leu Pro Arg Val Val Val Gly Asp Gln Ser Ala Gly Lys
305                 310                 315                 320

Thr Ser Val Leu Glu Met Ile Ala Gln Ala Arg Ile Phe Pro Arg Gly
                325                 330                 335

Ser Gly Glu Met Met Thr Arg Ser Pro Val Lys Val Thr Leu Ser Glu
                340                 345                 350

Gly Pro His His Val Ala Leu Phe Lys Asp Ser Ser Arg Glu Phe Asp
                355                 360                 365

Leu Thr Lys Glu Glu Asp Leu Ala Ala Leu Arg His Glu Ile Glu Leu
                370                 375                 380

Arg Met Arg Lys Asn Val Lys Glu Gly Cys Thr Val Ser Pro Glu Thr
385                 390                 395                 400

Ile Ser Leu Asn Val Lys Gly Pro Gly Leu Gln Arg Met Val Leu Val
                405                 410                 415

Asp Leu Pro Gly Val Ile Asn Thr Val Thr Ser Gly Met Ala Pro Asp
                420                 425                 430

Thr Lys Glu Thr Ile Phe Ser Ile Ser Lys Ala Tyr Met Gln Asn Pro
                435                 440                 445

Asn Ala Ile Ile Leu Cys Ile Gln Asp Gly Ser Val Asp Ala Glu Arg
                450                 455                 460

Ser Ile Val Thr Asp Leu Val Ser Gln Met Asp Pro His Gly Arg Arg
465                 470                 475                 480

Thr Ile Phe Val Leu Thr Lys Val Asp Leu Ala Glu Lys Asn Val Ala
                485                 490                 495

Ser Pro Ser Arg Ile Gln Gln Ile Ile Glu Gly Lys Leu Phe Pro Met
                500                 505                 510

Lys Ala Leu Gly Tyr Phe Ala Val Val Thr Gly Lys Gly Asn Ser Ser
                515                 520                 525

Glu Ser Ile Glu Ala Ile Arg Glu Tyr Glu Glu Phe Phe Gln Asn
                530                 535                 540

Ser Lys Leu Leu Lys Thr Ser Met Leu Lys Ala His Gln Val Thr Thr
545                 550                 555                 560
```

```
Arg Asn Leu Ser Leu Ala Val Ser Asp Cys Phe Trp Lys Met Val Arg
            565                 570                 575

Glu Ser Val Glu Gln Gln Ala Asp Ser Phe Lys Ala Thr Arg Phe Asn
        580                 585                 590

Leu Glu Thr Glu Trp Lys Asn Asn Tyr Pro Arg Leu Arg Glu Leu Asp
    595                 600                 605

Arg Asn Glu Leu Phe Glu Lys Ala Lys Asn Glu Ile Leu Asp Glu Val
610                 615                 620

Ile Ser Leu Ser Gln Val Thr Pro Lys His Trp Glu Glu Ile Leu Gln
625                 630                 635                 640

Gln Ser Leu Trp Glu Arg Val Ser Thr His Val Ile Glu Asn Ile Tyr
            645                 650                 655

Leu Pro Ala Ala Gln Thr Met Asn Ser Gly Thr Phe Asn Thr Thr Val
        660                 665                 670

Asp Ile Lys Leu Lys Gln Trp Thr Asp Lys Gln Leu Pro Asn Lys Ala
    675                 680                 685

Val Glu Val Ala Trp Glu Thr Leu Gln Glu Glu Phe Ser Arg Phe Met
690                 695                 700

Thr Glu Pro Lys Gly Lys Glu His Asp Ile Phe Asp Lys Leu Lys
705                 710                 715                 720

Glu Ala Val Lys Glu Glu Ser Ile Lys Arg His Lys Trp Asn Asp Phe
            725                 730                 735

Ala Glu Asp Ser Leu Arg Val Ile Gln His Asn Ala Leu Glu Asp Arg
        740                 745                 750

Ser Ile Ser Asp Lys Gln Gln Trp Asp Ala Ala Ile Tyr Phe Met Glu
    755                 760                 765

Glu Ala Leu Gln Ala Arg Leu Lys Asp Thr Glu Asn Ala Ile Glu Asn
770                 775                 780

Met Val Gly Pro Asp Trp Lys Lys Arg Trp Leu Tyr Trp Lys Asn Arg
785                 790                 795                 800

Thr Gln Glu Gln Cys Val His Asn Glu Thr Lys Asn Glu Leu Glu Lys
            805                 810                 815

Met Leu Lys Cys Asn Glu Glu His Pro Ala Tyr Leu Ala Ser Asp Glu
        820                 825                 830

Ile Thr Thr Val Arg Lys Asn Leu Glu Ser Arg Gly Val Glu Val Asp
    835                 840                 845

Pro Ser Leu Ile Lys Asp Thr Trp His Gln Val Tyr Arg Arg His Phe
850                 855                 860

Leu Lys Thr Ala Leu Asn His Cys Asn Leu Cys Arg Arg Gly Phe Tyr
865                 870                 875                 880

Tyr Tyr Gln Arg His Phe Val Asp Ser Glu Leu Glu Cys Asn Asp Val
            885                 890                 895

Val Leu Phe Trp Arg Ile Gln Arg Met Leu Ala Ile Thr Ala Asn Thr
        900                 905                 910

Leu Arg Gln Gln Leu Thr Asn Thr Glu Val Arg Arg Leu Glu Lys Asn
    915                 920                 925

Val Lys Glu Val Leu Glu Asp Phe Ala Glu Asp Gly Glu Lys Lys Ile
930                 935                 940

Lys Leu Leu Thr Gly Lys Arg Val Gln Leu Ala Glu Asp Leu Lys Lys
945                 950                 955                 960

Val Arg Glu Ile Gln Glu Lys Leu Asp Ala Phe Ile Glu Ala Leu His
            965                 970                 975
```

Gln Glu Lys

<210> SEQ ID NO 13
<211> LENGTH: 6456
<212> TYPE: DNA
<213> ORGANISM: Homo sapiens

<400> SEQUENCE: 13

| | | | | | |
|---|---|---|---|---|---|
| gtgctgcccg | cctagaaagg | gtgaagtggt | tgtttccgtg | acggactgag | tacgggtgcc | 60 |
| tgtcaggctc | ttgcggaagt | ccatgcgcca | ttgggagggc | ctcggccgcg | gctctgtgcc | 120 |
| cttgctgctg | agggccactt | cctgggtcat | tcctggaccg | ggagccgggc | tggggctcac | 180 |
| acggggctc | ccgcgtggcc | gtctcggcgc | ctgcgtgacc | tccccgccgg | cgggatgtgg | 240 |
| cgactacgtc | gggccgctgt | ggcctgtgag | gtctgccagt | cttagtgaa | acacagctct | 300 |
| ggaataaaag | gaagtttacc | actacaaaaa | ctacatctgg | tttcacgaag | catttatcat | 360 |
| tcacatcatc | ctaccttaaa | gcttcaacga | ccccaattaa | ggacatcctt | tcagcagttc | 420 |
| tcttctctga | caaaccttcc | tttacgtaaa | ctgaaattct | ctccaattaa | atatggctac | 480 |
| cagcctcgca | ggaattttg | gccagcaaga | ttagctacga | gactcttaaa | acttcgctat | 540 |
| ctcatactag | gatcggctgt | tggggtggc | tacacagcca | aaaagacttt | tgatcagtgg | 600 |
| aaagatatga | taccggacct | tagtgaatat | aaatggattg | tgcctgacat | tgtgtgggaa | 660 |
| attgatgagt | atatcgattt | tgagaaaatt | agaaaagccc | ttcctagttc | agaagacctt | 720 |
| gtaaagttag | caccagactt | tgacaagatt | gttgaaagcc | ttagcttatt | gaaggacttt | 780 |
| tttacctcag | gttctccgga | agaaacggcg | tttagagcaa | cagatcgtgg | atctgaaagt | 840 |
| gacaagcatt | ttagaaaggg | tctgcttggt | gagctcattc | tcttacaaca | acaaattcaa | 900 |
| gagcatgaag | aggaagcgcg | cagagccgct | ggccaatata | gcacgagcta | tgcccaacag | 960 |
| aagcgcaagg | tgtcagacaa | agagaaaatt | gaccaacttc | aggaagaact | tctgcacact | 1020 |
| cagttgaagt | atcagagaat | cttggaacga | ttagaaaagg | agaacaaaga | attgagaaaa | 1080 |
| ttagtattgc | agaaagatga | caaaggcatt | catcatagaa | agcttaagaa | atctttgatt | 1140 |
| gacatgtatt | ctgaagttct | tgatgttctc | tctgattatg | atgccagtta | taatacgcaa | 1200 |
| gatcatctgc | cacgggttgt | tgtggttgga | gatcagagtg | ctggaaagac | tagtgtgttg | 1260 |
| gaaatgattg | cccaagctcg | aatattccca | agaggatctg | gggagatgat | gacacgttct | 1320 |
| ccagttaagg | tgactctgag | tgaaggtcct | caccatgtgg | ccctatttaa | agatagttct | 1380 |
| cgggagtttg | atcttaccaa | agaagaagat | cttgcagcat | taagacatga | aatagaactt | 1440 |
| cgaatgagga | aaaatgtgaa | agaaggctgt | accgttagcc | ctgagaccat | atccttaaat | 1500 |
| gtaaaaggcc | ctggactaca | gaggatggtg | cttgttgact | taccaggtgt | gattaatact | 1560 |
| gtgacatcag | gcatggctcc | tgacacaaag | gaaactattt | tcagtatcag | caaagcttac | 1620 |
| atgcagaatc | ctaatgccat | catactgtgt | attcaagatg | gatctgtgga | tgctgaacgc | 1680 |
| agtattgtta | cagacttggt | cagtcaaatg | gaccctcatg | gaaggagaac | catattcgtt | 1740 |
| ttgaccaaag | tagacctggc | agagaaaaat | gtagccagtc | caagcaggat | tcagcagata | 1800 |
| attgaaggaa | agctcttccc | aatgaaagct | ttaggttatt | ttgctgttgt | aacaggaaaa | 1860 |
| gggaacagct | ctgaaagcat | tgaagctata | agagaatatg | aagaagagtt | ttttcagaat | 1920 |
| tcaaagctcc | taaagacaag | catgctaaag | gcacaccaag | tgactacaag | aaatttaagc | 1980 |
| cttgcagtat | cagactgctt | ttggaaaatg | gtacgagagt | ctgttgaaca | acaggctgat | 2040 |
| agtttcaaag | caacacgttt | taaccttgaa | actgaatgga | agaataacta | tcctcgcctg | 2100 |

```
cgggaacttg accggaatga actatttgaa aaagctaaaa atgaaatcct tgatgaagtt    2160
atcagtctga gccaggttac accaaaacat tgggaggaaa tccttcaaca atctttgtgg    2220
gaaagagtat caactcatgt gattgaaaac atctaccttc cagctgcgca gaccatgaat    2280
tcaggaactt ttaacaccac agtggatatc aagcttaaac agtggactga taaacaactt    2340
cctaataaag cagtagaggt tgcttgggag accctacaag aagaattttc ccgctttatg    2400
acagaaccga aagggaaaga gcatgatgac atatttgata aacttaaaga ggctgttaag    2460
gaagaaagta ttaaacgaca caagtggaat gactttgcgg aggacagctt gagggttatt    2520
caacacaatg ctttggaaga ccgatccata tctgataaac agcaatggga tgcagctatt    2580
tattttatgg aagaggctct gcaggctcgt ctcaaggata ctgaaaatgc aattgaaaac    2640
atggtgggtc cagactggaa aaagaggtgg ttatactgga agaatcggac ccaagaacag    2700
tgtgttcaca atgaaaccaa gaatgaattg gagaagatgt tgaaatgtaa tgaggagcac    2760
ccagcttatc ttgcaagtga tgaaataacc acagtccgga agaaccttga atcccgagga    2820
gtagaagtag atccaagctt gattaaggat acttggcatc aagtttatag aagacatttt    2880
ttaaaaacag ctctaaacca ttgtaacctt tgtcgaagag gttttttatta ctaccaaagg    2940
cattttgtag attctgagtt ggaatgcaat gatgtggtct tgttttggcg tatacagcgc    3000
atgcttgcta tcaccgcaaa tactttaagg caacaactta caaatactga agttaggcga    3060
ttagagaaaa atgttaaaga ggtattggaa gattttgctg aagatggtga agaagaagatt    3120
aaattgctta ctggtaaacg cgttcaactg gcggaagacc tcaagaaagt tagagaaatt    3180
caagaaaaac ttgatgcttt cattgaagct cttcatcagg agaaataaat taaaatcgta    3240
ctcataatca gctctgcata catctgaaga acaaaaacat caacgtcttt tgtccagcct    3300
cttttcttc tgctgttcca cctttctaaa catacaataa agtcatggga taaaaataat    3360
cgatgtatgt tacgggcgct ttaaccatca gctgcctctc gaatggaaga acagtggtaa    3420
tggattaaca tcctattttg ttgtactaaa gtgacaaatc ggaataatat aattggtatg    3480
gccattaggt tcagtccttg aagataagaa acttgttctc tgtttgttgt cttatttgtg    3540
gtggcactcg tttaatggat taactgaggt tgctcaatgt tcagtttctt ttccagaaat    3600
acaatgctag gtgttttgaa ataaaactta tatagcaatt gtttaaagtt atcaattgta    3660
tataaaatca cagtagcctg ctaaatcatt gtatgtgtct gtagtattct attcccagaa    3720
actatttgac catgataatt cagtttatat tcaccacatg aaagaaaaat gggtaacaga    3780
agaacccta aaacaggtta atttggattg taacgttcag tgaaagaaat ttcaaccctt    3840
catagccagc gaagaaattt gccttggaag ccaagtcagt accagcttac ctatttgatt    3900
cagttgctgt tttctcactc tctatatcca tttgaaattg atttatttta gatgttgtat    3960
acttacgtta ggctttctgt taatagtggt ttttctcctg ttgacagagc caccggatta    4020
tgacacagga tgaggaagat taaggataat caattgacta atttcattta gaatattatc    4080
aaacatttca actaggtatc agaaaaaggc tttctttcat aagactattt taaatagaaa    4140
ttatttcaac aattaaagta atgttgacca tccccctctc agctgaataa agaaaaattt    4200
agttcaattt attgcaattt aattacaata ctaccttcac aacatttca tgtgttttaa    4260
ataaatattt tttaattggc taaaggacat tcaagcaaag aaatgctttc tttacttaaa    4320
atgtctatct catttgctgc cttttcacta agcctttact tgttaataa aagtgtccat    4380
tgtgtgatgt ttttgatttt acagtttgct aaatcttatt ttcttggagt tgctttttgg    4440
```

| | | |
|---|---|---|
| taacagcccc attgctactc cccatttat tgttttacat caatgcatgc ttcgttgtga | 4500 | |
| tccctcaaga tgtaacactt ggtatgctcg gttgaggata tgaaaaaata cttccgaaac | 4560 | |
| caggaattca atgtatgttt gttttatact gtttgataag aaaagtaggt ccagccttaa | 4620 | |
| gcagcacaga tgcgctggta gatgcatagt caggaacttt ttttatttct tttaggtcta | 4680 | |
| gggacaggag tgaatagaaa gggaggagag ctctattatg ttctatacac agattaggag | 4740 | |
| atgaccttac tgggtacacc cctctaacca gtgcttacag gttaatgcat gttaatgaat | 4800 | |
| atttttgcag ttgtaaagca taacaattac aactacacat ctatttctaa agaataaaac | 4860 | |
| aggaccatat ttatttactt ctgtcaacta tagaaagaaa gaccttcagc tgtatttcca | 4920 | |
| cagatttctc ccaaggaaaa ggctaatatt agtcactact gttatcacat ccctttgtat | 4980 | |
| aagttttaaa aagagatgga gggagatctt catttctttg aggagatcag tattgtaacg | 5040 | |
| tatgtgaata gatgataaca attaatatta ctaaaagtcc cacatgagag tcctgacgcc | 5100 | |
| ctctccatgc cccacagtaa tgtggcttct ttcatgggtt ttttttttctt cttttttagct | 5160 | |
| gatctcatcc taagcatgct ttatttttcc ttgaaagcta ggtatttatc aactgcagat | 5220 | |
| gttattgaaa gaaataaaa ttcagtctca agagtaaacc ctgtgtcttg tgtctgtagt | 5280 | |
| tcaaaagtca gaaatgattc taatttaaac aaaaagatac taaatataca gaagttaaat | 5340 | |
| tcgaactagc cacagaatca tttgttttta tgtcagaatt tgcaaagagt ggagtggaca | 5400 | |
| aagctctgta tggaagactg aacaactgta aatagatgat atccaaactt aatttggcta | 5460 | |
| ggacttcaat tttaaaaatc agtgtaccta ggcagtgcac agcacgaaat aagtggccct | 5520 | |
| tgcagcttcc ccgtttaacc cactgtgcta tagttgcggg tggaacagtc aacctttcta | 5580 | |
| gtagtttatg atattgccct ctttgtattc ccatttctca cagttttttc cgcagacttc | 5640 | |
| tttctgcaaa ttattcagcc tccaaatgca atgaatgat ataaaaataa gtagggaaca | 5700 | |
| tggcagagag tggtgcttcc cagcctcaca atgtgggaat ttgacatagg atgagagtca | 5760 | |
| gagtataggt ttaaaagata aaatctttag ttaataattt tgtatttatt tattctagat | 5820 | |
| gtatgtatct gaggaaagaa atctggtatt tttgctttcc aataaagggg atcaaagtaa | 5880 | |
| tggttttct ctcagttctc taagctggtc tatgttatag ctctagcagt atggaaatgt | 5940 | |
| gctttaaaat atgcttacct tttgaatgat catggctata tgttgttgag atatttgaaa | 6000 | |
| cttaccttgt tttcacttgt gcactgtgaa tgaactttgt attatttttt taaaaccttc | 6060 | |
| acattacgtg tagatattat tgcaacttat attttgcctg agcttgatca aaggtcattt | 6120 | |
| gtgtagatga gtaattaaaa aatatttaaa tcacattata attctattat tggagagcat | 6180 | |
| cttttaaatt tttttctgtt ttaacgaggg aaagagaaac ctgtatacct agggtcatta | 6240 | |
| tttgaccca gtataacc agattcatgg tctaacaagc tctcagtgtg gcttttctct | 6300 | |
| gaatgcttga atttcacatg ccttgcattt cacagttgta ctccatggtc aaccggtgct | 6360 | |
| tttttcaca tcgtggtact tgtcaaaaca ttttgttatt ttccttggta aaatatataa | 6420 | |
| aaaaggtttt ctaatttcaa aaaaaaaaaa aaaaaa | 6456 | |

<210> SEQ ID NO 14
<211> LENGTH: 997
<212> TYPE: PRT
<213> ORGANISM: Homo sapiens

<400> SEQUENCE: 14

Met Trp Arg Leu Arg Arg Ala Ala Val Ala Cys Glu Val Cys Gln Ser
1               5                   10                  15

-continued

Leu Val Lys His Ser Gly Ile Lys Gly Ser Leu Pro Gln Lys
             20                  25              30

Leu His Leu Val Ser Arg Ser Ile Tyr His Ser His Pro Thr Leu
         35                  40              45

Lys Leu Gln Arg Pro Gln Leu Arg Thr Ser Phe Gln Gln Phe Ser Ser
 50                  55                  60

Leu Thr Asn Leu Pro Leu Arg Lys Leu Lys Phe Ser Pro Ile Lys Tyr
 65                  70                  75                  80

Gly Tyr Gln Pro Arg Arg Asn Phe Trp Pro Ala Arg Leu Ala Thr Arg
                 85                  90                  95

Leu Leu Lys Leu Arg Tyr Leu Ile Leu Gly Ser Ala Val Gly Gly Gly
             100                 105                 110

Tyr Thr Ala Lys Lys Thr Phe Asp Gln Trp Lys Asp Met Ile Pro Asp
             115                 120                 125

Leu Ser Glu Tyr Lys Trp Ile Val Pro Asp Ile Val Trp Glu Ile Asp
 130                 135                 140

Glu Tyr Ile Asp Phe Glu Lys Ile Arg Lys Ala Leu Pro Ser Ser Glu
145                 150                 155                 160

Asp Leu Val Lys Leu Ala Pro Asp Phe Asp Lys Ile Val Glu Ser Leu
             165                 170                 175

Ser Leu Leu Lys Asp Phe Phe Thr Ser Gly Ser Pro Glu Glu Thr Ala
             180                 185                 190

Phe Arg Ala Thr Asp Arg Gly Ser Glu Ser Asp Lys His Phe Arg Lys
         195                 200                 205

Gly Leu Leu Gly Glu Leu Ile Leu Leu Gln Gln Gln Ile Gln Glu His
 210                 215                 220

Glu Glu Glu Ala Arg Arg Ala Ala Gly Gln Tyr Ser Thr Ser Tyr Ala
225                 230                 235                 240

Gln Gln Lys Arg Lys Val Ser Asp Lys Glu Lys Ile Asp Gln Leu Gln
             245                 250                 255

Glu Glu Leu Leu His Thr Gln Leu Lys Tyr Gln Arg Ile Leu Glu Arg
             260                 265                 270

Leu Glu Lys Glu Asn Lys Glu Leu Arg Lys Leu Val Leu Gln Lys Asp
             275                 280                 285

Asp Lys Gly Ile His His Arg Lys Leu Lys Lys Ser Leu Ile Asp Met
 290                 295                 300

Tyr Ser Glu Val Leu Asp Val Leu Ser Asp Tyr Asp Ala Ser Tyr Asn
305                 310                 315                 320

Thr Gln Asp His Leu Pro Arg Val Val Val Gly Asp Gln Ser Ala
             325                 330                 335

Gly Lys Thr Ser Val Leu Glu Met Ile Ala Gln Ala Arg Ile Phe Pro
             340                 345                 350

Arg Gly Ser Gly Glu Met Met Thr Arg Ser Pro Val Lys Val Thr Leu
         355                 360                 365

Ser Glu Gly Pro His His Val Ala Leu Phe Lys Asp Ser Ser Arg Glu
 370                 375                 380

Phe Asp Leu Thr Lys Glu Glu Asp Leu Ala Ala Leu Arg His Glu Ile
385                 390                 395                 400

Glu Leu Arg Met Arg Lys Asn Val Lys Glu Gly Cys Thr Val Ser Pro
             405                 410                 415

Glu Thr Ile Ser Leu Asn Val Lys Gly Pro Gly Leu Gln Arg Met Val
             420                 425                 430

Leu Val Asp Leu Pro Gly Val Ile Asn Thr Val Thr Ser Gly Met Ala

-continued

```
            435                 440                 445
Pro Asp Thr Lys Glu Thr Ile Phe Ser Ile Ser Lys Ala Tyr Met Gln
450                 455                 460
Asn Pro Asn Ala Ile Ile Leu Cys Ile Gln Asp Gly Ser Val Asp Ala
465                 470                 475                 480
Glu Arg Ser Ile Val Thr Asp Leu Val Ser Gln Met Asp Pro His Gly
                    485                 490                 495
Arg Arg Thr Ile Phe Val Leu Thr Lys Val Asp Leu Ala Glu Lys Asn
                500                 505                 510
Val Ala Ser Pro Ser Arg Ile Gln Gln Ile Ile Glu Gly Lys Leu Phe
            515                 520                 525
Pro Met Lys Ala Leu Gly Tyr Phe Ala Val Val Thr Gly Lys Gly Asn
530                 535                 540
Ser Ser Glu Ser Ile Glu Ala Ile Arg Glu Tyr Glu Glu Glu Phe Phe
545                 550                 555                 560
Gln Asn Ser Lys Leu Leu Lys Thr Ser Met Leu Lys Ala His Gln Val
                565                 570                 575
Thr Thr Arg Asn Leu Ser Leu Ala Val Ser Asp Cys Phe Trp Lys Met
                580                 585                 590
Val Arg Glu Ser Val Glu Gln Gln Ala Asp Ser Phe Lys Ala Thr Arg
            595                 600                 605
Phe Asn Leu Glu Thr Glu Trp Lys Asn Asn Tyr Pro Arg Leu Arg Glu
610                 615                 620
Leu Asp Arg Asn Glu Leu Phe Glu Lys Ala Lys Asn Glu Ile Leu Asp
625                 630                 635                 640
Glu Val Ile Ser Leu Ser Gln Val Thr Pro Lys His Trp Glu Glu Ile
                645                 650                 655
Leu Gln Gln Ser Leu Trp Glu Arg Val Ser Thr His Val Ile Glu Asn
                660                 665                 670
Ile Tyr Leu Pro Ala Ala Gln Thr Met Asn Ser Gly Thr Phe Asn Thr
            675                 680                 685
Thr Val Asp Ile Lys Leu Lys Gln Trp Thr Asp Lys Gln Leu Pro Asn
690                 695                 700
Lys Ala Val Glu Val Ala Trp Glu Thr Leu Gln Glu Glu Phe Ser Arg
705                 710                 715                 720
Phe Met Thr Glu Pro Lys Gly Lys Glu His Asp Asp Ile Phe Asp Lys
                725                 730                 735
Leu Lys Glu Ala Val Lys Glu Glu Ser Ile Lys Arg His Lys Trp Asn
                740                 745                 750
Asp Phe Ala Glu Asp Ser Leu Arg Val Ile Gln His Asn Ala Leu Glu
            755                 760                 765
Asp Arg Ser Ile Ser Asp Lys Gln Gln Trp Asp Ala Ala Ile Tyr Phe
770                 775                 780
Met Glu Glu Ala Leu Gln Ala Arg Leu Lys Asp Thr Glu Asn Ala Ile
785                 790                 795                 800
Glu Asn Met Val Gly Pro Asp Trp Lys Lys Arg Trp Leu Tyr Trp Lys
                805                 810                 815
Asn Arg Thr Gln Glu Gln Cys Val His Asn Glu Thr Lys Asn Glu Leu
                820                 825                 830
Glu Lys Met Leu Lys Cys Asn Glu Glu His Pro Ala Tyr Leu Ala Ser
            835                 840                 845
Asp Glu Ile Thr Thr Val Arg Lys Asn Leu Glu Ser Arg Gly Val Glu
850                 855                 860
```

Val Asp Pro Ser Leu Ile Lys Asp Thr Trp His Gln Val Tyr Arg Arg
865                 870                 875                 880

His Phe Leu Lys Thr Ala Leu Asn His Cys Asn Leu Cys Arg Arg Gly
            885                 890                 895

Phe Tyr Tyr Tyr Gln Arg His Phe Val Asp Ser Glu Leu Glu Cys Asn
        900                 905                 910

Asp Val Val Leu Phe Trp Arg Ile Gln Arg Met Leu Ala Ile Thr Ala
            915                 920                 925

Asn Thr Leu Arg Gln Gln Leu Thr Asn Thr Glu Val Arg Arg Leu Glu
        930                 935                 940

Lys Asn Val Lys Glu Val Leu Glu Asp Phe Ala Glu Asp Gly Glu Lys
945                 950                 955                 960

Lys Ile Lys Leu Leu Thr Gly Lys Arg Val Gln Leu Ala Glu Asp Leu
            965                 970                 975

Lys Lys Val Arg Glu Ile Gln Glu Leu Asp Ala Phe Ile Glu Ala
        980                 985                 990

Leu His Gln Glu Lys
        995

<210> SEQ ID NO 15
<211> LENGTH: 6510
<212> TYPE: DNA
<213> ORGANISM: Homo sapiens

<400> SEQUENCE: 15

```
gtgctgcccg cctagaaagg gtgaagtggt tgtttccgtg acggactgag tacgggtgcc        60
tgtcaggctc ttgcggaagt ccatgcgcca ttgggagggc ctcggccgcg gctctgtgcc       120
cttgctgctg agggccactt cctgggtcat tcctggaccg ggagccgggc tggggctcac       180
acggggctc ccgcgtggcc gtctcggcgc ctgcgtgacc tccccgccgg cgggatgtgg        240
cgactacgtc gggccgctgt ggcctgtgag gtctgccagt ctttagtgaa acacagctct       300
ggaataaaag gaagtttacc actacaaaaa ctacatctgg tttcacgaag catttatcat       360
tcacatcatc ctaccttaaa gcttcaacga ccccaattaa ggacatcctt tcagcagttc       420
tcttctctga caaaccttcc tttacgtaaa ctgaaattct ctccaattaa atatggctac       480
cagcctcgca ggaattttg ccagcaagaa ttagctacga gactcttaaa acttcgctat        540
ctcatactag gatcggctgt tggggtggc tacacagcca aaaagacttt tgatcagtgg        600
aaagatatga taccggacct tagtgaatat aaatggattg tgcctgacat tgtgtgggaa       660
attgatgagt atatcgattt tgagaaaatt agaaaagccc ttcctagttc agaagacctt       720
gtaaagttag caccagactt tgacaagatt gttgaaagcc ttagcttatt gaaggacttt       780
tttacctcag gtcacaaatt ggttagtgaa gtcataggag cttctgaccct acttctcttg       840
ttaggttctc cggaagaaac ggcgtttaga gcaacagatc gtggatctga agtgacaag        900
cattttagaa agggtctgct tggtgagctc attctcttac aacaacaaat tcaagagcat       960
gaagaggaag cgcgcagagc cgctggccaa tatagcacga gctatgccca acagaagcgc      1020
aaggtgtcag acaaagagaa aattgaccaa cttcaggaag aacttctgca cactcagttg      1080
aagtatcaga gaatcttgga acgattagaa aaggagaaca agaattgag aaaattagta      1140
ttgcagaaag atgacaaagg cattcatcat agaaagctta gaaatctttt gattgacatg      1200
tattctgaag ttcttgatgt tctctctgat tatgatgcca gttataatac gcaagatcat      1260
ctgccacggg ttgttgtggt tggagatcag agtgctggaa agactagtgt gttggaaatg      1320
```

```
attgcccaag ctcgaatatt cccaagagga tctggggaga tgatgacacg ttctccagtt   1380
aaggtgactc tgagtgaagg tcctcaccat gtggccctat ttaaagatag ttctcgggag   1440
tttgatctta ccaaagaaga agatcttgca gcattaagac atgaaataga acttcgaatg   1500
aggaaaaatg tgaaagaagg ctgtaccgtt agccctgaga ccatatcctt aaatgtaaaa   1560
ggccctggac tacagaggat ggtgcttgtt gacttaccag gtgtgattaa tactgtgaca   1620
tcaggcatgg ctcctgacac aaaggaaact attttcagta tcagcaaagc ttacatgcag   1680
aatcctaatg ccatcatact gtgtattcaa gatggatctg tggatgctga acgcagtatt   1740
gttacagact tggtcagtca aatggaccct catggaagga gaaccatatt cgttttgacc   1800
aaagtagacc tggcagagaa aaatgtagcc agtccaagca ggattcagca gataattgaa   1860
ggaaagctct tcccaatgaa agctttaggt tattttgctg ttgtaacagg aaaagggaac   1920
agctctgaaa gcattgaagc tataagagaa tatgaagaag agttttttca gaattcaaag   1980
ctcctaaaga caagcatgct aaaggcacac caagtgacta caagaaattt aagccttgca   2040
gtatcagact gcttttggaa aatggtacga gagtctgttg aacaacaggc tgatagtttc   2100
aaagcaacac gttttaacct tgaaactgaa tggaagaata actatcctcg cctgcgggaa   2160
cttgaccgga atgaactatt tgaaaaagct aaaaatgaaa tccttgatga agttatcagt   2220
ctgagccagg ttacaccaaa acattgggag gaaatccttc aacaatcttt gtgggaaaga   2280
gtatcaactc atgtgattga aaacatctac cttccagctg cgcagaccat gaattcagga   2340
acttttaaca ccacagtgga tatcaagctt aaacagtgga ctgataaaca acttcctaat   2400
aaagcagtag aggttgcttg ggagacccta caagaagaat tttcccgctt tatgacagaa   2460
ccgaagggga aagagcatga tgacatattt gataaactta agaggctgt taaggaagaa   2520
```

```
ctaggtgttt tgaaataaaa cttatatagc aattgtttaa agttatcaat tgtatataaa    3720
atcacagtag cctgctaaat cattgtatgt gtctgtagta ttctattccc agaaactatt    3780
tgaccatgat aattcagttt atattcacca catgaaagaa aaatgggtaa cagaagaacc    3840
cttaaaacag gttaatttgg attgtaacgt tcagtgaaag aaatttcaac ccttcatagc    3900
cagcgaagaa atttgccttg gaagccaagt cagtaccagc ttacctattt gattcagttg    3960
ctgttttctc actctctata tccatttgaa attgatttat tttagatgtt gtatacttac    4020
gttaggcttt ctgttaatag tggttttttct cctgttgaca gagccaccgg attatgacac    4080
aggatgagga agattaagga taatcaattg actaatttca tttagaatat tatcaaacat    4140
ttcaactagg tatcagaaaa aggctttctt tcataagact attttaaata gaaattattt    4200
caacaattaa agtaatgttg accatccccc tctcagctga ataaagaaaa atttagttca    4260
atttattgca atttaattac aatactacct tcacaacatt ttcatgtgtt ttaaataaat    4320
attttttaat tggctaaagg acattcaagc aaagaaatgc tttctttact taaaatgtct    4380
atctcatttg ctgccttttc actaagcctt tactttgtta ataaaagtgt ccattgtgtg    4440 atgttttga ttttacagtt tgctaaatct tattttcttg gagttgcttt ttggtaacag    4500
ccccattgct actccccatt ttattgtttt acatcaatgc atgcttcgtt gtgatccctc    4560
aagatgtaac acttggtatg ctcggttgag gatatgaaaa aatacttccg aaaccaggaa    4620
ttcaatgtat gtttgtttta tactgtttga taagaaaagt aggtccagcc ttaagcagca    4680
cagatgcgct ggtagatgca tagtcaggaa ctttttttat ttcttttagg tctagggaca    4740
ggagtgaata gaaagggagg agagctctat tatgttctat acacagatta ggagatgacc    4800
ttactgggta caccccctcta accagtgctt acaggttaat gcatgttaat gaatattttt    4860
gcagttgtaa agcataacaa ttacaactac acatctattt ctaaagaata aaacaggacc    4920
atatttattt acttctgtca actatagaaa gaaagacctt cagctgtatt tccacagatt    4980
tctcccaagg aaaaggctaa tattagtcac tactgttatc acatcccttt gtataagttt    5040
taaaaagaga tggagggaga tcttcatttc tttgaggaga tcagtattgt aacgtatgtg    5100
aatagatgat aacaattaat attactaaaa gtcccacatg agagtcctga cgccctctcc    5160
atgccccaca gtaatgtggc ttctttcatg ggttttttttt tcttcttttt agctgatctc    5220
atcctaagca tgctttatt ttccttgaaa gctaggtatt tatcaactgc agatgttatt    5280
gaaagaaaat aaaattcagt ctcaagagta aaccctgtgt cttgtgtctg tagttcaaaa    5340
gtcagaaatg attctaattt aaacaaaaag atactaaata tacagaagtt aaattcgaac    5400
tagccacaga atcatttgtt tttatgtcag aatttgcaaa gagtggagtg gacaaagctc    5460
tgtatggaag actgaacaac tgtaaataga tgatatccaa acttaatttg gctaggactt    5520
caattttaaa aatcagtgta cctaggcagt gcacagcacg aaataagtgg cccttgcagc    5580
ttccccgttt aacccactgt gctatagttg cgggtggaac agtcaacctt tctagtagtt    5640
tatgatattg ccctctttgt attcccattt tctacagttt tttccgcaga cttctttctg    5700
caaattattc agcctccaaa tgcaaatgaa tgatataaaa ataagtaggg aacatggcag    5760
agagtggtgc ttcccagcct cacaatgtgg gaatttgaca taggatgaga gtcagagtat    5820
aggtttaaaa gataaaatct ttagttaata attttgtatt tatttattct agatgtatgt    5880
atctgaggaa agaaatctgg tatttttgct ttccaataaa ggggatcaaa gtaatggttt    5940
ttctctcagt tctctaagct ggtctatgtt atagctctag cagtatggaa atgtgcttta    6000
aaatatgctt accttttgaa tgatcatggc tatatgttgt tgagatattt gaaacttacc    6060
```

-continued

```
ttgttttcac ttgtgcactg tgaatgaact ttgtattatt ttttaaaac cttcacatta    6120 cgtgtagata ttattgcaac ttatattttg cctgagcttg atcaaaggtc atttgtgtag    6180
atgagtaatt aaaaaatatt taaatcacat tataattcta ttattggaga gcatctttta    6240
aatttttttc tgttttaacg agggaaagag aaacctgtat acctagggtc attatttgac    6300
cccatagtat aaccagattc atggtctaac aagctctcag tgtggctttt ctctgaatgc    6360
ttgaatttca catgccttgc atttcacagt tgtactccat ggtcaaccgg tgcttttttt    6420
cacatcgtgg tacttgtcaa aacattttgt tattttcctt ggtaaaatat ataaaaaagg    6480
ttttctaatt tcaaaaaaaa aaaaaaaaa                                      6510
```

<210> SEQ ID NO 16
<211> LENGTH: 1015
<212> TYPE: PRT
<213> ORGANISM: Homo sapiens

<400> SEQUENCE: 16

```
Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Glu Lys Ile Arg Lys Ala Leu Pro Ser Ser Glu
145                 150                 155                 160

Asp Leu Val Lys Leu Ala Pro Asp Phe Asp Lys Ile Val Glu Ser Leu
                165                 170                 175

Ser Leu Leu Lys Asp Phe Phe Thr Ser Gly His Lys Leu Val Ser Glu
            180                 185                 190

Val Ile Gly Ala Ser Asp Leu Leu Leu Leu Gly Ser Pro Glu Glu
        195                 200                 205

Thr Ala Phe Arg Ala Thr Asp Arg Gly Ser Glu Ser Asp Lys His Phe
    210                 215                 220

Arg Lys Gly Leu Leu Gly Glu Leu Ile Leu Gln Gln Gln Ile Gln
225                 230                 235                 240

Glu His Glu Glu Glu Ala Arg Arg Ala Ala Gly Gln Tyr Ser Thr Ser
                245                 250                 255

Tyr Ala Gln Gln Lys Arg Lys Val Ser Asp Lys Glu Lys Ile Asp Gln
            260                 265                 270

Leu Gln Glu Glu Leu Leu His Thr Gln Leu Lys Tyr Gln Arg Ile Leu
        275                 280                 285
```

```
Glu Arg Leu Glu Lys Glu Asn Lys Glu Leu Arg Lys Leu Val Leu Gln
    290                 295                 300

Lys Asp Asp Lys Gly Ile His His Arg Lys Leu Lys Lys Ser Leu Ile
305                 310                 315                 320

Asp Met Tyr Ser Glu Val Leu Asp Val Leu Ser Asp Tyr Asp Ala Ser
                325                 330                 335

Tyr Asn Thr Gln Asp His Leu Pro Arg Val Val Val Gly Asp Gln
            340                 345                 350

Ser Ala Gly Lys Thr Ser Val Leu Glu Met Ile Ala Gln Ala Arg Ile
        355                 360                 365

Phe Pro Arg Gly Ser Gly Glu Met Met Thr Arg Ser Pro Val Lys Val
370                 375                 380

Thr Leu Ser Glu Gly Pro His His Val Ala Leu Phe Lys Asp Ser Ser
385                 390                 395                 400

Arg Glu Phe Asp Leu Thr Lys Glu Glu Asp Leu Ala Ala Leu Arg His
                405                 410                 415

Glu Ile Glu Leu Arg Met Arg Lys Asn Val Lys Glu Gly Cys Thr Val
            420                 425                 430

Ser Pro Glu Thr Ile Ser Leu Asn Val Lys Gly Pro Gly Leu Gln Arg
        435                 440                 445

Met Val Leu Val Asp Leu Pro Gly Val Ile Asn Thr Val Thr Ser Gly
    450                 455                 460

Met Ala Pro Asp Thr Lys Glu Thr Ile Phe Ser Ile Ser Lys Ala Tyr
465                 470                 475                 480

Met Gln Asn Pro Asn Ala Ile Ile Leu Cys Ile Gln Asp Gly Ser Val
                485                 490                 495

Asp Ala Glu Arg Ser Ile Val Thr Asp Leu Val Ser Gln Met Asp Pro
            500                 505                 510

His Gly Arg Arg Thr Ile Phe Val Leu Thr Lys Val Asp Leu Ala Glu
        515                 520                 525

Lys Asn Val Ala Ser Pro Ser Arg Ile Gln Gln Ile Ile Glu Gly Lys
    530                 535                 540

Leu Phe Pro Met Lys Ala Leu Gly Tyr Phe Ala Val Val Thr Gly Lys
545                 550                 555                 560

Gly Asn Ser Ser Glu Ser Ile Glu Ala Ile Arg Glu Tyr Glu Glu Glu
                565                 570                 575

Phe Phe Gln Asn Ser Lys Leu Leu Lys Thr Ser Met Leu Lys Ala His
            580                 585                 590

Gln Val Thr Thr Arg Asn Leu Ser Leu Ala Val Ser Asp Cys Phe Trp
        595                 600                 605

Lys Met Val Arg Glu Ser Val Glu Gln Gln Ala Asp Ser Phe Lys Ala
    610                 615                 620

Thr Arg Phe Asn Leu Glu Thr Glu Trp Lys Asn Asn Tyr Pro Arg Leu
625                 630                 635                 640

Arg Glu Leu Asp Arg Asn Glu Leu Phe Glu Lys Ala Lys Asn Glu Ile
                645                 650                 655

Leu Asp Glu Val Ile Ser Leu Ser Gln Val Thr Pro Lys His Trp Glu
            660                 665                 670

Glu Ile Leu Gln Gln Ser Leu Trp Glu Arg Val Ser Thr His Val Ile
        675                 680                 685

Glu Asn Ile Tyr Leu Pro Ala Ala Gln Thr Met Asn Ser Gly Thr Phe
    690                 695                 700

Asn Thr Thr Val Asp Ile Lys Leu Lys Gln Trp Thr Asp Lys Gln Leu
```

```
             705                 710                 715                 720
      Pro Asn Lys Ala Val Glu Val Ala Trp Glu Thr Leu Gln Glu Glu Phe
                      725                 730                 735
      Ser Arg Phe Met Thr Glu Pro Lys Gly Lys Glu His Asp Asp Ile Phe
                      740                 745                 750
      Asp Lys Leu Lys Glu Ala Val Lys Glu Glu Ser Ile Lys Arg His Lys
                      755                 760                 765
      Trp Asn Asp Phe Ala Glu Asp Ser Leu Arg Val Ile Gln His Asn Ala
                      770                 775                 780
      Leu Glu Asp Arg Ser Ile Ser Asp Lys Gln Gln Trp Asp Ala Ala Ile
      785                 790                 795                 800
      Tyr Phe Met Glu Glu Ala Leu Gln Ala Arg Leu Lys Asp Thr Glu Asn
                      805                 810                 815
      Ala Ile Glu Asn Met Val Gly Pro Asp Trp Lys Lys Arg Trp Leu Tyr
                      820                 825                 830
      Trp Lys Asn Arg Thr Gln Glu Gln Cys Val His Asn Glu Thr Lys Asn
                      835                 840                 845
      Glu Leu Glu Lys Met Leu Lys Cys Asn Glu Glu His Pro Ala Tyr Leu
                      850                 855                 860
      Ala Ser Asp Glu Ile Thr Thr Val Arg Lys Asn Leu Glu Ser Arg Gly
      865                 870                 875                 880
      Val Glu Val Asp Pro Ser Leu Ile Lys Asp Thr Trp His Gln Val Tyr
                      885                 890                 895
      Arg Arg His Phe Leu Lys Thr Ala Leu Asn His Cys Asn Leu Cys Arg
                      900                 905                 910
      Arg Gly Phe Tyr Tyr Tyr Gln Arg His Phe Val Asp Ser Glu Leu Glu
                      915                 920                 925
      Cys Asn Asp Val Val Leu Phe Trp Arg Ile Gln Arg Met Leu Ala Ile
                      930                 935                 940
      Thr Ala Asn Thr Leu Arg Gln Gln Leu Thr Asn Thr Glu Val Arg Arg
      945                 950                 955                 960
      Leu Glu Lys Asn Val Lys Glu Val Leu Glu Asp Phe Ala Glu Asp Gly
                      965                 970                 975
      Glu Lys Lys Ile Lys Leu Leu Thr Gly Lys Arg Val Gln Leu Ala Glu
                      980                 985                 990
      Asp Leu Lys Lys Val Arg Glu Ile  Gln Glu Lys Leu Asp  Ala Phe Ile
                      995                1000                1005
      Glu Ala  Leu His Gln Glu Lys
         1010                1015

<210> SEQ ID NO 17
<211> LENGTH: 1953
<212> TYPE: DNA
<213> ORGANISM: Homo sapiens

<400> SEQUENCE: 17
gcgaagggcg ccccggccgg tatggcgggc aggaagtgcg ggtgcgcgcc tgcgcatagg      60
tcgggtctgc ggtgtcaccg ctttcgcttc tgcttgagta atcaagtgaa aaaatgagct     120
tcatctgtgg attgcagtct gctgctagaa accatgtttt cttccgattt aattcactgt     180
ctaactggag aaaatgtaac acattagcat ccacctcacg gggctgtcat caagtacaag     240
ttaaccatat agtaaataag tatcaggggac tgggagtaaa tcagtgtgac aggtggagtt     300
ttctgcctgg aaactttcat ttttatagta cttttaacaa caaaagaaca ggaggcctct     360
```

| | |
|---|---|
| caagtaccaa aagtaaggaa atttggagga ttaccagcaa atgtactgta tggaatgatg | 420 |
| cttttcaag acagctgcta ataaaagaag ttacagcagt ccctagtctg tcagtattgc | 480 |
| atcctctaag ccctgcttcc ataagagcta ttaggaattt ccatacttct ccacggtttc | 540 |
| aagctgctcc ggttcctctc ttgttgatga ttcttaaacc agtacagaag ttatttgcaa | 600 |
| tcattgtagg cagggcata aggaaatggt ggcaggcact tcctcctaac aagaaggaag | 660 |
| tagttaaaga aaatataagg aagaataaat ggaagctatt ccttggtttg agtagttttg | 720 |
| gattgctctt tgtggtgttt tatttactc acctggaagt aagtccaatc acaggaagga | 780 |
| gcaagctact attattgggg aaagaacagt tcagactttt atcggaactg aatatgaag | 840 |
| catggatgga agaatttaaa aatgatatgc taactgagaa agatgcccga tacctggctg | 900 |
| ttaaagaagt gctttgtcat ctaattgaat gcaataaaga tgttccaggg atctctcaga | 960 |
| tcaattgggt tattcatgtg gttgattccc caattattaa tgccttcgtg cttccaaatg | 1020 |
| gacaaatgtt tgttttcact ggatttttaa atagtgtaac cgatattcat caactttctt | 1080 |
| tccttctggg ccatgaaata gcacatgcag tacttgggca tgctgcagaa aaggctggca | 1140 |
| tggttcattt gttggatttc ctaggtatga ttttcctcac aatgatttgg gccatttgtc | 1200 |
| ctcgagatag cttggcactt tgtgccagt ggatacagtc taaattgcag gagtatatgt | 1260 |
| ttaatagacc atacagcaga aaattggagg ccgaagctga caaaattgga ctactgcttg | 1320 |
| ctgcaaaggc ttgtgcagac ataagagcca gttcagtgtt ttggcagcaa atggagttcg | 1380 |
| ttgatagcct gcatggccaa cccaagatgc agaatggtt atctacacac ccttctcatg | 1440 |
| gcaatcgagt tgagtacttg gatagactta tacctcaggc tctcaaaatt agagagatgt | 1500 |
| gtaattgtcc accactgtct aatccagacc ctcgattact attcaaactc agcacgaagc | 1560 |
| attttcttga agaatcagag aaagaagacc taaatatcac gaagaaacag aaaatggata | 1620 |
| ctcttcctat tcaaaaacag gagcaaatac cattaacata catagttgag aaaagaacgg | 1680 |
| gcagttgaat taaatttat gagacacaag atatatgaag aatgttgcag tccttatcat | 1740 |
| tttatgttac ttttaaaaa atgatgtttg aagtgaaaaa aaaaaggata ttcagggtca | 1800 |
| aatcatgtac attacagata ttatctaaat tcttctagaa tttatttttc atgaaatatt | 1860 |
| gatgtatttt aatctatgtt aaaatatctt caatgaggaa aatgtcacag aataaattta | 1920 |
| tattacacat tttaaaaaaa aaaaaaaaaa aaa | 1953 |

<210> SEQ ID NO 18
<211> LENGTH: 524
<212> TYPE: PRT
<213> ORGANISM: Homo sapiens

<400> SEQUENCE: 18

Met Ser Phe Ile Cys Gly Leu Gln Ser Ala Ala Arg Asn His Val Phe
1               5                   10                  15

Phe Arg Phe Asn Ser Leu Ser Asn Trp Arg Lys Cys Asn Thr Leu Ala
            20                  25                  30

Ser Thr Ser Arg Gly Cys His Gln Val Gln Val Asn His Ile Val Asn
        35                  40                  45

Lys Tyr Gln Gly Leu Gly Val Asn Gln Cys Asp Arg Trp Ser Phe Leu
    50                  55                  60

Pro Gly Asn Phe His Phe Tyr Ser Thr Phe Asn Lys Arg Thr Gly
65                  70                  75                  80

Gly Leu Ser Ser Thr Lys Ser Lys Glu Ile Trp Arg Ile Thr Ser Lys
                85                  90                  95

```
Cys Thr Val Trp Asn Asp Ala Phe Ser Arg Gln Leu Leu Ile Lys Glu
                100                 105                 110

Val Thr Ala Val Pro Ser Leu Ser Val Leu His Pro Leu Ser Pro Ala
            115                 120                 125

Ser Ile Arg Ala Ile Arg Asn Phe His Thr Ser Pro Arg Phe Gln Ala
130                 135                 140

Ala Pro Val Pro Leu Leu Leu Met Ile Leu Lys Pro Val Gln Lys Leu
145                 150                 155                 160

Phe Ala Ile Ile Val Gly Arg Gly Ile Arg Lys Trp Trp Gln Ala Leu
                165                 170                 175

Pro Pro Asn Lys Lys Glu Val Val Lys Glu Asn Ile Arg Lys Asn Lys
            180                 185                 190

Trp Lys Leu Phe Leu Gly Leu Ser Ser Phe Gly Leu Leu Phe Val Val
        195                 200                 205

Phe Tyr Phe Thr His Leu Glu Val Ser Pro Ile Thr Gly Arg Ser Lys
    210                 215                 220

Leu Leu Leu Leu Gly Lys Glu Gln Phe Arg Leu Leu Ser Glu Leu Glu
225                 230                 235                 240

Tyr Glu Ala Trp Met Glu Glu Phe Lys Asn Asp Met Leu Thr Glu Lys
                245                 250                 255

Asp Ala Arg Tyr Leu Ala Val Lys Glu Val Leu Cys His Leu Ile Glu
            260                 265                 270

Cys Asn Lys Asp Val Pro Gly Ile Ser Gln Ile Asn Trp Val Ile His
        275                 280                 285

Val Val Asp Ser Pro Ile Ile Asn Ala Phe Val Leu Pro Asn Gly Gln
    290                 295                 300

Met Phe Val Phe Thr Gly Phe Leu Asn Ser Val Thr Asp Ile His Gln
305                 310                 315                 320

Leu Ser Phe Leu Leu Gly His Glu Ile Ala His Ala Val Leu Gly His
                325                 330                 335

Ala Ala Glu Lys Ala Gly Met Val His Leu Leu Asp Phe Leu Gly Met
            340                 345                 350

Ile Phe Leu Thr Met Ile Trp Ala Ile Cys Pro Arg Asp Ser Leu Ala
        355                 360                 365

Leu Leu Cys Gln Trp Ile Gln Ser Lys Leu Gln Glu Tyr Met Phe Asn
    370                 375                 380

Arg Pro Tyr Ser Arg Lys Leu Glu Ala Glu Ala Asp Lys Ile Gly Leu
385                 390                 395                 400

Leu Leu Ala Ala Lys Ala Cys Ala Asp Ile Arg Ala Ser Ser Val Phe
                405                 410                 415

Trp Gln Gln Met Glu Phe Val Asp Ser Leu His Gly Gln Pro Lys Met
            420                 425                 430

Pro Glu Trp Leu Ser Thr His Pro Ser His Gly Asn Arg Val Glu Tyr
        435                 440                 445

Leu Asp Arg Leu Ile Pro Gln Ala Leu Lys Ile Arg Glu Met Cys Asn
    450                 455                 460

Cys Pro Pro Leu Ser Asn Pro Asp Pro Arg Leu Leu Phe Lys Leu Ser
465                 470                 475                 480

Thr Lys His Phe Leu Glu Glu Ser Glu Lys Glu Asp Leu Asn Ile Thr
                485                 490                 495

Lys Lys Gln Lys Met Asp Thr Leu Pro Ile Gln Lys Gln Glu Gln Ile
            500                 505                 510
```

Pro Leu Thr Tyr Ile Val Glu Lys Arg Thr Gly Ser
        515                 520

<210> SEQ ID NO 19
<211> LENGTH: 2952
<212> TYPE: DNA
<213> ORGANISM: Homo sapiens

<400> SEQUENCE: 19

| | | | | | |
|---|---|---|---|---|---|
| gctctaggta | agcgaaacaa | gccgggggac | tgcgagccag | ggactcgggc | cgcggggcgg | 60 |
| gaagaagtgg | ggcagcgctt | ggccaggccg | aaaggacttt | ggggtgggg | gctgggagtc | 120 |
| cgtgtctcga | atgagggagg | agaggtggag | ttgccgggc | tcaggcccgg | cctcgagcat | 180 |
| gggcggatga | gaggagtcgg | gagccgaggc | ctagggtcct | tcgggtgagg | ggagacggag | 240 |
| ccagcgagga | gatggagcag | aagcttgtgg | aggagattct | tcaagcaatc | actatgtcaa | 300 |
| cagacacagg | tgtttccctt | ccttcatatg | aggaagatca | gggatcaaaa | ctcattcgaa | 360 |
| aagctaaaga | ggcaccattc | gtacccgttg | aatagcggg | ttttgcagca | attgttgcat | 420 |
| atggattata | taaactgaag | agcagggaa | atactaaaat | gtccattcat | ctgatccaca | 480 |
| tgcgtgtggc | agcccaaggc | tttgttgtag | agcaatgac | tgttggtatg | ggctattcca | 540 |
| tgtatcggga | attctgggca | aaacctaagc | cttagaagaa | gagatgctgt | cttggtcttg | 600 |
| ttggaggagc | ttgctttagt | tagatgtctt | attattaaag | ttacctatta | ttgttggaaa | 660 |
| taaactaatt | tgtatgggtt | tagatggtaa | catggcattt | tgaatattgg | cttccttct | 720 |
| tgcaggcttg | atttgcttgg | tgaccgaatt | actagtgact | agtttactaa | ctaggtcatt | 780 |
| caaggaagtc | aagttaactt | aaacatgtca | cctaaatgca | cttgatggtg | ttgaaatgtc | 840 |
| caccttctta | aattttaag | atgaacttag | ttctaaagaa | gataacaggc | caatcctgaa | 900 |
| ggtactccct | gtttgctgca | gaatgtcaga | tattttggat | gttgcataag | agtcctattt | 960 |
| gccccagtta | attcaacttt | tgtctgcctg | ttttgtggac | tggctggctc | tgttagaact | 1020 |
| ctgtccaaaa | agtgcatgga | atataacttg | taaagcttcc | cacaattgac | aatatatatg | 1080 |
| catgtgttta | aaccaaatcc | agaaagctta | acaatagag | ctgcataata | gtatttatta | 1140 |
| aagaatcaca | actgtaaaca | tgagaataat | ttaaggattc | tagtttagtt | ttttgtaatt | 1200 |
| gcaaattata | tttttgctgc | tgatatatta | gaataatttt | taaatgtcat | cttgaaatag | 1260 |
| aaatatgtat | tttaagcact | cacgcaaagg | taaatgaaca | cgtttttaaat | gtgtgtgttg | 1320 |
| ctaattttt | ccataagaat | tgtaaacatt | gaactgaaca | aattacctat | aatggatttg | 1380 |
| gttaatgact | tatgagcaag | ctggtttggc | cagacagtat | acccaaactt | ttatataata | 1440 |
| tacagaaggc | tatcacactt | gtgaaattct | cttgtctaat | ctgaatttgc | attccatggt | 1500 |
| gttaacatgg | tatatgtatt | gttattaaag | taagtgaccc | atgtcaaatg | tcttttattt | 1560 |
| atttcatgag | gaaagctttc | tgtagagga | acaaatttga | aacaagttt | caggaaattg | 1620 |
| tcttttttgt | tgttgttctc | taatcatgtt | ctcctttctg | tttcaacgat | tttaaaaata | 1680 |
| ttttactta | tggtatgttt | tattttttt | ccttttgtgg | gtaattttg | ttctattgat | 1740 |
| tatccatata | aatttttttt | tttttttttt | gagacggagt | tattctctgt | catcttggct | 1800 |
| ggcgtgcagt | ggcacgatct | tggctcactg | caacttccat | ccccaggtt | caagtgattc | 1860 |
| tcttgcctca | gcctcctgag | tagctgtgat | tacaggcatg | caccaacatg | cctggctaat | 1920 |
| ttttgtatat | ttagtagaga | cgaggtttca | ccatgttggc | caggctgatc | ttgaattcct | 1980 |
| gacctcaggt | tatccacctg | cctcggcctc | ccaaagtgct | aggattacag | gcgtgagcca | 2040 |

| | |
|---|---:|
| ccacgcccag ctgattatcc atataattat aacactcttc tatttatttt cagtcaccaa | 2100 |
| taattccttt tgagcaatat ttaagcctag catatttctt ccttccctcc tcctctacta | 2160 |
| accagttctg gtcgatatat tattggattt tactcttata ctgtttgttt gtttgtttgt | 2220 |
| ttgtttattt tgagacagag tcttgctctg ttgctgaggc tggagtacag tggtgtgatc | 2280 |
| tgagctcacg gcaccctcca cctcctagct tcgtgcgatt ctgatgcttc aaccttccga | 2340 |
| gtagctggga ttacaggcat gcgccaccat gtcgggctaa tttttgtgtt tttagtaaag | 2400 |
| gcgaggtttc accatgttgg atgatcttga actcctggct tcaagagatc tatctgcctc | 2460 |
| agcctcccaa agtgctggga ttacaagcat aatccaccac acctgaccta cttttgtatg | 2520 |
| ttaaatgtga ttatacttct ctttgacttg tcagcttagc tttagctgat acactctggt | 2580 |
| gcccaactat tattgtatca gtgaacttcc actttctttt cctttctct caattttgt | 2640 |
| tgtatcattc ctaccttgtg aggacatata atatttacat tctgttgtca tcctcacatt | 2700 |
| tcttagttcc acagtttaaa tgtatttgaa actcaaaaca ttcccattaa tctcttggtc | 2760 |
| agctgaaatt aatgatttaa tagtttcctt aaaaaagact catggaacaa tttccctaaa | 2820 |
| tttttgccat gtcaaatatg tttatctgta gcctttacac agtaaaaaca atttggctag | 2880 |
| ataatacaat tctcagttca tattttctt tggaatatta agtattgct atagagaaaa | 2940 |
| aaaaaaaaaa aa | 2952 |

<210> SEQ ID NO 20
<211> LENGTH: 107
<212> TYPE: PRT
<213> ORGANISM: Homo sapiens

<400> SEQUENCE: 20

Met Glu Gln Lys Leu Val Glu Glu Ile Leu Gln Ala Ile Thr Met Ser
1               5                   10                  15

Thr Asp Thr Gly Val Ser Leu Pro Ser Tyr Glu Glu Asp Gln Gly Ser
            20                  25                  30

Lys Leu Ile Arg Lys Ala Lys Glu Ala Pro Phe Val Pro Val Gly Ile
        35                  40                  45

Ala Gly Phe Ala Ala Ile Val Ala Tyr Gly Leu Tyr Lys Leu Lys Ser
    50                  55                  60

Arg Gly Asn Thr Lys Met Ser Ile His Leu Ile His Met Arg Val Ala
65                  70                  75                  80

Ala Gln Gly Phe Val Val Gly Ala Met Thr Val Gly Met Gly Tyr Ser
                85                  90                  95

Met Tyr Arg Glu Phe Trp Ala Lys Pro Lys Pro
            100                 105

<210> SEQ ID NO 21
<211> LENGTH: 2805
<212> TYPE: DNA
<213> ORGANISM: Homo sapiens

<400> SEQUENCE: 21

| | |
|---|---:|
| gattggctgg gacggctgtg ggtggggaga agccgggagg actgggtgcg cctgcaggga | 60 |
| tcggaagccg gttgggtgt gagaggtttt ctcgctctag aacctcatag aaattctttc | 120 |
| tcagggagat tcttcaagca atcactatgt caacagacac aggtgtttcc cttccttcat | 180 |
| atgaggaaga tcaggcatca aaactcattc gaaaagctaa agaggcacca ttcgtacccg | 240 |
| ttggaatagc gggttttgca gcaattgttg catatggatt atataaactg aagagcaggg | 300 |

```
gaaatactaa aatgtccatt catctgatcc acatgcgtgt ggcagcccaa ggctttgttg    360
taggagcaat gactgttggt atgggctatt ccatgtatcg ggaattctgg gcaaaaccta    420
agccttagaa gaagagatgc tgtcttggtc ttgttggagg agcttgcttt agttagatgt    480
cttattatta aagttaccta ttattgttgg aaataaacta atttgtatgg gtttagatgg    540
taacatggca ttttgaatat tggcttcctt tcttgcaggc ttgatttgct tggtgaccga    600
attactagtg actagtttac taactaggtc attcaaggaa gtcaagttaa cttaaacatg    660
tcacctaaat gcacttgatg gtgttgaaat gtccaccttc ttaaatttt aagatgaact     720
tagttctaaa gaagataaca ggccaatcct gaaggtactc cctgttgct gcagaatgtc      780
agatattttg gatgttgcat aagagtccta ttgccccag ttaattcaac ttttgtctgc      840
ctgttttgtg gactggctgg ctctgttaga actctgtcca aaaagtgcat ggaatataac    900
ttgtaaagct tcccacaatt gacaatatat atgcatgtgt ttaaaccaaa tccagaaagc    960
ttaaacaata gagctgcata atagtattta ttaaagaatc acaactgtaa acatgagaat    1020
aatttaagga ttctagttta gttttttgta attgcaaatt atatttttgc tgctgatata    1080
ttagaataat tttaaatgt catcttgaaa tagaaatatg tatttaagc actcacgcaa      1140
aggtaaatga acacgtttta aatgtgtgtg ttgctaatt tttccataag aattgtaaac     1200
attgaactga acaaattacc tataatggat ttggttaatg acttatgagc aagctggttt    1260
ggccagacag tatacccaaa ctttatata atatacagaa ggctatcaca cttgtgaaat      1320
tctcttgtct aatctgaatt tgcattccat ggtgttaaca tggtatatgt attgttatta    1380
aagtaagtga cccatgtcaa atgtctttta tttatttcat gaggaaaagc tttctgtaga    1440
ggaacaaatt tgagaacaag tttcaggaaa ttgtcttttt tgttgttgtt ctctaatcat    1500
gttctccttt ctgtttcaac gattttaaaa atatttact ttatggtatg ttttatttt      1560
tttcctttg tgggtaattt ttgttctatt gattatccat ataaattttt tttttttt       1620
tttgagacgg agttattctc tgtcatcttg gctggcgtgc agtggcacga tcttggctca    1680
ctgcaacttc catccccag gttcaagtga ttctcttgcc tcagcctcct gagtagctgt      1740
gattacaggc atgcaccaac atgcctggct aatttttgta tatttagtag agacgaggtt    1800
tcaccatgtt ggccaggctg atcttgaatt cctgacctca ggttatccac ctgcctcggc    1860
ctcccaaagt gctaggatta caggcgtgag ccaccacgcc cagctgatta tccatataat    1920
tataacactc ttctattat tttcagtcac caataattcc ttttgagcaa tatttaagcc     1980
tagcatattt cttccttccc tcctcctcta ctaaccagtt ctggtcgata tattattgga    2040
ttttactctt atactgtttg tttgtttgtt tgtttgttta ttttgagaca gagtcttgct    2100
ctgttgctga ggctggagta cagtggtgtg atctgagctc acggcaccct ccacctccta    2160
gcttcgtgcg attctgatgc ttcaaccttc cgagtagctg ggattacagg catgcgccac    2220
catgtcgggc taattttgt gttttagta aaggcgaggt ttcaccatgt tggatgatct      2280
tgaactcctg gcttcaagag atctatctgc ctcagcctcc caaagtgctg ggattacaag    2340
cataatccac cacacctgac ctacttttgt atgttaaatg tgattatact tctctttgac    2400
ttgtcagctt agcttagct gatacactct ggtgcccaac tattattgta tcagtgaact     2460
tccactttct tttcctttc tctcaatttt tgttgtatca ttcctacctt gtgaggacat     2520
ataaatattta cattctgttg tcatcctcac atttcttagt tccacagttt aaatgtattt    2580
gaaactcaaa acattcccat taatctcttg gtcagctgaa attaatgatt taatagtttc    2640
cttaaaaaag actcatggaa caatttccct aaattttgc catgtcaaat atgtttatct     2700
```

| gtagccttta cacagtaaaa acaatttggc tagataatac aattctcagt tcatattttt | 2760 |
|---|---|
| ctttggaata ttaaagtatt gctatagaga aaaaaaaaaa aaaaa | 2805 |

<210> SEQ ID NO 22
<211> LENGTH: 93
<212> TYPE: PRT
<213> ORGANISM: Homo sapiens

<400> SEQUENCE: 22

```
Met Ser Thr Asp Thr Gly Val Ser Leu Pro Ser Tyr Glu Glu Asp Gln
1               5                  10                  15
Gly Ser Lys Leu Ile Arg Lys Ala Lys Glu Ala Pro Phe Val Pro Val
            20                  25                  30
Gly Ile Ala Gly Phe Ala Ala Ile Val Ala Tyr Gly Leu Tyr Lys Leu
        35                  40                  45
Lys Ser Arg Gly Asn Thr Lys Met Ser Ile His Leu Ile His Met Arg
    50                  55                  60
Val Ala Ala Gln Gly Phe Val Val Gly Ala Met Thr Val Gly Met Gly
65                  70                  75                  80
Tyr Ser Met Tyr Arg Glu Phe Trp Ala Lys Pro Lys Pro
                85                  90
```

<210> SEQ ID NO 23
<211> LENGTH: 1661
<212> TYPE: DNA
<213> ORGANISM: Homo sapiens

<400> SEQUENCE: 23

| aagtcgcggc caatgggcga cgcggccgca gatccgcccg gccccgccct gccctgtgag | 60 |
|---|---|
| ttcctccggc cgggctgcgg ggctccgctc agtccgggag cgcagctggg ccgcggcgct | 120 |
| ccgacctccg ctttcccacc gcccgcagct gaagcacatc ccgcagcccg cgcggactc | 180 |
| cgatcgccgc agttgccctc tggcgccatg tcgcagaacg gagcgcccgg gatgcaggag | 240 |
| gagagcctgc agggctcctg gtagaactga cacttcagca ataatgggaa cgggggcagc | 300 |
| gttccagcct cggtttctat ttataatgga gacatggaaa aaatactgct ggacgcacag | 360 |
| catgagtctg gacggagtag ctccaagagc tctcactgtg acagcccacc tcgctcgcag | 420 |
| acaccacaag ataccaacag agcttctgaa acagataccc atagcattgg agagaaaaac | 480 |
| agctcacagt ctgaggaaga tgatattgaa agaaggaaag aagttgaaag catcttgaag | 540 |
| aaaaactcag attggatatg ggattggtca agtcggccgg aaaatattcc ccccaaggag | 600 |
| ttcctcttta acacccgaa gcgcacggcc accctcagca tgaggaacac gagcgtcatg | 660 |
| aagaaagggg gcatattctc tgcagaattt ctgaaagttt tccttccatc tctgctgctc | 720 |
| tctcatttgc tggccatcgg attggggatc tatattggaa ggcgtctgac aacctccacc | 780 |
| agcaccttt tgatgaagaa ctggagtctga cttggttcgt tagtggatta cttctgagct | 840 |
| tgcaacatag ctcactgaag agctgttaga tcctggggtg gccacgtcac ttgtgtttat | 900 |
| ttgttctgta aatgctgcgt tcctaattta gtaaaataaa agaatagaca ctaaaatcat | 960 |
| gttgatctat aattacacct atgggatcaa taagcatgtc agactgatta atgtctactg | 1020 |
| tgaaaatttg gtagtaaatt ttcatttgat attagatata aatatctgaa tataaataat | 1080 |
| tttaatatac tagtcatgat gtgtgttgta ttttaaaaat tatctgcaac cttaattcag | 1140 |
| ctgaagtact ttatatttca aaagaatgaa taacattgat aataaaatcg ctactttaag | 1200 |

-continued

```
gggtttgtcc aaaataaata ttgtggcctt atatatcaca ctattgtaga aagtattatt    1260
taatttaaat ggatgcaggt tgtctactaa agaaagatta tatataacta tgctaattgt    1320
tcataatcaa cagaaaccaa gatagagcta caaactcagc tgtacagttc gtacactaaa    1380
ctcttcttgc ttttgcatta taaggaatta agtctccgat tattaggtga tcaccctgga    1440
tgatcagttt tctgctgaag gcacctactc agtatctttt cctctttatc actctgcatt    1500
ggtgaattta atcctctcct ttgtgttcaa cttttgtgtg cttttaaaat cagctttatt    1560
ctaagcaaat ctgtgtctac tttaaaaaac tggaaatgga aaaaaaaata aatctttgcc    1620
aaatccttca gataaaaaaa aaaaaaaaaa aaaaaaaaa a                         1661
```

<210> SEQ ID NO 24
<211> LENGTH: 259
<212> TYPE: PRT
<213> ORGANISM: Homo sapiens

<400> SEQUENCE: 24

```
Met Gly Asp Ala Ala Ala Asp Pro Pro Gly Pro Ala Leu Pro Cys Glu
1               5                   10                  15

Phe Leu Arg Pro Gly Cys Gly Ala Pro Leu Ser Pro Gly Ala Gln Leu
                20                  25                  30

Gly Arg Gly Ala Pro Thr Ser Ala Phe Pro Pro Ala Ala Glu Ala
        35                  40                  45

His Pro Ala Ala Arg Arg Gly Leu Arg Ser Pro Gln Leu Pro Ser Gly
    50                  55                  60

Ala Met Ser Gln Asn Gly Ala Pro Gly Met Gln Glu Glu Ser Leu Gln
65                  70                  75                  80

Gly Ser Trp Val Glu Leu His Phe Ser Asn Asn Gly Asn Gly Gly Ser
                85                  90                  95

Val Pro Ala Ser Val Ser Ile Tyr Asn Gly Asp Met Glu Lys Ile Leu
                100                 105                 110

Leu Asp Ala Gln His Glu Ser Gly Arg Ser Ser Ser Lys Ser Ser His
                115                 120                 125

Cys Asp Ser Pro Pro Arg Ser Gln Thr Pro Gln Asp Thr Asn Arg Ala
            130                 135                 140

Ser Glu Thr Asp Thr His Ser Ile Gly Glu Lys Asn Ser Ser Gln Ser
145                 150                 155                 160

Glu Glu Asp Asp Ile Glu Arg Arg Lys Glu Val Glu Ser Ile Leu Lys
                165                 170                 175

Lys Asn Ser Asp Trp Ile Trp Asp Trp Ser Ser Arg Pro Glu Asn Ile
                180                 185                 190

Pro Pro Lys Glu Phe Leu Phe Lys His Pro Lys Arg Thr Ala Thr Leu
            195                 200                 205

Ser Met Arg Asn Thr Ser Val Met Lys Lys Gly Gly Ile Phe Ser Ala
    210                 215                 220

Glu Phe Leu Lys Val Phe Leu Pro Ser Leu Leu Leu Ser His Leu Leu
225                 230                 235                 240

Ala Ile Gly Leu Gly Ile Tyr Ile Gly Arg Arg Leu Thr Thr Ser Thr
                245                 250                 255

Ser Thr Phe
```

<210> SEQ ID NO 25
<211> LENGTH: 4403
<212> TYPE: DNA
<213> ORGANISM: Homo sapiens

<400> SEQUENCE: 25

```
actgttgagt tagcgcctcg ccttccgggg cggattgtct gtcgttgcag tagctgtagg      60
aaggggaggc cattttccgt ttctgggagg agtgaggggc aacgggtcgg agaaaaagga     120
aaaaagaagg gctcagcgcc tccccgccgg gccgtggaca gaggggcaca gtttcggcag     180
gcgggtgagg tcgctgaggg cccgccggag atgttttcct tgtcgagcac ggtgcaaccc     240
caggttacag ttcctctgag tcatctcatc aatgccttcc atacaccaaa aaacacttct     300
gtttctctca gtggagtgtc agtttctcaa aaccagcatc gagatgtagt tcctgagcat     360
gaggctccca gcagtgagtg tatgttcagt gacttcctga cgaagcttaa cattgtttca     420
attggcaaag gaaaaatatt cgaagggtac agatccatgt tcatggagcc agcaaaaagg     480
atgaagaaga gcttggacac aaccgataac tggcacatcc gtccagaacc cttctccctc     540
tcaatccctc cttcacttaa cttaagggac cttggattat ctgaactaaa aattggacag     600
attgatcagc tggtagaaaa tctacttcct ggattttgta aaggcaaaaa catttcttcc     660
cattggcata catcccatgt ctctgcacaa tccttctttg aaaataaata tggtaactta     720
gatatattta gtacattacg ttcctcttgc ttgtatcgac atcattcaag agctcttcaa     780
agcatttgtt cagatcttca gtactggcca gttttcatac agtctcgggg ttttaaaact     840
ttgaaatcaa ggacacgacg tctccagtct acctccgaga gattagctga acacagaat      900
atagcgccat cattcgtgaa ggggtttctt tgcgggaca gaggatcaga tgttgagagt      960
ttggacaaac tcatgaaaac caaaatata cctgaagctc accagatgc atttaaaact     1020
ggttttgcgg aaggttttct gaaagctcaa gcactcacac aaaaaaccaa tgattcccta    1080
aggcgaaccc gtctgattct cttcgttctg ctgctattcg gcatttatgg acttctaaaa    1140
aacccatttt tatctgtccg cttccggaca acaacagggc ttgattctgc agtagatcct    1200
gtccagatga aaaatgtcac ctttgaacat gttaaagggg tggaggaagc taaacaagaa    1260
ttacaggaag ttgttgaatt cttgaaaaat ccacaaaaat ttactattct tggaggtaaa    1320
cttccaaaag gaattctttt agttggaccc ccagggactg gaaagacact tcttgcccga    1380
gctgtggcgg gagaagctga tgttcctttt tattatgctt ctggatccga atttgatgag    1440
atgtttgtgg gtgtgggagc cagccgtatc agaaatcttt ttagggaagc aaaggcgaat    1500
gctccttgtg ttatatttat tgatgaatta gattctgttg gtgggaagag aattgaatct    1560
ccaatgcatc catattcaag gcagaccata aatcaacttc ttgctgaaat ggatggtttt    1620
aaacccaatg aaggagttat cataatagga gccacaaact cccagaggc attagataat    1680
gccttaatac gtcctggtcg ttttgacatg caagttacag ttccaaggcc agatgtaaaa    1740
ggtcgaacag aaatttgaa atggtatctc aataaaataa agtttgatca atccgttgat    1800
ccagaaatta tagctcgagg tactgttggc ttttccggag cagagttgga gaatcttgtg    1860
aaccaggctg cattaaaagc agctgttgat ggaaaagaaa tggttaccat gaaggagctg    1920
gagttttcca agacaaaat tctaatgggg cctgaaagaa gaagtgtgga aattgataac    1980
aaaaacaaaa ccatcacagc atatcatgaa tctggtcatg ccattattgc atattcacac    2040
aaagatgcaa tgcctatcaa caaagctaca atcatgccac gggggccaac acttggacat    2100
gtgtccctgt tacctgagaa tgacagatgg aatgaaacta gagcccagct gcttgcacaa    2160
atggatgtta gtatgggagg aagagtggca gaggagctta tatttggaac cgaccatatt    2220
acaacaggtg cttccagtga ttttgataat gccactaaaa tagcaaagcg gatggttacc    2280
```

```
aaatttggaa tgagtgaaaa gcttggagtt atgacctaca gtgatacagg gaaactaagt    2340
ccagaaaccc aatctgccat cgaacaagaa ataagaatcc ttctaaggga ctctatgaa    2400 cgagcaaaac atatcttgaa aactcatgca aaggagcata agaatctcgc agaagcttta    2460
ttgacctatg agactttgga tgccaaagag attcaaattg ttcttgaggg gaaaaagttg    2520
gaagtgagat gataactctc ttgatatgga tgcttgctgg ttttattgca agaatacaag    2580
tagcattgca gtagtctact tttacaacgc tttcccctca ttcttgatgt ggtgtaattg    2640
aagggtgtga aatgctttgt caatcatttg tcacatttat ccagtttggg ttattctcat    2700
tatgacacct attgcaaatt agcatcccat ggcaaatata ttttgaaaaa ataaagaact    2760
atcaggattg aaaacagctc ttttgaggaa tgtcaattag ttattaagtt gaaagtaatt    2820
aatgatttta tgtttggtta ctctactaga tttgataaaa attgtgcctt tagccttcta    2880
tatacatcag tggaaactta agatgcagta attatgttcc agattgacca tgaataaaat    2940
attttttaat ctaaatgtag agaagttggg attaaaagca gtctcggaaa cacagagcca    3000
ggaatatagc cttttggcat ggtgccatgg ctcacatctg taatcccagc acttttggag    3060
gctgaggcgg gtggattgct tgaggccagg agttcgagac cagcctggcc aacgtggtga    3120
aacgctgtct ctactaaaat acaaaaaaat agggctgggc gcggttgctc acgcctgtaa    3180
tcccagcact tttcagaggc caaggcgggc aaatcacctg aggtcaagag tttgagacca    3240
gcctggccaa catggtgaaa ccccatctct actaaacatg caaaaattac ctgggcatgg    3300
tggcaggtgc ttataatccc agctactctg ggggccaagg caggagaatt gcttgagcct    3360
gggagatgga ggttgcagtg agctgagatc atgccactgc actccagcct gggcaacaga    3420
gcaagactct gcctcaaaaa aaaattaaaa taaatttaaa tacaaaaaaa aatagccagg    3480 tgtgggtgc atgcctggaa tcccagctac ttgagaggct gaggcacgag aattgcttga    3540
acccaggagg tggaggttgc agtgagccaa gatcacagga gccactgcac tccagcctgg    3600
gtgacagagt gagactctgt ctcaaaaaaa aattaaataa attattataa cctttcagaa    3660
atgctgtgtg cattttcatg ttcttttttt tagcattact gtcactctcc ctaatgaaat    3720
gtacttcaga gaagcagtat tttgttaaat aaatacataa cctcattctg aataatgtcc    3780
ctcattttga ctataactgt gcttggtttc aaaagcaaaa ttaaacaaaa atctcagtcc    3840
cctccgaagt gaactttgtg ttaccctgcg tcagaaatgc caagttgtgt ttacttttca    3900
ttcagatttt gtgaatatga acatgctgtt ataggatcta cagatgaata tttaactcaa    3960
tagaaaaatt attttagaac acattgtatt ggtattacaa ccagattata ttcttgacgt    4020
tgacttcatt aaaattatct acaatttcct aataatttaa gctgtatatg gtcttcattg    4080 aaaaagata gatattgtta caggaagctt gttacattat attcttgacc ttttggttga    4140
taatcttaaa tcttaatgta atttcaaact ggcagaaatg ttgccagcat aatacatgga    4200
tgtctcatat accctgcatc cagatttacc agttgttatc attctgcccg ttttttattg    4260
ccccaaacct gttctgtctc cctctctgta tgtacataca tacacgtata aaatattgat    4320
aaagtcttat ctgtcttaaa ttttttttaca tatttgttga ggtataattt acatatgata    4380
aaattcattt taaatgtaaa aaa                                            4403
```

<210> SEQ ID NO 26
<211> LENGTH: 773
<212> TYPE: PRT
<213> ORGANISM: Homo sapiens

<400> SEQUENCE: 26

-continued

```
Met Phe Ser Leu Ser Ser Thr Val Gln Pro Gln Val Thr Val Pro Leu
1               5                   10                  15

Ser His Leu Ile Asn Ala Phe His Thr Pro Lys Asn Thr Ser Val Ser
                20                  25                  30

Leu Ser Gly Val Ser Val Ser Gln Asn Gln His Arg Asp Val Val Pro
            35                  40                  45

Glu His Glu Ala Pro Ser Ser Glu Cys Met Phe Ser Asp Phe Leu Thr
50                      55                  60

Lys Leu Asn Ile Val Ser Ile Gly Lys Gly Lys Ile Phe Glu Gly Tyr
65                  70                  75                  80

Arg Ser Met Phe Met Glu Pro Ala Lys Arg Met Lys Lys Ser Leu Asp
                85                  90                  95

Thr Thr Asp Asn Trp His Ile Arg Pro Glu Pro Phe Ser Leu Ser Ile
                100                 105                 110

Pro Pro Ser Leu Asn Leu Arg Asp Leu Gly Leu Ser Glu Leu Lys Ile
            115                 120                 125

Gly Gln Ile Asp Gln Leu Val Glu Asn Leu Leu Pro Gly Phe Cys Lys
        130                 135                 140

Gly Lys Asn Ile Ser Ser His Trp His Thr Ser His Val Ser Ala Gln
145                 150                 155                 160

Ser Phe Phe Glu Asn Lys Tyr Gly Asn Leu Asp Ile Phe Ser Thr Leu
                165                 170                 175

Arg Ser Ser Cys Leu Tyr Arg His His Ser Arg Ala Leu Gln Ser Ile
                180                 185                 190

Cys Ser Asp Leu Gln Tyr Trp Pro Val Phe Ile Gln Ser Arg Gly Phe
            195                 200                 205

Lys Thr Leu Lys Ser Arg Thr Arg Arg Leu Gln Ser Thr Ser Glu Arg
210                 215                 220

Leu Ala Glu Thr Gln Asn Ile Ala Pro Ser Phe Val Lys Gly Phe Leu
225                 230                 235                 240

Leu Arg Asp Arg Gly Ser Asp Val Glu Ser Leu Asp Lys Leu Met Lys
                245                 250                 255

Thr Lys Asn Ile Pro Glu Ala His Gln Asp Ala Phe Lys Thr Gly Phe
                260                 265                 270

Ala Glu Gly Phe Leu Lys Ala Gln Ala Leu Thr Gln Lys Thr Asn Asp
            275                 280                 285

Ser Leu Arg Arg Thr Arg Leu Ile Leu Phe Val Leu Leu Leu Phe Gly
        290                 295                 300

Ile Tyr Gly Leu Leu Lys Asn Pro Phe Leu Ser Val Arg Phe Arg Thr
305                 310                 315                 320

Thr Thr Gly Leu Asp Ser Ala Val Asp Pro Val Gln Met Lys Asn Val
                325                 330                 335

Thr Phe Glu His Val Lys Gly Val Glu Glu Ala Lys Gln Glu Leu Gln
                340                 345                 350

Glu Val Val Glu Phe Leu Lys Asn Pro Gln Lys Phe Thr Ile Leu Gly
            355                 360                 365

Gly Lys Leu Pro Lys Gly Ile Leu Leu Val Gly Pro Pro Gly Thr Gly
        370                 375                 380

Lys Thr Leu Leu Ala Arg Ala Val Ala Gly Glu Ala Asp Val Pro Phe
385                 390                 395                 400

Tyr Tyr Ala Ser Gly Ser Glu Phe Asp Glu Met Phe Val Gly Val Gly
                405                 410                 415
```

```
Ala Ser Arg Ile Arg Asn Leu Phe Arg Glu Ala Lys Ala Asn Ala Pro
            420                 425                 430

Cys Val Ile Phe Ile Asp Glu Leu Asp Ser Val Gly Gly Lys Arg Ile
        435                 440                 445

Glu Ser Pro Met His Pro Tyr Ser Arg Gln Thr Ile Asn Gln Leu Leu
    450                 455                 460

Ala Glu Met Asp Gly Phe Lys Pro Asn Glu Gly Val Ile Ile Gly
465                 470                 475                 480

Ala Thr Asn Phe Pro Glu Ala Leu Asp Asn Ala Leu Ile Arg Pro Gly
                485                 490                 495

Arg Phe Asp Met Gln Val Thr Val Pro Arg Pro Asp Val Lys Gly Arg
            500                 505                 510

Thr Glu Ile Leu Lys Trp Tyr Leu Asn Lys Ile Lys Phe Asp Gln Ser
        515                 520                 525

Val Asp Pro Glu Ile Ile Ala Arg Gly Thr Val Gly Phe Ser Gly Ala
    530                 535                 540

Glu Leu Glu Asn Leu Val Asn Gln Ala Ala Leu Lys Ala Val Asp
545                 550                 555                 560

Gly Lys Glu Met Val Thr Met Lys Glu Leu Glu Phe Ser Lys Asp Lys
                565                 570                 575

Ile Leu Met Gly Pro Glu Arg Arg Ser Val Glu Ile Asp Asn Lys Asn
            580                 585                 590

Lys Thr Ile Thr Ala Tyr His Glu Ser Gly His Ala Ile Ile Ala Tyr
        595                 600                 605

Tyr Thr Lys Asp Ala Met Pro Ile Asn Lys Ala Thr Ile Met Pro Arg
    610                 615                 620

Gly Pro Thr Leu Gly His Val Ser Leu Leu Pro Glu Asn Asp Arg Trp
625                 630                 635                 640

Asn Glu Thr Arg Ala Gln Leu Leu Ala Gln Met Asp Val Ser Met Gly
                645                 650                 655

Gly Arg Val Ala Glu Glu Leu Ile Phe Gly Thr Asp His Ile Thr Thr
            660                 665                 670

Gly Ala Ser Ser Asp Phe Asp Asn Ala Thr Lys Ile Ala Lys Arg Met
        675                 680                 685

Val Thr Lys Phe Gly Met Ser Glu Lys Leu Gly Val Met Thr Tyr Ser
    690                 695                 700

Asp Thr Gly Lys Leu Ser Pro Glu Thr Gln Ser Ala Ile Glu Gln Glu
705                 710                 715                 720

Ile Arg Ile Leu Leu Arg Asp Ser Tyr Glu Arg Ala Lys His Ile Leu
                725                 730                 735

Lys Thr His Ala Lys Glu His Lys Asn Leu Ala Glu Ala Leu Leu Thr
            740                 745                 750

Tyr Glu Thr Leu Asp Ala Lys Glu Ile Gln Ile Val Leu Glu Gly Lys
        755                 760                 765

Lys Leu Glu Val Arg
    770

<210> SEQ ID NO 27
<211> LENGTH: 4232
<212> TYPE: DNA
<213> ORGANISM: Homo sapiens

<400> SEQUENCE: 27
actgttgagt tagcgcctcg ccttccgggg cggattgtct gtcgttgcag tagctgtagg      60
```

```
aagggagggc cattttccgt ttctgggagg agtgaggggc aacgggtcgg agaaaaagga    120
aaaaagaagg gctcagcgcc tccccgccgg gccgtggaca gaggggcaca gtttcggcag    180
gcgggtgagg tcgctgaggg cccgccggag atgttttcct tgtcgagcac ggtgcaaccc    240
caggttacag ttcctctgag tcatctcatc aatgccttcc atacaccaaa aaacacttct    300
gtttctctca gtggagtgtc agtttctcaa aaccagcatc gagatgtagt tcctgagcat    360
gaggctccca gcagtgagcc ttcacttaac ttaagggacc ttggattatc tgaactaaaa    420
attggacaga ttgatcagct ggtagaaaat ctacttcctg gattttgtaa aggcaaaaac    480
atttcttccc attggcatac atcccatgtc tctgcacaat ccttctttga aaataaatat    540
ggtaacttag atatatttag tacattacgt tcctcttgct tgtatcgaca tcattcaaga    600
gctcttcaaa gcatttgttc agatcttcag tactggccag ttttcataca gtctcggggt    660
tttaaaactt tgaaatcaag gacacgacgt ctccagtcta cctccgagag attagctgaa    720
acacagaata tagcgccatc attcgtgaag gggtttcttt tgcgggacag aggatcagat    780
gttgagagtt tggacaaact catgaaaacc aaaaatatac ctgaagctca ccaagatgca    840
tttaaaactg ttttgcgga aggttttctg aaagctcaag cactcacaca aaaaaccaat    900
gattccctaa ggcgaacccg tctgattctc ttcgttctgc tgctattcgg catttatgga    960
cttctaaaaa acccattttt atctgtccgc ttccggacaa caacagggct tgattctgca   1020
gtagatcctg tccagatgaa aaatgtcacc tttgaacatg ttaaagggga ggaggaagct   1080
aaacaagaat tacaggaagt tgttgaattc ttgaaaaatc cacaaaaatt tactattctt   1140
ggaggtaaac ttccaaaagg aattctttta gttggacccc cagggactgg aaagacactt   1200
cttgcccgag ctgtggcggg agaagctgat gttcctttttt attatgcttc tggatccgaa   1260
tttgatgaga tgtttgtggg tgtgggagcc agccgtatca gaaatctttt tagggaagca   1320
aaggcgaatg ctccttgtgt tatatttatt gatgaattag attctgttgg tgggaagaga   1380
attgaatctc caatgcatcc atattcaagg cagaccataa atcaacttct tgctgaaatg   1440
gatggtttta aacccaatga aggagttatc ataataggag ccacaaactt cccagaggca   1500
ttagataatg ccttaatacg tcctggtcgt tttgacatgc aagttacagt tccaaggcca   1560
gatgtaaaag gtcgaacaga aattttgaaa tggtatctca ataaaataaa gtttgatcaa   1620
tccgttgatc cagaaattat agctcgaggt actgttggct tttccggagc agagttggag   1680
aatcttgtga accaggctgc attaaaagca gctgttgatg gaaaagaaat ggttaccatg   1740
aaggagctgg agttttccaa agacaaaatt ctaatgggc ctgaaagaag aagtgtggaa   1800
attgataaca aaaacaaaac catcacagca tatcatgaat ctggtcatgc cattattgca   1860
tattacacaa aagatgcaat gcctatcaac aaagctacaa tcatgccacg ggggccaaca   1920
cttggacatg tgtccctgtt acctgagaat gacagatgga atgaaactag agcccagctg   1980
cttgcacaaa tggatgttag tatgggagga agagtggcag aggagcttat atttggaacc   2040
gaccatatta caacaggtgc ttccagtgat tttgataatg ccactaaaat agcaaagcgg   2100
atggttacca aatttggaat gagtgaaaag cttggagtta tgacctacag tgatacaggg   2160
aaactaagtc cagaaaccca atctgccatc gaacaagaaa taagaatcct tctaagggac   2220
tcatatgaac gagcaaaaca tatcttgaaa actcatgcaa aggagcataa gaatctcgca   2280
gaagctttat tgacctatga acttttggat gccaaagaga ttcaaattgt tcttgagggg   2340
aaaaagttgg aagtgagatg ataactctct tgatatggat gcttgctggt tttattgcaa   2400
gaatacaagt agcattgcag tagtctactt ttacaacgct ttcccctcat tcttgatgtg   2460
```

```
gtgtaattga agggtgtgaa atgctttgtc aatcatttgt cacatttatc cagtttgggt    2520
tattctcatt atgacaccta ttgcaaatta gcatcccatg gcaaatatat ttgaaaaaa    2580
taaagaacta tcaggattga aaacagctct tttgaggaat gtcaattagt tattaagttg    2640
aaagtaatta atgattttat gtttggttac tctactagat ttgataaaaa ttgtgccttt    2700
agccttctat atacatcagt ggaaacttaa gatgcagtaa ttatgttcca gattgaccat    2760
gaataaaata ttttttaatc taaatgtaga aagttgggga ttaaaagcag tctcggaaac    2820
acagagccag gaatatagcc ttttggcatg gtgccatggc tcacatctgt aatcccagca    2880
cttttggagg ctgaggcggg tggattgctt gaggccagga gttcgagacc agcctggcca    2940
acgtggtgaa acgctgtctc tactaaaata caaaaaaata gggctgggcg cggttgctca    3000
cgcctgtaat cccagcactt tcagaggcc aaggcgggca aatcacctga ggtcaagagt    3060
ttgagaccag cctggccaac atggtgaaac cccatctcta ctaaacatgc aaaaattacc    3120
tgggcatggt ggcaggtgct tataatccca gctactctgg gggccaaggc aggagaattg    3180
cttgagcctg ggagatggag gttgcagtga gctgagatca tgccactgca ctccagcctg    3240
ggcaacagag caagactctg cctcaaaaaa aaattaaaat aaatttaaat acaaaaaaaa    3300
atagccaggt gtggggtgca tgcctggaat cccagctact tgagaggctg aggcacgaga    3360
attgcttgaa cccaggaggt ggaggttgca gtgagccaag atcacaggag ccactgcact    3420
ccagcctggg tgacagagtg agactctgtc tcaaaaaaaa attaaataaa ttattataac    3480
cttttcagaaa tgctgtgtgc attttcatgt tcttttttt agcattactg tcactctccc    3540
taatgaaatg tacttcagag aagcagtatt ttgttaaata aatacataac ctcattctga    3600
ataatgtccc tcattttgac tataactgtg cttggtttca aaagcaaaat taaacaaaaa    3660
tctcagtccc ctccgaagtg aactttgtgt taccctgcgt cagaaatgcc aagttgtgtt    3720
tacttttcat tcagattttg tgaatatgaa catgctgtta taggatctac agatgaaatt    3780
ttaactcaat agaaaaatta ttttagaaca cattgtattg gtattacaac cagattatat    3840
tcttgacgtt gacttcatta aaattatcta caatttccta ataatttaag ctgtatatgg    3900
tcttcattga aaaaagatag atattgttac aggaagcttg ttacattata ttcttgacct    3960
tttggttgat aatcttaaat cttaatgtaa tttcaaactg gcagaaatgt tgccagcata    4020
atacatggat gtctcatata ccctgcatcc agatttacca gttgttatca ttctgcccgt    4080
tttttattgc cccaaacctg ttctgtctcc ctctctgtat gtacatacat acacgtataa    4140
aatattgata aagtcttatc tgtcttaaat tttttacat atttgttgag gtataattta    4200
catatgataa aattcatttt aaatgtaaaa aa                                  4232
```

<210> SEQ ID NO 28
<211> LENGTH: 716
<212> TYPE: PRT
<213> ORGANISM: Homo sapiens

<400> SEQUENCE: 28

```
Met Phe Ser Leu Ser Ser Thr Val Gln Pro Gln Val Thr Val Pro Leu
1               5                   10                  15

Ser His Leu Ile Asn Ala Phe His Thr Pro Lys Asn Thr Ser Val Ser
            20                  25                  30

Leu Ser Gly Val Ser Val Ser Gln Asn Gln His Arg Asp Val Val Pro
        35                  40                  45

Glu His Glu Ala Pro Ser Ser Glu Pro Ser Leu Asn Leu Arg Asp Leu
```

```
                 50                  55                  60
Gly Leu Ser Glu Leu Lys Ile Gly Gln Ile Asp Gln Leu Val Glu Asn
 65                  70                  75                  80

Leu Leu Pro Gly Phe Cys Lys Gly Lys Asn Ile Ser Ser His Trp His
                 85                  90                  95

Thr Ser His Val Ser Ala Gln Ser Phe Phe Glu Asn Lys Tyr Gly Asn
                100                 105                 110

Leu Asp Ile Phe Ser Thr Leu Arg Ser Ser Cys Leu Tyr Arg His His
                115                 120                 125

Ser Arg Ala Leu Gln Ser Ile Cys Ser Asp Leu Gln Tyr Trp Pro Val
            130                 135                 140

Phe Ile Gln Ser Arg Gly Phe Lys Thr Leu Lys Ser Arg Thr Arg Arg
145                 150                 155                 160

Leu Gln Ser Thr Ser Glu Arg Leu Ala Glu Thr Gln Asn Ile Ala Pro
                165                 170                 175

Ser Phe Val Lys Gly Phe Leu Leu Arg Asp Arg Gly Ser Asp Val Glu
            180                 185                 190

Ser Leu Asp Lys Leu Met Lys Thr Lys Asn Ile Pro Glu Ala His Gln
            195                 200                 205

Asp Ala Phe Lys Thr Gly Phe Ala Glu Gly Phe Leu Lys Ala Gln Ala
210                 215                 220

Leu Thr Gln Lys Thr Asn Asp Ser Leu Arg Arg Thr Arg Leu Ile Leu
225                 230                 235                 240

Phe Val Leu Leu Leu Phe Gly Ile Tyr Gly Leu Leu Lys Asn Pro Phe
                245                 250                 255

Leu Ser Val Arg Phe Arg Thr Thr Thr Gly Leu Asp Ser Ala Val Asp
                260                 265                 270

Pro Val Gln Met Lys Asn Val Thr Phe Glu His Val Lys Gly Val Glu
                275                 280                 285

Glu Ala Lys Gln Glu Leu Gln Glu Val Val Glu Phe Leu Lys Asn Pro
            290                 295                 300

Gln Lys Phe Thr Ile Leu Gly Gly Lys Leu Pro Lys Gly Ile Leu Leu
305                 310                 315                 320

Val Gly Pro Pro Gly Thr Gly Lys Thr Leu Leu Ala Arg Ala Val Ala
                325                 330                 335

Gly Glu Ala Asp Val Pro Phe Tyr Tyr Ala Ser Gly Ser Glu Phe Asp
                340                 345                 350

Glu Met Phe Val Gly Val Gly Ala Ser Arg Ile Arg Asn Leu Phe Arg
            355                 360                 365

Glu Ala Lys Ala Asn Ala Pro Cys Val Ile Phe Ile Asp Glu Leu Asp
            370                 375                 380

Ser Val Gly Gly Lys Arg Ile Glu Ser Pro Met His Pro Tyr Ser Arg
385                 390                 395                 400

Gln Thr Ile Asn Gln Leu Leu Ala Glu Met Asp Gly Phe Lys Pro Asn
                405                 410                 415

Glu Gly Val Ile Ile Ile Gly Ala Thr Asn Phe Pro Glu Ala Leu Asp
                420                 425                 430

Asn Ala Leu Ile Arg Pro Gly Arg Phe Asp Met Gln Val Thr Val Pro
            435                 440                 445

Arg Pro Asp Val Lys Gly Arg Thr Glu Ile Leu Lys Trp Tyr Leu Asn
450                 455                 460

Lys Ile Lys Phe Asp Gln Ser Val Asp Pro Glu Ile Ile Ala Arg Gly
465                 470                 475                 480
```

Thr Val Gly Phe Ser Gly Ala Glu Leu Glu Asn Leu Val Asn Gln Ala
            485                 490                 495

Ala Leu Lys Ala Ala Val Asp Gly Lys Glu Met Val Thr Met Lys Glu
        500                 505                 510

Leu Glu Phe Ser Lys Asp Lys Ile Leu Met Gly Pro Glu Arg Arg Ser
        515                 520                 525

Val Glu Ile Asp Asn Lys Asn Lys Thr Ile Thr Ala Tyr His Glu Ser
    530                 535                 540

Gly His Ala Ile Ile Ala Tyr Tyr Thr Lys Asp Ala Met Pro Ile Asn
545                 550                 555                 560

Lys Ala Thr Ile Met Pro Arg Gly Pro Thr Leu Gly His Val Ser Leu
            565                 570                 575

Leu Pro Glu Asn Asp Arg Trp Asn Glu Thr Arg Ala Gln Leu Leu Ala
        580                 585                 590

Gln Met Asp Val Ser Met Gly Gly Arg Val Ala Glu Glu Leu Ile Phe
    595                 600                 605

Gly Thr Asp His Ile Thr Thr Gly Ala Ser Ser Asp Phe Asp Asn Ala
    610                 615                 620

Thr Lys Ile Ala Lys Arg Met Val Thr Lys Phe Gly Met Ser Glu Lys
625                 630                 635                 640

Leu Gly Val Met Thr Tyr Ser Asp Thr Gly Lys Leu Ser Pro Glu Thr
            645                 650                 655

Gln Ser Ala Ile Glu Gln Ile Arg Ile Leu Leu Arg Asp Ser Tyr
        660                 665                 670

Glu Arg Ala Lys His Ile Leu Lys Thr His Ala Lys Glu His Lys Asn
    675                 680                 685

Leu Ala Glu Ala Leu Leu Thr Tyr Glu Thr Leu Asp Ala Lys Glu Ile
    690                 695                 700

Gln Ile Val Leu Glu Gly Lys Lys Leu Glu Val Arg
705                 710                 715

<210> SEQ ID NO 29
<211> LENGTH: 4133
<212> TYPE: DNA
<213> ORGANISM: Homo sapiens

<400> SEQUENCE: 29
actgttgagt tagcgcctcg ccttccgggg cggattgtct gtcgttgcag tagctgtagg      60
aaggggaggc cattttccgt ttctgggagg agtgaggggc aacgggtcgg agaaaaagga     120 aaaagaagg gctcagcgcc tccccgccgg gccgtggaca gaggggcaca gtttcggcag     180
gcgggtgagg tcgctgaggg cccgccggag atgttttcct tgtcgagcac ggtgcaaccc     240
caggttacag ttcctctgag tcatctcatc aatgccttcc atacaccaaa aaacacttct     300
gtttctctca gtggagtgtc agtttctcaa aaccagcatc gagatgtagt tcctgagcat     360
gaggctccca gcagtgagcc ttcacttaac ttaagggacc ttggattatc tgaactaaaa     420
attggacaga ttgatcagct ggtagaaaat ctacttcctg gattttgtaa aggcaaaaac     480
atttcttccc attggcatac atcccatgtc tctgcacaat ccttctttga aaataaatat     540
gttttcatac agtctcgggg ttttaaaact ttgaaatcaa ggacacgacg tctccagtct     600
acctccgaga gattagctga acacagaat atagcgccat cattcgtgaa ggggtttctt     660
ttgcgggaca gaggatcaga tgttgagagt ttggacaaac tcatgaaaac caaaatata     720 cctgaagctc accaagatgc atttaaaact ggttttgcgg aaggttttct gaaagctcaa     780

```
gcactcacac aaaaaaccaa tgattccta aggcgaaccc gtctgattct cttcgttctg    840
ctgctattcg gcatttatgg acttctaaaa aacccatttt tatctgtccg cttccggaca    900
acaacagggc ttgattctgc agtagatcct gtccagatga aaaatgtcac ctttgaacat    960
gttaaagggg tggaggaagc taaacaagaa ttacaggaag ttgttgaatt cttgaaaaat   1020
ccacaaaaat ttactattct tggaggtaaa cttccaaaag gaattctttt agttggaccc   1080
ccagggactg gaaagacact tcttgcccga gctgtggcgg gagaagctga tgttcctttt   1140
tattatgctt ctggatccga atttgatgag atgtttgtgg gtgtgggagc cagccgtatc   1200
agaaatcttt ttagggaagc aaaggcgaat gctccttgtg ttatatttat tgatgaatta   1260
gattctgttg gtgggaagag aattgaatct ccaatgcatc catattcaag gcagaccata   1320
aatcaacttc ttgctgaaat ggatggtttt aaacccaatg aaggagttat cataatagga   1380
gccacaaact tcccagaggc attagataat gccttaatac gtcctggtcg ttttgacatg   1440
caagttacag ttccaaggcc agatgtaaaa ggtcgaacag aaattttgaa atggtatctc   1500
aataaaataa agtttgatca atccgttgat ccagaaatta tagctcgagg tactgttggc   1560
ttttccggag cagagttgga gaatcttgtg aaccaggctg cattaaaagc agctgttgat   1620
ggaaaagaaa tggttaccat gaaggagctg gagttttcca aagacaaaat tctaatgggg   1680
cctgaaagaa gaagtgtgga aattgataac aaaaacaaaa ccatcacagc atatcatgaa   1740
tctggtcatg ccattattgc atattacaca aaagatgcaa tgcctatcaa caaagctaca   1800
atcatgccac gggggccaac acttggacat gtgtccctgt tacctgagaa tgacagatgg   1860
aatgaaacta gagcccagct gcttgcacaa atggatgtta tatgggagg aagagtggca   1920 gaggagctta tatttggaac cgaccatatt acaacaggtg cttccagtga ttttgataat   1980
gccactaaaa tagcaaagcg gatggttacc aaatttggaa tgagtgaaaa gcttggagtt   2040
atgacctaca gtgatacagg gaaactaagt ccagaacccc aatctgccat cgaacaagaa   2100
ataagaatcc ttctaaggga ctcatatgaa cgagcaaaac atatcttgaa aactcatgca   2160
aaggagcata gaatctcgc agaagcttta ttgacctatg agactttgga tgccaaagag   2220
attcaaattg ttcttgaggg gaaaaagttg gaagtgagat gataactctc ttgatatgga   2280
tgcttgctgg ttttattgca agaatacaag tagcattgca gtagtctact tttacaacgc   2340
tttcccctca ttcttgatgt ggtgtaattg aagggtgtga aatgctttgt caatcatttg   2400
tcacatttat ccagtttggg ttattctcat tatgacacct attgcaaatt agcatcccat   2460
ggcaaatata ttttgaaaaa ataaagaact atcaggattg aaaacagctc ttttgaggaa   2520
tgtcaattag ttattaagtt gaaagtaatt aatgatttta tgtttggtta ctctactaga   2580
tttgataaaa attgtgcctt tagccttcta tatacatcag tggaaactta agatgcagta   2640
attatgttcc agattgacca tgaataaaat attttttaat ctaaatgtag agaagttggg   2700
attaaaagca gtctcggaaa cacagagcca ggaatatagc cttttggcat ggtgccatgg   2760
ctcacatctg taatcccagc acttttggag gctgaggcgg gtggattgct tgaggccagg   2820
agttcgagac cagcctggcc aacgtggtga acgctgtct ctactaaaat acaaaaaaat   2880
agggctgggc gcggttgctc acgcctgtaa tcccagcact tttcagaggc caaggcgggc   2940
aaatcacctg aggtcaagag tttgagacca gcctggccaa catggtgaaa ccccatctct   3000
actaaacatg caaaaattac ctgggcatgg tggcaggtgc ttataatccc agctactctg   3060
ggggccaagg caggagaatt gcttgagcct gggagatgga ggttgcagtg agctgagatc   3120
```

```
atgccactgc actccagcct gggcaacaga gcaagactct gcctcaaaaa aaaattaaaa      3180
taaatttaaa tacaaaaaaa aatagccagg tgtggggtgc atgcctggaa tcccagctac      3240
ttgagaggct gaggcacgag aattgcttga acccaggagg tggaggttgc agtgagccaa      3300
gatcacagga gccactgcac tccagcctgg gtgacagagt gagactctgt ctcaaaaaaa      3360
aattaaataa attattataa cctttcagaa atgctgtgtg cattttcatg ttcttttttt      3420
tagcattact gtcactctcc ctaatgaaat gtacttcaga gaagcagtat tttgttaaat      3480
aaatacataa cctcattctg aataatgtcc ctcattttga ctataactgt gcttggtttc      3540
aaaagcaaaa ttaaacaaaa atctcagtcc cctccgaagt gaactttgtg ttaccctgcg      3600
tcagaaatgc caagttgtgt ttactttca ttcagatttt gtgaatatga acatgctgtt      3660
ataggatcta cagatgaata tttaactcaa tagaaaaatt attttagaac acattgtatt      3720
ggtattacaa ccagattata ttcttgacgt tgacttcatt aaaattatct acaatttcct      3780
aataatttaa gctgtatatg gtcttcattg aaaaagata gatattgtta caggaagctt      3840
gttacattat attcttgacc ttttggttga taatcttaaa tcttaatgta atttcaaact      3900
ggcagaaatg ttgccagcat aatacatgga tgtctcatat accctgcatc cagatttacc      3960
agttgttatc attctgcccg tttttattg ccccaaacct gttctgtctc cctctctgta      4020
tgtacataca tacacgtata aaatattgat aaagtcttat ctgtcttaaa ttttttaca      4080 tatttgttga ggtataattt acatgata aaattcattt taaatgtaaa aaa              4133
```

<210> SEQ ID NO 30
<211> LENGTH: 683
<212> TYPE: PRT
<213> ORGANISM: Homo sapiens

<400> SEQUENCE: 30

```
Met Phe Ser Leu Ser Ser Thr Val Gln Pro Gln Val Thr Val Pro Leu
1               5                   10                  15

Ser His Leu Ile Asn Ala Phe His Thr Pro Lys Asn Thr Ser Val Ser
            20                  25                  30

Leu Ser Gly Val Ser Val Ser Gln Asn Gln His Arg Asp Val Val Pro
        35                  40                  45

Glu His Glu Ala Pro Ser Ser Glu Pro Ser Leu Asn Leu Arg Asp Leu
    50                  55                  60

Gly Leu Ser Glu Leu Lys Ile Gly Gln Ile Asp Gln Leu Val Glu Asn
65                  70                  75                  80

Leu Leu Pro Gly Phe Cys Lys Gly Lys Asn Ile Ser Ser His Trp His
                85                  90                  95

Thr Ser His Val Ser Ala Gln Ser Phe Phe Glu Asn Lys Tyr Val Phe
            100                 105                 110

Ile Gln Ser Arg Gly Phe Lys Thr Leu Lys Ser Arg Thr Arg Arg Leu
        115                 120                 125

Gln Ser Thr Ser Glu Arg Leu Ala Glu Thr Gln Asn Ile Ala Pro Ser
    130                 135                 140

Phe Val Lys Gly Phe Leu Leu Arg Asp Arg Gly Ser Asp Val Glu Ser
145                 150                 155                 160

Leu Asp Lys Leu Met Lys Thr Lys Asn Ile Pro Glu Ala His Gln Asp
                165                 170                 175

Ala Phe Lys Thr Gly Phe Ala Glu Gly Phe Leu Lys Ala Gln Ala Leu
            180                 185                 190

Thr Gln Lys Thr Asn Asp Ser Leu Arg Arg Thr Arg Leu Ile Leu Phe
```

```
                195                 200                 205
Val Leu Leu Leu Phe Gly Ile Tyr Gly Leu Leu Lys Asn Pro Phe Leu
    210                 215                 220

Ser Val Arg Phe Arg Thr Thr Thr Gly Leu Asp Ser Ala Val Asp Pro
225                 230                 235                 240

Val Gln Met Lys Asn Val Thr Phe Glu His Val Lys Gly Val Glu Glu
                245                 250                 255

Ala Lys Gln Glu Leu Gln Glu Val Val Glu Phe Leu Lys Asn Pro Gln
            260                 265                 270

Lys Phe Thr Ile Leu Gly Gly Lys Leu Pro Lys Gly Ile Leu Leu Val
        275                 280                 285

Gly Pro Pro Gly Thr Gly Lys Thr Leu Leu Ala Arg Ala Val Ala Gly
    290                 295                 300

Glu Ala Asp Val Pro Phe Tyr Tyr Ala Ser Gly Ser Glu Phe Asp Glu
305                 310                 315                 320

Met Phe Val Gly Val Gly Ala Ser Arg Ile Arg Asn Leu Phe Arg Glu
                325                 330                 335

Ala Lys Ala Asn Ala Pro Cys Val Ile Phe Ile Asp Glu Leu Asp Ser
            340                 345                 350

Val Gly Gly Lys Arg Ile Glu Ser Pro Met His Pro Tyr Ser Arg Gln
        355                 360                 365

Thr Ile Asn Gln Leu Leu Ala Glu Met Asp Gly Phe Lys Pro Asn Glu
    370                 375                 380

Gly Val Ile Ile Ile Gly Ala Thr Asn Phe Pro Glu Ala Leu Asp Asn
385                 390                 395                 400

Ala Leu Ile Arg Pro Gly Arg Phe Asp Met Gln Val Thr Val Pro Arg
                405                 410                 415

Pro Asp Val Lys Gly Arg Thr Glu Ile Leu Lys Trp Tyr Leu Asn Lys
            420                 425                 430

Ile Lys Phe Asp Gln Ser Val Asp Pro Glu Ile Ile Ala Arg Gly Thr
        435                 440                 445

Val Gly Phe Ser Gly Ala Glu Leu Glu Asn Leu Val Asn Gln Ala Ala
    450                 455                 460

Leu Lys Ala Ala Val Asp Gly Lys Glu Met Val Thr Met Lys Glu Leu
465                 470                 475                 480

Glu Phe Ser Lys Asp Lys Ile Leu Met Gly Pro Glu Arg Arg Ser Val
                485                 490                 495

Glu Ile Asp Asn Lys Asn Lys Thr Ile Thr Ala Tyr His Glu Ser Gly
            500                 505                 510

His Ala Ile Ile Ala Tyr Tyr Thr Lys Asp Ala Met Pro Ile Asn Lys
        515                 520                 525

Ala Thr Ile Met Pro Arg Gly Pro Thr Leu Gly His Val Ser Leu Leu
    530                 535                 540

Pro Glu Asn Asp Arg Trp Asn Glu Thr Arg Ala Gln Leu Leu Ala Gln
545                 550                 555                 560

Met Asp Val Ser Met Gly Gly Arg Val Ala Glu Leu Ile Phe Gly
                565                 570                 575

Thr Asp His Ile Thr Thr Gly Ala Ser Ser Asp Phe Asn Ala Thr
            580                 585                 590

Lys Ile Ala Lys Arg Met Val Thr Lys Phe Gly Met Ser Glu Lys Leu
        595                 600                 605

Gly Val Met Thr Tyr Ser Asp Thr Gly Lys Leu Ser Pro Glu Thr Gln
    610                 615                 620
```

Ser Ala Ile Glu Gln Glu Ile Arg Ile Leu Leu Arg Asp Ser Tyr Glu
625                 630                 635                 640

Arg Ala Lys His Ile Leu Lys Thr His Ala Lys Glu His Lys Asn Leu
        645                 650                 655

Ala Glu Ala Leu Leu Thr Tyr Glu Thr Leu Asp Ala Lys Glu Ile Gln
            660                 665                 670

Ile Val Leu Glu Gly Lys Lys Leu Glu Val Arg
            675                 680

<210> SEQ ID NO 31
<211> LENGTH: 1919
<212> TYPE: DNA
<213> ORGANISM: Homo sapiens

<400> SEQUENCE: 31

| | |
|---|---|
| atgtggaggt cagagtggaa gcaggtgaga atggagggg cggcaaaggc tcgtttctgg | 60 |
| gcatctctgc agtcctcctc tgctccatga tgtgcacttt gggcgaggag agtgcgtgcg | 120 |
| tgtgagaggg tccagcagaa ggaaacatgg ctgccaaagt gtttgagtcc attggcaagt | 180 |
| ttggcctggc cttagctgtt gcaggaggcg tggtgaactc tgccttatat aatgtggatg | 240 |
| ctgggcacag agctgtcatc tttgaccgat ccgtggagt gcaggacatt gtggtagggg | 300 |
| aagggactca ttttctcatc ccgtgggtac agaaaccaat tatctttgac tgccgttctc | 360 |
| gaccacgtaa tgtgccagtc atcactggta gcaaagattt acagaatgtc aacatcacac | 420 |
| tgcgcatcct cttccggcct gtcgccagcc agcttcctcg catcttcacc agcatcggag | 480 |
| aggactatga tgagcgtgtg ctgccgtcca tcacaactga tcctcaag tcagtggtgg | 540 |
| ctcgctttga tgctggagaa ctaatcaccc agagagagct ggtctccagg caggtgagcg | 600 |
| acgaccttac agagcgagcc gccacctttg ggctcatcct ggatgacgtg tccttgacac | 660 |
| atctgacctt cgggaaggag ttcacagaag cggtggaagc caaacaggtg gctcagcagg | 720 |
| aagcagagag ggccagattt gtggtggaaa aggctgagca acagaaaaag gcggccatca | 780 |
| tctctgctga gggcgactcc aaggcagctg agctgattgc caactcactg gccactgcag | 840 |
| gggatggcct gatcgagctg cgcaagctgg aagctgcaga ggacatcgcg taccagctct | 900 |
| cacgctctcg gaacatcacc tacctgccag cggggcagtc cgtgctcctc cagctgcccc | 960 |
| agtgagggcc caccctgcct gcacctccgc gggctgactg ggccacagcc ccgatgattc | 1020 |
| ttaacacagc cttccttctg ctcccacccc agaaatcact gtgaaatttc atgattggct | 1080 |
| taaagtgaag gaaataaagg taaaatcact tcagatctct aattagtcta tcaaatgaaa | 1140 |
| ctctttcatt cttctcacat ccatctactt ttttatccac ctccctacca aaaattgcca | 1200 |
| agtgcctatg caaaccagct ttaggtccca attcggggcc tgctggagtt ccggcctggg | 1260 |
| caccagcatt tggcagcacg caggcggggc agtatgtgat ggactgggga gcacaggtgt | 1320 |
| ctgcctagat ccacgtgtgg cctccgtcct gtcactgatg gaaggtttgc ggatgagggc | 1380 |
| atgtgcggct gaactgagaa ggcaggcctc cgtcttccca gcggttcctg tgcagatgct | 1440 |
| gctgaagaga ggtgccgggg aggggcagag aggaagtggt ctgtctgtta ccataagtct | 1500 |
| gattctcttt aactgtgtga ccagcggaaa caggtgtgtg tgaactgggc acagattgaa | 1560 |
| gaatctgccc ctgttgaggt gggtgggcct gactgttgcc ccccagggtc ctaaaacttg | 1620 |
| gatggacttg tatagtgaga gaggaggcct ggaccgagat gtgagtcctg ttgaagactt | 1680 |
| cctctctacc ccccaccttg gtccctctca gatacccagt ggaattccaa cttgaaggat | 1740 |

```
tgcatcctgc tggggctgaa catgcctgcc aaagacgtgt ccgacctacg ttcctggccc   1800
cctcgttcag agactgccct tctcacgggc tctatgcctg cactgggaag gaaacaaatg   1860
tgtataaact gctgtcaata aatgacaccc agaccttccg gctcagccaa aaaaaaaaa    1919
```

<210> SEQ ID NO 32
<211> LENGTH: 272
<212> TYPE: PRT
<213> ORGANISM: Homo sapiens

<400> SEQUENCE: 32

```
Met Ala Ala Lys Val Phe Glu Ser Ile Gly Lys Phe Gly Leu Ala Leu
1               5                   10                  15

Ala Val Ala Gly Gly Val Val Asn Ser Ala Leu Tyr Asn Val Asp Ala
            20                  25                  30

Gly His Arg Ala Val Ile Phe Asp Arg Phe Arg Gly Val Gln Asp Ile
        35                  40                  45

Val Val Gly Glu Gly Thr His Phe Leu Ile Pro Trp Val Gln Lys Pro
    50                  55                  60

Ile Ile Phe Asp Cys Arg Ser Arg Pro Arg Asn Val Pro Val Ile Thr
65                  70                  75                  80

Gly Ser Lys Asp Leu Gln Asn Val Asn Ile Thr Leu Arg Ile Leu Phe
                85                  90                  95

Arg Pro Val Ala Ser Gln Leu Pro Arg Ile Phe Thr Ser Ile Gly Glu
            100                 105                 110

Asp Tyr Asp Glu Arg Val Leu Pro Ser Ile Thr Thr Glu Ile Leu Lys
        115                 120                 125

Ser Val Val Ala Arg Phe Asp Ala Gly Glu Leu Ile Thr Gln Arg Glu
    130                 135                 140

Leu Val Ser Arg Gln Val Ser Asp Leu Thr Glu Arg Ala Ala Thr
145                 150                 155                 160

Phe Gly Leu Ile Leu Asp Asp Val Ser Leu Thr His Leu Thr Phe Gly
                165                 170                 175

Lys Glu Phe Thr Glu Ala Val Glu Ala Lys Gln Val Ala Gln Gln Glu
            180                 185                 190

Ala Glu Arg Ala Arg Phe Val Val Glu Lys Ala Glu Gln Gln Lys Lys
        195                 200                 205

Ala Ala Ile Ile Ser Ala Glu Gly Asp Ser Lys Ala Ala Glu Leu Ile
    210                 215                 220

Ala Asn Ser Leu Ala Thr Ala Gly Asp Gly Leu Ile Glu Leu Arg Lys
225                 230                 235                 240

Leu Glu Ala Ala Glu Asp Ile Ala Tyr Gln Leu Ser Arg Ser Arg Asn
                245                 250                 255

Ile Thr Tyr Leu Pro Ala Gly Gln Ser Val Leu Leu Gln Leu Pro Gln
            260                 265                 270
```

<210> SEQ ID NO 33
<211> LENGTH: 1520
<212> TYPE: DNA
<213> ORGANISM: Homo sapiens

<400> SEQUENCE: 33

```
gggcgggca gaggagctca tgcgcagtat gtgtggttgg ggaattcatg tggaggtcag    60
agtggaagca ggtgtgagag ggtccagcag aaggaaacat ggctgccaaa gtgtttgagt   120
ccattggcaa gtttggcctg gccttagctg ttgcaggagg cgtggtgaac tctgccttat   180
```

```
ataatgtgga tgctgggcac agagctgtca tctttgaccg attccgtgga gtgcaggaca        240
ttgtggtagg ggaagggact cattttctca tcccgtgggt acagaaacca attatctttg        300
actgccgttc tcgaccacgt aatgtgccag tcatcactgg tagcaaagat ttacagaatg        360
tcaacatcac actgcgcatc ctcttccggc ctgtcgccag ccagcttcct cgcatcttca        420
ccagcatcgg agaggactat gatgagcgtg tgctgccgtc catcacaact gagatcctca        480
agtcagtggt ggctcgcttt gatgctggag aactaatcac ctacctgcca gcggggcagt        540
ccgtgctcct ccagctgccc cagtgagggc ccaccctgcc tgcacctccg cgggctgact        600
gggccacagc cccgatgatt cttaacacag ccttccttct gctcccaccc cagaaatcac        660
tgtgaaattt catgattggc ttaaagtgaa ggaaataaag gtaaaatcac ttcagatctc        720
taattagtct atcaaatgaa actctttcat tcttctcaca tccatctact tttttatcca        780
cctccctacc aaaaattgcc aagtgcctat gcaaaccagc tttaggtccc aattcggggc        840
ctgctggagt tccggcctgg gcaccagcat ttggcagcac gcaggcgggg cagtatgtga        900
tggactgggg agcacaggtg tctgcctaga tccacgtgtg gcctccgtcc tgtcactgat        960
ggaaggtttg cggatgaggg catgtgcggc tgaactgaga aggcaggcct ccgtcttccc       1020
agcggttcct gtgcagatgc tgctgaagag aggtgccggg gaggggcaga gaggaagtgg       1080
tctgtctgtt accataagtc tgattctctt taactgtgtg accagcggaa acaggtgtgt       1140
gtgaactggg cacagattga agaatctgcc cctgttgagg tgggtgggcc tgactgttgc       1200
cccccagggt cctaaaactt ggatggactt gtatagtgag agaggaggcc tggaccgaga       1260
tgtgagtcct gttgaagact tcctctctac cccccacctt ggtccctctc agatacccag       1320
tggaattcca acttgaagga ttgcatcctg ctggggctga acatgcctgc caaagacgtg       1380
tccgacctac gttcctggcc ccctcgttca gagactgccc ttctcacggg ctctatgcct       1440
gcactgggaa ggaaacaaat gtgtataaac tgctgtcaat aaatgacacc cagaccttcc       1500
ggctcagcca aaaaaaaaaa                                                   1520
```

<210> SEQ ID NO 34
<211> LENGTH: 155
<212> TYPE: PRT
<213> ORGANISM: Homo sapiens

<400> SEQUENCE: 34

```
Met Ala Ala Lys Val Phe Glu Ser Ile Gly Lys Phe Gly Leu Ala Leu
1               5                   10                  15

Ala Val Ala Gly Gly Val Val Asn Ser Ala Leu Tyr Asn Val Asp Ala
            20                  25                  30

Gly His Arg Ala Val Ile Phe Asp Arg Phe Arg Gly Val Gln Asp Ile
        35                  40                  45

Val Val Gly Glu Gly Thr His Phe Leu Ile Pro Trp Val Gln Lys Pro
    50                  55                  60

Ile Ile Phe Asp Cys Arg Ser Arg Pro Arg Asn Val Pro Val Ile Thr
65                  70                  75                  80

Gly Ser Lys Asp Leu Gln Asn Val Asn Ile Thr Leu Arg Ile Leu Phe
                85                  90                  95

Arg Pro Val Ala Ser Gln Leu Pro Arg Ile Phe Thr Ser Ile Gly Glu
            100                 105                 110

Asp Tyr Asp Glu Arg Val Leu Pro Ser Ile Thr Thr Glu Ile Leu Lys
        115                 120                 125

Ser Val Val Ala Arg Phe Asp Ala Gly Glu Leu Ile Thr Tyr Leu Pro
```

Ala Gly Gln Ser Val Leu Leu Gln Leu Pro Gln
145                 150                 155

<210> SEQ ID NO 35
<211> LENGTH: 1457
<212> TYPE: DNA
<213> ORGANISM: Homo sapiens

<400> SEQUENCE: 35

| | | | | | |
|---|---|---|---|---|---|
| tccgtatgcg | cgattcctgt | gcgcgaagtt | cgggtccgta | gtgggctaag | ggggagggtt | 60 |
| tcaaagggag | cgcacttccg | ctgcccttc | tttcgccagc | cttacgggcc | cgaaccctcg | 120 |
| tgtgaagggt | gcagtaccta | agccggagcg | gggtagaggc | gggccggcac | ccccttctga | 180 |
| cctccagtgc | cgccggcctc | aagatcagac | atggcccaga | acttgaagga | cttggcggga | 240 |
| cggctgcccg | ccgggccccg | gggcatgggc | acggccctga | agctgttgct | ggggccggc | 300 |
| gccgtggcct | acggtgtgcg | cgaatctgtg | ttcaccgtgg | aaggcgggca | cagagccatc | 360 |
| ttcttcaatc | ggatcggtgg | agtgcagcag | gacactatcc | tggccgaggg | ccttcacttc | 420 |
| aggatccctt | ggttccagta | ccccattatc | tatgacattc | gggccagacc | tcgaaaaatc | 480 |
| tcctcccta | caggctccaa | agacctacag | atggtgaata | tctccctgcg | agtgttgtct | 540 |
| cgacccaatg | ctcaggagct | tcctagcatg | taccagcgcc | tagggctgga | ctacgaggaa | 600 |
| cgagtgttgc | cgtccattgt | caacgaggtg | ctcaagagtg | tggtggccaa | gttcaatgcc | 660 |
| tcacagctga | tcacccagcg | ggcccaggta | tccctgttga | tccgccggga | gctgacagag | 720 |
| agggccaagg | acttcagcct | catcctggat | gatgtggcca | tcacagagct | gagctttagc | 780 |
| cgagagtaca | cagctgctgt | agaagccaaa | caagtggccc | agcaggaggc | ccagcgggcc | 840 |
| caattcttgg | tagaaaaagc | aaagcaggaa | cagcggcaga | aaattgtgca | ggccgagggt | 900 |
| gaggccgagg | ctgccaagat | gcttggagaa | gcactgagca | agaaccctgg | ctacatcaaa | 960 |
| cttcgcaaga | ttcgagcagc | ccagaatatc | tccaagacga | tcgccacatc | acagaatcgt | 1020 |
| atctatctca | cagctgacaa | ccttgtgctg | aacctacagg | atgaaagttt | caccaggga | 1080 |
| agtgacagcc | tcatcaaggg | taagaaatga | gcctagtcac | caagaactcc | accccagag | 1140 |
| gaagtggatc | tgcttctcca | gttttttgagg | agccagccag | gggtccagca | cagccctacc | 1200 |
| ccgcccagt | atcatgcgat | ggtccccac | accggttccc | tgaaccctc | ttggattaag | 1260 |
| gaagactgaa | gactagcccc | ttttctgggg | aattactttc | ctcctccctg | tgttaactgg | 1320 |
| ggctgttggg | gacagtgcgt | gatttctcag | tgatttccta | cagtgttgtt | ccctccctca | 1380 |
| aggctgggag | gagataaaca | ccaacccagg | aattctcaat | aaattttat | tacttaacct | 1440 |
| gaaaaaaaaa | aaaaaaa | | | | | 1457 |

<210> SEQ ID NO 36
<211> LENGTH: 299
<212> TYPE: PRT
<213> ORGANISM: Homo sapiens

<400> SEQUENCE: 36

Met Ala Gln Asn Leu Lys Asp Leu Ala Gly Arg Leu Pro Ala Gly Pro
1               5                   10                  15

Arg Gly Met Gly Thr Ala Leu Lys Leu Leu Gly Ala Gly Ala Val
            20                  25                  30

Ala Tyr Gly Val Arg Glu Ser Val Phe Thr Val Glu Gly Gly His Arg
        35                  40                  45

```
Ala Ile Phe Phe Asn Arg Ile Gly Gly Val Gln Gln Asp Thr Ile Leu
    50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Ser Ser Pro Thr Gly Ser
                85                  90                  95

Lys Asp Leu Gln Met Val Asn Ile Ser Leu Arg Val Leu Ser Arg Pro
            100                 105                 110

Asn Ala Gln Glu Leu Pro Ser Met Tyr Gln Arg Leu Gly Leu Asp Tyr
        115                 120                 125

Glu Glu Arg Val Leu Pro Ser Ile Val Asn Val Leu Lys Ser Val
130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
            180                 185                 190

Tyr Thr Ala Ala Val Glu Ala Lys Gln Val Ala Gln Gln Ala Gln
        195                 200                 205

Arg Ala Gln Phe Leu Val Glu Lys Ala Lys Gln Glu Gln Arg Gln Lys
210                 215                 220

Ile Val Gln Ala Glu Gly Glu Ala Glu Ala Lys Met Leu Gly Glu
225                 230                 235                 240

Ala Leu Ser Lys Asn Pro Gly Tyr Ile Lys Leu Arg Lys Ile Arg Ala
                245                 250                 255

Ala Gln Asn Ile Ser Lys Thr Ile Ala Thr Ser Gln Asn Arg Ile Tyr
            260                 265                 270

Leu Thr Ala Asp Asn Leu Val Leu Asn Leu Gln Asp Glu Ser Phe Thr
        275                 280                 285

Arg Gly Ser Asp Ser Leu Ile Lys Gly Lys Lys
    290                 295
```

<210> SEQ ID NO 37
<211> LENGTH: 1343
<212> TYPE: DNA
<213> ORGANISM: Homo sapiens

<400> SEQUENCE: 37

```
tccgtatgcg cgattcctgt gcgcgaagtt cgggtccgta gtgggctaag ggggagggtt      60
tcaaagggag cgcacttccg ctgccctttc tttcgccagc cttacgggcc cgaaccctcg     120
tgtgaagggt gcagtaccta agccggagcg gggtagaggc gggccggcac ccccttctga     180
cctccagtgc cgccggcctc aagatcagac atggcccaga acttgaagga cttggcggga     240
cggctgcccg ccgggccccg gggcatgggc acgccctga gctgttgct ggggccggc       300 gccgtggcct acggtgtgcg cgaatctgtg ttcaccgtgg aaggcgggca cagagccatc     360
ttcttcaatc ggatcggtgg agtgcagcag gacactatcc tggccgaggg ccttcacttc     420
aggatcccct tggttccagta cccccattatc tatgacattc gggccagacc tcgaaaaatc     480
tcctccccta caggctccaa agacctacag atggtgaata tctccctgcg agtgttgtct     540
cgacccaatg ctcaggagct tcctagcatg taccagcgcc tagggctgga ctacgaggaa     600
cgagtgttgc cgtccattgt caacgaggtg ctcaagagtg tggtggccaa gttcaatgcc     660
```

```
tcacagctga tcacccagcg ggcccaggta tccctgttga tccgccggga gctgacagag    720
agggccaagg acttcagcct catcctggat gatgtggcca tcacagagct gagctttagc    780
cgagagtaca cagctgctgt agaagccaaa caagtggcac tgagcaagaa ccctggctac    840
atcaaacttc gcaagattcg agcagcccag aatatctcca agacgatcgc acatcacag    900 aatcgtatct atctcacagc tgacaacctt gtgctgaacc tacaggatga agtttcacc    960 aggggaagtg acagcctcat caagggtaag aaatgagcct agtcaccaag aactccaccc   1020
ccagaggaag tggatctgct tctccagttt ttgaggagcc agccaggggt ccagcacagc   1080
cctaccccgc cccagtatca tgcgatggtc ccccacaccg gttccctgaa cccctcttgg   1140
attaaggaag actgaagact agccccttt ctggggaatt actttcctcc tccctgtgtt   1200
aactggggct gttggggaca gtgcgtgatt tctcagtgat ttcctacagt gttgttccct   1260
ccctcaaggc tgggaggaga taaacaccaa cccaggaatt ctcaataaat ttttattact   1320
taacctgaaa aaaaaaaaaa aaa                                           1343
```

<210> SEQ ID NO 38
<211> LENGTH: 261
<212> TYPE: PRT
<213> ORGANISM: Homo sapiens

<400> SEQUENCE: 38

```
Met Ala Gln Asn Leu Lys Asp Leu Ala Gly Arg Leu Pro Ala Gly Pro
1               5                   10                  15

Arg Gly Met Gly Thr Ala Leu Lys Leu Leu Gly Ala Gly Ala Val
            20                  25                  30

Ala Tyr Gly Val Arg Glu Ser Val Phe Thr Val Glu Gly Gly His Arg
        35                  40                  45

Ala Ile Phe Phe Asn Arg Ile Gly Gly Val Gln Gln Asp Thr Ile Leu
    50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Ser Ser Pro Thr Gly Ser
                85                  90                  95

Lys Asp Leu Gln Met Val Asn Ile Ser Leu Arg Val Leu Ser Arg Pro
            100                 105                 110

Asn Ala Gln Glu Leu Pro Ser Met Tyr Gln Arg Leu Gly Leu Asp Tyr
        115                 120                 125

Glu Glu Arg Val Leu Pro Ser Ile Val Asn Glu Val Leu Lys Ser Val
    130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
            180                 185                 190

Tyr Thr Ala Ala Val Glu Ala Lys Gln Val Ala Leu Ser Lys Asn Pro
        195                 200                 205

Gly Tyr Ile Lys Leu Arg Lys Ile Arg Ala Ala Gln Asn Ile Ser Lys
    210                 215                 220

Thr Ile Ala Thr Ser Gln Asn Arg Ile Tyr Leu Thr Ala Asp Asn Leu
225                 230                 235                 240

Val Leu Asn Leu Gln Asp Glu Ser Phe Thr Arg Gly Ser Asp Ser Leu
                245                 250                 255
```

Ile Lys Gly Lys Lys
        260

<210> SEQ ID NO 39
<211> LENGTH: 1773
<212> TYPE: DNA
<213> ORGANISM: Homo sapiens

<400> SEQUENCE: 39

| | | | | | |
|---|---|---|---|---|---|
| aatgagcgaa | ggcatcgcga | gccagggggc | gcggagaagg | cggggaatca | tggccgcccc | 60 |
| cagtgttccg | cgtccggggg | tttgtgggag | ttgccttgac | ctgcagctcc | gccaccgcgg | 120 |
| acccgccttc | tgccctcagc | agcagacgct | ctgtcccgcc | cgggcagctc | tgcgaggcag | 180 |
| cggctggaga | gggaaccatg | gggactgtgc | acgcccggag | tttggagcct | cttccatcaa | 240 |
| gtggacctga | ttttggagga | ttaggagaag | aagctgaatt | tgttgaagtt | gagcctgaag | 300 |
| ctaaacagga | aattcttgaa | aacaaagatg | tggttgttca | acatgttcat | tttgatggac | 360 |
| ttggaaggac | taaagatgat | atcatcattt | gtgaaattgg | agatgttttc | aaggccaaaa | 420 |
| acctaattga | ggtaatgcgg | aaatctcatg | aagcccgtga | aaaattgctc | cgtcttggaa | 480 |
| tttttagaca | agtggatgtt | ttgattgaca | catgtcaagg | tgatgacgca | cttccaaatg | 540 |
| ggttagacgt | tacctttgaa | gtaactgaat | tgaggagatt | aacgggcagt | tataacacca | 600 |
| tggttggaaa | caatgaaggc | agtatggtac | ttggcctcaa | gcttcctaat | cttcttggtc | 660 |
| gtgcagaaaa | ggtgaccttt | cagttttcct | atggaacaaa | agaaacttcg | tatggcctgt | 720 |
| ccttcttcaa | accacggccc | ggaaacttcg | aaagaaattt | ctctgtaaac | ttatataaag | 780 |
| ttactggaca | gttcccttgg | agctcactgc | gggagacgga | cagaggaatg | tcagctgagt | 840 |
| acagttttcc | catatggaag | accagccaca | ctgtcaagtg | ggaaggcgta | tggcgagaac | 900 |
| tgggctgcct | ctcaaggacg | gcgtcatttg | ctgttcgaaa | agaaagcgga | cattcactga | 960 |
| aatcatctct | ttcgcacgcc | atggtcatcg | attctcggaa | tcttccatc | ttaccaagga | 1020 |
| gaggtgcttt | gctgaaagtt | aaccaggaac | tggcaggcta | cactggcggg | gatgtgagct | 1080 |
| tcatcaaaga | agattttgaa | cttcagttga | acaagcaact | catatttgat | tcagtttttt | 1140 |
| cagcgtctt | ctggggcgga | atgttggtac | ccattggtga | taagccgtca | agcattgctg | 1200 |
| ataggtttta | ccttggggga | cccacaagca | tccgcggatt | cagcatgcac | agcatcgggc | 1260 |
| cacagagcga | aggagactac | ctaggtggag | aagcgtactg | ggccggcggc | ctgcacctct | 1320 |
| acaccccatt | acctttccgg | ccaggccagg | gtggctttgg | agaacttttc | cgaacacact | 1380 |
| tctttctcaa | cgcaggaaac | ctctgcaacc | tcaactatgg | ggagggcccc | aaagctcata | 1440 |
| ttcgtaagct | ggctgagtgc | atccgctggt | cgtacgggc | cgggattgtc | ctcaggcttg | 1500 |
| gcaacatcgc | tcggttggaa | cttaattact | gcgtccccat | gggagtacag | acaggcgaca | 1560 |
| ggatatgtga | tggcgtccag | tttggagctg | ggataaggtt | cctgtagccg | acaccctac | 1620 |
| aggagaagct | ctgggactgg | ggcagcagca | aggcgcccat | gccacacacc | gtctctcgag | 1680 |
| gaaacgcggt | tcagcgattc | tttgactgcg | gaccctgtgg | gaaacccccgt | caataaatgt | 1740 |
| taaagacaca | ctccgaaaaa | aaaaaaaaaa | aaa | | | 1773 |

<210> SEQ ID NO 40
<211> LENGTH: 469
<212> TYPE: PRT
<213> ORGANISM: Homo sapiens

<400> SEQUENCE: 40

```
Met Gly Thr Val His Ala Arg Ser Leu Glu Pro Leu Pro Ser Ser Gly
1               5                   10                  15

Pro Asp Phe Gly Gly Leu Gly Glu Glu Ala Glu Phe Val Glu Val Glu
            20                  25                  30

Pro Glu Ala Lys Gln Glu Ile Leu Glu Asn Lys Asp Val Val Val Gln
            35                  40                  45

His Val His Phe Asp Gly Leu Gly Arg Thr Lys Asp Ile Ile Ile
    50                  55                  60

Cys Glu Ile Gly Asp Val Phe Lys Ala Lys Asn Leu Ile Glu Val Met
65                  70                  75                  80

Arg Lys Ser His Glu Ala Arg Glu Lys Leu Leu Arg Leu Gly Ile Phe
                85                  90                  95

Arg Gln Val Asp Val Leu Ile Asp Thr Cys Gln Gly Asp Ala Leu
                100                 105                 110

Pro Asn Gly Leu Asp Val Thr Phe Glu Val Thr Glu Leu Arg Arg Leu
            115                 120                 125

Thr Gly Ser Tyr Asn Thr Met Val Gly Asn Asn Glu Gly Ser Met Val
    130                 135                 140

Leu Gly Leu Lys Leu Pro Asn Leu Leu Gly Arg Ala Glu Lys Val Thr
145                 150                 155                 160

Phe Gln Phe Ser Tyr Gly Thr Lys Glu Thr Ser Tyr Gly Leu Ser Phe
                165                 170                 175

Phe Lys Pro Arg Pro Gly Asn Phe Glu Arg Asn Phe Ser Val Asn Leu
            180                 185                 190

Tyr Lys Val Thr Gly Gln Phe Pro Trp Ser Ser Leu Arg Glu Thr Asp
        195                 200                 205

Arg Gly Met Ser Ala Glu Tyr Ser Phe Pro Ile Trp Lys Thr Ser His
    210                 215                 220

Thr Val Lys Trp Glu Gly Val Trp Arg Glu Leu Gly Cys Leu Ser Arg
225                 230                 235                 240

Thr Ala Ser Phe Ala Val Arg Lys Glu Ser Gly His Ser Leu Lys Ser
                245                 250                 255

Ser Leu Ser His Ala Met Val Ile Asp Ser Arg Asn Ser Ser Ile Leu
            260                 265                 270

Pro Arg Arg Gly Ala Leu Leu Lys Val Asn Gln Glu Leu Ala Gly Tyr
        275                 280                 285

Thr Gly Gly Asp Val Ser Phe Ile Lys Glu Asp Phe Glu Leu Gln Leu
    290                 295                 300

Asn Lys Gln Leu Ile Phe Asp Ser Val Phe Ser Ala Ser Phe Trp Gly
305                 310                 315                 320

Gly Met Leu Val Pro Ile Gly Asp Lys Pro Ser Ser Ile Ala Asp Arg
                325                 330                 335

Phe Tyr Leu Gly Gly Pro Thr Ser Ile Arg Gly Phe Ser Met His Ser
            340                 345                 350

Ile Gly Pro Gln Ser Glu Gly Asp Tyr Leu Gly Gly Glu Ala Tyr Trp
        355                 360                 365

Ala Gly Gly Leu His Leu Tyr Thr Pro Leu Pro Phe Arg Pro Gly Gln
    370                 375                 380

Gly Gly Phe Gly Glu Leu Phe Arg Thr His Phe Phe Leu Asn Ala Gly
385                 390                 395                 400

Asn Leu Cys Asn Leu Asn Tyr Gly Glu Gly Pro Lys Ala His Ile Arg
                405                 410                 415
```

```
Lys Leu Ala Glu Cys Ile Arg Trp Ser Tyr Gly Ala Gly Ile Val Leu
            420                 425                 430

Arg Leu Gly Asn Ile Ala Arg Leu Glu Leu Asn Tyr Cys Val Pro Met
            435                 440                 445

Gly Val Gln Thr Gly Asp Arg Ile Cys Asp Gly Val Gln Phe Gly Ala
    450                 455                 460

Gly Ile Arg Phe Leu
465

<210> SEQ ID NO 41
<211> LENGTH: 3018
<212> TYPE: DNA
<213> ORGANISM: Homo sapiens

<400> SEQUENCE: 41
```

| | | | | |
|---|---|---|---|---|
| aattctcttt | aagagtcaca | gctgtccatt | ttccacgtgc | ggctgaagaa tggatttcag | 60 |
| agcgctctcc | ctccggcagt | gttcacctag | taacccttc | cggataagga cctgcagccc | 120 |
| gggcgcgacc | cggaaaggga | atccgccctt | ttcgcctcct | tcgcgccaat cgcctggagt | 180 |
| tggcgttccc | gcagccggga | cacagcccac | cctctaagag | ccgcggagtc ggggacggta | 240 |
| gaaggggccg | cgcgtgcgca | gtggcgtccg | ctgtgcttcc | ggtgcgccgg gcgcggacgc | 300 |
| gggcacgcac | acacgcaagc | acgcctccac | ttaactcgcg | ccgccgcggc agctcgagtc | 360 |
| caccagcagc | gccgtccgct | tgaccgagat | gctgcgggcc | tgtcagttat cgggtgtgac | 420 |
| cgccgccgcc | cagagttgtc | tctgtgggaa | gtttgtcctc | cgtccattgc gaccatgccg | 480 |
| cagatactct | acttcaggca | gctctgggtt | gactactggc | aaaattgctg gagctggcct | 540 |
| tttgtttgtt | ggtggaggta | ttggtggcac | tatcctatat | gccaaatggg attcccattt | 600 |
| ccgggaaagt | gtagagaaaa | ccataccctta | ctcagacaaa | ctcttcgaga tggttcttgg | 660 |
| tcctgcagct | tataatgttc | cattgccaaa | gaaatcgatt | cagtcgggtc cactaaaaat | 720 |
| ctctagtgta | tcagaagtaa | tgaaagaatc | taaacagcct | gcctcacaac tccaaaaaca | 780 |
| aaagggagat | actccagctt | cagcaacagc | acctacagaa | gcggctcaaa ttatttctgc | 840 |
| agcaggtgat | accctgtcgg | tcccagcccc | tgcagttcag | cctgaggaat ctttaaaaac | 900 |
| tgatcaccct | gaaattggtg | aaggaaaacc | cacacctgca | ctttcagaag aagcatcctc | 960 |
| atcttctata | agggagcgac | cacctgaaga | agttgcagct | cgccttgcac aacaggaaaa | 1020 |
| acaagaacaa | gttaaaattg | agtctctagc | caagagctta | gaagatgctc tgaggcaaac | 1080 |
| tgcaagtgtc | actctgcagg | ctattgcagc | tcagaatgct | gcggtccagg ctgtcaatgc | 1140 |
| acactccaac | atattgaaag | ccgccatgga | caattctgag | attgcaggcg agaagaaatc | 1200 |
| tgctcagtgg | cgcacagtgg | agggtgcatt | gaaggaacgc | agaaaggcag tagatgaagc | 1260 |
| tgccgatgcc | cttctcaaag | ccaaagaaga | gttagagaag | atgaaaagtg tgattgaaaa | 1320 |
| tgcaaagaaa | aaagaggttg | ctggggccaa | gcctcatata | actgctgcag agggtaaact | 1380 |
| tcacaacatg | atagttgatc | tggataatgt | ggtcaaaaag | gtccaagcag ctcagtctga | 1440 |
| ggctaaggtt | gtatctcagt | atcatgagct | ggtggtccaa | gctcgggatg actttaaacg | 1500 |
| agagctggac | agtattactc | cagaagtcct | tcctgggtgg | aaaggaatga gtgtttcaga | 1560 |
| cttagctgac | aagctctcta | ctgatgatct | gaactccctc | attgctcatg cacatcgtcg | 1620 |
| tattgatcag | ctgaacagag | agctggcaga | acagaaggcc | accgaaaagc agcacatcac | 1680 |
| gttagccttg | gagaaacaaa | agctggaaga | aaagcgggca | tttgactctg cagtagcaaa | 1740 |
| agcattagaa | catcacagaa | gtgaaatcac | ggctgaacag | gacagaaaga tagaagaagt | 1800 |

```
cagagatgcc atggaaaatg aaatgagaac ccagcttcgc cgacaggcag ctgcccacac   1860
tgatcacttg cgagatgtcc ttagggtaca agaacaggaa ttgaagtctg aatttgagca   1920
gaacctgtct gagaaactct ctgaacaaga attacaattt cgtcgtctca gtcaagagca   1980
agttgacaac tttactctgg atataaatac tgcctatgcc agactcagag gaatcgaaca   2040
ggctgttcag agccatgcag ttgctgaaga ggaagccaga aaagcccacc aactctggct   2100
ttcagtggag gcattaaagt acagcatgaa gacctcatct gcagaaacac ctactatccc   2160
gctgggtagt gcagttgagg ccatcaaagc caactgttct gataatgaat tcacccaagc   2220
tttaaccgca gctatccctc cagagtccct gacccgtggg gtgtacagtg aagagaccct   2280
tagagcccgt ttctatgctg ttcaaaaact ggcccgaagg gtagcaatga ttgatgaaac   2340
cagaaatagc ttgtaccagt acttcctctc ctacctacag tccctgctcc tattcccacc   2400
tcagcaactg aagccgcccc cagagctctg ccctgaggat ataaacacat ttaaattact   2460
gtcatatgct tcctattgca ttgagcatgg tgatctggag ctagcagcaa agtttgtcaa   2520
tcagctgaag ggggaatcca gacgagtggc acaggactgg ctgaaggaag cccgaatgac   2580
cctagaaacg aaacagatag tggaaatcct gacagcatat gccagcgccg taggaatagg   2640
aaccactcag gtgcagccag agtgaggttt aggaagattt catcaaagtc atatttcatg   2700
tcaaaggaaa tcagcagtga tagatgaagg gttcgcagcg agagtcccgg acttgtctag   2760
aaatgagcag gtttacaagt actgttctaa atgttaacac ctgttgcatt tatattcttt   2820
ccatttgcta tcatgtcagt gaacgccagg agtgctttct ttgcaacttg tgtaacattt   2880
tctgtttttt caggttttac tgatgaggct tgtgaggcca atcaaaataa tgtttgtgat   2940
ctctactact gttgattttg ccctcggagc aaactgaata aagcaacaag atgaaaactg   3000
aaaaaaaaaa aaaaaaaa                                                 3018
```

<210> SEQ ID NO 42
<211> LENGTH: 758
<212> TYPE: PRT
<213> ORGANISM: Homo sapiens

<400> SEQUENCE: 42

```
Met Leu Arg Ala Cys Gln Leu Ser Gly Val Thr Ala Ala Gln Ser
1               5                   10                  15

Cys Leu Cys Gly Lys Phe Val Leu Arg Pro Leu Arg Pro Cys Arg Arg
                20                  25                  30

Tyr Ser Thr Ser Gly Ser Ser Gly Leu Thr Thr Gly Lys Ile Ala Gly
            35                  40                  45

Ala Gly Leu Leu Phe Val Gly Gly Ile Gly Gly Thr Ile Leu Tyr
        50                  55                  60

Ala Lys Trp Asp Ser His Phe Arg Glu Ser Val Glu Lys Thr Ile Pro
65                  70                  75                  80

Tyr Ser Asp Lys Leu Phe Glu Met Val Leu Gly Pro Ala Ala Tyr Asn
                85                  90                  95

Val Pro Leu Pro Lys Lys Ser Ile Gln Ser Gly Pro Leu Lys Ile Ser
            100                 105                 110

Ser Val Ser Glu Val Met Lys Glu Ser Lys Gln Pro Ala Ser Gln Leu
        115                 120                 125

Gln Lys Gln Lys Gly Asp Thr Pro Ala Ser Ala Thr Ala Pro Thr Glu
    130                 135                 140

Ala Ala Gln Ile Ile Ser Ala Ala Gly Asp Thr Leu Ser Val Pro Ala
```

```
            145                 150                 155                 160
        Pro Ala Val Gln Pro Glu Glu Ser Leu Lys Thr Asp His Pro Glu Ile
                        165                 170                 175
        Gly Glu Gly Lys Pro Thr Pro Ala Leu Ser Glu Glu Ala Ser Ser Ser
                        180                 185                 190
        Ser Ile Arg Glu Arg Pro Pro Glu Val Ala Ala Arg Leu Ala Gln
                    195                 200                 205
        Gln Glu Lys Gln Glu Gln Val Lys Ile Glu Ser Leu Ala Lys Ser Leu
                    210                 215                 220
        Glu Asp Ala Leu Arg Gln Thr Ala Ser Val Thr Leu Gln Ala Ile Ala
        225                 230                 235                 240
        Ala Gln Asn Ala Ala Val Gln Ala Val Asn Ala His Ser Asn Ile Leu
                        245                 250                 255
        Lys Ala Ala Met Asp Asn Ser Glu Ile Ala Gly Glu Lys Lys Ser Ala
                        260                 265                 270
        Gln Trp Arg Thr Val Glu Gly Ala Leu Lys Glu Arg Arg Lys Ala Val
                    275                 280                 285
        Asp Glu Ala Ala Asp Ala Leu Leu Lys Ala Lys Glu Glu Leu Glu Lys
                    290                 295                 300
        Met Lys Ser Val Ile Glu Asn Ala Lys Lys Lys Glu Val Ala Gly Ala
        305                 310                 315                 320
        Lys Pro His Ile Thr Ala Ala Glu Gly Lys Leu His Asn Met Ile Val
                        325                 330                 335
        Asp Leu Asp Asn Val Val Lys Lys Val Gln Ala Ala Gln Ser Glu Ala
                        340                 345                 350
        Lys Val Val Ser Gln Tyr His Glu Leu Val Val Gln Ala Arg Asp Asp
                    355                 360                 365
        Phe Lys Arg Glu Leu Asp Ser Ile Thr Pro Glu Val Leu Pro Gly Trp
                    370                 375                 380
        Lys Gly Met Ser Val Ser Asp Leu Ala Asp Lys Leu Ser Thr Asp Asp
        385                 390                 395                 400
        Leu Asn Ser Leu Ile Ala His Ala His Arg Arg Ile Asp Gln Leu Asn
                        405                 410                 415
        Arg Glu Leu Ala Glu Gln Lys Ala Thr Glu Lys Gln His Ile Thr Leu
                        420                 425                 430
        Ala Leu Glu Lys Gln Lys Leu Glu Glu Lys Arg Ala Phe Asp Ser Ala
                    435                 440                 445
        Val Ala Lys Ala Leu Glu His His Arg Ser Glu Ile Gln Ala Glu Gln
                    450                 455                 460
        Asp Arg Lys Ile Glu Glu Val Arg Asp Ala Met Glu Asn Glu Met Arg
        465                 470                 475                 480
        Thr Gln Leu Arg Arg Gln Ala Ala Ala His Thr Asp His Leu Arg Asp
                        485                 490                 495
        Val Leu Arg Val Gln Glu Gln Leu Lys Ser Glu Phe Glu Gln Asn
                        500                 505                 510
        Leu Ser Glu Lys Leu Ser Glu Gln Leu Gln Phe Arg Arg Leu Ser
                    515                 520                 525
        Gln Glu Gln Val Asp Asn Phe Thr Leu Asp Ile Asn Thr Ala Tyr Ala
                    530                 535                 540
        Arg Leu Arg Gly Ile Glu Gln Ala Val Gln Ser His Ala Val Ala Glu
        545                 550                 555                 560
        Glu Glu Ala Arg Lys Ala His Gln Leu Trp Leu Ser Val Glu Ala Leu
                        565                 570                 575
```

Lys Tyr Ser Met Lys Thr Ser Ser Ala Glu Thr Pro Thr Ile Pro Leu
                580                 585                 590

Gly Ser Ala Val Glu Ala Ile Lys Ala Asn Cys Ser Asp Asn Glu Phe
            595                 600                 605

Thr Gln Ala Leu Thr Ala Ala Ile Pro Pro Glu Ser Leu Thr Arg Gly
        610                 615                 620

Val Tyr Ser Glu Glu Thr Leu Arg Ala Arg Phe Tyr Ala Val Gln Lys
625                 630                 635                 640

Leu Ala Arg Arg Val Ala Met Ile Asp Glu Thr Arg Asn Ser Leu Tyr
                645                 650                 655

Gln Tyr Phe Leu Ser Tyr Leu Gln Ser Leu Leu Leu Phe Pro Pro Gln
            660                 665                 670

Gln Leu Lys Pro Pro Glu Leu Cys Pro Glu Asp Ile Asn Thr Phe
        675                 680                 685

Lys Leu Leu Ser Tyr Ala Ser Tyr Cys Ile Glu His Gly Asp Leu Glu
            690                 695                 700

Leu Ala Ala Lys Phe Val Asn Gln Leu Lys Gly Glu Ser Arg Arg Val
705                 710                 715                 720

Ala Gln Asp Trp Leu Lys Glu Ala Arg Met Thr Leu Glu Thr Lys Gln
                725                 730                 735

Ile Val Glu Ile Leu Thr Ala Tyr Ala Ser Ala Val Gly Ile Gly Thr
            740                 745                 750

Thr Gln Val Gln Pro Glu
        755

<210> SEQ ID NO 43
<211> LENGTH: 3015
<212> TYPE: DNA
<213> ORGANISM: Homo sapiens

<400> SEQUENCE: 43

```
aattctcttt aagagtcaca gctgtccatt ttccacgtgc ggctgaagaa tggatttcag      60
agcgctctcc ctccggcagt gttcacctag taacccttc cggataagga cctgcagccc     120
gggcgcgacc cggaaaggga atccgccctt ttcgcctcct tcgcgccaat cgcctggagt     180
tggcgtttcc gcagccggga cacagcccac cctctaagag ccgcggagtc ggggacggta     240
gaaggggccg cgcgtgcgca gtggcgtccg ctgtgcttcc ggtgcgccgg gcgcggacgc     300
gggcacgcac acacgcaagc acgcctccac ttaactcgcg ccgccgcggc agctcgagtc     360
caccagcagc gccgtccgct tgaccgagat gctgcgggcc tgtcagttat cgggtgtgac     420
cgccgccgcc cagagttgtc tctgtgggaa gtttgtcctc cgtccattgc gaccatgccg     480
cagatactct acttcaggca gctctgggtt gactactggc aaaattgctg gagctggcct     540
tttgtttgtt ggtggaggta ttggtggcac tatcctatat gccaaatggg attcccattt     600
ccgggaaagt gtagagaaaa ccataccta ctcagacaaa ctcttcgaga tggttcttgg     660
tcctgcagct tataatgttc cattgccaaa gaaatcgatt cagtcgggtc cactaaaaat     720
ctctagtgta tcagaagtaa tgaaagaatc taaacagcct gcctcacaac tccaaaaaca     780
aaagggagat actccagctt cagcaacagc acctacagaa gcggctcaaa ttatttctgc     840
agcaggtgat accctgtcgg tcccagcccc tgcagttcag cctgaggaat cttttaaaaac     900
tgatcaccct gaaattggtg aaggaaaacc cacacctgca ctttcagaag catcctcatc     960
ttctataagg gagcgaccac ctgaagaagt tgcagctcgc cttgcacaac aggaaaaaca    1020
```

```
agaacaagtt aaaattgagt ctctagccaa gagcttagaa gatgctctga ggcaaactgc    1080
aagtgtcact ctgcaggcta ttgcagctca gaatgctgcg gtccaggctg tcaatgcaca    1140
ctccaacata ttgaaagccg ccatggacaa ttctgagatt gcaggcgaga gaaatctgc     1200
tcagtggcgc acagtggagg gtgcattgaa ggaacgcaga aaggcagtag atgaagctgc    1260
cgatgcccctt ctcaaagcca agaagagtt agagaagatg aaaagtgtga ttgaaaatgc    1320
aaagaaaaaa gaggttgctg gggccaagcc tcatataact gctgcagagg gtaaacttca    1380
caacatgata gttgatctgg ataatgtggt caaaaaggtc caagcagctc agtctgaggc    1440
taaggttgta tctcagtatc atgagctggt ggtccaagct cgggatgact ttaaacgaga    1500
gctggacagt attactccag aagtccttcc tgggtggaaa ggaatgagtg tttcagactt    1560
agctgacaag ctctctactg atgatctgaa ctccctcatt gctcatgcac atcgtcgtat    1620
tgatcagctg aacagagagc tggcagaaca gaaggccacc gaaaagcagc acatcacgtt    1680
agccttggag aaacaaaagc tggaagaaaa gcgggcattt gactctgcag tagcaaaagc    1740
attagaacat cacagaagtg aaatacaggc tgaacaggac agaaagatag aagaagtcag    1800
agatgccatg gaaaatgaaa tgagaaccca gcttcgccga caggcagctg cccacactga    1860
tcacttgcga gatgtcctta gggtacaaga acaggaattg aagtctgaat ttgagcagaa    1920
cctgtctgag aaactctctg aacaagaatt acaatttcgt cgtctcagtc aagagcaagt    1980
tgacaacttt actctggata taaatactgc ctatgccaga ctcagaggaa tcgaacaggc    2040
tgttcagagc catgcagttg ctgaagagga agccagaaaa gcccaccaac tctggctttc    2100
agtggaggca ttaaagtaca gcatgaagac ctcatctgca gaaacaccta ctatcccgct    2160
gggtagtgca gttgaggcca tcaaagccaa ctgttctgat aatgaattca cccaagcttt    2220
aaccgcagct atccctccag agtccctgac ccgtggggtg tacagtgaag agacccttag    2280
agcccgtttc tatgctgttc aaaaactggc ccgaagggta gcaatgattg atgaaaccag    2340
aaatagcttg taccagtact tcctctccta cctacagtcc ctgctcctat cccacctca    2400
gcaactgaag ccgcccccag agctctgccc tgaggatata aacacattta aattactgtc    2460
atatgcttcc tattgcattg agcatggtga tctggagcta gcagcaaagt ttgtcaatca    2520
gctgaagggg gaatccagac gagtggcaca ggactggctg aaggaagccc gaatgaccct    2580
agaaacgaaa cagatagtgg aaatcctgac agcatatgcc agcgccgtag gaataggaac    2640
cactcaggtg cagccagagt gaggtttagg aagattttca taaagtcata tttcatgtca    2700
aaggaaatca gcagtgatag atgaagggtt cgcagcgaga gtcccggact tgtctagaaa    2760
tgagcaggtt tacaagtact gttctaaatg ttaacacctg ttgcatttat attctttcca    2820
tttgctatca tgtcagtgaa cgccaggagt gctttctttg caacttgtgt aacatttct     2880
gttttttcag gttttactga tgaggcttgt gaggccaatc aaaataatgt ttgtgatctc    2940
tactactgtt gattttgccc tcggagcaaa ctgaataaag caacaagatg aaaactgaaa    3000
aaaaaaaaaa aaaaa                                                     3015
```

<210> SEQ ID NO 44
<211> LENGTH: 757
<212> TYPE: PRT
<213> ORGANISM: Homo sapiens

<400> SEQUENCE: 44

Met Leu Arg Ala Cys Gln Leu Ser Gly Val Thr Ala Ala Ala Gln Ser
 1               5                  10                  15

```
Cys Leu Cys Gly Lys Phe Val Leu Arg Pro Leu Arg Pro Cys Arg Arg
             20                  25                  30

Tyr Ser Thr Ser Gly Ser Ser Gly Leu Thr Thr Gly Lys Ile Ala Gly
         35                  40                  45

Ala Gly Leu Leu Phe Val Gly Gly Ile Gly Gly Thr Ile Leu Tyr
 50                  55                  60

Ala Lys Trp Asp Ser His Phe Arg Glu Ser Val Glu Lys Thr Ile Pro
 65              70                  75                  80

Tyr Ser Asp Lys Leu Phe Glu Met Val Leu Gly Pro Ala Ala Tyr Asn
             85                  90                  95

Val Pro Leu Pro Lys Lys Ser Ile Gln Ser Gly Pro Leu Lys Ile Ser
            100                 105                 110

Ser Val Ser Glu Val Met Lys Glu Ser Lys Gln Pro Ala Ser Gln Leu
        115                 120                 125

Gln Lys Gln Lys Gly Asp Thr Pro Ala Ser Ala Thr Ala Pro Thr Glu
    130                 135                 140

Ala Ala Gln Ile Ile Ser Ala Ala Gly Asp Thr Leu Ser Val Pro Ala
145                 150                 155                 160

Pro Ala Val Gln Pro Glu Glu Ser Leu Lys Thr Asp His Pro Glu Ile
                165                 170                 175

Gly Glu Gly Lys Pro Thr Pro Ala Leu Ser Glu Ala Ser Ser Ser Ser
            180                 185                 190

Ile Arg Glu Arg Pro Pro Glu Val Ala Ala Arg Leu Ala Gln Gln
        195                 200                 205

Glu Lys Gln Glu Gln Val Lys Ile Glu Ser Leu Ala Lys Ser Leu Glu
    210                 215                 220

Asp Ala Leu Arg Gln Thr Ala Ser Val Thr Leu Gln Ala Ile Ala Ala
225                 230                 235                 240

Gln Asn Ala Ala Val Gln Ala Val Asn Ala His Ser Asn Ile Leu Lys
                245                 250                 255

Ala Ala Met Asp Asn Ser Glu Ile Ala Gly Lys Lys Ser Ala Gln
            260                 265                 270

Trp Arg Thr Val Glu Gly Ala Leu Lys Glu Arg Arg Lys Ala Val Asp
    275                 280                 285

Glu Ala Ala Asp Ala Leu Leu Lys Ala Lys Glu Glu Leu Glu Lys Met
290                 295                 300

Lys Ser Val Ile Glu Asn Ala Lys Lys Glu Val Ala Gly Ala Lys
305                 310                 315                 320

Pro His Ile Thr Ala Ala Glu Gly Lys Leu His Asn Met Ile Val Asp
            325                 330                 335

Leu Asp Asn Val Val Lys Lys Val Gln Ala Ala Gln Ser Glu Ala Lys
        340                 345                 350

Val Val Ser Gln Tyr His Glu Leu Val Val Gln Ala Arg Asp Asp Phe
    355                 360                 365

Lys Arg Glu Leu Asp Ser Ile Thr Pro Glu Val Leu Pro Gly Trp Lys
370                 375                 380

Gly Met Ser Val Ser Asp Leu Ala Asp Lys Leu Ser Thr Asp Asp Leu
385                 390                 395                 400

Asn Ser Leu Ile Ala His Ala His Arg Ile Asp Gln Leu Asn Arg
                405                 410                 415

Glu Leu Ala Glu Gln Lys Ala Thr Glu Lys Gln His Ile Thr Leu Ala
            420                 425                 430

Leu Glu Lys Gln Lys Leu Glu Glu Lys Arg Ala Phe Asp Ser Ala Val
```

```
             435                 440                 445
Ala Lys Ala Leu Glu His His Arg Ser Glu Ile Gln Ala Glu Gln Asp
450                 455                 460

Arg Lys Ile Glu Glu Val Arg Asp Ala Met Glu Asn Glu Met Arg Thr
465                 470                 475                 480

Gln Leu Arg Arg Gln Ala Ala His Thr Asp His Leu Arg Asp Val
                485                 490                 495

Leu Arg Val Gln Glu Gln Glu Leu Lys Ser Glu Phe Glu Gln Asn Leu
                500                 505                 510

Ser Glu Lys Leu Ser Glu Gln Glu Leu Gln Phe Arg Arg Leu Ser Gln
            515                 520                 525

Glu Gln Val Asp Asn Phe Thr Leu Asp Ile Asn Thr Ala Tyr Ala Arg
        530                 535                 540

Leu Arg Gly Ile Glu Gln Ala Val Gln Ser His Ala Val Ala Glu Glu
545                 550                 555                 560

Glu Ala Arg Lys Ala His Gln Leu Trp Leu Ser Val Glu Ala Leu Lys
                565                 570                 575

Tyr Ser Met Lys Thr Ser Ser Ala Glu Thr Pro Thr Ile Pro Leu Gly
                580                 585                 590

Ser Ala Val Glu Ala Ile Lys Ala Asn Cys Ser Asp Asn Glu Phe Thr
            595                 600                 605

Gln Ala Leu Thr Ala Ala Ile Pro Pro Glu Ser Leu Thr Arg Gly Val
        610                 615                 620

Tyr Ser Glu Glu Thr Leu Arg Ala Arg Phe Tyr Ala Val Gln Lys Leu
625                 630                 635                 640

Ala Arg Arg Val Ala Met Ile Asp Glu Thr Arg Asn Ser Leu Tyr Gln
                645                 650                 655

Tyr Phe Leu Ser Tyr Leu Gln Ser Leu Leu Phe Pro Pro Gln Gln
                660                 665                 670

Leu Lys Pro Pro Glu Leu Cys Pro Glu Asp Ile Asn Thr Phe Lys
            675                 680                 685

Leu Leu Ser Tyr Ala Ser Tyr Cys Ile Glu His Gly Asp Leu Glu Leu
        690                 695                 700

Ala Ala Lys Phe Val Asn Gln Leu Lys Gly Glu Ser Arg Arg Val Ala
705                 710                 715                 720

Gln Asp Trp Leu Lys Glu Ala Arg Met Thr Leu Glu Thr Lys Gln Ile
                725                 730                 735

Val Glu Ile Leu Thr Ala Tyr Ala Ser Ala Val Gly Ile Gly Thr Thr
                740                 745                 750

Gln Val Gln Pro Glu
        755

<210> SEQ ID NO 45
<211> LENGTH: 2985
<212> TYPE: DNA
<213> ORGANISM: Homo sapiens

<400> SEQUENCE: 45
aattctcttt aagagtcaca gctgtccatt ttccacgtgc ggctgaagaa tggatttcag      60
agcgctctcc ctccggcagt gttcacctag taaccccttc cggataagga cctgcagccc     120
gggcgcgacc cggaaaggga atccgcccct ttcgcctcct tcgcgccaat cgcctggagt     180
tggcgtttcc gcagccggga cacagcccac cctctaagag ccgcggagtc ggggacggta     240
gaaggggccg cgcgtgcgca gtggcgtccg ctgtgcttcc ggtgcgccgg gcgcggacgc     300
```

```
gggcacgcac acacgcaagc acgcctccac ttaactcgcg ccgccgcggc agctcgagtc    360
caccagcagc gccgtccgct tgaccgagat gctgcgggcc tgtcagttat cgggtgtgac    420
cgccgccgcc cagagttgtc tctgtgggaa gtttgtcctc cgtccattgc gaccatgccg    480
cagatactct acttcaggca gctctgggtt gactactggc aaaattgctg gagctggcct    540
tttgtttgtt ggtggaggta ttggtggcac tatcctatat gccaaatggg attcccattt    600
ccgggaaagt gtagagaaaa ccataccctta ctcagacaaa ctcttcgaga tggttcttgg    660
tcctgcagct tataatgttc cattgccaaa gaaatcgatt cagtcgggtc cactaaaaat    720
ctctagtgta tcagaagtaa tgaaagaatc taaacagcct gcctcacaac tccaaaaaca    780
aaagggagat actccagctt cagcaacagc aggtgatacc ctgtcggtcc cagcccctgc    840
agttcagcct gaggaatctt taaaaactga tcaccctgaa attggtgaag aaaacccac     900 acctgcactt tcagaagaag catcctcatc ttctataagg gagcgaccac ctgaagaagt    960
tgcagctcgc cttgcacaac aggaaaaaca agaacaagtt aaaattgagt ctctagccaa   1020
gagcttagaa gatgctctga ggcaaactgc aagtgtcact ctgcaggcta ttgcagctca   1080
gaatgctgcg gtccaggctg tcaatgcaca ctccaacata ttgaaagccg ccatggacaa   1140
ttctgagatt gcaggcgaga gaaatctgc tcagtggcgc acagtggagg gtgcattgaa    1200
ggaacgcaga aaggcagtag atgaagctgc cgatgcccct ctcaaagcca agaagagtt    1260 agagaagatg aaaagtgtga ttgaaaatgc aaagaaaaaa gaggttgctg ggccaagcc    1320 tcatataact gctgcagagg gtaaacttca acatgatga gttgatctgg ataatgtggt    1380
caaaaaggtc caagcagctc agtctgaggc taaggttgta tctcagtatc atgagctggt   1440
ggtccaagct cgggatgact ttaaacgaga gctggacagt attactccag aagtccttcc   1500
tgggtggaaa ggaatgagtg tttcagactt agctgacaag ctctctactg atgatctgaa   1560
ctccctcatt gctcatgcac atcgtcgtat tgatcagctg aacagagagc tggcagaaca   1620
gaaggccacc gaaaagcagc acatcacgtt agccttggag aaacaaaagc tggaagaaaa   1680
gcgggcattt gactctgcag tagcaaaagc attagaacat cacagaagtg aaatacaggc   1740
tgaacaggac agaaagatag aagaagtcag agatgccatg gaaaatgaaa tgagaaccca   1800
gcttcgccga caggcagctg cccacactga tcacttgcga gatgtcctta gggtacaaga   1860
acaggaattg aagtctgaat ttgagcagaa cctgtctgag aaactctctg aacaagaatt   1920
acaatttcgt cgtctcagtc aagagcaagt tgacaacttt actctggata taaatactgc   1980
ctatgccaga ctcagaggaa tcgaacaggc tgttcagagc catgcagttg ctgaagagga   2040
agccagaaaa gcccaccaac tctggctttc agtggaggca ttaaagtaca gcatgaagac   2100
ctcatctgca gaaacaccta ctatcccgct gggtagtgca gttgaggcca tcaaagccaa   2160
ctgttctgat aatgaattca cccaagcttt aaccgcagct atccctccag agtccctgac   2220 ccgtgggtg tacagtgaag agaccctag agcccgtttc tatgctgttc aaaaactggc   2280
ccgaagggta gcaatgattg atgaaaccag aaatagcttg taccagtact tcctctccta   2340
cctacagtcc ctgctcctat tcccacctca gcaactgaag ccgcccccag agctctgccc   2400
tgaggatata aacacattta aattactgtc atatgcttcc tattgcattg agcatggtga   2460
tctggagcta gcagcaaagt ttgtcaatca gctgaagggg gaatccagac gagtggcaca   2520
ggactggctg aaggaagccc gaatgaccct agaaacgaaa cagatagtgg aaatcctgac   2580
agcatatgcc agcgccgtag gaataggaac cactcaggtg cagccagagt gaggtttagg   2640
```

-continued

```
aagattttca taaagtcata tttcatgtca aaggaaatca gcagtgatag atgaagggtt    2700
cgcagcgaga gtcccggact tgtctagaaa tgagcaggtt tacaagtact gttctaaatg    2760
ttaacacctg ttgcatttat attctttcca tttgctatca tgtcagtgaa cgccaggagt    2820
gctttctttg caacttgtgt aacattttct gttttttcag gttttactga tgaggcttgt    2880
gaggccaatc aaaataatgt ttgtgatctc tactactgtt gattttgccc tcggagcaaa    2940
ctgaataaag caacaagatg aaaactgaaa aaaaaaaaa aaaaa                     2985
```

<210> SEQ ID NO 46
<211> LENGTH: 747
<212> TYPE: PRT
<213> ORGANISM: Homo sapiens

<400> SEQUENCE: 46

```
Met Leu Arg Ala Cys Gln Leu Ser Gly Val Thr Ala Ala Ala Gln Ser
1               5                   10                  15

Cys Leu Cys Gly Lys Phe Val Leu Arg Pro Leu Arg Pro Cys Arg Arg
            20                  25                  30

Tyr Ser Thr Ser Gly Ser Gly Leu Thr Thr Gly Lys Ile Ala Gly
        35                  40                  45

Ala Gly Leu Leu Phe Val Gly Gly Ile Gly Gly Thr Ile Leu Tyr
    50                  55                  60

Ala Lys Trp Asp Ser His Phe Arg Glu Ser Val Glu Lys Thr Ile Pro
65                  70                  75                  80

Tyr Ser Asp Lys Leu Phe Glu Met Val Leu Gly Pro Ala Ala Tyr Asn
                85                  90                  95

Val Pro Leu Pro Lys Lys Ser Ile Gln Ser Gly Pro Leu Lys Ile Ser
            100                 105                 110

Ser Val Ser Glu Val Met Lys Glu Ser Lys Gln Pro Ala Ser Gln Leu
        115                 120                 125

Gln Lys Gln Lys Gly Asp Thr Pro Ala Ser Ala Thr Ala Gly Asp Thr
    130                 135                 140

Leu Ser Val Pro Ala Pro Ala Val Gln Pro Glu Glu Ser Leu Lys Thr
145                 150                 155                 160

Asp His Pro Glu Ile Gly Glu Gly Lys Pro Thr Pro Ala Leu Ser Glu
                165                 170                 175

Glu Ala Ser Ser Ser Ile Arg Glu Arg Pro Pro Glu Glu Val Ala
            180                 185                 190

Ala Arg Leu Ala Gln Gln Glu Lys Gln Glu Gln Val Lys Ile Glu Ser
        195                 200                 205

Leu Ala Lys Ser Leu Glu Asp Ala Leu Arg Gln Thr Ala Ser Val Thr
    210                 215                 220

Leu Gln Ala Ile Ala Gln Asn Ala Val Gln Val Asn Ala
225                 230                 235                 240

His Ser Asn Ile Leu Lys Ala Ala Met Asp Asn Ser Glu Ile Ala Gly
                245                 250                 255

Glu Lys Lys Ser Ala Gln Trp Arg Thr Val Glu Gly Ala Leu Lys Glu
            260                 265                 270

Arg Arg Lys Ala Val Asp Glu Ala Asp Ala Leu Leu Lys Ala Lys
        275                 280                 285

Glu Glu Leu Glu Lys Met Lys Ser Val Ile Glu Asn Ala Lys Lys Lys
    290                 295                 300

Glu Val Ala Gly Ala Lys Pro His Ile Thr Ala Ala Glu Gly Lys Leu
305                 310                 315                 320
```

```
His Asn Met Ile Val Asp Leu Asp Asn Val Val Lys Val Gln Ala
                325                 330                 335

Ala Gln Ser Glu Ala Lys Val Val Ser Gln Tyr His Glu Leu Val Val
            340                 345                 350

Gln Ala Arg Asp Asp Phe Lys Arg Glu Leu Asp Ser Ile Thr Pro Glu
            355                 360                 365

Val Leu Pro Gly Trp Lys Gly Met Ser Val Ser Asp Leu Ala Asp Lys
    370                 375                 380

Leu Ser Thr Asp Asp Leu Asn Ser Leu Ile Ala His Ala His Arg Arg
385                 390                 395                 400

Ile Asp Gln Leu Asn Arg Glu Leu Ala Glu Gln Lys Ala Thr Glu Lys
                405                 410                 415

Gln His Ile Thr Leu Ala Leu Glu Lys Gln Lys Leu Glu Glu Lys Arg
            420                 425                 430

Ala Phe Asp Ser Ala Val Ala Lys Ala Leu Glu His His Arg Ser Glu
            435                 440                 445

Ile Gln Ala Glu Gln Asp Arg Lys Ile Glu Glu Val Arg Asp Ala Met
    450                 455                 460

Glu Asn Glu Met Arg Thr Gln Leu Arg Arg Gln Ala Ala Ala His Thr
465                 470                 475                 480

Asp His Leu Arg Asp Val Leu Arg Val Gln Glu Gln Glu Leu Lys Ser
                485                 490                 495

Glu Phe Glu Gln Asn Leu Ser Glu Lys Leu Ser Glu Gln Glu Leu Gln
            500                 505                 510

Phe Arg Arg Leu Ser Gln Glu Gln Val Asp Asn Phe Thr Leu Asp Ile
            515                 520                 525

Asn Thr Ala Tyr Ala Arg Leu Arg Gly Ile Glu Gln Ala Val Gln Ser
    530                 535                 540

His Ala Val Ala Glu Glu Ala Arg Lys Ala His Gln Leu Trp Leu
545                 550                 555                 560

Ser Val Glu Ala Leu Lys Tyr Ser Met Lys Thr Ser Ser Ala Glu Thr
                565                 570                 575

Pro Thr Ile Pro Leu Gly Ser Ala Val Glu Ala Ile Lys Ala Asn Cys
            580                 585                 590

Ser Asp Asn Glu Phe Thr Gln Ala Leu Thr Ala Ile Pro Pro Glu
            595                 600                 605

Ser Leu Thr Arg Gly Val Tyr Ser Glu Glu Thr Leu Arg Ala Arg Phe
    610                 615                 620

Tyr Ala Val Gln Lys Leu Ala Arg Arg Val Ala Met Ile Asp Glu Thr
625                 630                 635                 640

Arg Asn Ser Leu Tyr Gln Tyr Phe Leu Ser Tyr Leu Gln Ser Leu Leu
                645                 650                 655

Leu Phe Pro Pro Gln Gln Leu Lys Pro Pro Glu Leu Cys Pro Glu
            660                 665                 670

Asp Ile Asn Thr Phe Lys Leu Leu Ser Tyr Ala Ser Tyr Cys Ile Glu
            675                 680                 685

His Gly Asp Leu Glu Leu Ala Ala Lys Phe Val Asn Gln Leu Lys Gly
    690                 695                 700

Glu Ser Arg Arg Val Ala Gln Asp Trp Leu Lys Glu Ala Arg Met Thr
705                 710                 715                 720

Leu Glu Thr Lys Gln Ile Val Glu Ile Leu Thr Ala Tyr Ala Ser Ala
                725                 730                 735
```

```
Val Gly Ile Gly Thr Thr Gln Val Gln Pro Glu
          740                 745
```

<210> SEQ ID NO 47
<211> LENGTH: 15
<212> TYPE: PRT
<213> ORGANISM: Homo sapiens

<400> SEQUENCE: 47

```
Tyr Leu Ile Leu Gly Ser Ala Val Gly Gly Tyr Thr Ala Lys
1               5                   10                  15
```

<210> SEQ ID NO 48
<211> LENGTH: 6
<212> TYPE: PRT
<213> ORGANISM: Homo sapiens

<400> SEQUENCE: 48

```
Thr Phe Asp Gln Trp Lys
1               5
```

<210> SEQ ID NO 49
<211> LENGTH: 10
<212> TYPE: PRT
<213> ORGANISM: Homo sapiens

<400> SEQUENCE: 49

```
Asp Met Ile Pro Asp Leu Ser Glu Tyr Lys
1               5                   10
```

<210> SEQ ID NO 50
<211> LENGTH: 18
<212> TYPE: PRT
<213> ORGANISM: Homo sapiens

<400> SEQUENCE: 50

```
Trp Ile Val Pro Asp Ile Val Trp Glu Ile Asp Glu Tyr Ile Asp Phe
1               5                   10                  15

Glu Lys
```

<210> SEQ ID NO 51
<211> LENGTH: 7
<212> TYPE: PRT
<213> ORGANISM: Homo sapiens

<400> SEQUENCE: 51

```
Leu Ala Pro Asp Phe Asp Lys
1               5
```

<210> SEQ ID NO 52
<211> LENGTH: 9
<212> TYPE: PRT
<213> ORGANISM: Homo sapiens

<400> SEQUENCE: 52

```
Ile Val Glu Ser Leu Ser Leu Leu Lys
1               5
```

<210> SEQ ID NO 53
<211> LENGTH: 10
<212> TYPE: PRT
<213> ORGANISM: Homo sapiens

<400> SEQUENCE: 53

```
Ala Leu Pro Asn Ser Glu Asp Leu Val Lys
1               5                   10
```

<210> SEQ ID NO 54
<211> LENGTH: 14
<212> TYPE: PRT
<213> ORGANISM: Homo sapiens

<400> SEQUENCE: 54

```
Asp Phe Phe Thr Ser Gly Ser Pro Glu Glu Thr Ala Phe Arg
1               5                   10
```

<210> SEQ ID NO 55
<211> LENGTH: 13
<212> TYPE: PRT
<213> ORGANISM: Homo sapiens

<400> SEQUENCE: 55

```
Thr Arg Leu Leu Lys Leu Arg Tyr Leu Ile Leu Gly Ser
1               5                   10
```

<210> SEQ ID NO 56
<211> LENGTH: 20
<212> TYPE: PRT
<213> ORGANISM: Homo sapiens

<400> SEQUENCE: 56

```
Phe Trp Pro Ala Arg Leu Ala Thr Arg Leu Leu Lys Leu Arg Tyr Leu
1               5                   10                  15

Ile Leu Gly Ser
            20
```

<210> SEQ ID NO 57
<211> LENGTH: 21
<212> TYPE: PRT
<213> ORGANISM: Homo sapiens

<400> SEQUENCE: 57

```
Gly Leu Leu Gly Glu Leu Ile Leu Leu Gln Gln Gln Ile Gln Glu His
1               5                   10                  15

Glu Glu Glu Ala Arg
            20
```

<210> SEQ ID NO 58
<211> LENGTH: 13
<212> TYPE: PRT
<213> ORGANISM: Homo sapiens

<400> SEQUENCE: 58

```
Ala Ala Gly Gln Tyr Ser Thr Ser Tyr Ala Gln Gln Lys
1               5                   10
```

<210> SEQ ID NO 59
<211> LENGTH: 14
<212> TYPE: PRT
<213> ORGANISM: Homo sapiens

<400> SEQUENCE: 59

```
Ile Asp Gln Leu Gln Glu Glu Leu Leu His Thr Gln Leu Lys
1               5                   10
```

<210> SEQ ID NO 60
<211> LENGTH: 37
<212> TYPE: PRT

```
<213> ORGANISM: Homo sapiens

<400> SEQUENCE: 60

Glu Tyr Lys Trp Ile Val Pro Asp Ile Val Trp Glu Ile Asp Glu Tyr
1               5                   10                  15

Ile Asp Phe Gly His Lys Leu Val Ser Glu Val Ile Gly Ala Ser Asp
            20                  25                  30

Leu Leu Leu Leu Leu
            35

<210> SEQ ID NO 61
<211> LENGTH: 42
<212> TYPE: PRT
<213> ORGANISM: Homo sapiens

<400> SEQUENCE: 61

Glu Tyr Lys Trp Ile Val Pro Asp Ile Val Trp Glu Ile Asp Glu Tyr
1               5                   10                  15

Ile Asp Phe Gly Ser Pro Glu Glu Thr Ala Phe Arg Ala Thr Asp Arg
            20                  25                  30

Gly Ser Glu Ser Asp Lys His Phe Arg Lys
            35                  40

<210> SEQ ID NO 62
<211> LENGTH: 59
<212> TYPE: PRT
<213> ORGANISM: Homo sapiens

<400> SEQUENCE: 62

Glu Lys Ile Arg Lys Ala Leu Pro Asn Ser Glu Asp Leu Val Lys Leu
1               5                   10                  15

Ala Pro Asp Phe Asp Lys Ile Val Glu Ser Leu Ser Leu Leu Lys Asp
            20                  25                  30

Phe Phe Thr Ser Gly Ser Pro Glu Glu Thr Ala Phe Arg Ala Thr Asp
            35                  40                  45

Arg Gly Ser Glu Ser Asp Lys His Phe Arg Lys
        50                  55

<210> SEQ ID NO 63
<211> LENGTH: 60
<212> TYPE: PRT
<213> ORGANISM: Homo sapiens

<400> SEQUENCE: 63

Gly Ser Pro Glu Glu Thr Ala Phe Arg Ala Thr Asp Arg Gly Ser Glu
1               5                   10                  15

Ser Asp Lys His Phe Arg Lys Val Ser Asp Lys Glu Lys Ile Asp Gln
            20                  25                  30

Leu Gln Glu Glu Leu Leu His Thr Gln Leu Lys Tyr Gln Arg Ile Leu
            35                  40                  45

Glu Arg Leu Glu Lys Glu Asn Lys Glu Leu Arg Lys
        50                  55                  60
```

METHODS FOR TREATING DISEASES RELATED TO MITOCHONDRIAL STRESS

This application is a Continuation of PCT International Application No. PCT/US2017/064195 with an international filing date of Dec. 1, 2017, which claims the benefit under 35 U.S.C. § 119(e) of U.S. Provisional Application No. 62/581,723 filed on Nov. 5, 2017, U.S. Provisional Application No. 62/481,392 filed on Apr. 4, 2017, and U.S. Provisional Application No. 62/429,846 filed on Dec. 4, 2016, each of which is incorporated by reference in its entirety.

FIELD

The present disclosure relates to means and methods for therapeutic intervention of mitochondrial disorders or diseases, in particular to a method for the treatment, prevention and/or amelioration of a disorder or disease correlated with mitochondrial stress or dysfunction, a mitochondrial disorder or disease, or a disorder or disease characterized by OPA1 alterations. Thereby, a pharmaceutically active amount of a compound capable of modulating the activity of OMA1 and/or an oligomeric complex comprising OMA1 is administered to a patient in need of medical intervention. The present invention also relates to a method of screening for a compound capable of modulating the activity of OMA1 and/or an oligomeric complex comprising OMA1. The present invention further relates to a method for determining the susceptibility for, predisposition for, or the presence of such a disorder or disease and whether a person in need will benefit from the therapeutic intervention, i.e. personalized medicine.

BACKGROUND

Mitochondria are essential for cells; their proper function is an absolute requirement for cell survival. Mitochondria form large networks of dynamic interconnected tubules that are maintained by balanced fission and fusion events. Morphological alterations of mitochondria and the mitochondrial network have been reported in human disorders. Impairment of mitochondrial fusion or fission is causative of various neurodegenerative diseases such as Charcot-Marie-Tooth disease type 2A and 4A, familial Parkinson's disease, Alzheimer's disease, Autosomal Dominant Optic Atrophy (ADOA) and other optic neuropathies (Alexander et al. 2000; Delettre et al. 2000; Carelli et al. 2002; Sadun 2002; Carelli et al. 2004; Zuchner et al. 2004; Niemann et al. 2005; Kong et al. 2009; Lenaers et al. 2009; Osborne 2010; Lee et al. 2011; Chrysostomou et al. 2013; Maresca et al. 2013; Burte et al. 2015; Salminen et al. 2015; Bose and Beal 2016; Voigt et al. 2016; Zhang et al. 2016). There is strong evidence in particular for a causal relationship between mitochondrial dysfunction and Parkinson's disease (Schapira et al. 1990; Keeney et al. 2006; Parker et al. 2008; Santos et al. 2015; Dolle et al. 2016). On the other hand, dysfunctional mitochondria have been recognized for many years in brains from deceased patients with Alzheimer's disease as well (Parker et al. 1990; Smith et al. 1996; Gibson et al. 1998; Maurer et al. 2000; Butterfield et al. 2001; Devi et al. 2006). Cumulative evidence also exists for mitochondrial fusion/fission being necessary for normal cardiac function (Dorn 2013; Piquereau et al. 2013; Burke et al. 2015; Mann-Garcia and Akhmedov 2016; Ong et al. 2017). Another example for a mitochondrial disorder is cancer. Research over the past century or so has generated a complex and rich body of knowledge revealing cancer to be a disease correlated to mitochondrial dysfunction (Alirol and Martinou 2006; Frezza and Gottlieb 2009; Hanahan and Weinberg 2011; Wallace 2012; Vyas et al. 2016).

OPA1 is a mitochondrial pro-fusion protein with two functions in mitochondrial inner membrane fusion/cristae remodeling and cytochrome C release/cell death (Alavi and Fuhrmann 2013). Proteolytic cleavage of long OPA1 isoforms (OPA1L) produces short OPA1 isoforms (OPA1S). OPA1's dual functions in mitochondrial inner membrane remodeling and cytochrome C release (Olichon et al. 2003; Frezza et al. 2006) are regulated by the ratio of OPA1L-to-OPA1S (Song et al. 2007). OPA1 forms a complex together with IMMT at the inner membrane termed MICOS complex to regulate mitochondrial cristae morphology (Barrera et al. 2016; Glytsou et al. 2016; Hessenberger et al. 2017). This complex is associated with the mitochondrial outer membrane by binding to SAMM50 (Koob et al. 2015; Ott et al. 2015). OPA1 interacts with the apoptotic machinery at the mitochondrial outer membrane through the interaction with BNIP3 (Landes et al. 2010). OPA1L cleavage and OPA1S can promote mitochondrial fragmentation, cytochrome C release and correlates with cell death (Olichon et al. 2003; Duvezin-Caubet et al. 2006; Ishihara et al. 2006; Griparic et al. 2007; Song et al. 2007; Merkwirth et al. 2008; Ehses et al. 2009; Head et al. 2009). Several proteases are directly or indirectly involved in this conversion, such as YME1L1, PARL, HTRA2, and OMA1, which plays the key role during stress-induced OPA1 cleavage (Cipolat et al. 2006; Duvezin-Caubet et al. 2006; Ishihara et al. 2006; Griparic et al. 2007; Song et al. 2007; Ehses et al. 2009; Head et al. 2009).

OMA1 is a zinc metallo-endopeptidase located in the mitochondrial inner membrane (Kaser et al. 2003). Heterozygous mutations in conserved OMA1 residues have been reported in several patients afflicted with familial and sporadic forms of amyotrophic lateral sclerosis (ALS) (Daoud et al. 2011). OMA1 is activated upon cellular stress events, such as increased reactive oxygen species or loss of mitochondrial function (Richter et al. 2015; Bohovych et al. 2016; Rainbolt et al. 2016). In the case of chronic or high stress, there is prolonged OMA1 activation, which in turn triggers the release of cytochrome C, ultimately leading to cell death (Jiang et al. 2014). OMA1 and YME1L1, which proteolytically cleaves OPA1 at the S2 cleavage site, are organized and regulated in the inner mitochondrial membrane by PHB and PHB2 (Wai et al. 2016).

Cells have an innate regulatory feedback loop to counterbalance stress-induced OPA1 cleavage by OMA1 (Alavi and Fuhrmann 2013) (Alavi and Fuhrmann 2013)(Alavi and Fuhrmann 2013)(Alavi and Fuhrmann 2013)(Alavi and Fuhrmann 2013) (Alavi and Fuhrmann 2013). Hypoxic conditions can cause decreased mitochondrial membrane potential, which activates OMA1 (Richter et al. 2015; Bohovych et al. 2016; Rainbolt et al. 2016). HIGD1A is a mitochondrial protein upregulated under hypoxic conditions by HIF1α (Amen et al. 2015; Amen and Maltepe 2015). HIGD1A can bind to the S1 cleavage site thereby protecting OPA1 from proteolytic cleavage by OMA1 (An et al. 2011; An et al. 2013), while HIGD1A translocates to the nucleus in cells undergoing apoptosis (Amen et al. 2013).

SUMMARY

There remains an unmet medical need for therapeutic intervention because at present we still have no method for the treatment, prevention and/or amelioration of a disorder or disease correlated with mitochondrial dysfunction, for a mitochondrial disorder or disease; or for a disorder or disease characterized by OPA1 alterations.

Clinical and/or pathological examples for a disorder or disease correlated with mitochondrial dysfunction, for a mitochondrial disorder or disease; or for a disorder or disease characterized by OPA1 alterations and hence, intended to be therapeutically intervened in context of this invention, are given in the non-exhaustive table below.

- Ageing; in particular pathological and/or pre-mature aging
- Age-related Macular Degeneration (AMD)
- Alzheimer's disease
- Amyotrophic lateral sclerosis (ALS)
- Apoptosis
- Ataxia
- Autism
- Autosomal Dominant Optic Atrophy (ADOA)
- Barth syndrome, (familial)
- Bipolar disorder
- Cancer (e.g. renal cell and colorectal carcinoma, early liver, protasta, breast, bladder, primary lung, head and neck tumours, astrocytomas, adenocarcinomas in Barrett's esophagus)
- Cardiomyopathy
- Charcot-Marie-Tooth disease (e.g., Charcot-Marie-Tooth disease type 2a and type 4a)
- Congenital lactic acidosis
- Crohn disease
- Deafness
- Diabetes
- Diabetic sensory neuropathy
- Encephalomyopathy
- Endotoxemia
- External ophthalmoplegia (e.g. PEO)
- Eye diseases
- Friedreich's ataxia
- Glaucoma
- Heart disease
- Hepatopathy (e.g. defects in SCO1)
- Hepato-cerebral form of mtDNA depletion syndrome
- Hereditary sensory neuropathy
- Hereditary spastic paraplegia
- Infantile encephalopathy
- Infantile myopathy
- Infectious diseases
- Inflammatory diseases
- Ischemia-reperfusion injury/Hypoxic damage/Oxidative damage
- Kearns-Sayre syndrome
- Lactic acidosis
- Leber's hereditary opticus neuropathy (LHON)
- Leigh's syndrome
- Leukodystrophy
- Metabolic disorders (e.g. defective glucose and fatty acid metabolism)
- Mitochondrial neurogastrointestinal-encephalomyopathy
- Mohr-Tranebjaerg-syndrome
- Motor neuron disorders
- mtDNA depletion syndrome
- Multiple Sclerosis (MS)
- Myoclonus epilepsy and ragged-red fibers syndrome (MERRF)
- Myopathy
- Myopathy encephalopathy lactic acidosis and stroke-like episodes (MELAS)
- Myositis
- Neurodegenerative disorders
- Non-alcoholic fatty liver disease
- Obesity
- Ocular myopathy
- Optic neuropathy
- Optic atrophy type 1
- Optic atrophy types 2 to 11
- Paraganglioma (e.g. defects in complex II/SDH)
- Parkinson's disease
- Pearson's syndrome
- Respiratory chain disorder
- Rhabdomyolysis
- Schizophrenia
- Sideroblastic anemia
- Stroke
- Tubulopathy (e.g. defects in BCS1L)
- Viral and bacterial infections
- Wolf-Hirschhorn syndrome
- Wolfram syndrome However, the disorders or diseases to be medically intervened in context of this invention are not strictly construed to the clinical and/or pathological situations described above.

The technical problem underlying the present invention is the provision of suitable means and methods for therapeutic intervention against mitochondrial dysfunction and diseases or disorders related thereto. Further, means and methods for determining the susceptibility for, predisposition for, and/or the presence of such a disease or disorder are of need.

The solution to the above technical problem is achieved by providing the embodiments characterized in the claims.

The present invention solves the above identified technical problem since, as documented herein below and in the appended examples, it was found that:

i) a disorder or disease correlated with mitochondrial dysfunction, or a mitochondrial disorder or disease, or a disorder or disease characterized by OPA1 alterations also correlated with changes in the activity of OMA1 and/or an oligomeric complex comprising OMA1 and/or HIDG1A and/or OPA1 and/or BNIP3 and/or YME1L1 and/or PHB and/or SAMM50 and/or IMMT and/or PHB2 or (a) variant(s) thereof.

ii) measurements of the changes of OMA1 and/or an oligomeric complex comprising OMA1 and/or HIDG1A and/or OPA1 and/or BNIP3 and/or YME1L1 and/or PHB and/or SAMM50 and/or IMMT and/or PHB2 or (a) variant(s) thereof informed selection of suitable interventions for patients with such a disorder or disease and in need of medical intervention.

iii) administering a pharmaceutically active amount of a compound capable of adjusting said changes of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof ameliorated, prevented and/or treated said disorder or disease.

In this context, it is evident that measuring the activity and/or the gene expression levels and/or the protein levels of OMA1 and/or an oligomeric complex comprising OMA1 and/or HIDG1A and/or OPA1 and/or BNIP3 and/or YME1L1 and/or PHB and/or SAMM50 and/or IMMT and/or PHB2 or (a) variant(s) thereof can be utilized for determining the susceptibility for, predisposition for or the presence of a disorder or disease correlated with mitochondrial dysfunction or characterized by OPA1 alterations, as well as for selecting the appropriate medical interventions. The term biomarker(s) may be utilized mutatis mutandis to describe the result from such measurements.

It is of note that the present invention is particularly useful in the treatment, prevention and/or amelioration of a disease or disorder described herein before any clinical and/or pathological symptoms are diagnosed or determined or can be diagnosed or determined by the attending physician. Thereby, prior to the herein disclosed medical interventions, particular advantage can and shall also be taken of the means and methods disclosed herein for determining the susceptibility for, predisposition for or the presence of a corresponding disorder or disease.

In an additional main aspect, the present invention relates to a method of screening for a compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof comprising the steps of (a) contacting OPA1 with OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof in the presence of said compound to be screened for under conditions allowing OPA1 processing to occur; and (b) evaluating whether OPA1 processing is altered compared to a control, wherein OPA1 and OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof are contacted in the absence of said compound to be screened for under conditions allowing OPA1 processing to occur (herein referred to as "control sample").

The herein disclosed method of screening may further comprise the step of determining the extent of OPA1 processing in the test sample and in the control sample and/or the step of comparing the corresponding results from the test sample with those of the control sample. Thereby, if the extent of OPA1 processing in the test sample differs from that of the control sample, the compound to be screened for is considered to be a modulator of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, i.e. a "compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof in accordance with the present invention.

If the extend of OPA1 processing in the test sample exceeds that of the control sample, the compound screened is considered to be an "agonist" of said oligomeric complex in accordance with the present invention. If the extend of OPA1 processing in the test sample falls short of that of the control sample, the compound screened is considered to be an "antagonist" of said oligomeric complex in accordance with the present invention.

The terms "agonist" and "antagonist" are known in the arts and it is to be understood that both agonists as well as antagonists capable of modulating the activity of OMA1 and/or an oligomeric complex comprising OMA1 and/or HIDG1A and/or OPA1 and/or BNIP3 and/or YME1L1 and/or PHB and/or SAMM50 and/or IMMT and/or PHB2 or (a) variant(s) thereof can provide desirable effects for a patient in need of medical intervention.

A person skilled in the art is, based on the teaching provided herein, readily in a position to select the appropriate medical intervention, i.e. agonist or antagonist, for a patient in need of such intervention based on the evaluation of said biomarker(s). Suitable means and methods for therapeutic intervention and selection of these interventions based on the disclosed biomarker(s) may be referred to as personalized medicine and/or precision medicine.

According to the present invention, methods for the treatment, prevention and/or amelioration of (i) a disorder or disease correlated with mitochondrial dysfunction, or a mitochondrial disorder or disease; or (ii) a disorder or disease characterized by OPA1 alterations, comprise the administration to a patient in need of medical intervention a pharmaceutically active amount of a compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

According to the present invention, methods of screening for a compound capable of modulating the activity of OMA1 and/or an oligomeric complex comprising OMA1 and/or HIGD1A and/or OPAL and/or BNIP3 and/or YME1L1 and/or PHB and/or PHB2 and/or SAMM50 and/or IMMT or (a) variant(s) thereof comprise the steps of (a) contacting OPA1 with said OMA1 and/or oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof in the presence of said compound to be screened for under conditions allowing OPA1 processing to occur; and (b) evaluating whether OPA1 processing is altered compared to a control, where OPA1 and OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof are contacted in the absence of said compound to be screened for under conditions allowing OPAL processing to occur.

According to the present invention, methods for determining the susceptibility for, predisposition for or the presence of (i) a disorder or disease correlated with mitochondrial dysfunction or a mitochondrial disorder or disease; or (ii) a disorder or disease characterized by OPA1 alterations, comprise the steps of (a) obtaining a sample from the subject and measuring the activity of OMA1 and/or YME1L1 or (a) combination(s) thereof in the sample, and/or measuring the gene expression levels of OMA1, HIGD1A, OPA1, BNIP3, YME1L1, PHB, SAMM50, IMMT and/or PHB2 or (a) combination(s) thereof in the sample, and/or measuring the protein levels of OMA1, HIGD1A, OPA1, BNIP3, YME1L1, PHB, SAMM50, IMMT and/or PHB2 or (a) combination(s) thereof in the sample;

(b) comparing the increase and/or decrease of measured activity and/or gene expression levels and/or protein levels of OMA1 and/or HIGD1A and/or OPA1 and/or BNIP3 and/or YME1L1 and/or PHB and/or SAMM50 and/or IMMT and/or PHB2 or (a) combination(s) thereof in the sample compared to a reference;

(c) integrating the results of these measurements through combination of 3 or more genes selected from the group of OMA1, HIGD1A, OPA1, BNIP3, YME1L1, PHB, SAMM50, IMMT and PHB2.

According to the present invention, compounds are capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof for the treatment, prevention and/or amelioration of:

(i) a disorder or disease correlated with mitochondrial dysfunction or a mitochondrial disorder or disease; or (ii) a disorder or disease characterized by OPA1 alterations, wherein said oligomeric complex is defined as in claim 1, said compound is defined as in claim 1, said disorder or disease is defined as in claim 3 and/or said OPA1 alterations, wherein said altered OPA1 processing is characterized by an altered (decrease of a) certain amount of at least one large isoform of OPA1, an altered (increase of a) certain amount of at least one small isoform of OPA1 and/or an altered (decrease of a) certain ratio of at least one large versus at least one small isoform of OPA1 compared to a control/standard.

According to the present invention, methods of treating a disease or disorder in a patient comprise administering to a patient in need of such treatment a therapeutically effective amount of a compound according to the present invention.

According to the present invention, pharmaceutical compositions comprise a compound according to the present invention and a pharmaceutically acceptable excipient.

According to the present invention, methods of treating a disease or disorder in a patient comprise administering to a patient in need of such treatment a therapeutically effective amount of the pharmaceutical composition according to the present invention.

According to the present invention, a combination two or more methods according to the present invention result in a medical intervention individualized for one or more patients and that may be referred to as personalized medicine and/or precision medicine.

BRIEF DESCRIPTION OF THE DRAWINGS

The drawings described herein are for illustration purposes only. The drawings are not intended to limit the scope of the present disclosure.

FIGS. 4A-4B shows expression levels of ONA1 in human hepatocytes for Huh7.5.1 cells not exposed and exposed to Ribavirin (CAS #36791-04-5).

FIG. 8 shows data ranges for OPA1, OMA1, HIGD1A, BNIP3, YME1L1, PHB, PHB2, SAMM50 and IMMT gene expression levels in tissue samples from patients with breast cancer (top) and lung cancer (bottom).

FIG. 9 shows data ranges for OPA1, OMA1, HIGD1A, BNIP3, YME1L1, PHB, PHB2, SAMM50 and IMMT gene expression levels in tissue samples from patients with gastric cancer (top) and ovarian cancer (bottom).

FIG. 20 shows a list of different drugs and compounds that can modify OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

FIGS. 22A-22B shows OMA1 gene expression levels of SUM139 cells following exposure to micro-RNA miR-203 (NCBI Reference Sequence: NR_029620.1).

FIGS. 24A-24B shows OMA1 gene expression levels in monocyte derived macrophages following exposure to small cytokine CXCL4.

DETAILED DESCRIPTION

Figure 1:
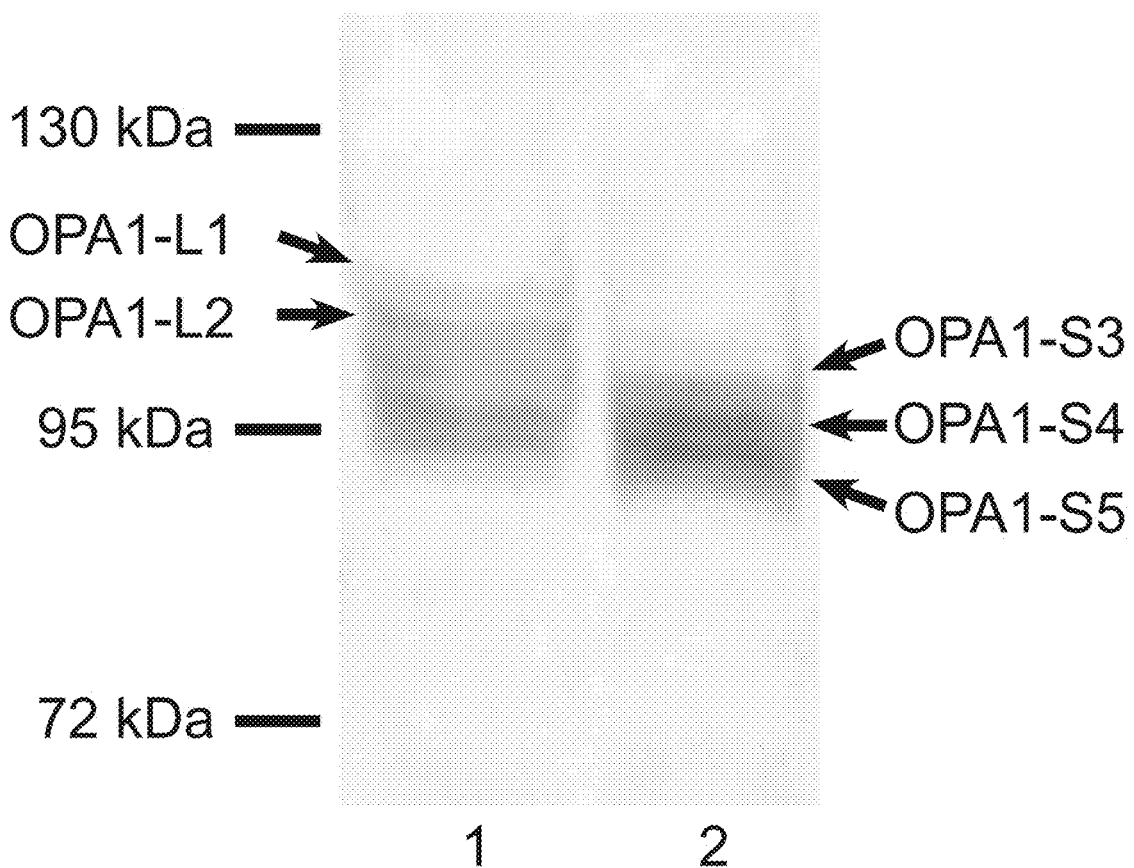
FIG. 1 shows an Illustration of the 5 human OPA1 isoforms resolved by SDS-PAGE/Western-blot.

The terms "personalized medicine" and "precision medicine" are known in the arts and involve, inter alia, the use of molecular markers that characterize a patient's disease to direct the medical care the patient receives.

The terms "agonist" and "antagonist" are known in the arts. If the extend of OPA1 processing in the test sample exceeds that of the control sample, the compound screened is considered to be an "agonist" of said oligomeric complex in accordance with the present invention. If the extend of OPA1 processing in the test sample falls short of that of the control sample, the compound screened is considered to be an "antagonist" of said oligomeric complex in accordance with the present invention.

The term "conditions allowing OPA1 processing to occur" means that OPA1, i.e. one or more of its spliceforms, can be proteolytically cleaved to form one or more of the OPA1 isoforms, whenever an agent/compound capable to cleave OPA1, i.e. capable to trigger OPA1 processing, is present. In other words, said "conditions" are such that said agent/compound capable to cleave OPA1 is active.

In general, the term "oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof" as described and defined in context of this invention (also referred to herein as "oligomeric complex") refers to a certain kind of protease, OMA1 and any interacting protein.

It is of note that at least one subunit comprised in the herein defined oligomeric complex must be proteolytically active regardless whether the remaining subunits are. Otherwise said oligomeric complex would not be proteolytically active. Irrespective whether active or not, all subunits, however, must be assembly competent with respect to said oligomeric complex.

From the above, it is evident that the herein described "oligomeric complex" can be a homo-oligomeric complex or a hetero-oligomeric complex.

The meaning of the terms "OMA1" and "HIGD1A" and "BNIP3" and "OPA1" and "YME1L1" and "PHB" and "SAMM50" and "IMMT" and "PHB2" is well known in the art and is, if not explicitly prescribed differentially, used accordingly in context of the present invention. In context of this invention, these terms are likewise used to refer to the corresponding nucleotide sequences (e.g. the genes) as well as to the corresponding polypeptides (e.g. the polypeptides encoded by said genes). In a specific embodiment of this invention, the oligomeric complex as defined and described herein comprises a polypeptide selected from the group consisting of:

(a) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(b) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.

(c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(d) a polypeptide comprising an amino acid sequence being homologous to the polypeptide of any one of (a) to (c);

(e) a polypeptide comprising an amino acid sequence encoded by a nucleic acid molecule being homologous to the nucleic acid molecule as defined in any one of (b) to (c);

(f) a polypeptide comprising an amino acid sequence encoded by a nucleic acid molecule hybridizing (under stringent conditions) to the complement stand of a nucleic acid molecule as defined in any one of (b) to (c); and (g) fragment of a polypeptide of any one of (a) to (f).

The polypeptides as defined in (d) to (g) and the nucleic acid molecule as defined in (c) to (g) are, for example, "variants" in accordance with the present invention.

"Homologous" or "homology" as used in context of this invention, for example, means at least 50%, at least 60%, at least 70%, at least 80%, at least 85%, at least 90%, at least 95%, at least 98% or at least 99% identical on the level of the amino acid or nucleic acid sequence. Thereby, the higher values of percentage are preferred.

It is of note that the meaning of the terms "nucleic acid molecule", "nucleic acid sequence" or "nucleotide sequence", and the like, as used herein are well known in the art and, for example, comprise DNA (e.g. cDNA or gDNA) and RNA (e.g. mRNA or siRNA).

The term "variant(s)" of the subunits comprised in the "oligomeric complex" is also intended to encompass "(a) fragment(s)" of said subunits (or of the mentioned variants thereof). Thereby, the term "fragment(s)" means amino acid stretches of at least 50, at least 100, at least 150, at least 200, at least 300, at least 500 or at least 700 amino acids of the "subunits" defined herein, or nucleotide stretches of at least 150, at least 300, at least 450, at least 600, at least 900, at least 1500 or at least 2100 nucleotides of the corresponding nucleic acid sequences defined herein.

In context of the present invention the meaning of the mentioned term "variant(s)" also encompasses conservative amino acid exchanges and further known modifications.

The meanings of terms like "OPA1", "OPA1 alterations", "OPA1 processing", "proteolytic cleavage of OPA1", "large/small OPA1 isoforms", and the like, are known in the art (Duvezin-Caubet et al. 2006; Ishihara et al. 2006) and can also be deduced from PCT/EP2007/004466 (claiming priority to U.S. 60/801,484) and PCT/EP2008/005400 (claiming priority to U.S. Ser. No. 12/667,329). Moreover, the corresponding definitions given herein-below, apply here mutatis mutandis.

As mentioned above, a "compound" to be employed, i.e. to be administered, in context of this invention can be any compound "capable of (specifically) modulating the activity, function and/or expression of OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof".

In one specific embodiment, such a "compound" is intended to be a compound screened for by the corresponding method of screening of this invention.

Generally, it is intended herein that a "compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof" as employed herein is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

The definitions of the term "activity" given herein-above apply here, mutatis mutandis. In a specific embodiment of this invention an "agonist" or "antagonist" is a molecule compound selected from the group consisting of:

(a) a binding molecule that (specifically) binds to/interacts with OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined herein or (specifically) binds to/interacts with a nucleic acid molecule encoding ((a) subunit(s) of) OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined herein;

(b) a nucleic acid molecule capable of specifically introducing an insertion of a heterologous sequence or a mutation into a nucleic acid molecule encoding ((a) subunit(s) of) OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined herein via in vivo mutagenesis;

(c) a nucleic acid molecule capable of specifically reducing the expression of mRNA encoding ((a) subunit(s) of) OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined herein by cosuppression; and (d) a low molecular weight compound or a small molecule, for example being capable of inhibiting the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined herein.

Non-limiting examples of a binding molecule as employed in context of this invention are is selected form the group consisting of antibodies, affybodies, trinectins, anticalins, aptamers, PNA, DNA or RNA, and the like.

Based on prior art literature, the person skilled in the art is familiar with obtaining specific binding molecules that may be useful in the context of the present invention. These molecules are directed and bind/interact specifically to or specifically label the oligomeric complex as defined herein or nucleotide sequences encoding (a) subunit(s) thereof.

For example, such binding molecules may, inter alia, be selected from the group consisting of:

(a) an antibody that specifically binds to the polypeptide or the nucleic acid molecule as defined herein-above or to ((a) subunit(s) of) OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined herein;

(b) an antisense nucleotide sequence that specifically hybridizes to the nucleic acid molecule as defined herein-above;

(c) a siRNA that specifically interacts with the nucleic acid molecule as defined herein-above;

(d) an aptamer that specifically binds to the polypeptide or the nucleic acid molecule as defined herein-above or to ((a) subunit(s) of) OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined herein; and (e) a ribozyme that specifically interacts with the nucleic acid molecule as defined herein-above.

A binding molecule (for example an antibody) to be employed in context of this invention may, for example, (specifically) bind to a particular epitope of the herein defined (subunit(s) of) OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof. Preferably, this particular epitope is essential for the activity of said complex, like, for example, an epitope comprising the active center of said complex. Moreover, such an epitope may, for example, comprise the consensus amino acid sequence of the metal binding site.

In this context, it is to be understood that the person skilled in the art is, based on the teaching provided herein, readily in a position to deduce (further) amino acid stretches/peptides being specific for (a particular subunit of) the oligomeric complex defined herein and therefore, representing an "epitope" as employed herein.

The antibody useful as a binding molecule in context of the present invention (commonly known as therapeutic antibody) can be, for example, polyclonal or monoclonal. The term "antibody" also comprises derivatives or fragments thereof which still retain the binding specificity. Techniques for the production of antibodies are well known in the art and described, e.g. in Harlow and Lane "Antibodies, A Laboratory Manual", CSH Press, Cold Spring Harbor, 1988. These antibodies can be used as particular binding molecules defined herein. Surface plasmon resonance as employed in the BIAcore system can be used to increase the efficiency of phage antibodies which bind to an epitope of the polypeptide/complex employed in this invention. Accordingly, also phage antibodies can be used in context of this invention.

The present invention furthermore includes the use of chimeric, single chain and humanized antibodies, as well as antibody fragments, like, inter alia, Fab fragments. Antibody fragments or derivatives further comprise F(ab')2, Fv or scFv fragments. Accordingly, in context of the present invention, the term "antibody molecule" relates to full immunoglobulin molecules as well as to parts of such immunoglobulin molecules. Furthermore, the term relates, as discussed above, to modified and/or altered antibody molecules, like chimeric and humanized antibodies. The term also relates to monoclonal or polyclonal antibodies as well as to recombinantly or synthetically generated/synthesized antibodies. The term also relates to intact antibodies as well as to antibody fragments thereof, like, separated light and heavy chains, Fab, Fab/c, Fv, Fab', F(ab')2. The term "antibody molecule" also comprises bifunctional antibodies, trifunctional antibodies and antibody constructs, like single chain Fvs (scFv) or antibody-fusion proteins.

Non-limiting examples of a low molecular weight compound or a small molecule to be employed as "agonist" or "antagonists" herein are any protease inhibitors or metal chelators, such as EDTA (CAS #60-00-4), phenanthroline (CAS #66-71-7), Deferiprone (CAS #30652-11-0), Deferasirox (CAS #201530-41-8) capable of inhibiting, preferably specifically inhibiting, the activity of the oligomeric complex described herein.

Particularly, metalloprotease inhibitors (like phenantrolin, DCI, and the like) are intended to be employed as low molecular weight compound or a small molecule in context of the present invention.

A further low molecular weight compound or a small molecule as employed in context of this invention may, for example, be a nucleotide analog, such as, for example, ATPγS, and the like.

As mentioned, in one particular embodiment, the "agonist" or "antagonist" to be employed is a nucleic acid molecule that leads to a reduction or depletion of the activity of the oligomeric complex defined herein via in vivo mutagenesis. Thereby, without being bound by theory, an insertion of a heterologous sequence or a mutation into a nucleotide sequence encoding a subunit of said complex, leads to a reduction of the amount of said subunit and hence, to a reduced expression of the intact complex. Generally, methods of "in vivo mutagenesis" (also known as "chimeroplasty") are known in the art. In such methods, a hybrid RNA/DNA oligonucleotide (chimeroplast) is introduced into cells (WO 95/15972; Kren, Hepatology 25 (21997), 1462-1468; Cole-Stauss, Science 273 (1996), 1386-1389). Without being bound by theory, a part of the DNA component of the RNA/DNA oligonucleotide is thereby homologous to a nucleotide sequence occurring endogenously in the cell and encoding a corresponding protein, but displays a mutation or comprises a heterologous part which lies within the homologous region. Due to base pairing of the regions of the RNA/DNA oligonucleotide which are homologous to the endogenous sequence with these sequences, followed by homologous recombination, the mutation or the heterologous part contained in the DNA component of the oligonucleotide can be introduced into the cell genome. This leads to a reduction of the activity, i.e. expression, of the gene, into which the heterologous part or the mutation has been introduced.

In view of the above, it is clear that the nucleic acid molecule causing in vivo mutagenesis may comprise a heterologous sequence or a sequence carrying a mutation flanked by parts of a nucleotide sequence encoding a subunit of the oligomeric complex defined herein.

In a further particular embodiment of the invention, the "agonist" or "antagonist" to be employed is a nucleic acid molecule that leads to a reduction or depletion of the activity of the oligomeric complex defined herein by a cosuppression effect. "Cosuppression effect" means that the synthesis of a nucleotide sequence, particularly of an RNA, in a living cell reduces the expression of a gene being homologous to said nucleotide sequence. The general principle of cosuppression and corresponding methods are well known to the person skilled in the art and are described, for example, in Pal-Bhadra (Cell 90, 1997), 479-490) and Birchler (Nature Genetics 21 (1999), 148-149). In a particular embodiment, the nucleic acid molecule causing a cosuppression effect comprises a nucleotide sequence encoding a subunit of the oligomeric complex defined herein or a fragment of said nucleotide sequence.

In another specific embodiment of this invention an "agonist" is a molecule selected from the group consisting of:

(a) a polypeptide as defined herein above, for example a subunit of the herein defined oligomeric complex or said oligomeric complex itself, or a nucleotide sequence comprising a nucleic acid molecule as defined herein above, for example a nucleic acid molecule encoding a subunit of the herein defined oligomeric complex;

(b) a low molecular weight compound or a small molecule, for example being capable of enhancing the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined herein; and (c) a binding molecule as defined herein, wherein said binding molecule is agonistic with respect to the activity of the oligomeric complex as defined and described herein (for example an agonistic antibody or agonistic aptamer).

Particularly, a low molecular weight compound or a small molecule as employed in context of this invention may be a compound/molecule having a molecular weight of less than about 2500 g/mol, preferably less than about 1500 g/mol, more preferably less than about 1000 g/mol and most preferably less than about 500 g/mol.

The skilled person is readily in the position to find out whether a certain binding molecule as defined herein is an agonist (for example an agonistic antibody or agonistic aptamer) or an antagonistm1 (for example an antisense nucleotide sequence, siRNA or ribozyme).

Based on the findings provided herein, it is envisaged in one embodiment of this invention that particular such oligomeric complexes are administered, the subunit composition of which varies dependent on the tissue affected by the disease or disorder to be addressed, i.e. dependent on cell type specific mitochondrial defects. In other words, based on the teaching provided herein, the subunit composition of the oligomeric complex may be adjusted to (a) particular tissue(s) affected by a disorder or disease described herein.

It is envisaged herein that the compound to be administered in accordance with this invention may, optionally, comprise a pharmaceutically acceptable carrier and/or diluent.

Examples of suitable pharmaceutically acceptable carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. The resulting pharmaceutical compositions can be administered to the subject at a suitable dose, i.e. a dose leading to a pharmaceutically active amount of the compound to be employed/used herein at its desired site of effect.

Administration of the compound to be administered in accordance with the present invention may be effected by different ways, e.g., by intravenous, intraperitoneal, subcutaneous, intramuscular, topical, intradermal, intranasal or intrabronchial administration (for example as effected by inhalation) or by direct administration (for example injection) into a particular tissue or organ.

The dosage regimen of the compound to be administered in accordance with this invention will be determined by the attending physician and clinical factors. As it is well known in the medical arts, dosages for any one patient depends upon many factors, including the patient's size, body surface area, age, the particular compound to be administered, sex, time and route of administration, general health, and other drugs being administered concurrently. A person skilled in the art is aware of and is able to test the relevant doses, the compounds to be used in terms of the present invention are to be administered in.

In the context of the invention, it is of note that a preferred subject/patient in the context of the present invention is a mammalian subject/patient, more preferably a primate subject/patient, most preferably a human being, preferably in need of medical intervention, either in form of treatment, prevention and/or amelioration.

In a particular embodiment, the method for medical intervention provided, and hence the corresponding compound to be administered, are envisaged to be employed in context of gene therapy. This is particularly envisaged, when the "compound" as employed herein is or comprises (a) nucleic acid molecule(s) or is encoded by (a) nucleic acid molecule(s). For example, such corresponding nucleic acid molecule(s) may then be employed in form of an insert comprised in a vector, particularly in an expression vector. Such (expression) vector may particularly be a vector suitable for gene therapy approaches (for example a viral (expression) vector).

Gene therapy, which is based on introducing therapeutic genes into cells by ex-vivo or in-vivo techniques is one of the most important applications of gene transfer. Suitable vectors, methods or gene-delivering systems for in-vitro or in-vivo gene therapy are described in the literature and are known to the person skilled in the art.

In another particular embodiment, the method for medical intervention provided, and hence the corresponding compound to be administered, are envisaged to be employed in context of gene silencing through RNAi (RNA-interference) by use of short interfering RNA (siRNA) or any other approach suitable to suppress gene expression and/or protein levels by at least 5%, 10%, 20%, 30%, 40%, 50%, 60%, 70% 80%, 90% 95%, or 99%.

The CRISPR/Cas9 systems has emerged as a powerful tool for genomic modification and regulation of gene expression in mammalian cells. In other aspects, the invention is envisioned to also provide compositions and methods for targeted regulation of endogenous genes encoding OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof as defined herein by use of the CRISPR-Cas reagents. Like the compositions and methods for genome editing, the compositions and methods for genome modulation by transcription regulation utilize the highly targeted DNA binding activity of artificial CRISPR-Cas components, where targeting of a modified Cas9 protein to a promoter region of interest can result in either transcriptional activation or transcriptional repression. The invention also provides for multiplex gene regulation, where more than one gene can be simultaneously targeted for transcriptional modulation (either up regulation or down regulation).

The nucleic acid molecules and vectors may be designed for direct introduction or for introduction via liposomes, viral vectors (e.g. adenoviral, retroviral), electroporation, ballistic (e.g. gene gun) or other delivery systems into the cell. Additionally, a baculoviral system can be used as eukaryotic expression system for the above-defined nucleic acid molecules. The introduction and gene therapeutic approach should, preferably, lead to the expression of a functional "compound" in accordance with this invention (for example an antisense or siRNA construct), whereby said expressed "compound" is particularly useful in the treatment, amelioration and/or prevention of the diseases or disorders defined herein.

The term "vector" as used herein particularly refers to plasmids, cosmids, viruses, bacteriophages and other vectors commonly used in genetic engineering. In a preferred embodiment, the vectors of the invention are suitable for the transformation of cells, like fungal cells, cells of microorganisms such as yeast or bacterial cells or animal cells. As mentioned, in a particularly preferred embodiment such vectors are suitable for use in gene therapy.

In one aspect of the invention, the vector to be employed is suitable for stable transformation of an organism, and hence is an expression vector. Generally, expression vectors have been widely described in the literature. As a rule, they may not only contain a selection marker gene and a replication-origin ensuring replication in the host selected, but also a promoter, for example a promoter as defined herein, and in most cases a termination signal for transcription. Between the promoter and the termination signal there is in general at least one restriction site or a polylinker which enables the insertion of a nucleotide sequence desired to be expressed.

Examples of vectors suitable to comprise the nucleic acid molecule(s) as employed in context of the present invention are known in the art.

As mentioned, the meanings of terms like "OPA1 alterations", "OPA1 processing" and "proteolytic cleavage of OPA1" are known in the art and can also be deduced from PCT/EP2007/004466 and PCT/EP2008/005400. These known definitions apply in context of this invention, if not explicitly defined otherwise.

In view of this, "OPA1 alterations" as defined herein is intended to be characterized by a certain amount of at least one large isoform of OPA1, a certain amount of at least one small isoform of OPA1 and/or a certain ratio of at least one large versus at least one small isoform of OPA1. Thereby, the OPA1 isoforms are formed by proteolytic cleavage of OPA1, i.e. of one or more of the OPA1 spliceforms. Usually, in mammalian cells, "OPA1 processing" usually occurs to a relatively moderate extent, referred to herein as "normal OPA1 processing" or simply "OPA1 processing". In difference to this, "altered OPA1 processing" or "OPA1 alterations" as defined herein is intended to be characterized by an altered amount of at least one large and/or at least one small isoform of OPA1 and/or an altered ratio of at least one large versus at least one small isoform of OPA1 (due to an altered proteolytic cleavage of OPA1) as compared to a control/standard. "Control/standard" in this context means a physiological condition, where "normal OPA1 processing" or simply "OPA1 processing" occurs (For example in healthy living cells, like the HEK293T cells cells employed herein).

Large isoform(s) of OPA1 as defined herein have an apparent molecular weight of more than about 95 kD and small isoform(s) as defined herein have an apparent molecular weight of less than about 95 kD, when said molecular weights being determined by SDS-PAGE analysis, as disclosed herein and described in the appended drawings (FIG. 1).

It is evident for the person skilled in the art that also other SDS gels and means (in particular Western-Blot analysis and the like) are useful and envisaged in context of the present invention. It is of note that the herein given value of 91 kD is, accordingly, an illustrative example and the person skilled in the art can also use other means to deduce the identity, amount and/or ratio of the herein described OPA1 isoforms (e.g. the presence or absence of said OPA1-isoforms) in a given sample to be analyzed. For example, said large OPA1 isoforms have an apparent molecular weight of more than about 95 kD or, preferably, of more than about 99 kD and the small OPA1 isoforms have an apparent molecular weight of less than about 95 kD or, preferably, of more than about 99 kD, when said molecular weights being determined by peptide analysis, e.g. mass spectrometry.

In context of the present invention, "OPA" or "OPAL" means the optic atrophy 1 protein/gene, in particular OPA1 of human origin. Yet, in certain embodiments it is also envisaged that OPA1 of other organisms, e.g. of mouse, rat, pig, dog, bovine species or fruit fly, be assessed in context of this invention. The nucleotide and amino acid sequences of human OPA1, particularly of the eight spliceforms of OPA1, are given in the appended sequence listing and examples.

The same applies for "OMA1", "HIGD1A", "YME1L1", "SAMM50", "IMMT", "PHB", "PHB2", and "BNIP3", the nucleotide and amino acid sequences of human OMA1, HIGD1A, YME1L1, SAMM50, IMMT, PHB, PHB2, and BNIP3 are given in the appended sequence listing.

It is of note that the nucleotide and amino acid sequences of OPA1, OMA1, HIGD1A, YME1L1, SAMM50, IMMT, PHB, PHB2, and BNIP3 given herein below are not limiting. Accordingly, the terms "OPA1", "OMA1", "HIGD1A", "YME1L1", "SAMM50", "IMMT", "PHB", "PHB2", and "BNIP3" also encompasses OPA1, OMA1, HIGD1A, YME1L1, SAMM50, IMMT, PHB, PHB2, and BNIP3 proteins/genes having amino acid or nucleotide sequences being derivatives of those given sequences.

In terms of the present invention the term "derivatives" or "derivatives thereof" or "variants" refers to amino acid or nucleotide sequences being homologous to the amino acid or nucleotide sequences shown herein, e.g. those of human OPA1, and/or amino acid or nucleotide sequences as shown herein, e.g. those of human OPA1, but having (a) particular (conservative) amino acid(s) exchanged. For instance, in context of the present invention, "homologous" means that amino acid or nucleotide sequences have identities of at least 50%, 60%, 70%, 80%, 90%, 95%, 98% or 99% to the sequences shown herein, e.g. those of human OPA1, wherein the higher identity values are preferred upon the lower ones.

As shown herein and in the arts, upon drug-induced apoptosis, processing of OPA1 and mitochondrial fragmentation precedes cytochrome c release. When the mitochondrial membrane potential is dissipated, processing of OPA1 and fragmentation of mitochondria can be observed.

Yet, based on the teaching provided in context of this invention, mitochondrial dysfunction (or a corresponding mitochondrial disease or disorder) is not merely correlated with decrease of any one of OPA1 isoforms, but with a decrease of particularly the large isoforms, e.g. OPA1-L1 (as defined herein) and OPA1-L2 (as defined herein), accompanied by an increase of the small isoforms, e.g. OPA1-S3 (as defined herein), OPA1-S4 (as defined herein), and OPA1-S5 (as defined herein).

In context of the present invention, the term "about", with respect to certain given molecular weight values, means +/−3 kD, preferably +/−2 kD, more preferably +/−1 kD, more preferably +/−0.5 kD and most preferably +/−0.1 kD. Moreover, in context of the present invention, it is envisaged that the term "less than about xx kD", for example "less than about 91 kD", "less than about 95 kD" or "less than about 99 kD", also comprises molecular weight values being equal to xx kD, for example equal to 91, 95 kD or 99 kD.

It is evident for the person skilled in the art that certain given molecular weight values may vary, dependent on the preparational/experimental conditions employed, or, for example with respect to mass spectrometry, dependent on the information content resulting from the preparational/experimental method employed or dependent on an employed modification of the proteins/peptides to be analyzed due to a specific preparational/experimental procedure. It is, for example, known in the art that proteins/peptides to be analyzed via mass spectrometry can be modified, i.e. their theoretical molecular weight can be increased (e.g. by certain chemical modifications) or decreased (e.g. by using (a) certain protease(s)) by a certain value. It is therefore of note in context of the present invention that the molecular weight values given for certain OPA1 isoforms can change, dependent on the particular preparational/experimental conditions employed during the corresponding mass spectrometry experiment (or other methods for determining molecular weights). The skilled person is readily in the position to deduce whether certain changes/differences of given molecular weight values result from the particular preparational/experimental method employed or form a specific composition of the protein/peptide analyzed.

In context of the present invention, the term "isoform" of OPA1 means a certain form of the OPA1 protein. Without bound by theory, an OPA1 isoform derives from (a protein encoded by) any one of spliceforms 1 to 8 of OPA1, e.g. by posttranslational processing (e.g. proteolytical processing). Without bound by theory, said posttranslational processing (e.g. proteolytical processing) leads to a shortened N-terminus of OPA1, particularly of the spliceforms thereof, wherein the C-terminus remains complete. The "isoforms" of OPA1 to be scrutinized in context of the present invention are described herein in more detail. Accordingly, the term "corresponding" in context of OPA1 isoforms and OPA1 spliceforms, e.g. in the term "an OPA1 isoform having an apparent molecular weight calculated from amino acid sequences of the corresponding spliceform(s)", means that the respective OPA1 isoform can be related to or may be derived from said OPA1 spliceform(s). These spliceforms are also described herein below.

In context of the present invention, the term "spliceform" or "splice variant" of OPA1 means a form of OPA1 that emerges by alternative splicing of the primary transcript transcribed from the OPA1 gene. It is envisaged herein, that the term "spliceform" either refers to the mature transcript generated by alternative splicing, but also refers to the corresponding protein which has been translated from said mature transcript. Accordingly, the term "isoform being derived from (corresponding) spliceform" means that an OPA1 isoform originates from a protein that has been translated from a mature (alternatively spliced) transcript of the OPA1 gene. Thereby, posttranslational processing (e.g. proteolytical processing) of said protein that has been translated from a mature (alternatively spliced) transcript of the OPA1 gene may occur. However, an OPA1 isoform may also directly originate from said protein, without further posttranslational processing. In such specific case, said protein then is said OPA1 isoform.

At present, 8 spliceforms of OPA1 are known in the art, which emerge by alternative splicing of exon 4, exon 4b and/or exon 5. The corresponding amino acid sequences of these 8 spliceforms are given in SEQ ID NO: 2, 4, 6, 8, 10, 12, 14 and 16. Their corresponding nucleotide acid sequences are given in SEQ ID NO: 1, 3, 5, 7, 9, 11, 13 and 15.

Dependent whether exon 4, exon 4b and/or exon 5 is comprised, the OPA1 spliceforms can be defined by specific amino acid sequences, e.g. by one of the following amino acid sequences:

EYKWIVPDIVWEIDEYIDFGHKLVSEVIG-ASDLLLLL (SEQ ID NO: 60) corresponds to the amino acid sequences from exon 3 to exon 4b (lack of exon 4) and is comprised in spliceforms 3 and 6.

EYKWIVPDIVWEIDEYIDFGSPEETAFRATDRGS-ESDKHFRK (SEQ ID NO: 61) corresponds to the amino acid sequences from exon 3 to exon 5 (lack of exon 4 and 4b) and is comprised in spliceforms 2 and 4.

EKIRKALPNSEDLVKLAPDFD-KIVESLSLLKDFFTSGSPEETAFRATDRGSESDKHFRK (SEQ ID NO: 62) corresponds to the amino acid sequences from exon 4 to exon 5 (lack of exon 4b) and is comprised in spliceforms 1 and 7.

GSPEETAFRATDRGSESDKHFRKVSD-KEKIDQLQEELLHTQLKYQRILERLEKENKELRK (SEQ ID NO: 63) corresponds to the amino acid sequences from exon 5 to exon 6 (lack of exon 5b) and is comprised in spliceforms 1, 2, 3 and 5.

Other amino acid sequences specific for a certain OPA1 spliceform can be derived from the amino acid sequences of the OPA1 spliceforms given herein below.

Since an OPA1 isoform to be employed in context of the present invention may be derive from one particular OPA1 spliceform, the above mentioned amino acid sequences defining the different OPA1 spliceforms may also be used to determine the identity, amount and/or ratio (e.g. the presence or absence) of a given OPA1 isoform as defined herein. For example, since the present invention provides evidence that OPA1-L1 be derived from spliceform 7 and OPA1-L2 be derived from spliceform 1, OPA1-L1 may, e.g. be characterized in that it comprises the amino acid sequence EKIRKALPNSEDLVKLAPDFD-KIVESLSLLKDFFTSGSPEETAFRATDRGSESDKHFRK (SEQ ID NO: 62) and in that it not comprises the amino acid sequence. GSPEETAFRATDRGSESDKHFRKVSD-KEKIDQLQEELLHTQLKYQRILERLEKENKELRK (SEQ ID NO: 63) and OPA1-L2 may, e.g. be characterized in that it comprises the amino acid sequence EKIRKA-LPNSEDLVKLAPDFD-KIVESLSLLKDFFTSGSPEETAFRATDRGSESDKHFRK (SEQ ID NO: 62) and GSPEETAFRATDRGS-ESDKHFRKVSDKEKIDQLQEELLHTQLKYQRILER-LEKENKELRK (SEQ ID NO: 63).

However, since the OPA1 isoforms to be employed in context of the present invention may derive from the OPA1 spliceforms by (proteolytical) processing, not the complete amino acid sequences as given above, but fragments or derivatives thereof, may be used to determine a certain OPA1 isoform.

The meaning of the term "Mass spectrometry" (MS) is, and corresponding methods, are known in the art. Particularly useful "mass spectrometry" methods to be employed in context of the present invention are MALDI-MS or LC-MS/MS. Further "mass spectrometry" methods are known in the art and can easily be adapted to the specific needs of the present invention by a person skilled in the art.

The term "molecular weights being determined by mass spectrometry" means that the apparent molecular weight of a certain OPA1 isoform is determined by performing mass spectrometry analysis on said OPA1 isoform and using the results of said mass spectrometry analysis to calculate said apparent molecular weight of said certain OPA1 isoform on the basis of the amino acid sequence of OPA1 Since eight alternative spliceforms exist of OPA1, having different amino acid sequences, the result of said calculation may vary, dependent on the spliceform, the amino acid sequence of which is used for said calculation.

It is of note that the so determined theoretical molecular weight may be further increased by the presence of a few further N-terminally located amino acid residues present in the (proteolytically) processed mature OPA1 isoform. The person skilled in the art is readily in the position to determine said slightly increased molecular weight, by taking advantage of the teaching of the present invention.

In context of the present invention, the large isoforms of OPA1 may comprise two isoforms (e.g. OPA1-L1 and OPA1-L2) and the small isoforms of OPA1 may comprise three isoforms (e.g. OPA1-S3, OPA1-S4 and OPA1-S5). However, it is also envisaged that further, possibly existing isoforms may be assigned as large or small isoforms in context of the present invention. For instance, it is evident for a skilled person that, e.g., single bands of an SDS-PAGE/Western-blot as exemplified herein, may represent not only one, but several different isoforms and/or that further isoforms, larger or smaller than the particular isoforms defined herein may be present. For example, particularly the band corresponding to OPA1-S4 as defined herein may correspond to (a) further OPA1 isoform(s). Again, the gist of the present invention is based on the fact the determination of "small" versus "large" isoforms is illustrative for mitochondrial dysfunction and corresponding related disorders/diseases. Therefore, further, possibly existing isoforms may, e.g., be detectable by alternative comparable methods known in the art and may also be taken into consideration in the herein provided methods and means. For example, such methods may be SDS-PAGEs taking advantage of gels having very low polyacrylamide concentrations (e.g. 1%, 2%, 3% or 4%) and/or Western-blots taking advantage of radionuclide labelling, e.g. radionucleotide labelling of (secondary) antibodies used in said Western-blots, or other labelling approaches known in the art, e.g. other very sensitive labelling approaches being suitable for the detection of proteins being present in low amount(s)/concentration(s). Moreover, such methods may be a two dimensional gelelectrophoresis methods. These and other alternative methods for detecting isoforms of certain proteins/genes, like OPA1, are known in the art. It is envisaged that such alternative methods may also be employed in context of the present invention.

However, it is preferred that each single band as evident from the SDS-PAGE analysis as employed and exemplified herein represents one single OPA1 isoform. Accordingly, in one embodiment of the present invention, the two large OPA1 isoforms as defined herein (e.g. OPA1-L1 and OPA1-L2) are represented by two single bands, and the three small OPA1 isoforms as defined herein (e.g. OPA1-S3, OPA1-S4 and OPA1-S5) are represented by three single bands occurring in an SDS-PAGE, e.g. an SDS-PAGE as exemplified herein (FIG. 1).

FIG. 1 shows an illustration of the 5 human OPA1 isoforms resolved by SDS-PAGE/Western-blot. Human HEK293T cells were harvested, solubilized in RIPA buffer, and separated utilizing an 8% Tris-Glycine Gel (Novex, ThermoFisher Scientific, CA). The large bands of OPA1 comprise two isoforms, OPA1-L1 and OPA1-L2, and the small bands of OPA1 comprise three isoforms, OPA1-S3, OPA1-S4 and OPA1-S5 (lane 1). Under conditions allowing OPA1 processing to occur, large OPA1 isoforms are proteolytically cleaved and convert into one or more of the small OPA1 isoforms. OPA1 processing was evoked in this particular non-limiting example by uncoupling of the oxidative phosphorylation through addition of 10 μMCCCP for 30 minutes at 37° C. (lane 2).

In context of the present invention, the two large OPA1 isoforms are indicated by numbers 1 and 2, namely 1 for the largest and 2 for the second largest OPA1 isoform. The three small OPA1 isoforms are indicated by numbers 3, 4 and 5, namely 3 for the largest of the three small isoforms, 4 for the second largest of the three small isoforms and 5 for the smallest isoform. The numbering of the OPA1 isoforms to be employed in context of the present invention is also given in FIG. 1. In accordance thereto the OPA1 isoforms as employed in context of the present invention are termed as follows: OPA1-L/l1, L/l-OPA1 #1, OPA1 #1 or L/l1-OPA1 for the largest OPA1 isoform. OPA1-L/l2, L/l-OPA1 #2, OPA1 #2 or L/l2-OPA1 for the second largest OPA1 isoform. Large isoform(s) in context of the present invention is (are), e.g., OPA1-L1 and/or OPA1-L2. OPA1-S/s3, S/s-OPA1 #3, OPA1 #3 or S/s3-OPA1 for the largest of the three small OPA1 isoforms. OPA1-S/s4, S/s-OPA1 #4, OPA1 #4 or S/s4-OPA1 for the second largest of the three small isoforms. OPA1-S/s5, S/s-OPA1 #5, OPA1 #5 or S/s5-OPA1 for the smallest OPA1 isoform. Accordingly, small isoform(s) in context of the present invention is (are), e.g., OPA1-S3, OPA1-S4 and/or OPA1-S5.

It is of note that the specific numbering is indicative for the specific OPA1 isoform, and that the additional terming, like "l" for large; "s" for small or "OPA", "OPA1" or "OPA1 #" for OPA1 may slightly vary. However, the abbreviations "L" or "l" indicate large isoforms and "S" or "s" indicate small isoforms of OPA1.

In view of the teaching provided herein, also in the appended examples, the OPA1 isoforms employed in context of the present invention are defined as follows:

In one aspect of the present invention, the term "OPA1 isoform" means a protein encoded by the OPA1 gene, but particularly be derived from at least one of the different spliceforms of OPA1 (e.g. from at least one of spliceforms 1 to 8), e.g. by posttranslational (e.g. proteolytical) processing, wherein said proteins are distinguishable by their molecular weight and/or (a) certain amino acid sequence(s). From the above, it is, inter alia, evident that an "OPA1 isoform" as employed in context of the present invention comprises (an) amino acid stretche(s) which unambiguously characterize it as a polypeptide/protein derived from OPA1. In this context, "derived from OPA1" particularly means encoded by the OPA1 gene and/or generated from OPA1 by the herein described and defined OPA1 processing. Thus, an "OPA1 isoform" as employed can particularly be characterized by (a) certain amino acid stretch(es) of any one of SEQ ID NO: 2, 4, 6, 8, 10, 12, 14 or 16 or by (a) certain amino acid stretch(es) encoded by any one of SEQ ID NO: 1, 3, 5, 7, 9, 11, 13 or 15.

In context of the present invention, the term "molecular weight" may, inter alia, refer to the apparent molecular weight. Said apparent molecular weight can be determined by methods known in the art. E.g., said apparent molecular weight can be determined by SDS-PAGE, and, accordingly, also from Western-blots, or can be calculated from the amino acid sequence of OPA1, particularly from the amino acid sequence(s) of the corresponding spliceform(s) by taking advantage of mass spectrometry methods. Examples of the determination of the OPA1 isoforms by using these techniques are given in the appended examples.

As already mentioned above, in context of the present invention, certain given molecular weight values are apparent molecular weight values. It is envisaged, that the certain molecular weight values given herein may slightly vary, e.g. with respect to the molecular weight of the protein present in vivo. Said variation may by in the range of 5 kD, 4 kD, 3 kD, 2 kD, 1 kD, 0.5 kD, 0.4 kD, 0.3 kD, 0.2 kD or 0.1 kD, whereby the smaller variations are preferred over the larger variations. The definitions given for the term "about" with respect to molecular weight values herein above, apply here, mutatis mutandis.

In context of the present invention, large isoforms comprise an isoform having an apparent molecular weight of about 97 kD (96.8 kD) (defined as OPA1-L1) or an isoform having an apparent molecular weight of about 92 kD (92.3 kD) (defined as OPA1-L2), said molecular weights being determined by SDS-PAGE analysis. Moreover, in context of the present invention large isoforms comprise an isoform having an apparent molecular weight of about 104 kD (104.0 kD) or, preferably, of about 105 kD (105.1 kD) (defined as OPA1-L1) or an isoform having an apparent molecular weight of about 99 kD (99.2 kD) or, preferably, of about 100 kD (100.0 kD) (defined as OPA1-L2), said molecular weights being determined by mass spectrometry.

In context of the present invention, small isoforms comprise an isoform having an apparent molecular weight of about 88 kD (88.1 kD) (defined as OPA1-S3), an isoform having an apparent molecular weight of about 84 kD (84.4 kD) (defined as OPA1-S4) or an isoform having an apparent molecular weight of about 81 kD (80.9 kD) (defined as OPA1-S5), said molecular weights being determined by SDS-PAGE analysis. Moreover, in context of the present invention small isoforms comprise an isoform having an apparent molecular weight of about 92 kD (91.8 kD) or, preferably, of about 96 kD (95.9 kD) (defined as OPA1-S3), an isoform having an apparent molecular weight of about 89 kD (89.2 kD) or, preferably, of about 92 kD (91.8 kD) (defined as OPA1-S4) or an isoform having an apparent molecular weight of about 87 kD (86.8 kD) or, preferably, of about 87 kD (86.8 kD) (defined as OPA1-S5), said molecular weights being determined by mass spectrometry.

It is of note that the molecular weight values of the OPA1 isoforms scrutinized herein are given as averaged values corresponding to the molecular weight values of different isoform bands within an SD S-PAGE/Western-blot.

The term "derivatives" or "derivatives thereof" as well as "homologous" as defined here in above, also apply, mutatis mutandis, in context of the peptides shown above, e.g. the peptides comprised in the OPA1 isoforms or the peptides that characterize the OPA1 spliceforms. Moreover, the term "derivatives" or "derivatives thereof" also refers to (a) fragment(s), e.g. (a) fragment(s) of the peptides shown above, e.g. the peptides comprised in the OPA1 isoforms or the peptides that characterize the OPA1 spliceforms. The term "fragment(s)" means amino acid stretches of at least 3, 4, 5, 6, 7, 8, 9, 10, 11, 12, 13, 14, 15, 20, 30, 50, 100 or 150 amino acids. Also, amino acid stretches having other numbers of amino acids are envisaged.

In terms of the present invention the term "derivatives" or "derivatives thereof" also comprises homologies as well as conservative amino acid exchanges and further known modifications.

In a non-limiting example, it is envisaged in context of the present invention that the identity, amount and/or ratio of the large OPA1 isoforms as defined herein, namely OPA1-L1 and OPA1-L2, can be determined via specific detection of any amino acid stretch of the large OPA1 isoforms lying in N-terminal direction to the amino acid stretches corresponding to the N-terminal amino acids of the "most N-terminal peptide(s)" defined herein of the small OPA1 isoform(s), alternatively and preferred lying in N-terminal direction to the amino acid stretches corresponding to the N-terminal amino acid of the small OPA1 isoforms. In analogy to the above, said amino acid stretch to be detected may be any epitope-bearing portion, or, e.g. any other portion to which a binding molecule as defined herein can bind and said detection may be a detection method as defined and exemplified herein, e.g. a detection method taking advantage of corresponding OPA1 antibodies as defined and exemplified herein, or a detection method taking advantage of other corresponding OPA1 binding molecules as defined herein.

In another particular embodiment of this invention, it is envisaged to distinguish between various types of mitochondrial dysfunction(s)/disease(s). In particular, it is envisaged to differentiate between mitochondrial dysfunction(s)/disease(s) dependent on depletion of mitochondrial DNA and other types of mitochondrial dysfunction(s)/disease(s). Moreover, a quantitative measure of mitochondrial dysfunction and the employment of a corresponding adapted medical intervention is also envisaged.

In context of the present invention, it is intended that the identity, amount or ratio of large and/or small isoforms of OPA1 is determined by optical, spectrophotometric and/or densitometric measurements or analysis. Such determination methods are well known in the art. A particular choice of such methods is described in the appended examples. For instance, such methods comprise the SDS-PAGE analysis, Western blots, ELISA, RIA, CLIA, IRMA and/or EIA. These and further methods are known in the art and are, e.g., described in "Cell Biology: Laboratory manual 3rd edition" (2005, J. Celis, editor. Academic Press, New York).

It is also intended that the identity, amount or ratio of large and/or small isoforms of OPA1 is determined by peptide analysis. Again, such peptide analysis methods are well known in the art. For example, such peptide analysis methods comprise mass spectrometry methods, like MALDI-MS or LC-MS/MS. The use of these particular mass spectrometry methods are described in the appended examples.

As detailed herein one gist of the present invention is based on the finding that a determined reduction of large OPA1 isoforms as described herein (OPA1-L1 and/or -L2) and/or a determined increase of small OPA1 isoforms as described herein (OPA1-S3, OPA1-S4 and/or OPA1-S5) is indicative for the presence of or the susceptibility to a mitochondrial disease/disorder/dysfunction.

Ratios between large and small OPA1 isoforms can be deduced from the the activity of OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof as defined herein.

It is understood that the ratios to be determined in context of the present invention may also differ from the ones exemplified above. As already mentioned above, examples that, in a non-limiting manner, describe the evaluation of such ratios are given herein below.

Inter alia, in context of the present invention, the term "ratio" or "density ratio", inter alia, refers to a comparison of density values of bands corresponding to OPA1 isoforms, as, e.g., derived from an SDS-PAGE/Western-blot. Methods how such density values can be obtained are known in the art and exemplified in the appended non-limiting examples.

It is to be understood that not only the comparison of small (OPA1-S3, -S4 and/or -S5) versus large isoforms of OPA1 (OPA1-L1 and/or -L2) or small or large versus other or all OPA1 isoforms derived from an individual patient sample or sample to be tested is of relevance with respect to a certain disorder or disease, but that also a comparison to a healthy control or a corresponding standard is of relevance and can, in accordance with the teachings provided herein, be obtained. This applies, mutatis mutandis, for all methods provided herein.

The person skilled in the art is readily in a position to determine the ratio of individual (or more) OPA1 isoforms as described herein by methods known in the art, like for example densitometric, spectrophotometric, luminescent, autoradiographic or fluorescent quantification methods. Also in this context, methods comprising tests with specific anti-OPA1 isoform antibodies (also specific antibodies against individual OPA1-isoforms as provided herein) are useful. Accordingly, methods, like Western-blot analysis or ELISA/RIA-tests may be employed to determine the OPA1 isoform ratio(s). Corresponding non-limiting examples are illustrated in the appended experimental part.

In context of the present invention, the amount or ratio of large and/or small isoforms of OPA1 can be, inter alia, derived from measurements of the enzymatic activity and/or the gene expression levels and/or the protein levels of OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof. In an embodiment, these different measurements can be integrated to determine the subject's prognosis based on said integration, wherein depending on the disorder or disease an increase and/or decrease of any of the aforementioned activities and/or levels indicates the subject has a favorable or unfavorable susceptibility for, predisposition for or the presence of the disorder or disease and therefore requires and/or responds to a treatment, prevention and/or amelioration of the disorder or disease. The term "biomarker" refers to such a prognostic method and is well known to the person skilled in the art.

As used herein, the term "subject" and "patient" are used interchangeably and refer to both human and non-human animals. The term "non-human animals" of the disclosure includes all vertebrates, e.g., mammals and non-mammals, such as nonhuman primates, sheep, dog, cat, horse, cow, chickens, rodents, amphibians, reptiles, and the like. Preferably, the subject is a human patient.

As used herein the term, "integration" refers to providing a probability based analysis of how a particular subject will develop a disorder or disease and/or how a particular subject will require or respond to a treatment. The prediction of responsiveness is not a guarantee or absolute, only a statistically probable indication of the responsiveness of the subject.

The prediction of responsiveness to a therapy may indicate that the subject is likely to be responsive to a therapy or alternatively may indicate that the subject is not likely to be responsive to a therapy. Alternatively, the prediction, may indicate that a method for the treatment, prevention and/or amelioration of a disorder or disease correlated with mitochondrial dysfunction or a mitochondrial disorder or disease, or a disorder or disease characterized by OPA1 alterations regime may be counter-productive and lead to a worse result for the subject than if no therapy was used or a placebo was used. Responsiveness includes but is not limited to, any measure of a likelihood of clinical benefit. For example, clinical benefits include an increase in overall survival, an increase in progression free survival, an increase in time to progression, increased response, decreased symptoms, or other quality of live benefits.

In one embodiment, the method includes determining the expression levels of the proteins or the RNA transcripts for the biomarkers in a sample from a patient with cancer or any other disorder or disease. Biomarker expression in some instances may be normalized against the expression levels of all proteins or RNA transcripts in the sample, or against a reference set of proteins or RNA transcripts in the sample. The level of expression of the biomarkers is indicative of the prognosis for the subject or predictive of the effectiveness of a particular treatment.

The methods of the present disclosure can also be used to assist in selecting appropriate courses of treatment and to identify patients that would benefit; from a particular course of therapy. Thus, the expression of the particular biomarkers described herein provides insight into which treatment regimens will be most effective for the patient. This information can be used, to generate treatment plans for the patient to prolong survival and minimize side effects or therapy related toxicity.

In some embodiments described herein, prognostic performance of the biomarkers and/or other clinical parameters was assessed by determining the threshold of OMA1 activation and/or the activation threshold of an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof upon induction of inner membrane permeabilization through addition of mitochondrial uncouplers, such as carbonyl cyanide m-chlorophenyl hydrazine (CCCP; CAS #555-60-2).

It is to be understood that any binding molecule capable of lowering or increasing the threshold levels is an agonist or antagonist in the context of the present invention and therefore administration of such a binding molecule to a patient in need of medical intervention is a method of treatment, prevention and/or amelioration of a disorder or disease correlated with mitochondrial dysfunction or a mitochondrial disorder or disease; or a disorder or disease characterized by OPA1 alterations.

"Sample" is intended to include a sampling of cells, tissues, or bodily fluids in which expression of a biomarker can be detected. Examples of such samples include, but are not limited to, biopsies, cerebrospinal fluid, blood, lymph, urine, saliva, or any other bodily secretion or derivative thereof. Blood can include whole blood, plasma (citrate, EDTA, heparin), serum, or any derivative of blood. Samples may be obtained from a patient by a variety of techniques available to those skilled in the art. Methods for collecting various samples are well known in the art.

Any methods available in the art for detecting expression of biomarkers are encompassed herein. The expression of a biomarker of the invention can be detected on a nucleic acid level (e.g., as an RNA transcript) or a protein level. By "detecting or determining expression" is intended determining the quantity or presence of a protein or its RNA transcript for any combination of at least two genes/proteins from the list compromising OMA1, HIGD1A, OPA1, BNIP3, YME1L1, PHB, SAMM50, IMMT or PHB2. Thus, "detecting expression" encompasses instances where a biomarker is determined not to be expressed, not to be detectably expressed, expressed at a low level, expressed at a normal level, or overexpressed.

Methods suitable for detecting or determining the expression levels of biomarkers are known to those of skill in the art and include, but are not limited to, ELISA, immunofluorescence, FACS analysis, Western blot, magnetic Immunoassays, and both antibody-based micro arrays and non-antibody-based microarrays. Methods for detecting expression of the biomarkers described herein are not limited to protein expression. Gene expression profiling including methods based on hybridization analysis of polynucleotides, methods based on sequencing of polynucleotides, immunohistochemistry methods, and proteomics-based methods may also be used. Alternatively, antibodies may be employed that can recognize specific duplexes, including DNA duplexes, RNA duplexes, and DNA-RNA hybrid duplexes, or DNA-protein duplexes. Representative methods for sequencing-based gene expression analysis include Serial Analysis of Gene Expression (SAGE) and gene expression analysis by massively parallel signature sequencing.

The term "probe" refers to any molecule that is capable of selectively binding to a specifically intended target biomolecule, for example, a nucleotide transcript or a protein encoded by or corresponding to a biomarker. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

EXAMPLES

Example 1

In view of the teaching provided herein, it is envisioned that measurements of OMA1, HIGD1A, OPA1, BNIP3, YME1L1, PHB, SAMM50, IMMT and/or PHB2 gene expression levels are utilized for determining the susceptibility for, predisposition for, or the presence of a disorder or disease correlated with mitochondrial dysfunction, or a mitochondrial disorder or disease; or a disorder or disease characterized by OPA1 alterations.

A non-limiting example for such a disorder or disease is Alzheimer's disease. It is known in the arts that mitochondrial damage and dysfunction are early features of Alzheimer's disease and other neurodegenerative diseases. Briefly, the two neuropathological hall marks of Alzheimer's disease are extracellular amyloid-β deposits and intracellular tau accumulation causing plaques and neurofibrillary tangles, respectively (Taylor et al. 2002). However, dysfunctional mitochondria also have been recognized for many years in brains from deceased patients with Alzheimer's disease suggesting a direct connection between mitochondrial homeostasis and Alzheimer's disease. (Parker et al. 1990; Smith et al. 1996; Gibson et al. 1998; Maurer et al. 2000; Butterfield et al. 2001; Devi et al. 2006). Different genetic mouse models (Aliev et al. 2003; Li et al. 2004; Lustbader et al. 2004; Reddy et al. 2004; Caspersen et al. 2005; Manczak et al. 2006; Eckert et al. 2008; Yao et al. 2009) and cellular models for Alzheimer's disease showed mitochondrial impairments as well (Butterfield et al. 2001; Cardoso et al. 2004; Diana et al. 2008; Eckert et al. 2008; Schmidt et al. 2008; Wang et al. 2008). Amyloid-β overexpression in cell culture studies decreased levels of DRP1 and OPA1, two key regulators of the dynamic mitochondrial network (Wang et al. 2008). Subsequent studies revealed that both amyloid-β and tau can interact with DRP1 and OPA1 leading to altered OPA1 processing, impaired mitochondrial dynamics and function (Wang et al. 2008; Manczak et al. 2011; Manczak and Reddy 2012; Shields et al. 2015; Akhtar et al. 2016; Yang et al. 2017). Moreover, neuronal damage in Amyloid-β and tau mouse models could be delayed by blocking DRP1-mediated mitochondrial fission or OMA1 knock-out (Merkwirth et al. 2008; Yan et al. 2015; Kandimalla et al. 2016; Korwitz et al. 2016; Manczak et al. 2016; Baek et al. 2017; Reddy et al. 2017).

We mined all gene expression data available through the NCBI GEO database (Edgar et al. 2002) for studies comparing human brain samples from patients with and without Alzheimer's disease. We obtained the data set from the Hisayama study (GEO accession number: GDS4758), which examined 88 autopsy samples from Hisayama residents obtained between 15 Dec. 2008 and 24 Feb. 2011 (Hokama et al. 2014). We also obtained the data set from a large-scale transcriptional analysis of postmortem brain samples from deceased patients with late-onset Alzheimer's disease provided by two tissue centers (Alzheimer's Disease Center, Oregon Health and Sciences University, and Human Brain and Spinal Fluid Resource Center; GEO accession number: GSE29378) (Miller et al. 2013). We then analyzed the gene expression levels of OMA1, OPA1, HIGD1A, BNIP3, SAMM50, IMMT, YME1L1, PHB and PHB2 in the different brain regions of patients with and without Alzheimer's disease. We calculated the differential expression with respect to region, disease, and sex. Differences were considered statistically significant for P-values of ≤0.05 using a Student's T-test.

We also mined the data repositories for FDA-approved drugs that modify the gene expression levels of OMA1, OPA1, HIGD1A, BNIP3, SAMM50, IMMT, YME1L1, PHB or PHB2. In addition, we searched for interventions that would modify the gene expression levels of OMA1, OPA1, HIGD1A, BNIP3, SAMM50, IMMT, YME1L1, PHB or PHB2. We identified Ribavirin (CAS #: 36791-04-5) as OMA1 antagonist in a study of human hepatocytes (Huh7.5.1 cells; GEO accession number: GSE23031) (Thomas et al. 2011). Ribavirin is approved by the regulatory authorities for the use as antiviral for patients with hepatitis C.

In context of the present invention it was, inter alia, found that OMA1, OPA1, BNIP3, SAMM50, IMMT and HIGD1A gene expression levels are differentially regulated in Alzheimer's disease brains in a sex-specific manner Therefore, susceptibility and/or presence of Alzheimer's disease as well as treatment selection can be predicted by integrating these sex-specific expression profiles.

In one particular embodiment, we found significant gene expression changes in postmortem brain tissue from patients pathologically diagnosed as having Alzheimer's disease. OMA1 expression was significantly reduced in the hippocampus and temporal cortex of male individuals without Alzheimer's disease (FIGS. 2A and 2B), while OPA1 was significantly reduced in the hippocampus and temporal cortex of female Alzheimer's disease patients (FIG. 2C and FIG. 2D). BNIP3 levels were significantly reduced in the hippocampus of both male and female Alzheimer's disease patients (FIG. 2E), but not in the temporal cortex (FIG. 2F).

Figure 2:
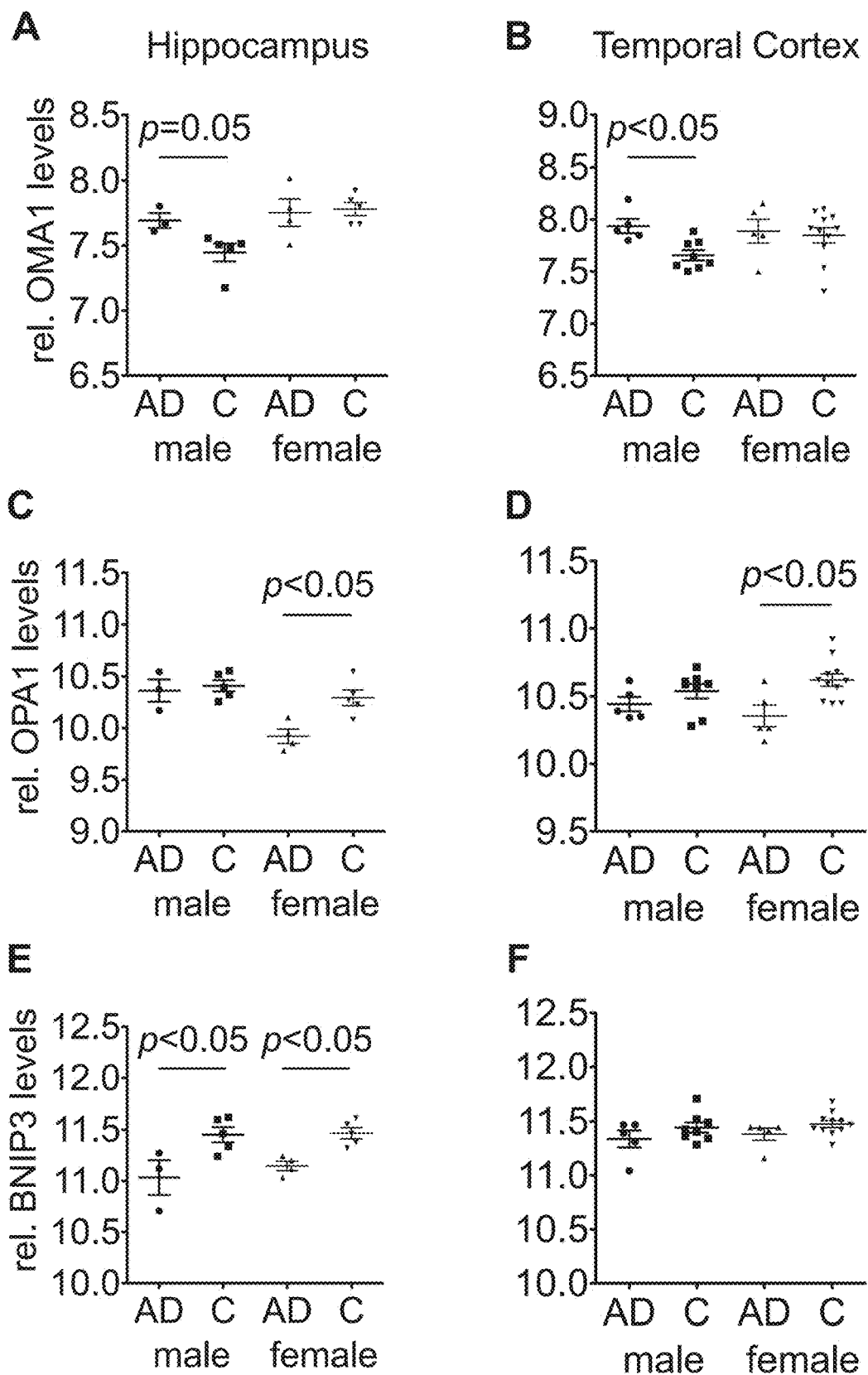
FIGS. 2A-2F show gene expression levels in the hippocampus (AD: n=8; C: n=9) and temporal cortex (AD: n=13; C: n=16) from post-mortem samples of patients with Alzheimer's disease (AD) and control subjects (C).

FIGS. 2A-2F show gene expression levels in the hippocampus (AD: n=8; C: n=9) and temporal cortex (AD: n=13; C: n=16) from post-mortem samples of patients with Alzheimer's disease (AD) and control subjects (C). OMA1 expression levels were significantly increased in males with Alzheimer's disease in the hippocampus by 3.3% (FIG. 2A) and the temporal cortex by 3.7% (FIG. 2B). Females appeared to have overall elevated OMA1 levels compared to males and there was no difference between Alzheimer's samples and controls. OPA1 levels were significantly reduced in the hippocampus of female patients with Alzheimer's by 3.7% (FIG. 2C) and the temporal cortex by 2.5% (FIG. 2C and FIG. 2D). BNIP3 levels were significantly reduced in the hippocampus from both male and female Alzheimer's patients by 3.7% and 2.8%, respectively (FIG. 2E), while there were no differences in the temporal cortex (FIG. 2F).

Figure 3:
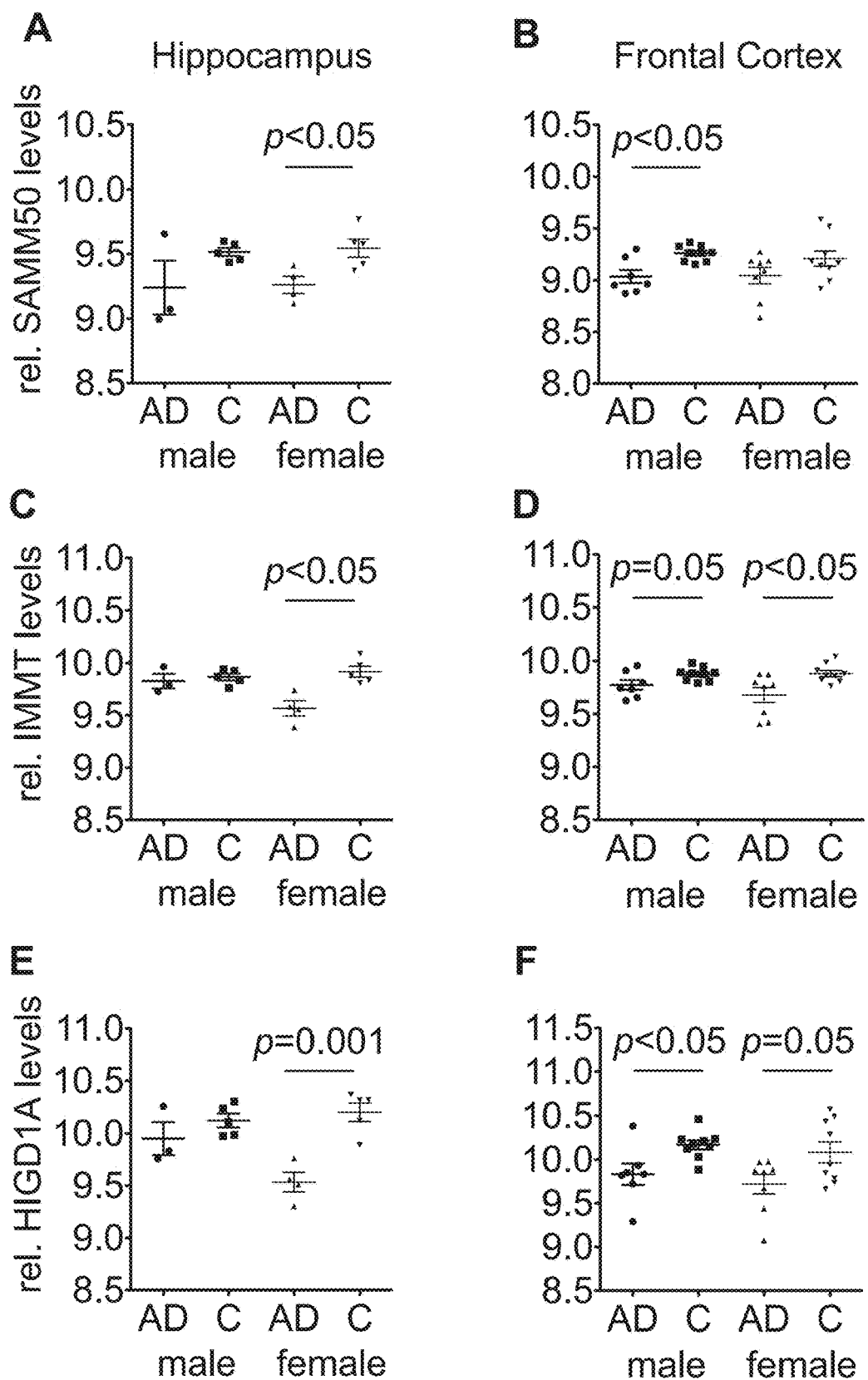
FIGS. 3A-3F show gene expression levels in the hippocampus (AD: n=8; C: n=9) and frontal cortex (AD: n=16; C: n=17) from post-mortem samples of patients with Alzheimer's disease (AD) and control subjects (C).

Expression of SAMM50 was significantly reduced in the hippocampus of female Alzheimer's disease patients (FIG. 3A) and the frontal cortex of male Alzheimer's disease patients (FIG. 3B). IMMT levels were significantly reduced in the hippocampus of female Alzheimer's disease patients (FIG. 3C) and in the frontal cortex of both male and female Alzheimer's disease patients (FIG. 3D). Expression of the endogenous OMA1 antagonist HIGD1A was also significantly reduced in the hippocampus of female Alzheimer's disease patients (FIG. 3E) and the frontal cortex of both male and female Alzheimer's disease patients (FIG. 3F).

FIGS. 3A-3F show gene expression levels in the hippocampus (AD: n=8; C: n=9) and frontal cortex (AD: n=16; C: n=17) from post-mortem samples of patients with Alzheimer's disease (AD) and control subjects C. SAMM50 expression levels appeared to be reduced in patients with Alzheimer's disease. They were significantly reduced by 3.0% in the hippocampus from Alzheimer's females (FIG. 3A) and by 2.4% in the frontal cortex from Alzheimer's males (FIG. 3B). IMMT levels were significantly reduced by 3.5% in the hippocampus from female subjects with Alzheimer's disease (FIG. 3C), while in the frontal cortex both males and females had significantly reduced IMMT levels by 2.0% and 1.0%, respectively (FIG. 3D). HIGD1A levels were significantly reduced by 6.6% in the hippocampus of female Alzheimer's patients (FIG. 3E). and in the frontal cortex of both male and female Alzheimer's patients by 3.3% and 3.6%, respectively (FIG. 3F).

In another embodiment, we found gene expression changes in the hippocampus from deceased late-onset Alzheimer's patients acquired at the Oregon Health and Sciences University (GEO accession number: GSE29378) (Miller et al. 2013). Again, OMA1 expression was significantly reduced in the hippocampus of non-Alzheimer's disease males (88.4%±15.1% S.D., p=0.05). We also found a trend for reduced HIGD1A levels in Alzheimer's brains at Oregon (86.3%±16.3% S.D., p=0.07), which agrees with the above data.

The specific changes in the gene expression of the genes OMA1, OPA1, BNIP3, SAMM50, IMMT and HIGD1A depends on the sex of a subject and the brain region. The specific expression profile and/or gene signature of these sex-dependent changes therefore represent a biomarker according to the definitions given above and is envisioned to be utilized, inter alia, for differentiation of Alzheimer's disease from other mitochondrial disorders or diseases, such as Parkinson's disease.

In view of the teaching provided herein, the means and methods of the present disclosure can also be used to inform selection and/or assist in selecting appropriate courses of treatment and/or medical interventions for patients in need of such interventions.

In one particular embodiment it was, inter alia, found that Ribavirin (CAS #: 36791-04-5) significantly decreases the gene expression levels of OMA1 by 15% to 17% (FIG. 4; Student's T-test: p≤0.05). Human hepatocytes (Huh7.5.1 cells) were cultured with or without 100 µg/mL Ribavirin (Thomas et al. 2011). Cells without Ribavirin (FIG. 4; PBS) expressed OMA1 at 7.89 (±0.21 S.D.; Spot ID: 226019_at) and 9.17 (±0.17 S.D. (FIG. 4A); Spot ID: 226020_s_at), while Ribavirin-treated cells had significantly reduced OMA1 levels at 6.52 (±0.22 S.D.; Spot ID: 226019_at) and 7.76 (±0.12 S.D.; Spot ID: 226020_s_at) (FIG. 4B), respectively.

Referring to FIGS. 4A and 4B, the antiviral Ribavirin (CAS #36791-04-5) represents an antagonist of OMA1. Ribavirin can significantly decrease the expression levels of OMA1 in human hepatocytes by 15% to 17%. Huh7.5.1 cells were cultured with either the addition of PBS or 100 µg/mL Ribavirin for 24 hours, after which mRNA was isolated and analyzed by gene expression microarrays. Vehicle treated cells (PBS) expressed OMA1 at 7.89 (±0.21 S.D.; Spot ID: 226019_at) and 9.17 (±0.17 S.D.; Spot ID: 226020_s_at) (FIG. 4A), while Ribavirin significantly reduced OMA1 levels to 6.52 (±0.22 S.D.; Spot ID: 226019_at) and 7.76 (±0.12 S.D.; Spot ID: 226020_s_at) (FIG. 4B), respectively.

Ribavirin is known in the arts as an antiviral agent that also possesses immunosuppressant activity. Neurotrophic activity of Ribavirin and analogs thereof are also known in the arts (WO 00/30656). However, the finding that Ribavirin can decrease OMA1 levels was unexpected and is non-obvious to a person skilled in the arts.

In context of the present invention Ribavirin thus represents an antagonist of OMA1. Accordingly, Ribavirin represent a medical intervention in particular for the treatment, of patients with Alzheimer's disease. Apovir is a combination drug of Ribavirin and Pleconaril that has been tested in a clinical study on patients with Alzheimer's disease (EudraCT number: 2013-002126-23) to investigate its effect on disease progression as assessed by the Alzheimer's Disease Assessment Scale-Cognitive Subscale [ADAS-cog]. Patients that received 600 mg Apovir per day (n=18) showed an improvement of −1.963 (±4.398 S.D.) points on the ADAS-cog. Subscale after 9 months, compared to placebo-treated patients (n=31), which showed worsening of 1.817 (±8.623 S.D.) points. Although these changes did not achieve statistical significance (P=0.1809), these results validate our method for the treatment of a mitochondrial disease, on the basis of Alzheimer's disease as an example for such a disease.

Example 2

Another non-limiting example for a disease correlated with altered OPA1 processing is Parkinson's disease for which there is strong evidence for mitochondrial dysfunction (Schapira et al. 1990; Keeney et al. 2006; Parker et al. 2008; Santos et al. 2015; Dolle et al. 2016). Briefly, familial forms of Parkinson's disease are associated with several proteins that directly impact mitochondrial fission and fusion. For example, α-synuclein can localize to mitochondria, and mitochondria associated ER membranes (Imaizumi et al. 2012; Nakamura 2013; Guardia-Laguarta et al. 2014; Ghio et al. 2016). Overexpression of mutant α-synuclein increased mitophagy in cortical neurons along with mitochondrial fragmentation and neuronal cell death by promoting OPA1 cleavage (Guardia-Laguarta et al. 2014). The adverse effects of mutant α-synuclein could be rescued in part by inhibiting mitophagy (Choubey et al. 2011; Nakamura et al. 2011). Pink1, Parkin and DJ-1 form an E3 ubiquitin-ligase complex on the mitochondrial surface that initiates mitophagy by ubiquitinating, among other proteins, DRP1 (Yang et al. 2008; Lutz et al. 2009; Wang et al. 2011). Mutations in any of the genes result in frustrated clearance and accumulation of damaged mitochondria leading to neuronal loss in the substantia nigra and other parts of the brain (Mukherjee et al. 2015). LRRK2 also resides on the mitochondrial outer membrane where it affects mitochondrial network dynamics through interactions with DRP1 and OPA1 (Stafa et al. 2014). As is the case for Alzheimer's disease, preventing mitochondrial fission through DRP1 inhibition also can attenuate neurotoxicity in animal models of Parkinson's disease (Rappold et al. 2014).

We mined all gene expression data available through the NCBI GEO database (Edgar et al. 2002) for studies comparing human brain samples from patients with and without Parkinson's disease. We obtained gene expression data from 16 patients with Parkinson's disease for which post mortem brain specimens were investigated. These patients were enrolled prospectively at the Department of Neurology of the Mayo Clinic in Rochester, Minn., from June 1996 through May 2004 (GEO accession number: GDS2821) (Maraganore et al. 2005; Lesnick et al. 2007). We also obtained an independent second data set from postmortem brain tissue of 11 subjects diagnosed with neuropathologically confirmed Parkinson's disease. The tissue blocks were acquired from the University of Maryland Brain and Tissue Bank, the New York Brain Bank at Columbia University, the Human Brain and Spinal Fluid Resource Center at the West Los Angeles VA Medical Center, McLean Hospital of Harvard University, and the Miami Brain and Tissue Bank (GEO accession number: GSE20168) (Zhang et al. 2005). We then analyzed the gene expression levels of OMA1, OPA1, HIGD1A, BNIP3, SAMM50, IMMT, YME1L1, PHB and PHB2 in the different brain regions of patients with and without Parkinson's disease. We calculated the differential expression with respect to region, disease, and sex. Differences were considered statistically significant for P-values of ≤0.05 using a Student's T-test.

Figure 5:
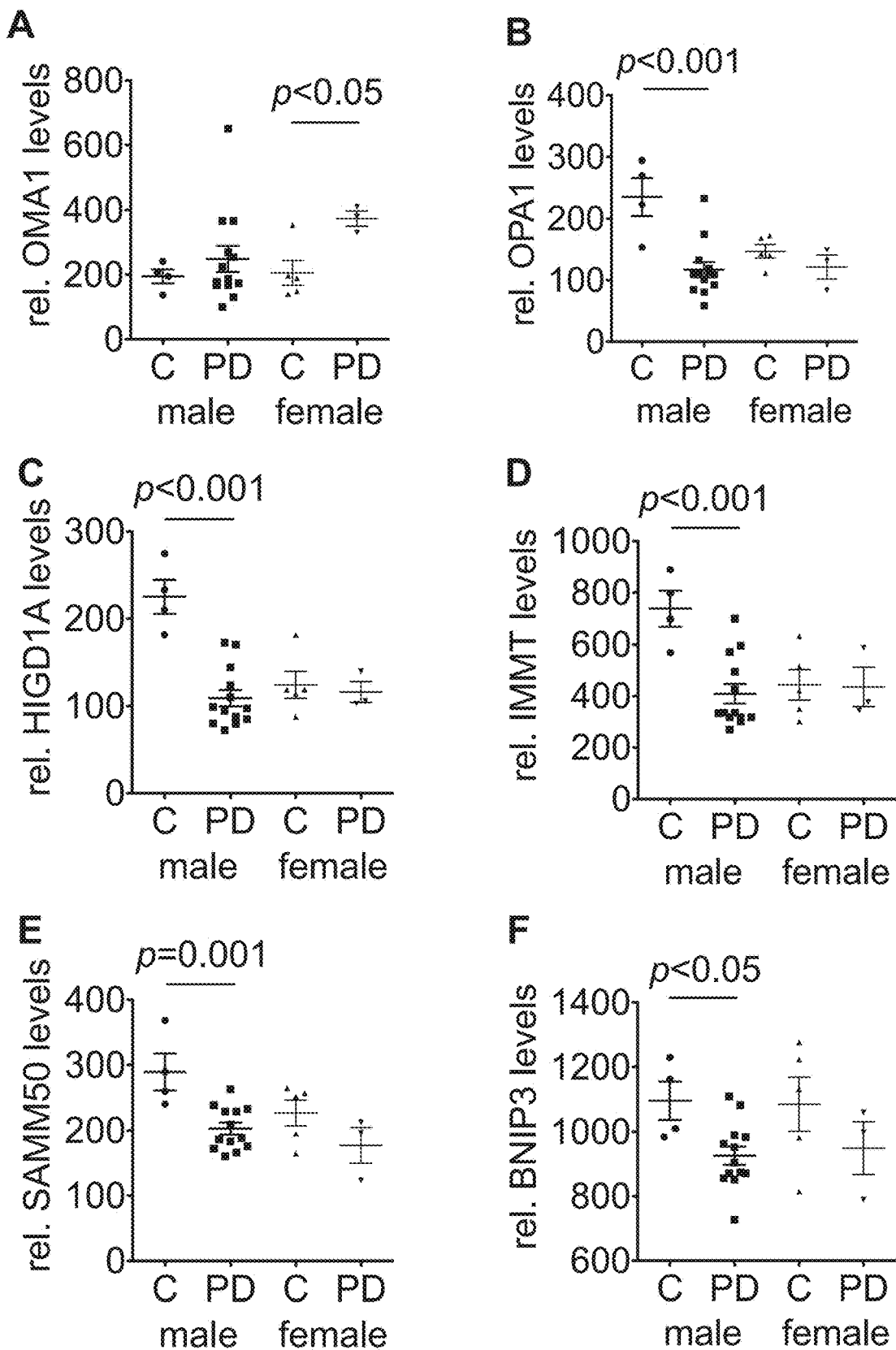
FIGS. 5A-5F show gene expression levels in post mortem samples of the substantia nigra from a cohort of healthy subjects (C; n=9) and patients with Parkinson's disease (PD; n=16) collected at Rochester, Minn. (GEO accession number: GDS2821).

In one particular embodiment, we found significant gene expression changes in samples of the substantia nigra from postmortem brain tissue from patients with Parkinson's disease (GEO accession number: GDS2821). OMA1 gene expression levels were significantly increased in samples of the substantia nigra from female Parkinson's patients (FIG. 5A). OPA1 gene expression levels, on the other hand, were significantly decreased in Parkinson's samples from male subjects (FIG. 5B). Females had overall lower OPA1 expression levels and there was no significant difference between non-PD and PD samples (FIG. 5B). HIGD1A levels were also significantly decreased in males with Parkinson's, while females had overall lower HIGD1A levels and did not show any significant differences (FIG. 5C). IMMT levels were significantly decreased in male Parkinson's samples to about the levels of healthy females and females with Parkinson's (FIG. 5D). SAMM50 was decreased in Parkinson's samples; this difference was statistically significant for males, while females showed lower overall levels (FIG. 5E). PHB2 levels appeared to be reduced in Parkinson's samples, which was statistically significant for male subjects (FIG. 5F).

FIGS. 5A-5F show gene expression levels in post mortem samples of the substantia nigra from a cohort of healthy subjects (C; n=9) and patients with Parkinson's disease (PD; n=16) collected at Rochester, Minn. (GEO accession number: GDS2821). OMA1 gene expression levels appeared to be increased in Parkinson's samples; they were significantly increased by 27.6% in samples from female Parkinson's patients (FIG. 5A). OPA1 gene expression levels were significantly decreased by 50.3% in samples from male Parkinson's subjects (FIG. 5B). Females had overall lower OPA1 expression levels in the substantia nigra than males and there was no significant difference between C and PD samples (5B). HIGD1A levels were significantly decreased by 51.5% in males with Parkinson's (FIG. 5C). Again, females had overall lower HIGD1A levels and did not show any significant differences. IMMT levels were also significantly decreased in males with Parkinson's by 44.6%, while females had overall lower IMMT levels and no significant changes (FIG. 5D). SAMM50 levels appeared to be decreased in Parkinson's samples; this difference was statistically significant for males (29.9% reduction), while females again showed lower overall levels (FIG. 5E). PHB2 levels appeared to be reduced in Parkinson's samples as well, which was statistically significant for males (FIG. 5F; 15.5% reduction).

Figure 6:
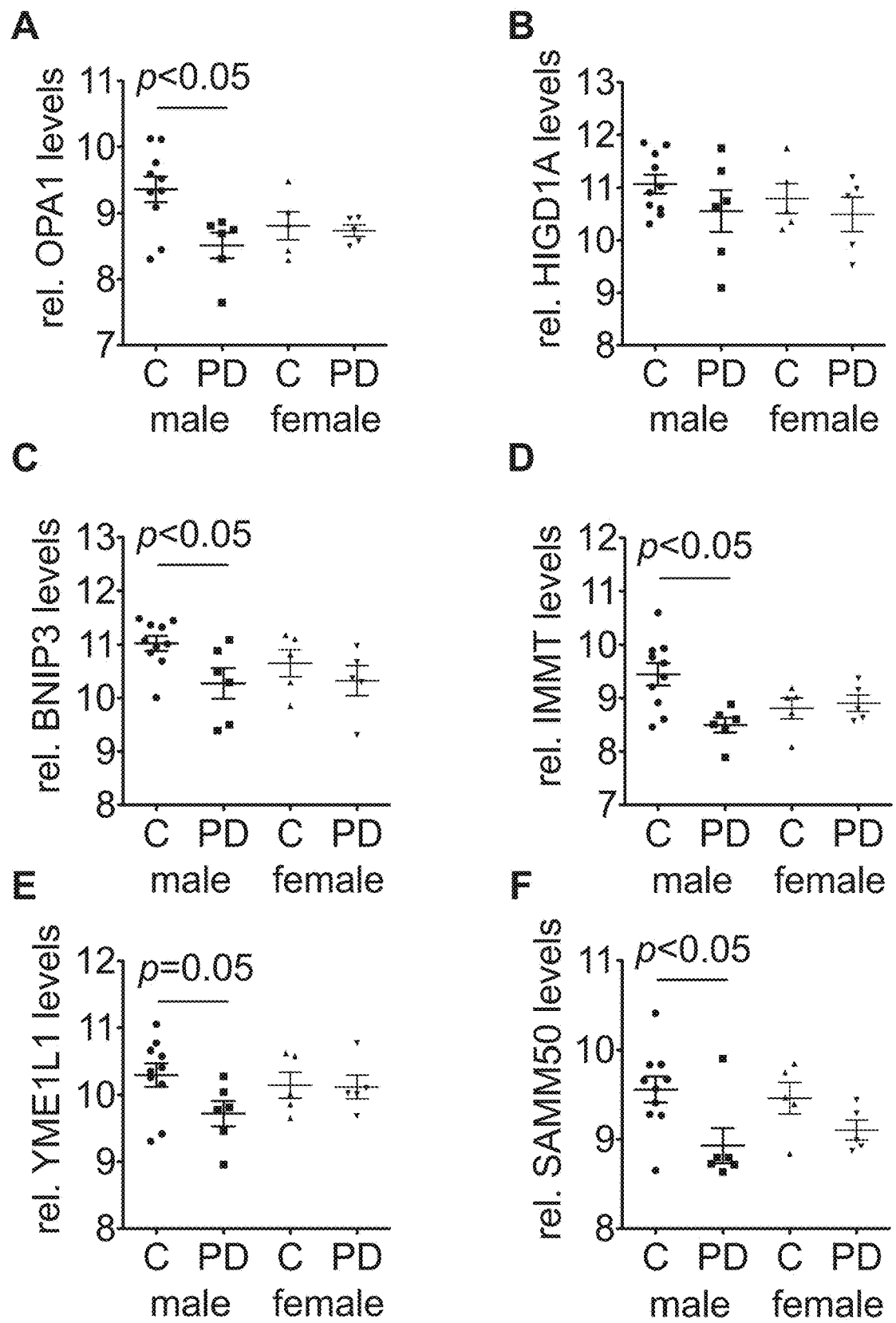
FIGS. 6A-6F show gene expression levels in post mortem samples of the substantia nigra from an independent cohort of healthy subjects (C; n=15) and patients with Parkinson's disease (PD; n=11) collected at Syracuse, N.Y. (GEO accession number: GSE20292).

In another embodiment, we found significant gene expression changes in an independent set of samples from the substantia nigra of postmortem brain tissue from patients with Parkinson's disease (GEO accession number: GSE20292). In agreement with the data obtained from the first study, OPAL gene expression levels were significantly decreased in Parkinson's samples from male subjects (FIG. 6A). Females had overall lower OPA1 expression levels and there was no significant difference between non-PD and PD samples (FIG. 6A). HIGD1A levels were overall lower in Parkinson's samples but did not reach statistical significance (FIG. 6B). BNIP3 gene expression levels were significantly reduced in male Parkinson's samples and females appear to have overall lower BNIP3 expression levels and there was no significant difference (FIG. 6C). Also, IMMT levels were significantly decreased in males with Parkinson's, while females had overall lower levels and did not show any significant differences (FIG. 6D). YME1L1 levels showed a small but significant decrease in male Parkinson's samples (FIG. 6E). SAMM50 was decreased in Parkinson's samples and this difference was statistically significant for males (FIG. 6F).

FIGS. 6A-6F show gene expression levels in post mortem samples of the substantia nigra from an independent cohort of healthy subjects (C; n=15) and patients with Parkinson's disease (PD; n=11) collected at Syracuse, N.Y. (GEO accession number: GSE20292). OPA1 gene expression levels were significantly decreased by 9.1% in Parkinson's samples from male subjects (FIG. 6A). HIGD1A levels were overall lower in Parkinson's samples but did not reach statistical significance (FIG. 6B). BNIP3 gene expression levels were significantly reduced by 6.8% in male Parkinson's samples (FIG. 6C). Females appear to have overall lower BNIP3 expression levels and there was no significant difference. IMMT levels were significantly decreased by 10.1% in males with Parkinson's, while females had overall lower levels and again did not show any significant differences (FIG. 6D). YME1L1 levels were significantly reduced by 5.6% in male Parkinson's samples (FIG. 6E). Overall SAMM50 levels were decreased in Parkinson's samples; males had a significant reduction by 6.6% while the difference between female samples did not reach statistical significance (FIG. 6F).

Figure 7:
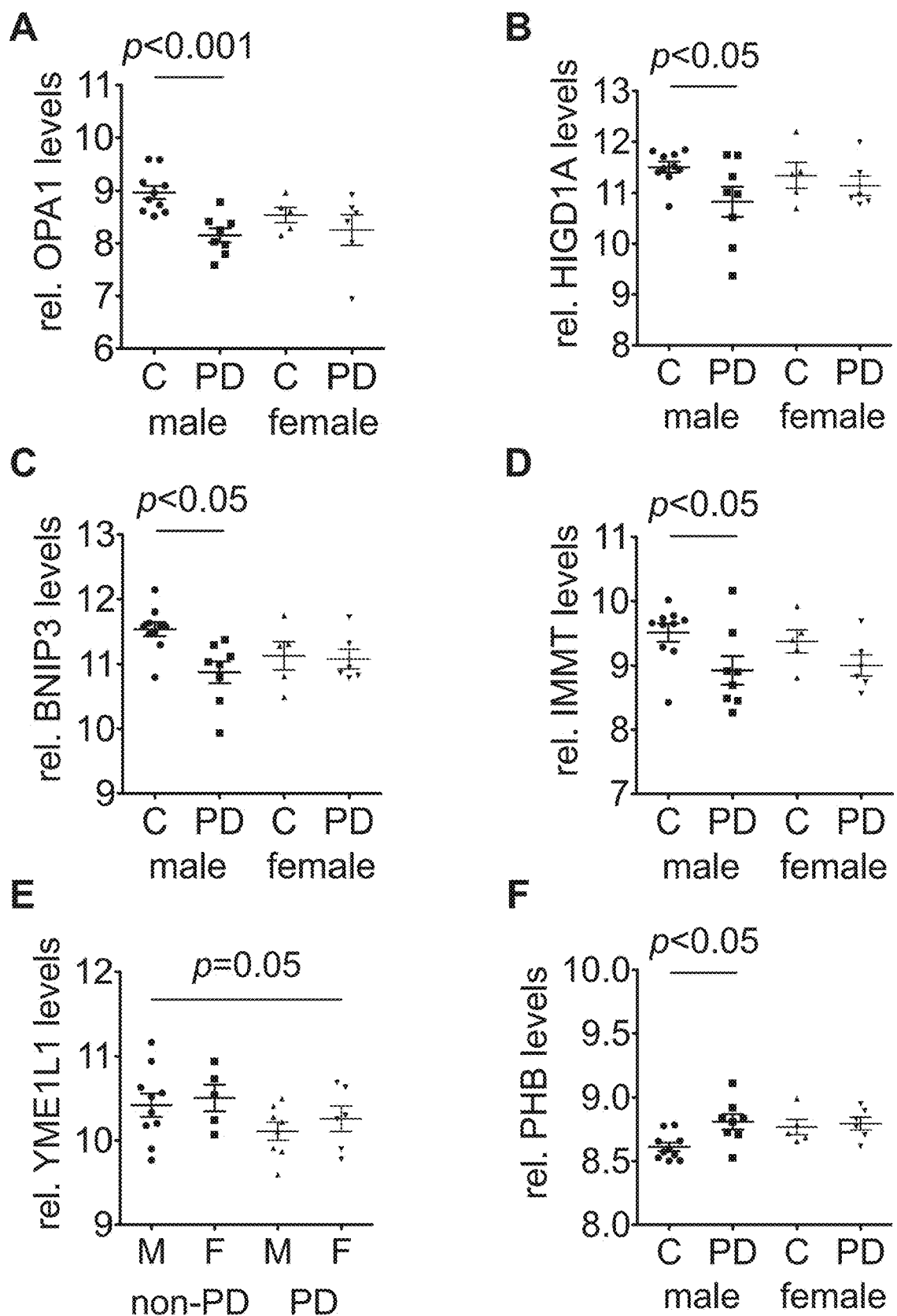
FIGS. 7A-7F show gene expression levels in the prefrontal cortex from healthy subjects (C; n=15) and patients with Parkinson's disease (PD; n=11) from Syracuse, N.Y. (GEO accession number: GSE20168).

In yet another embodiment, we found significant gene expression changes in post mortem samples of the prefrontal cortex from patients with Parkinson's disease (GEO accession number: GSE20168). OPA1 gene expression levels were also significantly decreased in the prefrontal cortex of male patients with Parkinson's (FIG. 7A). HIGD1A levels were significantly lower in male Parkinson's samples (FIG. 7B). BNIP3 gene expression levels were significantly reduced in male Parkinson's samples (FIG. 7C). IMMT levels appeared to be lower in Parkinson's samples and there was a statistically significant reduction in male samples (FIG. 7D). YME1L1 levels showed a small but significant reduction in Parkinson's samples when male and female samples were analyzed together (FIG. 7E). Females tended to have lower overall expression levels and did not show any significant changes for these genes. PHB showed a small but significant increase in the prefrontal cortex of males with Parkinson's (FIG. 7F).

FIGS. 7A-7F show gene expression levels in the prefrontal cortex from healthy subjects (C; n=15) and patients with Parkinson's disease (PD; n=11) from Syracuse, N.Y. (GEO accession number: GSE20168). OPA1 gene expression levels were significantly decreased by 9.1% in Parkinson's samples from male subjects (FIG. 7A). HIGD1A levels were significantly reduced by 5.9% in male Parkinson's samples (FIG. 7B). BNIP3 gene expression levels were significantly reduced by 5.8% in male Parkinson's samples (FIG. 7C). IMMT levels appeared to be lower in Parkinson's samples and there was a statistically significant reduction by 6.2% in male samples (FIG. 7D). There was a 2.6% decrease of YME1L1 levels, in Parkinson's samples, which was significant when male and female samples were analyzed together (FIG. 7E). PHB was significantly increased in the prefrontal cortex from male Parkinson's patients by 2.3% (FIG. 7F).

We have demonstrated above that Parkinson's disease correlates with specific changes in the gene expression levels of OMA1, OPA1, HIGD1A, BNIP3, SAMM50, IMMT, YME1L1, PHB and PHB2. These changes depend on the sex of a subject and the brain region. In context of the present invention it is envisioned that measuring and integrating these gene expression changes can be utilized, inter alia, for determining the susceptibility for, predisposition for, or the presence of Parkinson's disease. These measurements also can be utilized for differentiation of Parkinson's disease from other disorders or diseases correlated with mitochondrial dysfunction, such as Alzheimer's disease. Moreover, this biomarker is envisioned to guide treatment selection.

Example 3

Yet another non-limiting example for a mitochondrial disorder or disease is cancer. Research over the past century or so has generated a complex and rich body of knowledge revealing cancer to be a disease correlated to mitochondrial dysfunction (Alirol and Martinou 2006; Frezza and Gottlieb 2009; Hanahan and Weinberg 2011; Wallace 2012; Vyas et al. 2016). Uncontrolled cell proliferation represents the essence of neoplastic disease and entails adjustments of energy metabolism in order to fuel cell growth and division. Aerobic glycolysis is an anomalous characteristic of cancer cell energy metabolism referred to as "Warburg effect": even in the presence of oxygen, cancer cells largely adopt glycolysis (Warburg 1956). The existence of this metabolic switch in cancer cells has been substantiated and other mitochondrial changes have been described in the ensuing decades (Alirol and Martinou 2006; Frezza and Gottlieb 2009; Hanahan and Weinberg 2011; Wallace 2012; Vyas et al. 2016). It is also known in the arts that changes in energy metabolism are tightly correlation with alterations in mitochondrial morphology (Hackenbrock 1966; Jakobs et al. 2003; Cogliati et al. 2013). Changes in OPA1 levels and OPA1 processing have been found in various cancers, accordingly (Zhao et al. 2013; Kong et al. 2014; Faccenda et al. 2017). These mitochondrial alterations might not be the primary cause for cancer. And yet, they are functionally important for the development and progression of many forms of human cancer. Therefore, mitochondrial dynamics can adjust chemoresistance in cancer (Kong et al. 2015) and regulate tumorgenesis, metastatic spread and overall survival of cancer cells.

We obtained gene-expression data paired with survival data for different tumor samples through public data repositories and conducted meta studies on 1764 patients with breast cancer (GEO accession numbers: E-MTAB-365, GSE12276, GSE16391, GSE16446, GSE17907, GSE19615, GSE20685, GSE20711, GSE21653, GSE42568, GSE9195), on 1145 patients with lung cancer (GEO accession numbers: GSE19188, GSE3141, GSE50081, GSE37745, GSE29013, GSE30219, GSE31210), on 631 patients with gastric cancer (GEO accession numbers: GSE22377, GSE15459, GSE51105, GSE62254, GSE62254), and on 1435 patients with ovarian cancer (GEO accession numbers: GSE51373, GSE9891, GSE15622, GSE26712, GSE26193, GSE63885, GSE65986, GSE30161, GSE14764, TCGA). We analyzed different gene signatures for their predictive value on patient survival. To this end we calculated the median gene-expression levels for OMA1, HIGD1A, OPA1, BNIP3, YME1L1, PHB, SAMM50, IMMT and/or PHB2 in the different datasets and defined two groups of patients, depending on whether a subject's expression levels were below (group "low") or above the median gene expression levels (group "high"). The minimum, maximum and median gene expression levels for OPA1, OMA1, HIGD1A, BNIP3, YME1L1, PHB, PHB2, SAMM50 and IMMT for each of the 4 investigated cancer types (i.e., breast cancer, lung cancer, gastric cancer, ovarian cancer) are given in the tables depicted in FIG. 8 and FIG. 9, respectively. Also, the data range for each group, "low" or "high", for each gene is depicted in FIG. 8 and FIG. 9. Based on these classifications we tested the predictive value of different combinations of at least 3 genes. We termed these groups of 3 or more combinations of gene expression groups "gene signatures" (e.g., OMA1: high, HIGD1A: high, BNIP3: low). We tested whether patients with particular gene signatures had an increased chance of overall survival using a Log-rank Test. Differences were considered statistically significant for P-values of ≤0.05.

FIG. 8 shows data ranges for OPA1, OMA1, HIGD1A, BNIP3, YME1L1, PHB, PHB2, SAMM50 and IMMT gene expression levels in tissue samples from patients with breast cancer (top) and lung cancer (bottom). The median expression levels and the data range for the classification of patients, depending on whether a subject's expression levels were below (group "low") or above the median gene expression levels (group "high") are given as well.

FIG. 9 shows data ranges for OPA1, OMA1, HIGD1A, BNIP3, YME1L1, PHB, PHB2, SAMM50 and IMMT gene expression levels in tissue samples from patients with gastric cancer (top) and ovarian cancer (bottom). The median expression levels and the data range for the classification of patients, depending on whether a subject's expression levels were below (group "low") or above the median gene expression levels (group "high") are given as well.

Figure 10:
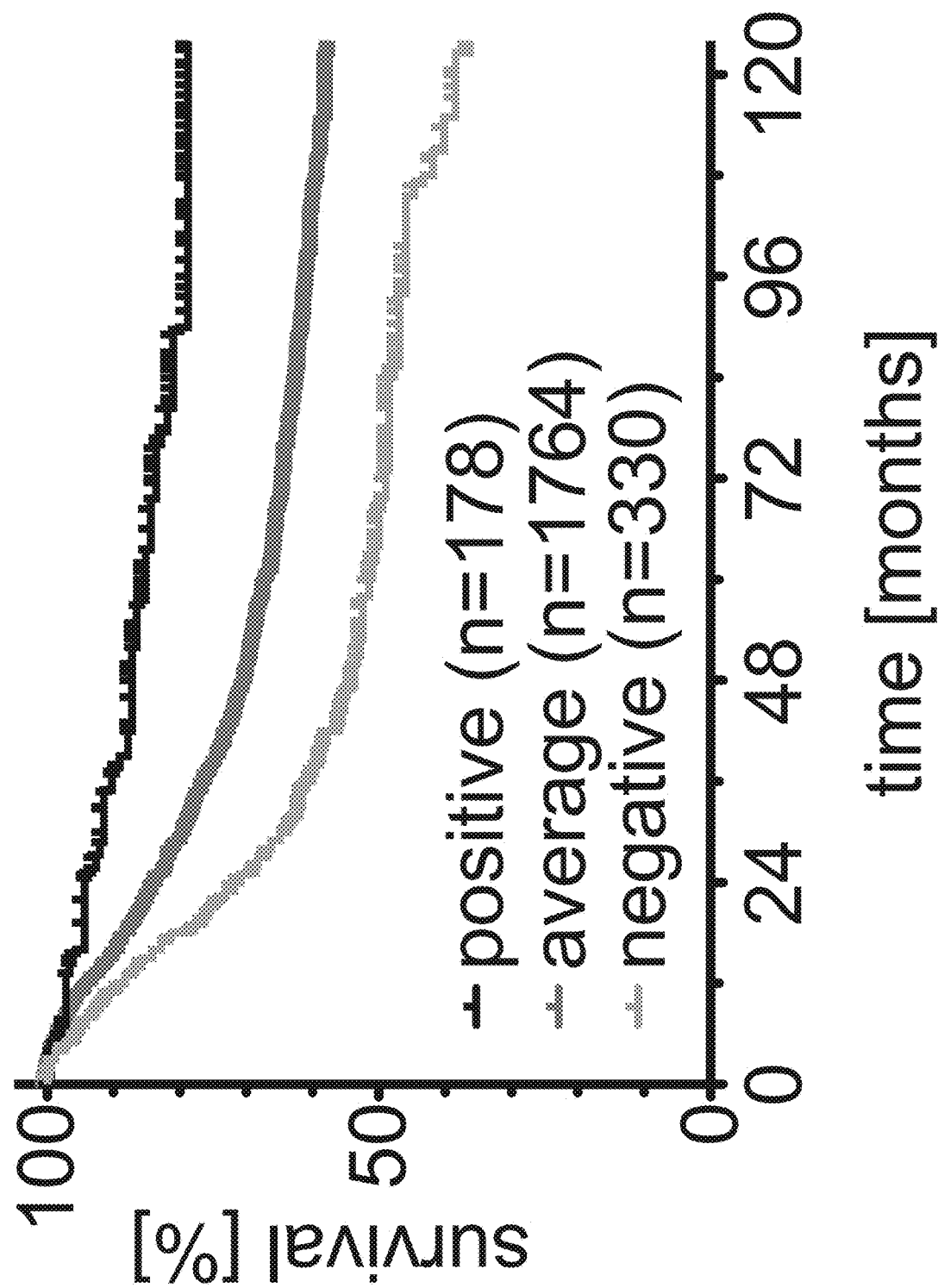
FIG. 10 shows Kaplan-Meier curves showing the overall survival of 1764 patients with breast cancer (average; dark grey, solid line; GEO accession numbers: E-MTAB-365, GSE12276, GSE16391, GSE16446, GSE17907, GSE19615, GSE20685, GSE20711, GSE21653, GSE42568, GSE9195) stratified by a proprietary 3-gene signature based on OMA1, HIGD1A and BNIP3 expression levels (i.e., OMA1: high, HIGD1A: high, BNIP3: low).

In one particular embodiment we have invented a 3-gene expression signature particularly useful for the prognosis of survival of patients with cancer. This 3-gene signature comprises OMA1, HIGD1A and BNIP3, wherein OMA1 and HIGD1A expression levels are elevated and BNIP3 expression levels are reduced compared to the median expression levels. This particular 3-gene signature can stratify patients with breast cancer based on whether the expression levels of OMA1, HIGD1A and BNIP3 matched (positive; i.e., OMA1: high; HIGD1A: high; BNIP3 low) or did not match (negative; i.e., OMA1: low; HIGD1A: low; BNIP3: high) the signature (FIG. 10). The median survival of patients with a negative gene signature was only 68 months, while patients with a positive signature had a significantly higher chance of survival (FIG. 10; Log-rank Test: p<0.0001; Chi square=65.60; df=2). This particular 3-gene signature has also been proven useful to stratify patients with lung cancer (FIG. 11) and gastric cancer (FIG. 12). Patients with lung cancer survived on average 78 months, while subjects with a negative signature survived only 52 months and subjects with a positive signature had significantly better chances of survival (FIG. 11; Log-rank Test: p<0.0001; Chi square=21.77; df=2). On the other hand, patients with gastric cancer had on average 53 months to survive, while subjects with a negative signature survived only 28 months and subjects with a positive signature had significantly better chances of survival (FIG. 12; Log-rank Test: p<0.0001; Chi square=24.12; df=2).

FIG. 10 shows Kaplan-Meier curves showing the overall survival of 1764 patients with breast cancer (average; dark grey, solid line; GEO accession numbers: E-MTAB-365, GSE12276, GSE16391, GSE16446, GSE17907, GSE19615, GSE20685, GSE20711, GSE21653, GSE42568, GSE9195) stratified by a proprietary 3-gene signature based on OMA1, HIGD1A and BNIP3 expression levels (i.e., OMA1: high, HIGD1A: high, BNIP3: low). Patients whose signature matched all 3 genes (positive; black, solid line) had a 100% chance of survival, while patients whose signature was inverted (i.e., OMA1: low, HIGD1A: low, BNIP3: high; negative; light grey, dotted line) had only a 60% chance with a median survival of 42 months (Log-rank Test: p<0.0001; Chi square=65.60; df=2).

Figure 11:
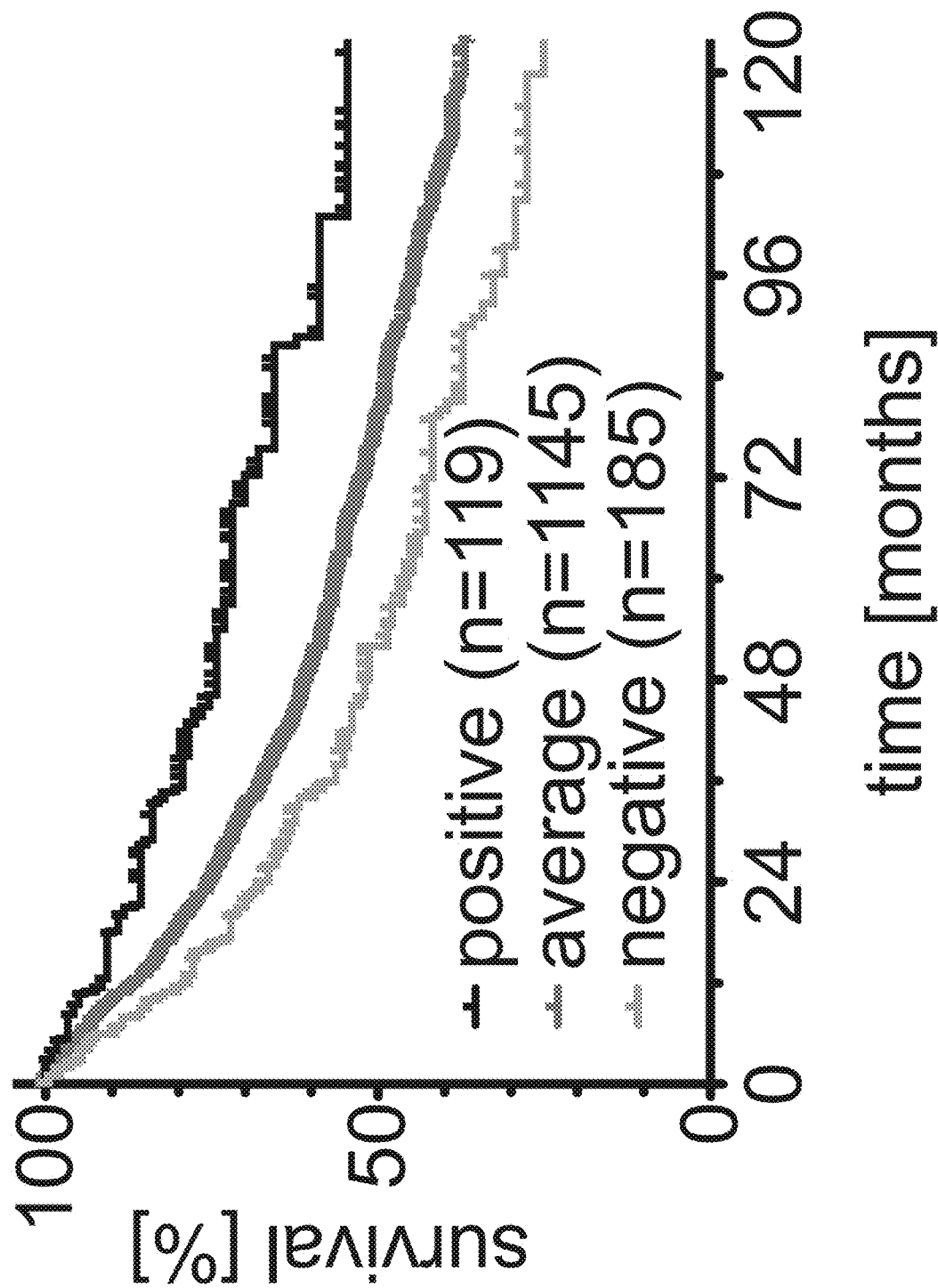
FIG. 11 shows Kaplan-Meier curves showing the overall survival of 1145 patients with lung cancer (average; dark grey, solid line; GEO accession numbers: GSE19188, GSE3141, GSE50081, GSE37745, GSE29013, GSE30219, GSE31210) stratified by the proprietary 3-gene signature (i.e., OMA1: high, HIGD1A: high, BNIP3: low).
Figure 12:
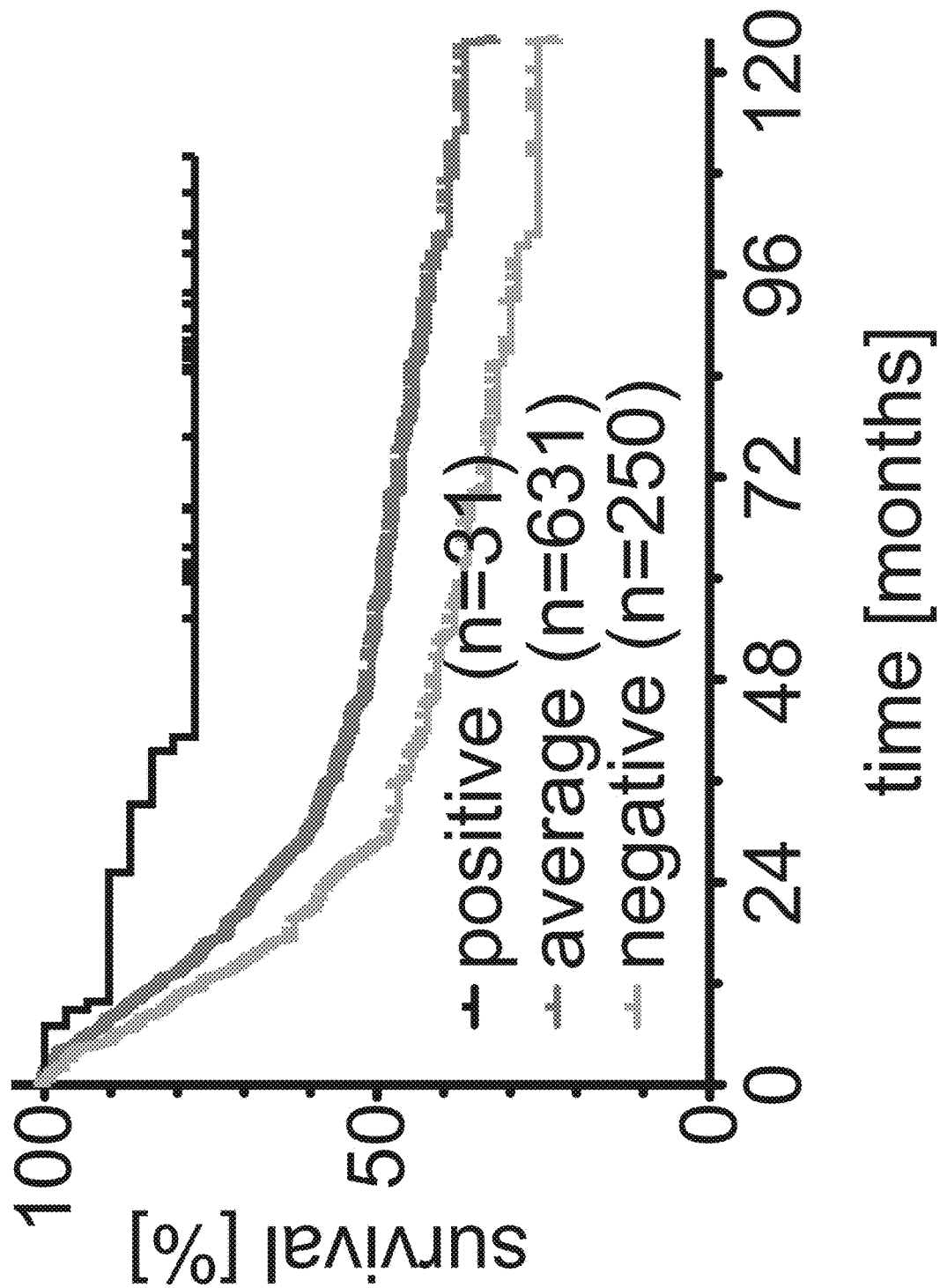
FIG. 12 shows Kaplan-Meier curves showing the overall survival of 631 patients with gastric cancer (average; dark grey, solid line; GEO accession numbers: GSE22377, GSE15459, GSE51105, GSE62254, GSE62254) stratified by the proprietary 3-gene signature (i.e., OMA1: high, HIGD1A: high, BNIP3: low).

FIG. 11 shows Kaplan-Meier curves showing the overall survival of 1145 patients with lung cancer (average; dark grey, solid line; GEO accession numbers: GSE19188, GSE3141, GSE50081, GSE37745, GSE29013, GSE30219, GSE31210) stratified by the proprietary 3-gene signature (i.e., OMA1: high, HIGD1A: high, BNIP3: low). Patients whose signature matched all 3 genes (positive; black, solid line) had an 82% chance of survival, while patients whose signature was inverted (i.e., OMA1: low, HIGD1A: low, BNIP3: high; negative; light grey, dotted line) had only a 55% chance with a median survival of 25 months (Log-rank Test: p<0.0001; Chi square=21.77; df=2).

FIG. 12 shows Kaplan-Meier curves showing the overall survival of 631 patients with gastric cancer (average; dark grey, solid line; GEO accession numbers: GSE22377, GSE15459, GSE51105, GSE62254, GSE62254) stratified by the proprietary 3-gene signature (i.e., OMA1: high, HIGD1A: high, BNIP3: low). Patients whose signature matched all 3 genes (positive; black, solid line) had an 84% chance of survival, while patients whose whose signature was inverted (i.e., OMA1: low, HIGD1A: low, BNIP3: high; negative; light grey, dotted line) had only a 53% chance with a median survival of 25 months (Log-rank Test: p<0.0001; Chi square=24.12; df=2).

Figure 13:
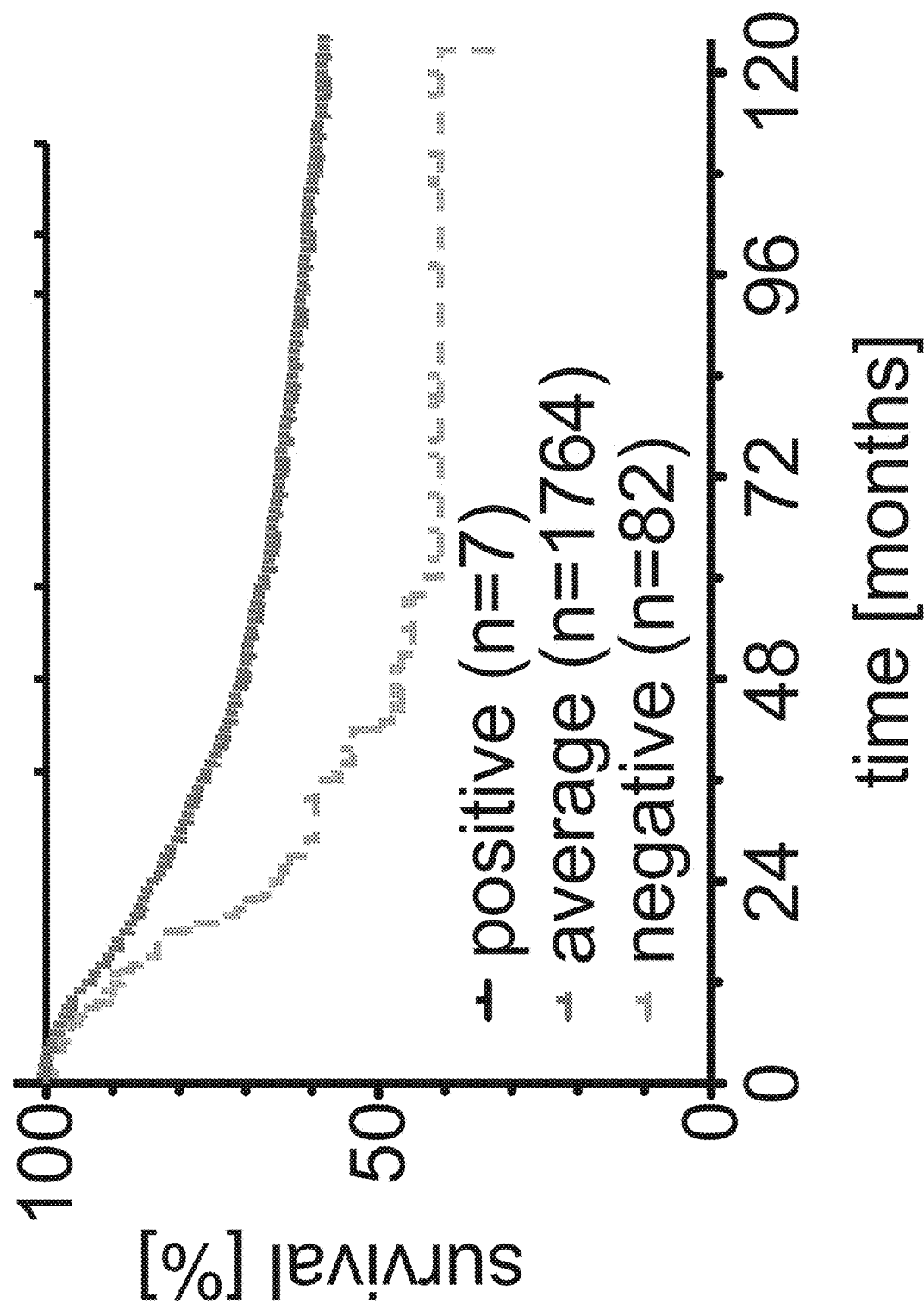
FIG. 13 shows Kaplan-Meier curves showing the overall survival of 1764 patients with breast cancer (average; dark grey, solid line; GEO accession numbers: E-MTAB-365, GSE12276, GSE16391, GSE16446, GSE17907, GSE19615, GSE20685, GSE20711, GSE21653, GSE42568, GSE9195) stratified by a proprietary 6-gene signature based on OMA1, HIGD1A, OPA1, BNIP3, YME1L1 and IMMT expression levels.

In another particular embodiment we have invented a more refined 6-gene expression signature particularly useful for the prognosis of survival of patients with breast cancer (FIG. 13). This 6-gene signature comprises OMA1, HIGD1A, BNIP3, OPA1, YME1L1 and IMMT, wherein OMA1 and HIGD1A expression levels are elevated and BNIP3, OPA1, YME1L1 and IMMT expression levels are reduced compared to the median expression levels (i.e., OMA1: high, HIGD1A: high, BNIP3: low, OPA1: low, YME1L1: low, IMMT: low). In a meta-study of 1764 patients with breast cancer, we were able to identify patients with 100% chance of survival provided that all 6 genes matched the 6-gene signature (FIG. 13, positive). Subjects whose gene expression profile did not match the 6-gene signature (negative; i.e., OMA1: low, HIGD1A: low, BNIP3: high, OPA1: high, YME1L1: high, IMMT: high) had only a 60.26% (±21.61 S.D.) chance of survival, and the median survival was 42 months (Log-rank Test: p<0.0001; Chi square=93.45; df=6). When the expression levels of 5 genes matched the 6-gene signature (5/6), patients had on average a chance of 87.19% (±7.188 S.D.). When 4 genes matched the 6-gene signature (4/6), the chance was 79.59% (±9.399 S.D.). When 3 genes matched the 6-gene signature (3/6), the chance was 73.12% (±12.70 S.D.). When 2 genes matched the 6-gene signature (2/6), the chance was 69.15% (±13.49 S.D.). And when only 1 gene matched the 6-gene signature (1/6), there was a 60.72% (±17.04 S.D.) chance of survival with a median survival of 73 months.

FIG. 13 shows Kaplan-Meier curves showing the overall survival of 1764 patients with breast cancer (average; dark grey, solid line; GEO accession numbers: E-MTAB-365, GSE12276, GSE16391, GSE16446, GSE17907, GSE19615, GSE20685, GSE20711, GSE21653, GSE42568, GSE9195) stratified by a proprietary 6-gene signature based on OMA1, HIGD1A, OPA1, BNIP3, YME1L1 and IMMT expression levels. Patients whose signature matched all 6 genes (positive; black, solid line) had a 100% chance of survival, while patients whose signature did not match any of the 6 genes (negative; light grey, dotted line) had only a 60% chance with a median survival of 42 months (Log-rank Test: p<0.0001; Chi square=93.45; df=6).

Figure 14:
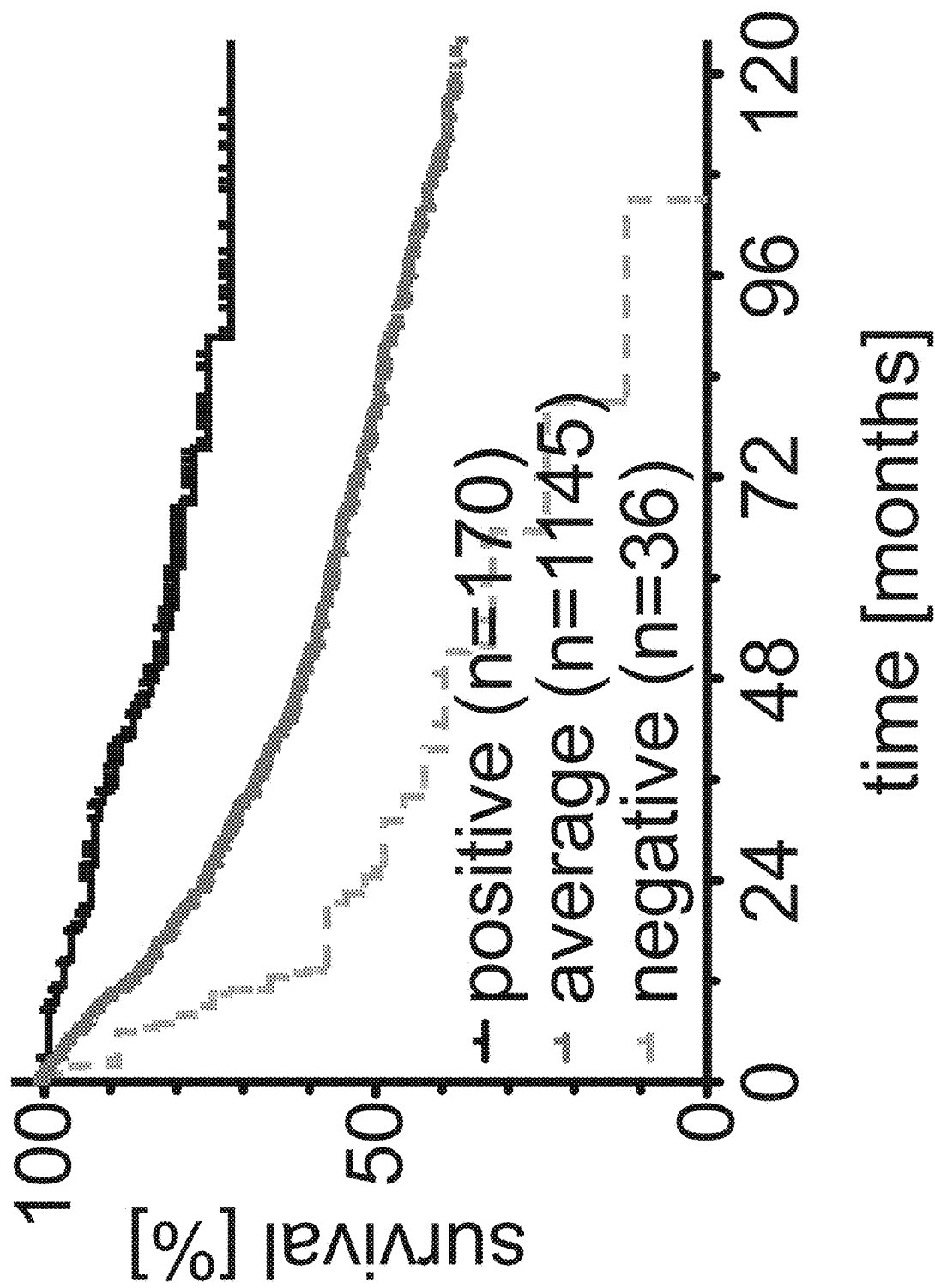
FIG. 14 shows Kaplan-Meier curves showing the overall survival of 1145 patients with lung cancer (average; dark grey, solid line; GEO accession numbers: GSE19188, GSE3141, GSE50081, GSE37745, GSE29013, GSE30219, GSE31210) stratified by a proprietary 6-gene signature based on OMA1, HIGD1A, YME1L1, PHB, SAMM50 and PHB2 expression levels.

In another embodiment it was, inter alia, found that a proprietary 6-gene signature has proven useful for the prognosis of survival of patients with lung cancer (FIG. 14). The 6-gene signature comprises elevated levels of OMA1, HIGD1A, YME1L1, PHB and SAMM50 compared to the median expression levels, and reduced PHB2 levels compared to the median expression levels (i.e., OMA1: high, HIGD1A: high, YME1L1: high, PHB: high, SAMM50: high, PHB2: low). In a meta-study of 1145 patients with lung cancer, we were able to identify patients with an 81.73% (±7.114 S.D.) chance of survival provided that all 6 genes matched the 6-gene signature (FIG. 14, positive). Subjects whose gene expression profile did not match the 6-gene signature (negative; i.e., OMA1: low, HIGD1A: low, YME1L1: low, PHB: low, SAMM50: low, PHB2: high) had only a 54.67% (±25.63 S.D.) chance of survival, and the median survival was 25 months (Log-rank Test: p<0.0001; Chi square=85.40; df=6). When expression levels of 5 genes matched the 6-gene signature (5/6), there was a 69.72% (±16.07 S.D.) chance and the median survival was 110 months. When 4 genes matched the 6-gene signature (4/6), the chance was 62.50% (±19.47 S.D.) and the median survival was 89 months. When 3 genes matched the 6-gene signature (3/6), there was a 57.84% (±20.73 S.D.) chance and the median survival was 55 months. When 2 genes matched the 6-gene signature (2/6), there was a 58.82% (±22.90 S.D.) chance and the median survival was 57 months. When only 1 gene matched the 6-gene signature (1/6), there was a 58.11% (±21.49 S.D.) chance and a subject's median survival was 45 months.

FIG. 14 shows Kaplan-Meier curves showing the overall survival of 1145 patients with lung cancer (average; dark grey, solid line; GEO accession numbers: GSE19188, GSE3141, GSE50081, GSE37745, GSE29013, GSE30219, GSE31210) stratified by a proprietary 6-gene signature based on OMA1, HIGD1A, YME1L1, PHB, SAMM50 and PHB2 expression levels. Patients whose signature matched all 6 genes (positive; black, solid line) had an 82% chance of survival, while patients whose signature did not match any of the 6 genes (negative; light grey, dotted line) had only a 55% chance with a median survival of 25 months (Log-rank Test: p<0.0001; Chi square=85.40; df=6).

Figure 15:
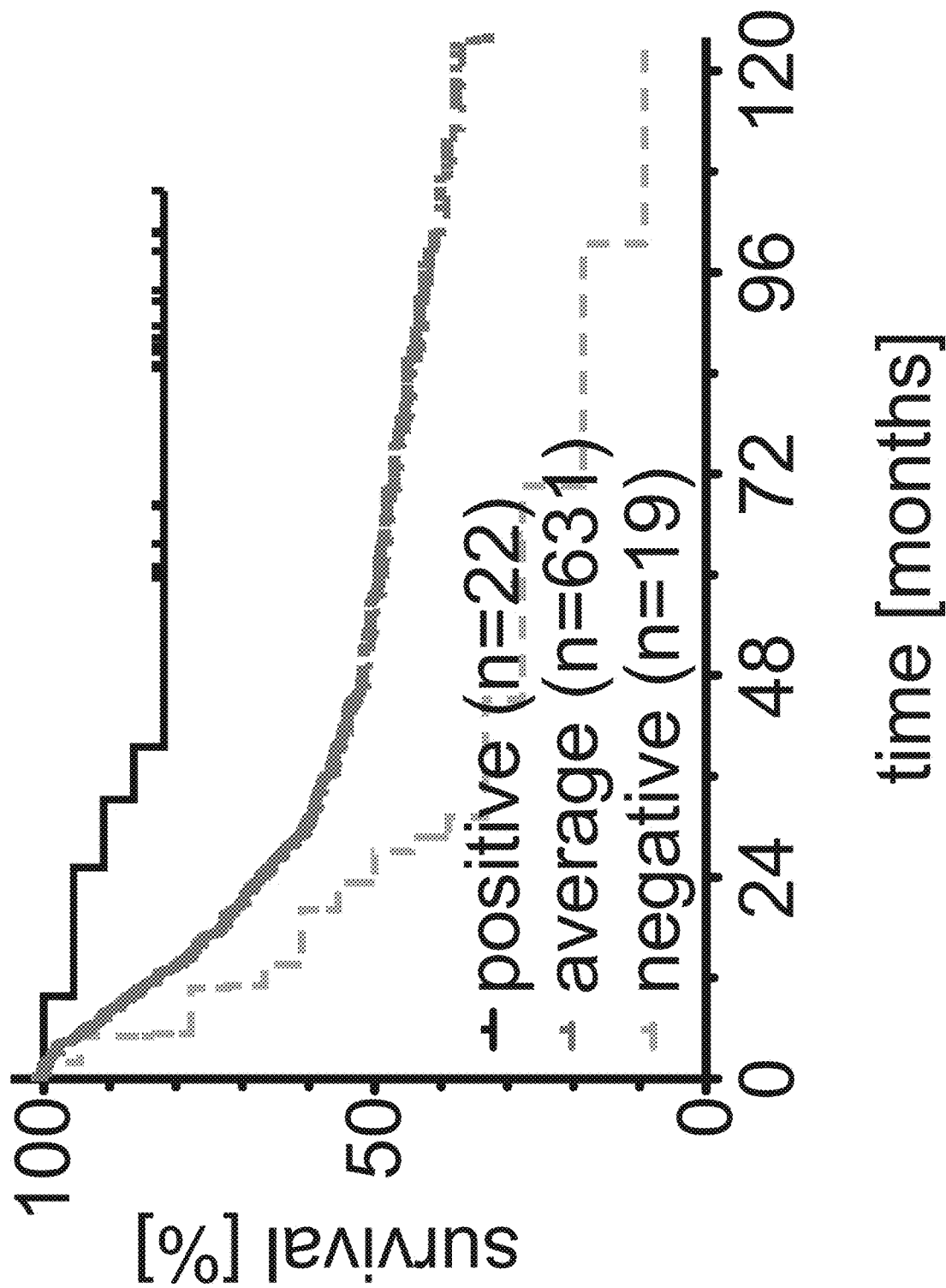
FIG. 15 shows Kaplan-Meier curves showing the overall survival of 631 patients with gastric cancer (average; dark grey, solid line; GEO accession numbers: GSE22377, GSE15459, GSE51105, GSE62254, GSE62254) stratified by a proprietary 7-gene signature based on OMA1, HIGD1A, YME1L1, PHB, SAMM50 and PHB2 expression levels.

In yet another embodiment it was, inter alia, found that a proprietary 7-gene signature has proven useful for the prognosis of survival of patients with gastric cancer (FIG. 15). The 7-gene signature comprises OMA1, HIGD1A, OPA1, BNIP3, YME1L1, SAMM50 and IMMT, wherein expression levels of BNIP3 are elevated while OMA1, HIGD1A, OPA1, YME1L1, SAMM50 and IMMT levels are decreased compared to the median levels (i.e., OMA1: low, HIGD1A: low, OPA1: low, YME1L1: low, SAMM50: low, IMMT: low, BNIP3: high). In a meta-study of 631 patients with gastric cancer, we were able to identify patients with an 83.79% (±4.908 S.D.) chance of survival provided that all 7 genes matched the 7-gene signature (FIG. 15, positive). Subjects whose gene expression profile did not match the 7-gene signature (negative; i.e., OMA1: high, HIGD1A: high, OPA1: high, YME1L1: high, SAMM50: high, IMMT: high, BNIP3: low) had only a 52.53% (±29.71 S.D.) chance of survival, and the median survival was 25 months (Log-rank Test: p<0.0001; Chi square=50.81; df=7). When 6 genes matched the 7-gene signature (6/7), there was a 74.68% (±11.29 S.D.) chance of survival. When 5 genes matched the 7-gene signature (5/7), there was a 67.07% (±14.17 S.D.) chance of survival. When 4 genes matched the 7-gene signature (4/7), there was a 69.22% (±14.48 S.D.) chance of survival. When 3 genes matched the 7-gene signature (3/7), the likelihood to survive was 61.61% (±21.79 S.D.) and the median survival was 38 months. When 2 genes matched the 7-gene signature (2/7), there was a 58.66% (±25.76 S.D.) chance and the median survival was 31 months. When only 1 gene matched the 7-gene signature (1/7), there was a 57.70% (±23.51 S.D.) chance and the median survival was 29 months.

FIG. 15 shows Kaplan-Meier curves showing the overall survival of 631 patients with gastric cancer (average; dark grey, solid line; GEO accession numbers: GSE22377, GSE15459, GSE51105, GSE62254, GSE62254) stratified by a proprietary 7-gene signature based on OMA1, HIGD1A, YME1L1, PHB, SAMM50 and PHB2 expression levels. Patients whose signature matched all 7 genes (positive; black, solid line) had an 84% chance of survival, while patients whose signature did not match any of the 7 genes (negative; light grey, dotted line) had only a 53% chance with a median survival of 25 months (Log-rank Test: p<0.0001; Chi square=50.81; df=7).

Figure 16:
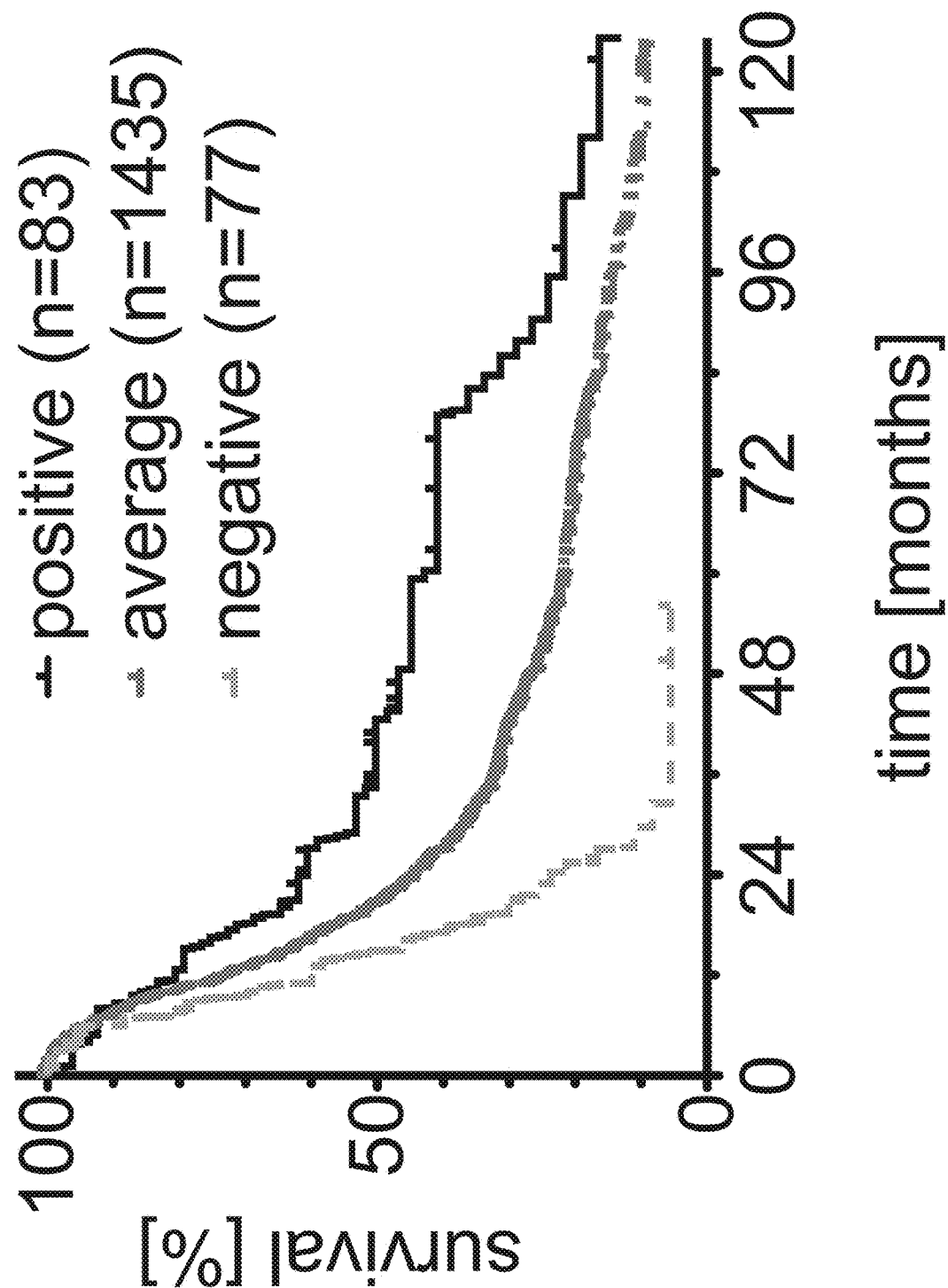
FIG. 16 shows Kaplan-Meier curves showing the overall survival of 1435 patients with ovarian cancer (average; dark grey, solid line; GEO accession numbers: GSE51373, GSE9891, GSE15622, GSE26712, GSE26193, GSE63885, GSE65986, GSE30161, GSE14764, TCGA) stratified by a proprietary 5-gene signature based on OPA1, BNIP3, YME1L1, IMMT, SAMM50 and PHB expression levels.

In yet another embodiment it was, inter alia, found that a proprietary 5-gene signature has proven useful for the prognosis of survival for patients with ovarian cancer (FIG. 16). The 5-gene expression signature comprises OPA1, BNIP3, YME1L1 and IMMT, which are reduced in their gene expression levels, and PHB, which has elevated levels compared to the median expression levels (i.e., OPA1: low, BNIP3: low, YME1L1: low, IMMT: low, PHB: high). In a meta-study of 1435 patients with ovarian cancer, we were able to identify patients with a 58.25% (±25.15 S.D) chance of survival provided that all 5 genes matched the 5-gene signature (FIG. 16, positive). These patients had a median survival of 43 months. When no gene matched the 5-gene signature (negative; i.e., OPA1: high, BNIP3: high, YME1L1: high, IMMT: high, PHB: low), there was a 56.81% (±28.46 S.D.) chance of survival and subjects had a median survival of 15 months (Log-rank Test: p<0.0001; Chi square=34.92; df=5). Patients had a 55.13% (±25.97 S.D.) chance of survival with a median survival of 24 months provided that 4 genes matched the 5-gene signature (4/5). When 3 genes matched the 5-gene signature (3/5), there was a 53.06% (±27.76 S.D.) chance and the median survival was 21 months. When 2 genes matched the 5-gene signature (2/5), there was a 57.53% (±28.81 S.D.) chance and the median survival was 19 months. When only 1 gene matched the 5-gene signature (1/5), there was a 60.48% (±28.47 S.D.) chance of survival and a subject's median survival was 19 months.

FIG. 16 shows Kaplan-Meier curves showing the overall survival of 1435 patients with ovarian cancer (average; dark grey, solid line; GEO accession numbers: GSE51373, GSE9891, GSE15622, GSE26712, GSE26193, GSE63885, GSE65986, GSE30161, GSE14764, TCGA) stratified by a proprietary 5-gene signature based on OPA1, BNIP3, YME1L1, IMMT, SAMM50 and PHB expression levels. Patients whose signature matched all 5 genes (positive; black, solid line) had a median survival of 43 months, while patients whose signature did not match any of the 5 genes (negative; light grey, dotted line) had only a median survival of 15 months (Log-rank Test: $p<0.0001$; Chi square=34.92; df=5).

It is known in the arts, and has been summarized above, that cancer also is a disorder correlated with mitochondrial dysfunction. In the context of the present invention it was, inter alia, found that measurements of OMA1, HIGD1A, OPA1, BNIP3, YME1L1, PHB, SAMM50, IMMT and/or PHB2 gene expression levels can be utilized for the prognosis of survival of a patient with cancer.

Cumulative evidence also exists for mitochondrial fusion/fission being necessary for normal cardiac function (Dorn 2013; Piquereau et al. 2013; Burke et al. 2015; Mann-Garcia and Akhmedov 2016; Ong et al. 2017). The first studies to investigate the role of OPA1 in the heart revealed reduced myocardial levels of OPA1 in ischemic heart failure patients and in a rat model of ischemic heart failure (Chen et al. 2009). OPA1 deficient mice show late onset cardiomyopathy with a decrease in cardiac output, reduced fractional shortening, and a blunted response to a β-adrenergic stimulus (Chen et al. 2012; Le Page et al. 2016). These findings were associated with mitochondrial fragmentation, impaired mitochondrial respiration, increased oxidative stress, attenuated calcium transients, and a reduction in mitochondrial DNA copy number (Chen et al. 2012). OPA1 deficient mice are also more susceptible to total aortic constriction, developing twice the extent of left ventricular hypertrophy, when compared to wild-type mice (Piquereau et al. 2012). These findings were associated with clustering of large mitochondria with abnormal cristae morphology, which were demonstrated to be resistant to calcium-induced mitochondrial permeability transition pore (MPTP) opening (Piquereau et al. 2012) Furthermore, cardiomyocytes from OPA1 deficient mice were more susceptible to cell death induced by ischemia/reperfusion injury (Chen et al. 2012; Le Page et al. 2016). Cardiac-specific ablation of YME1L1 in mice activated OMA1 and triggered OPA1 proteolysis, leading to a dilated cardiomyopathy and heart failure with mitochondrial fragmentation and altered cardiac metabolism (Wai et al. 2015). Genetic OMA1 deletion prevented OPA1 cleavage and cardio myopathy (Wai et al. 2015).

It is envisioned that comparable gene signatures can be developed based on the activity and/or expression of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

Example 4

The means and methods of the present disclosure can also be used to inform selection and/or assist in selecting appropriate courses of treatment and/or medical interventions for patients in need of such interventions.

We studied the OPA1 protein and its isoforms in fibroblast cell lines derived from patients that harbor a duplication of the exons 7 to 9 (c.678-984dup306) in the OPA1 gene (Fuhrmann et al. 2010). Exons 7 to 9 code for 102 amino acids in frame and one would expect a larger OPA1 protein. However, OPA1 protein levels were significantly reduced compared to healthy subjects and the ratios of the different OPA1 isoforms were altered. We could rule out nonsense mediated mRNA decay by qPCR analysis (Fuhrmann et al. 2010). Also mouse embryonic fibroblast cell lines with a splice-site mutation leading to skipping of Opa1 exon 10 (c.1065+5G>A) showed significantly reduced OPA1 protein levels despite no changes in the abundance of the mRNA (Alavi et al. 2007). These findings led us to the conclusion that OPA1 is regulated on protein levels and that only fully functional OPA1 is stable.

Co-culture experiments of mouse embryo fibroblasts from mutant OPA1 mice and wild-type control mice with epoxomycin, a specific inhibitor of the ubiquitin-proteasome degradation system, did not change OPA1 levels or the ratio of OPA1L to OPA1S isoforms, indicating that OPA1 is not regulated by the ubiquitin-proteasome pathway (Alavi et al. 2007). Phenanthroline is a chelator that sequesters divalent metal ions like zinc, which is crucial for the function of metallo-endopeptidases. When we cultured cells in the presence of phenantroline, we found an increase in the OPA1L isoform indicating that OPA1 is regulated by proteolytic turnover (Alavi et al. 2007). Indeed, when we investigated the OPA1 protein in pulse-chase experiments we found a degradation of OPA1L to OPA1S and changes in the protein half-life depending on single amino acid substitutions.

Stress-induced OPA1 cleavage caused cell death in different experimental paradigms (Olichon et al. 2003; Duvezin-Caubet et al. 2006; Ishihara et al. 2006; Griparic et al. 2007; Song et al. 2007; Merkwirth et al. 2008; Ehses et al. 2009; Head et al. 2009), and expression of non-cleavable OPA1 isoforms could prevent cell death in these experiments (Ishihara et al. 2006; Griparic et al. 2007; Song et al. 2007; Merkwirth et al. 2008). OMA1 knock-down or knock-out also can prevent cell death while prolonged activation of OMA1 will cause cell death. OMA1 is activated upon stress in pre-clinical disease models for ischemic kidney injury (Xiao et al. 2014), myocardial infarct (Piquereau et al. 2012; Wai et al. 2015), cancer (Kong et al. 2014), and neurodegeneration (Merkwirth et al. 2008; Korwitz et al. 2016). Knock-down or knock-out of OMA1 could prevent cell death in these models (Ehses et al. 2009; Head et al. 2009; Wai et al. 2015; Korwitz et al. 2016). We therefore screened for compounds that can modify OMA1 protease activity in a way that reduces OMA1 activity (i.e., OMA1 antagonists).

HEK293T cells were cultured and maintained in Dulbecco's Modified Eagle's Medium supplemented with 10% fetal bovine serum (FBS) and 2 mM 1-glutamine in a 95% air-5% $CO_2$ humidified atmosphere at 37° C. To test potential OMA1 antagonists, cells were seeded in 24-well plates and incubated over night to achieve around 90% confluency. For experiments the culture medium was replaced with Minimal Essential Medium and cells were pre-incubated with variable concentrations of the different test-compounds for 2 hours in a 95% air-5% $CO_2$ humidified atmosphere at 37° C. After 2 hours, OMA1 protease was activated through the addition of carbonyl cyanide m-chlorophenyl hydrazone (CCCP; 10 µM final concentration) for 30 min in the presence of different concentrations of compounds to be tested. After 30 minutes, cells were immediately placed on ice, the medium removed, and cells harvested through addition of 100 µl RIPA buffer supplemented with protease inhibitor cocktail. Samples were separated on 8% tris-glycine gels and transferred onto nitro-cellulose membranes by Wester blotting. Membranes were immunolabeled with anti-OPA1 Antibodies (1:1,000) and with goat-anti-mouse Alkaline Phosphatase conjugated secondary antibodies (1:5, 000). OPA1 protein was visualized with NBT/BCIP between 5 and 15 minutes before the reaction was stopped with an excess of distilled water.

As illustrated in FIG. 1, lane 1, and described in more details above, 5 different OPA1 isoforms (i.e., OPA1-L1, OPA1-L2, OPA1-S3, OPA1-S4, OPA1-S5) can be detected in HEK293T cells under standard culture conditions. CCCP is a potent mitochondrial oxidative phosphorylation uncoupler that activates OMA1 and creates conditions that allow OPA1 cleavage to occur. As illustrated in FIG. 1, lane 2, 30 minutes of CCCP treatment resulted in cleavage of both large OPA1-L1 and OPA1-L2 isoforms so that only the small OPA1-S3, OPA1-S4 and OPA1-S5 isoforms were detectable.

Figure 17:
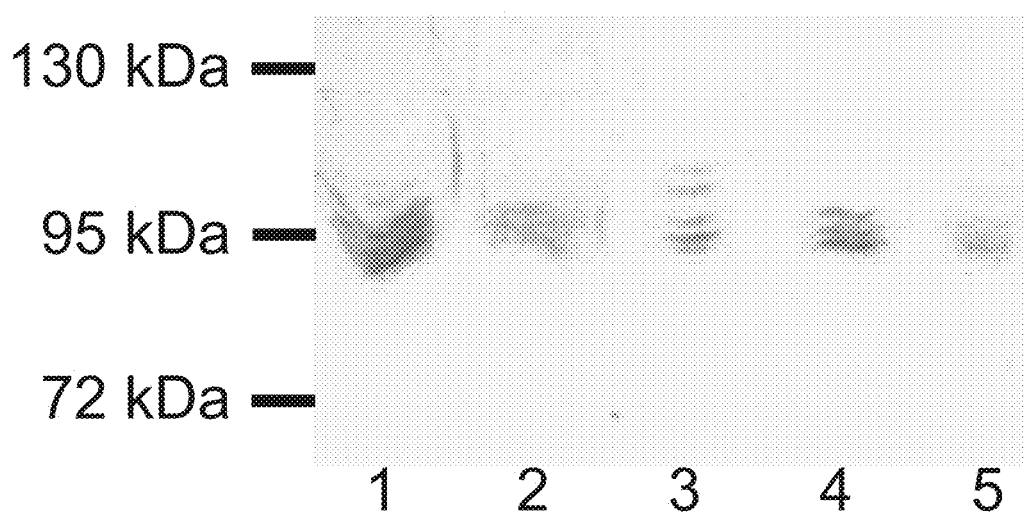
FIG. 17 shows the cleavage of OPA isoforms following exposure of HEK293T cells to thiophan.

In a non-limiting example it was, inter alia, found that Thiorphan (CAS #76721-89-6) can inhibit proteolytic cleavage of large OPA1 isoforms under conditions allowing OPA1 processing to occur (FIG. 17). As illustrated in FIG. 17, lanes 1, 2, 4 and 5, only the small OPA1 isoforms OPA1-S3, OPA1-S4 and OPA1-S5 were detectable by SDS-PAGE/Western-blotting upon treatment with 10 µM CCCP. In samples treated with 100 µM Thiorphan, however, all OPA1 isoforms including the two large OPA1-L1 and OPA1-L2 isoforms were readily detectable (FIG. 17, lane 3), which demonstrates that Thiorphan can affect proteolytic cleavage of OPA1 by OMA1 upon dissipation of the mitochondrial membrane potential. Thiorphan thus represent an antagonist of OMA1 and/or an oligomeric complex comprising OMA1.

Referring to FIG. 17, thiorphan (CAS #76721-89-6) is a non-limiting example of an OMA1 antagonists. In HEK293T cells, 10 µM CCCP could activate OMA1, which resulted in the cleavage of the OPA1-L1 and OPA1-L2 isoforms so that only the smaller three isoforms OPA1-S3, OPA1-S4 and OPA1-S5 were detectable by SDS-PAGE/Western-blot (lanes 1, 2, 4 and 5). The large OPA1-L1 and OPA1-L2 isoforms were still readily detectable when cells were treated with 100 µM Thiorphan (lane 3) for 2 hours prior OMA1 activation.

Figure 18:
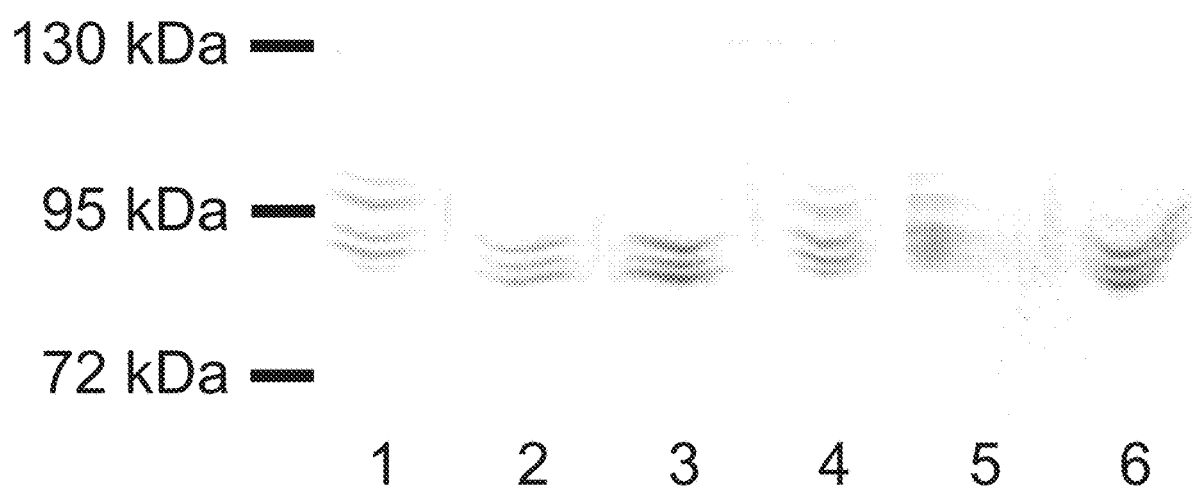
FIG. 18 shows the cleavage of OPA isoforms following exposure of HEK293T cells to phenanthroline.

In another non-limiting example it was, inter alia, found that ARP100 (CAS #704888-90-4) can inhibit proteolytic cleavage of large OPA1 isoforms under conditions allowing OPA1 processing to occur (FIG. 18). Again, only the small OPA1 isoforms OPA1-S3, OPA1-S4 and OPA1-S5 were detectable by SDS-PAGE/Western-blotting upon CCCP treatment (FIG. 18, lanes 2, 3 and 6), while in samples treated with 70 µM ARP100 all OPA1 isoforms including the large OPA1-L1 and OPA1-L2 isoforms were readily detectable (FIG. 18, lane 4). This demonstrates that ARP100 can inhibit proteolytic cleavage of OPA1 by OMA1. ARP100 thus represent an antagonist of OMA1 and/or an oligomeric complex comprising OMA1.

Referring to FIG. 18, phenanthroline (CAS #66-71-7) and ARP100 (CAS #704888-90-4) are non-limiting examples of OMA1 antagonists. In HEK293T cells, 10 µM CCCP could activate OMA1, which resulted in the cleavage of the OPA1-L1 and OPA1-L2 isoforms so that only the smaller three isoforms OPA1-S3, OPA1-S4 and OPA1-S5 were detectable by SDS-PAGE/Western-blot (lanes 2, 3 and 6). The large OPA1-L1 and OPA1-L2 isoforms were still readily detectable when cells were treated with 500 µM phenanthroline (lane 1) or 70 µM ARP100 (lane 4) for 2 hours prior OMA1 activation.

We controlled the experiments with phenanthroline, a chelator with inhibitory effects on metallo-enzymes. As expected, 500 µM phenanthroline also inhibited proteolytic cleavage of OPA1 by OMA1 (FIG. 18, lane 1).

Thiorphan is a potent inhibitor of neprilysin, a membrane metallo-endopeptidase that cleaves peptide hormones, such as enkephalins, glucagon, and bradykinin (Eberlin et al. 2012). Thiorphan is known in the arts also for its neuroprotective activity against excitotoxic neuronal cell death (Medja et al. 2006), which supports the OMA1 protease as genuine target for neuroprotective therapies. Moreover, this validates our approach of developing means and methods for the development of therapies for patients with mitochondrial disease. ARP 100 is a biphenylsulfonamide that acts as a selective inhibitor of MMP-2 (Rossello et al. 2004; Tuccinardi et al. 2006). The antagonistic effects of ARP100 on OMA1 were not known and are non-obvious to a person skilled in the arts.

Example 5

Cancer is a non-limiting example for a mitochondrial disorder or disease characterized by OPA1 alterations. As laid out in more details above, alterations in OMA1 and/or a heterooligomeric complex compromising OMA1 have a prognostic value for patients with various types of cancer. Certain cancer types were characterized, inter alia, by a 3-gene signature of increased OMA1 and HIGD1A levels and decreased BNIP3 levels. Patients with increased with this particular 3-gene signature had a significantly better prognosis of overall survival than patients without this signature. Moreover, patients that would have an inverted 3-gene signature of reduced OMA1 and HIGD1A levels and increased BNIP3 levels had a significantly worse prognosis of overall survival. In accordance with our results are findings of a study that compared cancer cells that are resistant against platin-based therapies with cancer cells that are amenable to these therapies. Chemoresistant cancer cells show significantly reduced OMA1 activity, which correlated with tumorogenesis, metastatic spread and overall survival of the cancer cells (Kong et al. 2015). Taken together, these data demonstrate that certain mitochondrial disorders or diseases are characterized by decreased OMA1 and that OMA1 agonists represent genuine medical interventions for these diseases. We therefore also screened for compounds that can modify OMA1 protease activity in a way that increases OMA1 activity (i.e., OMA1 agonists).

HEK293T cells were cultured and maintained in Dulbecco's Modified Eagle's Medium supplemented with 10% fetal bovine serum (FBS) and 2 mM 1-glutamine in a 95% air-5% $CO_2$ humidified atmosphere at 37° C. To test potential OMA1 antagonists, cells were seeded in 24-well plates and incubated over night to achieve around 90% confluency. For experiments the culture medium was replaced with Minimal Essential Medium and cells were pre-incubated with 100 µM compounds to be tested for their effects on OMA1 protease for 2 hours in a 95% air-5% $CO_2$ humidified atmosphere at 37° C. After 2 hours, cells were treated with increasing concentrations of 0 µM, 3 µM, 5 µM or 7 µM CCCP for 20 minutes to determine the minimum CCCP concentration that would lead to OMA1 activation and OPA1 cleavage, and whether this threshold level could be modified by the compound at question. After 20 minutes, cells were immediately placed on ice, the medium removed, and cells harvested through addition of 100 μl RIPA buffer supplemented with protease inhibitor cocktail. Samples were separated on 8% tris-glycine gels and transferred onto nitro-cellulose membranes by Wester blotting. Membranes were immunolabeled with anti-OPA1 Antibodies (1:1,000) and with goat-anti-mouse Alkaline Phosphatase conjugated secondary antibodies (1:5,000). OPA1 protein was visualized with NBT/BCIP between 5 and 15 minutes before the reaction was stopped with an excess of distilled water.

Figure 19:
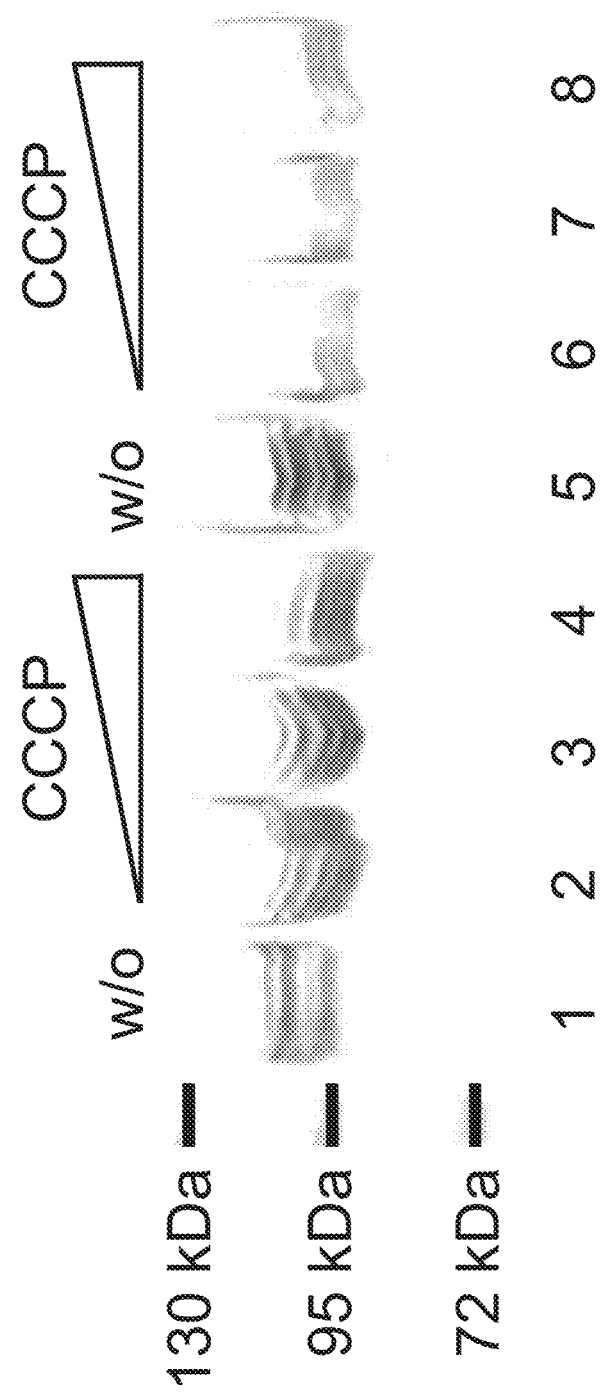
FIG. 19 shows the cleavage of OPA isoforms following exposure of HEK293T cells to SB-3CT.

In one particular embodiment it was, inter alia, found that SB-3CT (CAS #292605-14-2) reduced the threshold levels of OMA1 activation and allowed for proteolytic cleavage of large OPA1 isoforms to occur under conditions that otherwise would not allow for OPA1 cleavage to occur. HEK293T cells were cultured in MEM only or in MEM supplemented with increasing concentrations of 0 μM, 3 μM, 5 μM or 7 μM CCCP. As illustrated in FIG. 19, 0 μM, 3 μM and 5 μM CCCP had no effect on OPA1 processing in untreated cells (lanes 1, 2 and 3). In untreated cells OPA1 was cleaved only at the highest concentration of 7 μM CCCP (FIG. 19, lane 4). SB-3CT by itself had no effect on OPA1 under normal conditions that do not allow for OPA1 cleavage to occur, because cells that only were treated with 100 μM SB-3CT and that were not exposed to CCCP did not show OPA1 alterations (FIG. 19, lane 5). All 5 isoforms were readily detectable in these samples by SDS-PAGE/Western-blotting (FIG. 19, lane 5). To our surprise and against all expectations we found that 100 μM SB-3CT caused OPA1 cleavage to occur already at 3 μM and 5 μM CCCP (FIG. 19, lanes 6 and 7). As illustrated in FIG. 19, OPA1 cleavage in SB-3CT-treated cells, in particular at low CCCP concentrations, exceeded that of the control cells (FIG. 19, lanes 2 and 3, "vehicle-only".)

Referring to FIG. 19, SB-3CT (CAS #292605-14-2) represents an OMA1 agonist because SB-3CT reduces the threshold levels of OMA1 activation and allows for proteolytic cleavage of large OPA1 isoforms to occur under conditions that otherwise would not allow for OPA1 cleavage to occur. HEK293T cells were cultured with increasing concentrations of 0 μM, 3 μM, 5 μM and 7 μM CCCP (lanes 1-4 & 5-8). In "vehicle-only" treated cells (lanes 1-4), OMA1 was activated at the highest concentration of 7 μM CCCP (lane 4). In cells treated with 100 μM SB-3CT (lanes 5-8), OMA1 was already activated at lower concentrations of 3 μM and 5 μM CCCP (lanes 6 & 7). 100 μM SB-3CT did not induce OPA1 cleavage without CCCP (lane 5) demonstrating that SB-3CT acts through the stress-dependent modulation of the OMA1 complex.

SB-3CT is known in the arts for its inhibitory effects on proteases (US 2009/0209615 and US 2013/0052184) and the above-mentioned finding that SB-3CT can activate the OMA1 protease under conditions that otherwise would not allow for OPA1 cleavage to occur was surprising and against all expectations. In context of the present invention SB-3CT thus represents an agonist of OMA1 and/or an oligomeric complex comprising OMA1 as defined above. Accordingly, SB-3CT represents a medical intervention in particular for the treatment, prevention and/or amelioration of a disorder or disease correlated with mitochondrial stress or dysfunction, a mitochondrial disorder or disease, or a disorder or disease characterized by OPA1 alterations.

Example 6

An important aspect of the invention disclosed herein is that mitochondrial diseases or disorders or diseases can be characterized by alterations of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof. Measurements of these alterations can support diagnosis and guide therapy selection. Moreover, compounds and/or interventions that can mitigate alterations in OMA1, HIGD1A, OPA1, BNIP3, YME1L1, PHB, PHB2, SAMM50 or IMMT present suitable medical interventions for patients suffering from such a disorder or disease.

In an in silico approach we aimed to identify compounds and/or interventions that affect OMA1 and/or a heterooligomeric complex compromising OMA1. To this end, we mined publicly available data repositories for compounds that can modulate OMA1, HIGD1A, OPA1, BNIP3, YME1L1, PHB, PHB2, SAMM50 or IMMT. The findings are summarized in the table depicted in FIG. 20, which provides a list of compounds and treatments that are suitable medical interventions for patients with a mitochondrial disease or disorder.

FIG. 20 shows a list of different drugs and compounds that can modify OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof. These drugs represent non-limiting examples for therapies and medical interventions for patients with mitochondrial disease or disorder.

Figure 21:
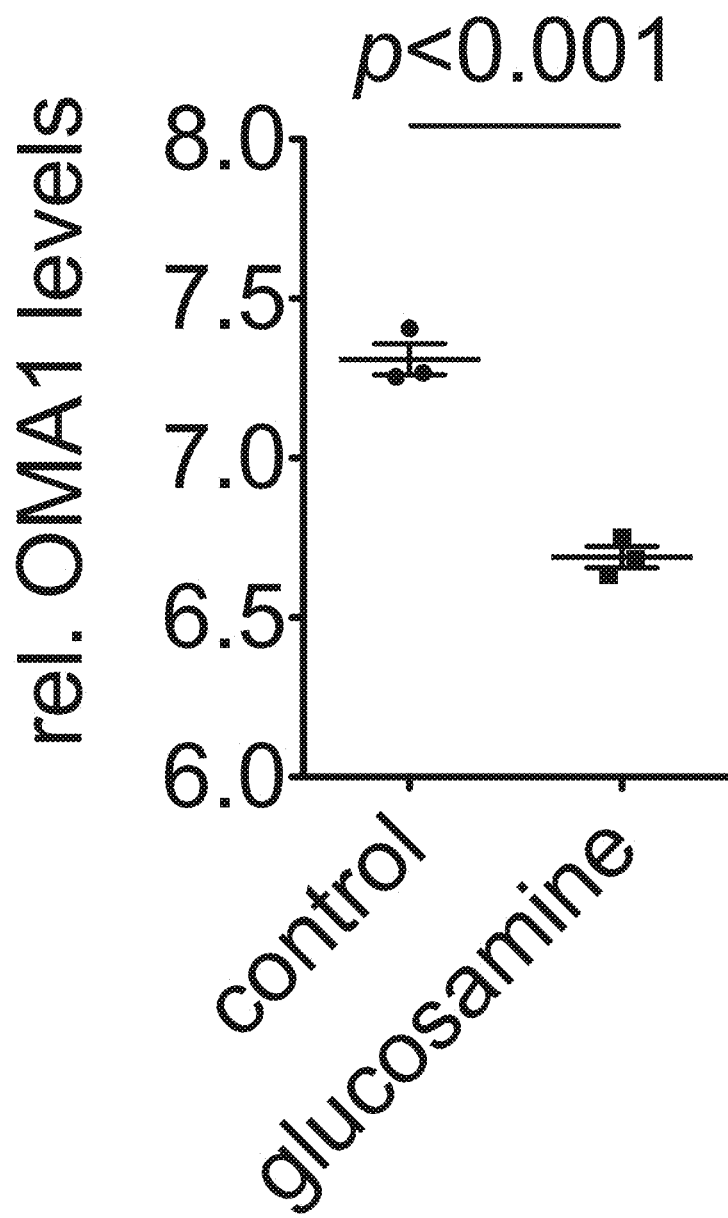
FIG. 21 shows OMA1 gene expression levels of KMH2 cells following exposure to glucosamine.

In one embodiment it was, inter alia, found that glucosamine (CAS #3416-24-8) significantly decreases the gene expression levels of OMA1 by 8.5% (FIG. 21; Student's T-test: $p \leq 0.001$). Human malignant lymphocytes (KMH2 cells) were cultured without or with 20 mM glucosamine (Carvalho et al. 2014). After 24 hours mRNA was isolated and analyzed by gene expression microarrays. Controls expressed OMA1 at 7.31 (±0.08 S.D.) and glucosamine treated cells expressed OMA1 at 6.69 (±0.06 S.D.). Glucosamine is a dietary supplement and its effects on mitochondria are known to a person skilled in the arts (Carvalho et al. 2014; Bond and Hanover 2015; Tan et al. 2017). However, the finding that glucosamine can significantly decrease OMA1 levels was unexpected and is non-obvious to a person skilled in the arts. In context of the present invention glucosamine thus represents an antagonist of OMA1 and/or an oligomeric complex comprising OMA1 as defined above. Accordingly, glucosamine represents a medical intervention in particular for the treatment, prevention and/or amelioration of a disorder or disease correlated with mitochondrial stress or dysfunction, a mitochondrial disorder or disease, or a disorder or disease characterized by OPA1 alterations.

Referring to FIG. 21, the dietary supplement glucosamine (CAS #3416-24-8) represents an antagonist of OMA1. Glucosamine can significantly decrease the gene expression levels of OMA1 in human malignant lymphocytes by 8.5% (Student's T-test: $p \leq 0.001$; GEO accession number: GDS5388). KMH2 cells were cultured for 24 hours without or with 20 mM glucosamine, after which mRNA was isolated and analyzed by gene expression microarrays. Controls expressed OMA1 at 7.31 (±0.08 S.D.) and glucosamine treated cells expressed OMA1 at 6.69 (±0.06 S.D.).

In another embodiment it was, inter alia, found that the micro-RNA miR-203 (NCBI Reference Sequence: NR_029620.1) significantly reduced the gene expression levels of OMA1 by 22% to 27% (FIGS. 22A and 22B); Student's T-test: $p \leq 0.05$). miR-203 was overexpressed in the breast cancer cell line SUM159 using a retrovirus (Taube et al. 2013). SUM159 control cells expressed OMA1 at 1219.5 (±109.3 S.D.; Spot ID: 226019_at) and 718.4 (±50.0 S.D. (FIG. 22A); Spot ID: 226020_s_at), while SUM159 cells expressing miR-203 had significantly reduced OMA1 levels at 891.7 (±54.1 S.D.; Spot ID: 226019_at) and 557.8 (±59.1 S.D.; Spot ID: 226020_s_at) (FIG. 22B), respectively. A person skilled in the arts knows miR-203 for its role in the epithelial-mesenchymal transition (EMT). The finding that miR-203 can decrease OMA1 levels was unexpected and is non-obvious to a person skilled in the arts. In context of the present invention miR-203 thus represents an antagonist of OMA1 and/or an oligomeric complex comprising OMA1 as defined above. Accordingly, miR-203 represents a medical intervention in particular for the treatment, prevention and/or amelioration of a disorder or disease correlated with mitochondrial stress or dysfunction, a mitochondrial disorder or disease, or a disorder or disease characterized by OPA1 alterations.

Referring to FIGS. 22A and 22B, the micro-RNA miR-203 (NCBI Reference Sequence: NR_029620.1) represents an antagonist of OMA1. miR-203 can significantly decrease the expression levels of OMA1 in human SUM159 mesenchymal-like breast cancer cells by 22% to 27% (Student's T-test: p≤0.05; GEO accession number: GSE23031). SUM159 control cells expressed OMA1 at 1219.5 (±109.3 S.D.; Spot ID: 226019_at) and 718.4 (±50.0 S.D. (FIG. 22A); Spot ID: 226020_s_at), while SUM159 cells expressing miR-203 had significantly reduced OMA1 levels at 891.7 (±54.1 S.D.; Spot ID: 226019_at) and 557.8 (±59.1 S.D.; Spot ID: 226020_s_at) (FIG. 22B), respectively.

Figure 23:
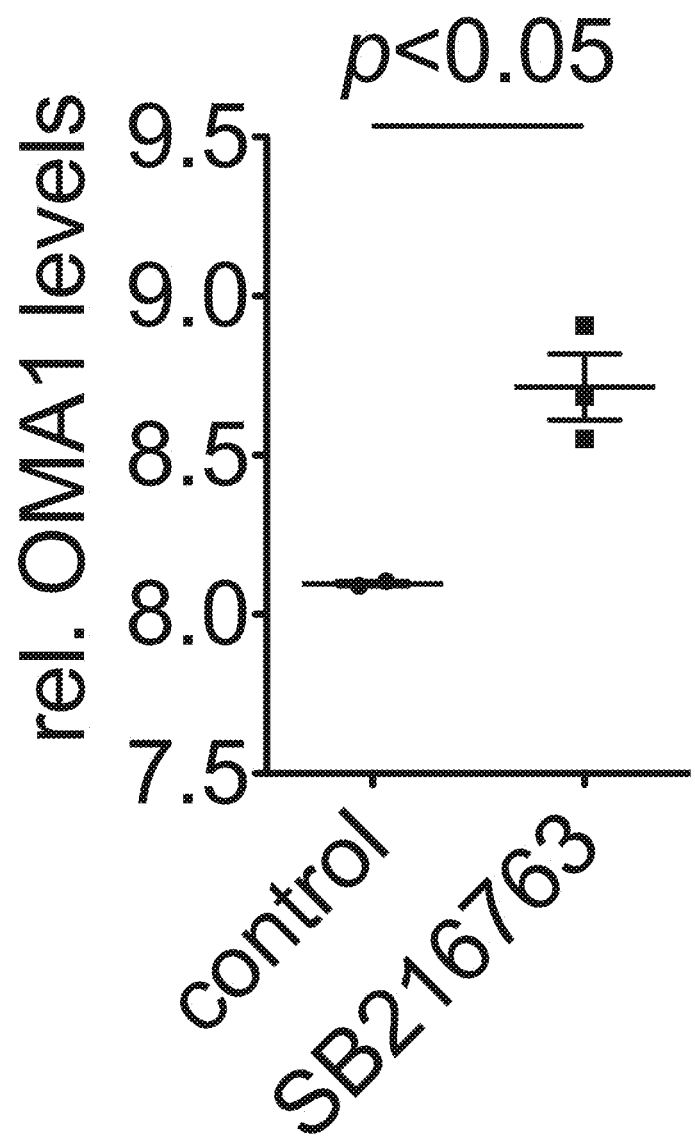
FIG. 23 shows OMA1 gene expression levels of RS4.11 cells following exposure to GSK-3 inhibitor SB216763.

In another particular embodiment it was, inter alia, found that the GSK-3 inhibitor SB216763 (CAS #280744-09-4) significantly increased gene expression levels of OMA1 by 7.6% (FIG. 23; Student's T-test: p≤0.05). Human MLL leukemia RS4.11 cells were cultured without or with 10 µM SB216763 for 20 hours (Wang et al. 2010). Gene expression analyses by microarrays demonstrated that controls expressed OMA1 at 8.10 (±0.01 S.D.), while cells treated with SB216763 expressed OMA1 at 8.7 (±0.18 S.D.). SB216763 is a kinase inhibitor and the finding that SB216763 can increase OMA1 levels was unexpected and is non-obvious to a person skilled in the arts. In context of the present invention SB216763 thus represents an agonist of OMA1 and/or an oligomeric complex comprising OMA1 as defined above. Accordingly, SB216763 represents a medical intervention in particular for the treatment, prevention and/or amelioration of a disorder or disease correlated with mitochondrial stress or dysfunction, a mitochondrial disorder or disease, or a disorder or disease characterized by OPA1 alterations.

Referring to FIG. 23, the GSK-3 inhibitor SB216763 (CAS #280744-09-4) represents an agonist of OMA1. SB216763 can significantly increase OMA1 gene expression levels in human MLL leukemia cells (RS4.11 cells) by 7.6% (Student's T-test: p≤0.05; GEO accession number: GDS4043). RS4.11 cells were cultured for 20 hours without or with 10 µM SB216763, after which mRNA was isolated and analyzed by gene expression microarrays. Controls expressed OMA1 at 8.10 (±0.01 S.D.) and SB216763 treated cells expressed OMA1 at 8.7 (±0.18 S.D.).

In one particular embodiment it was, inter alia, found that the cytokine CXCL4 (UniProt: P02776) significantly increased the gene expression levels of OMA1 in monocyte derived macrophages by 42% to 103% (FIGS. 24A and 24B; Student's T-test: p≤0.05). Monocytes were cultured for 6 days without or with 1 µM CXCL4 (Gleissner et al. 2010). Controls expressed OMA1 at 279.0 (±30.9 S.D.; Spot ID: 226019_at) and 327.3 (±20.8 S.D.; Spot ID: 226020_s_at), while CXCL4 treated cells had significantly increased OMA1 levels at 566.8 (±94.5 S.D. (FIG. 24A); Spot ID: 226019_at) and 465.3 (±23.3 S.D.; Spot ID: 226020_s_at) (FIG. 24B), respectively. CXCL4 is a small cytokine belonging to the CXC chemokine family that is also known in the arts as platelet factor 4 (PF4). The finding that CXCL4 can increase OMA1 levels was unexpected and is non-obvious to a person skilled in the arts. In context of the present invention CXCL4 thus represents an agonist of OMA1 and/or an oligomeric complex comprising OMA1 as defined above. Accordingly, CXCL4 represents a medical intervention in particular for the treatment, prevention and/or amelioration of a disorder or disease correlated with mitochondrial stress or dysfunction, a mitochondrial disorder or disease, or a disorder or disease characterized by OPA1 alterations.

Referring to FIGS. 24A and 24B, the small cytokine CXCL4 (UniProt: P02776) represents an agonist of OMA1. CXCL4 can significantly increase the gene expression levels of OMA1 in monocyte derived macrophages by 42% to 103% (Student's T-test: p≤0.05; GEO accession number: GDS3787). Controls expressed OMA1 at 279.0 (±30.9 S.D.; Spot ID: 226019_at) and 327.3 (±20.8 S.D. (FIG. 24A); Spot ID: 226020_s_at), while CXCL4 treated cells had significantly increased OMA1 levels at 566.8 (±94.5 S.D.; Spot ID: 226019_at) and 465.3 (±23.3 S.D.; Spot ID: 226020_s_at) (FIG. 24B), respectively.

Figure 25:
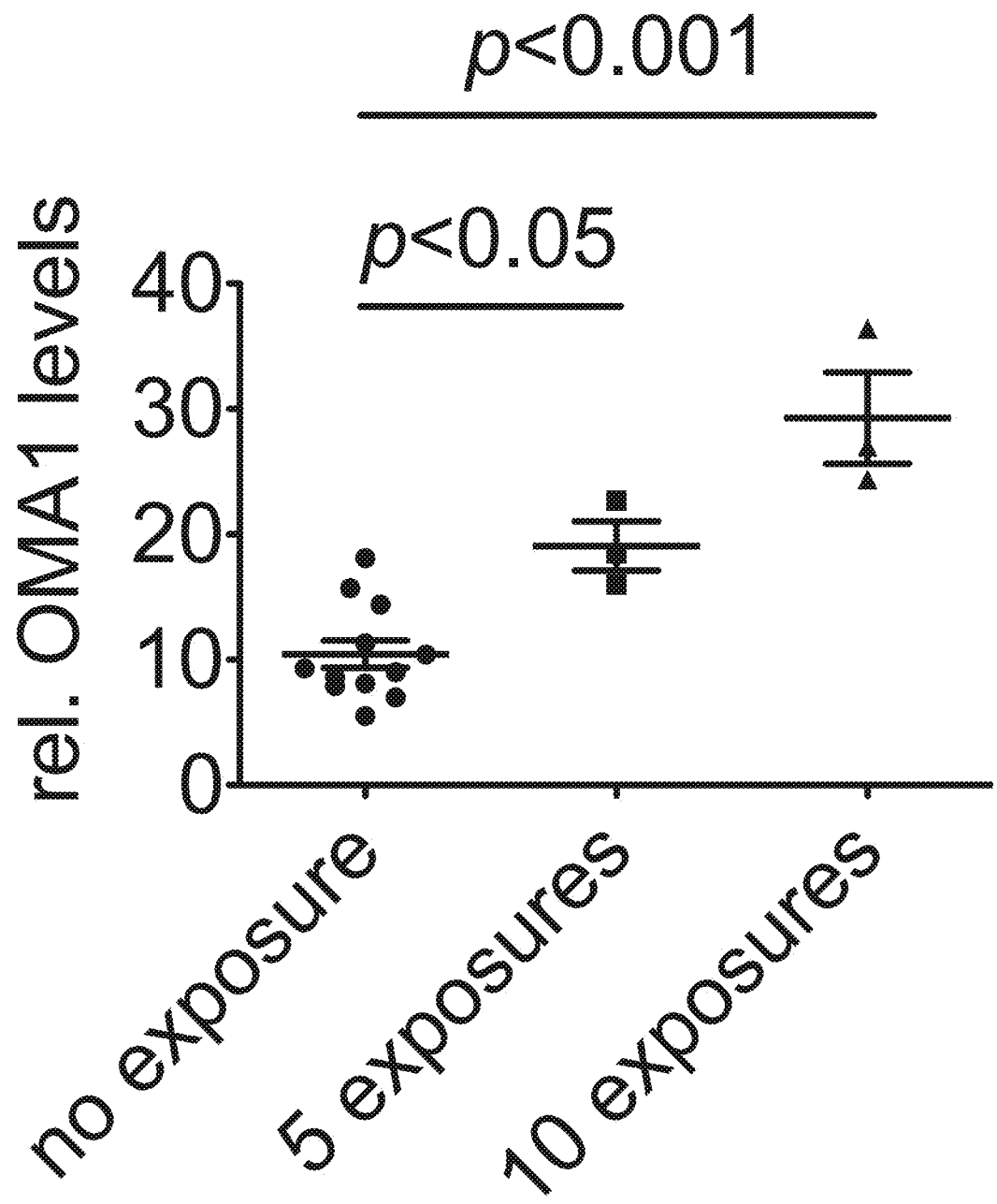
FIG. 25 shows OMA1 gene expression levels in rat brain following exposure to isoflurane.

In another particular embodiment it was, inter alia, found that Isoflurane increased the gene expression levels of OMA1 in rat brains in a dose-dependent manner (FIG. 25). Rats were exposed to 1% Isoflurane for 90 minutes twice daily for a total of 5 or 10 exposures, after which animals were sacrificed and brain samples analyzed by gene expression micro-arrays (Pan et al. 2006). Control rats expressed OMA1 at 10.4 (±3.8 S.D.), while rats exposed to Isoflurane for 5-times expressed OMA1 at elevated levels of 19.1 (±3.4 S.D.). Rats exposed to Isoflurane for 10-times showed even higher OMA1 expression levels of 29.3 (±6.3 S.D.) The dose-dependent increase by 83% and 180%, respectively, was statistically significant (FIG. 25; Student's T-test: p≤0.05). Isoflurane belongs to the halogenated ether family of medication and was approved for medical use in the United States in 1979. Isoflurane is a general anesthetic administered in conjunction with air and/or pure oxygen through inhalation. The exact mechanism of the action has not been clearly delineated. Isoflurane likely binds to GABA, glutamate and glycine receptors. It also binds to the D subunit of ATP synthase and NADH dehydrogenase. The finding that Isoflurane can increase OMA1 levels was unexpected and is non-obvious to a person skilled in the arts. In context of the present invention Isoflurane thus represents an agonist of OMA1 and/or an oligomeric complex comprising OMA1 as defined above. Accordingly, Isoflurane represents a medical intervention in particular for the treatment, prevention and/or amelioration of a disorder or disease correlated with mitochondrial stress or dysfunction, a mitochondrial disorder or disease, or a disorder or disease characterized by OPA1 alterations.

Referring to FIG. 25, isoflurane represents an agonist of OMA1. Isoflurane exposure can increase the gene expression levels of OMA1 in rat brains in a dose-dependent manner (GEO accession number: GDS364). Control rats expressed OMA1 at 10.4 (±3.8 S.D.), while rats exposed to Isoflurane for 5-times expressed OMA1 at elevated levels of 19.1 (±3.4 S.D.). Rats exposed to Isoflurane for 10-times showed even higher OMA1 expression levels of 29.3 (±6.3

S.D.). The dose-dependent increase of 183% and 280%, respectively, was statistically significant (Student's T-test: p<0.05).

Figure 26:
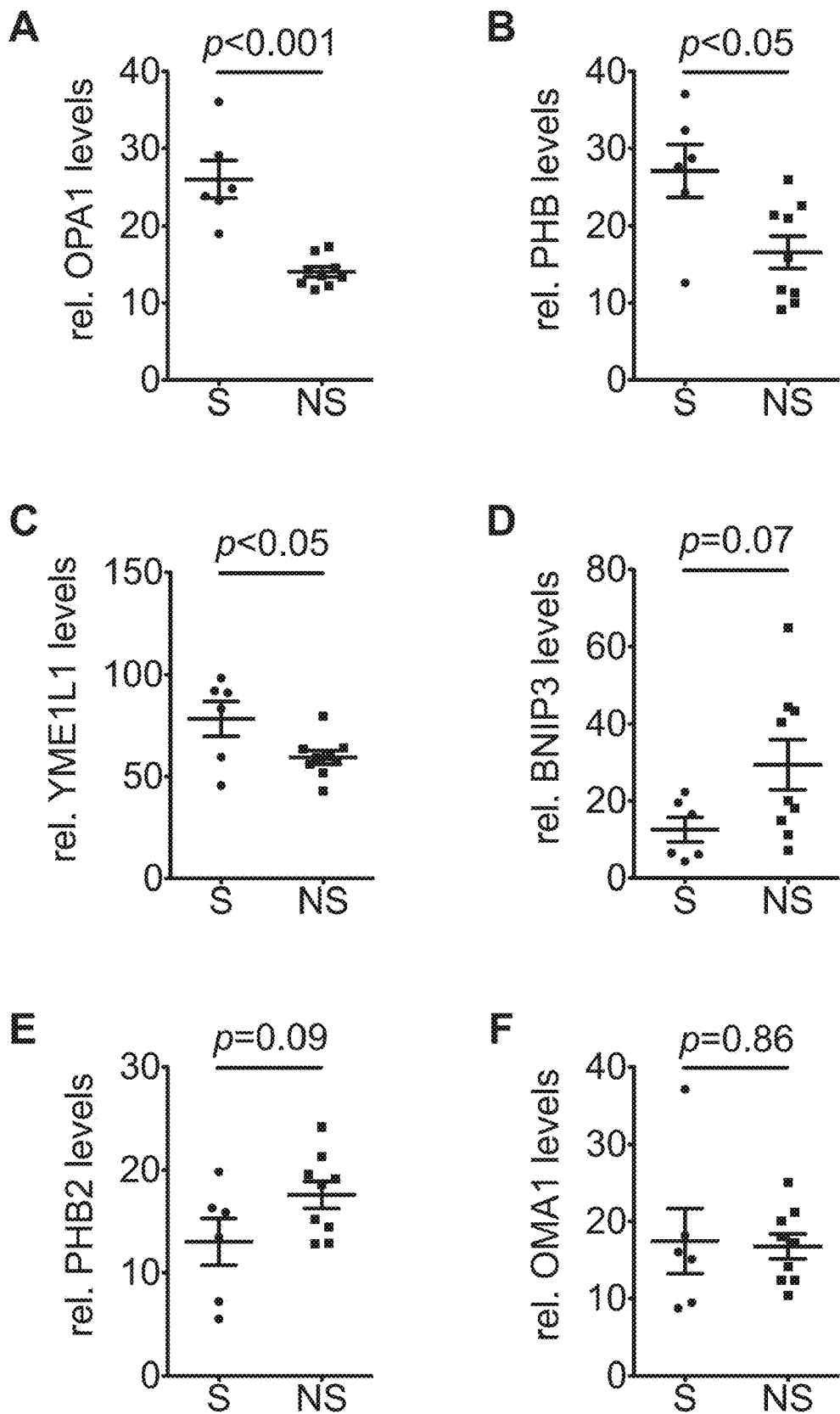
FIGS. 26A-26F show gene expression levels in tobacco smokers and non-smokers.

In another non-limiting and merely illustrative example it was, inter alia, found that OPA1, PHB and YME1L1 gene expression levels were significantly elevated in tobacco smokers (FIGS. 26A-26F). Gene expression levels were determined in blood samples from tobacco smokers (n=6) and non-smokers (n=9) by micro array analysis (Philibert et al. 2007). OPA1 levels were highly significantly elevated by 85% in smokers (26.0±5.9 S.D.) compared to non-smokers (14.0±1.9 S.D.; FIG. 26A; Student's T-test: p<0.001). PHB levels were significantly elevated by 64% in smokers (27.1±8.3 S.D.) compared to non-smokers (16.6±6.3 S.D.; FIG. 26B; Student's T-test: p<0.05). And also YME1L1 levels were significantly increased by 32% in smokers (78.3±20.0 S.D.) compared to non-smokers (59.4±10.0 S.D.; FIG. 26C; Student's T-test: p<0.05). BNIP3 levels and PHB2 levels appeared to be reduced in smokers (FIGS. 26D and E), while OMA1 expression was not changed (FIG. 26F). In view of the teaching provided herein, it is envisioned that smoking, and more preferably one or more pharmaceutically active compound(s) contained in tobacco smoke, will be administered to a patient in need of medical intervention for the treatment, prevention and/or amelioration of a disorder or disease correlated with mitochondrial stress or dysfunction, a mitochondrial disorder or disease, or a disorder or disease characterized by OPA1 alterations.

Referring to FIGS. 26A-26F, tobacco smoking alters OPA1, PHB and YME1L1 gene expression. Smoking can increase the OPA1 (26A), PHB (26B) and YME1L1 gene expression levels (C) in blood samples by 85%, 64% and 32%, respectively (Student's T-test: $p \leq 0.05$; GEO accession number: GDS2447). FIG. 26A: Non-smokers (NS) expressed OPA1 at 14.0 (±1.9 S.D.) and smokers (S) at 26.0 (±5.9 S.D.). FIG. 26B: Non-smokers expressed PHB at 16.6 (±6.3 S.D.) and smokers at 27.1 (±8.3 S.D.). FIG. 26C: And non-smokers expressed YME1L1 at 59.4 (±10.0 S.D.) and smokers at 78.3 (±20.0 S.D.). FIG. 26D: BNIP3 levels appeared to be reduced in smokers (12.6±10.0 S.D.) compared to non-smokers (29.4±19.5 S.D.) though the difference did not reach statistical significance. FIG. 26E: PHB2 levels also appeared to be reduced in smokers (13.0±5.6 S.D.) compared to non-smokers (17.6±4.0 S.D.). FIG. 26F: OMA1 levels were not changed (smokers: 17.4±10.3 S.D.; non-smokers: 16.8±4.9 S.D.).

Preferentially the susceptibility for, predisposition for, and/or presence of, such a disorder or disease has been determined by measurements of OMA1, HIGD1A, OPA1, BNIP3, YME1L1, PHB, SAMM50, IMMT and/or PHB2 levels as disclosed herein and the medical intervention has been selected based on these biomarkers. The skilled person is readily in the position to select the medical intervention for the patient in need of medical intervention based on these biomarkers.

ASPECTS OF THE INVENTION

Aspect 1. A method for the treatment, prevention and/or amelioration of
(i) a disorder or disease correlated with mitochondrial dysfunction, or a mitochondrial disorder or disease; or
(ii) a disorder or disease characterized by OPA1 alterations,
wherein said method comprises the administration to a patient in need of medical intervention a pharmaceutically active amount of a compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

Aspect 2. The method of aspect 1, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof comprises a polypeptide selected from the group consisting of:

(a) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.

(b) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(d) a polypeptide comprising an amino acid sequence having at least 50% sequence identity to the polypeptide of any one of (a) to (c);

(e) a polypeptide comprising an amino acid sequence encoded by a nucleic acid molecule having at least 50% sequence identity to the nucleic acid molecule as defined in any one of (a) to (c);

(f) a polypeptide comprising an amino acid sequence encoded by a nucleic acid molecule hybridizing under stringent conditions to the complement stand of a nucleic acid molecule as defined in any one of (a) to (c); and (g) fragment of a polypeptide of any one of (a) to (f).

Aspect 3. The method of aspect 1, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a homo-oligomeric complex or a hetero-oligomeric complex.

Aspect 4. The method of aspect 1, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof comprises a polypeptide selected from the group consisting of:

(a) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.

(b) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(d) a polypeptide comprising an amino acid sequence having at least 50% sequence identity to the polypeptide of any one of (a) to (c);

(e) a polypeptide comprising an amino acid sequence encoded by a nucleic acid molecule having at least 50% sequence identity to the nucleic acid molecule as defined in any one of (a) to (c);

(f) a polypeptide comprising an amino acid sequence encoded by a nucleic acid molecule hybridizing under stringent conditions to the complement stand of a nucleic acid molecule as defined in any one of (a) to (c); and (g) fragment of a polypeptide of any one of (a) to (f).

Aspect 5. The method of aspect 1, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a homo-oligomeric complex or a hetero-oligomeric complex.

Aspect 6. The method of aspect 5, wherein said hetero-oligomeric complex comprises AFG311 and/or AFG312 and/or paraplegin and/or HIGD1a and/or OPA1 and/or BNIP3 and/or YME1L1 and/or PHB and/or PHB2 or a variant thereof.

Aspect 7. The method of any one of aspects 1 to 6, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a compound obtained by a method comprising the steps of:

(a) contacting OPA1 with OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof in the presence of said compound to be screened for under conditions allowing OPA1 processing to occur; and (b) evaluating whether OPA1 processing is altered compared to a control, where OPA1 and OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof are contacted in the absence of said compound to be screened for under conditions allowing OPA1 processing to occur.

Aspect 8. The method of any one of aspects 1 to 6, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

Aspect 9. The method of any one of aspects 1 to 6, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, wherein said agonist or antagonist is a molecule selected from the group consisting of:

(a) a binding molecule that binds to/interacts with OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 or binds to/interacts with a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1;

(b) a nucleic acid molecule capable of introducing an insertion of a heterologous sequence or a mutation into a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 via in vivo mutagenesis;

(c) a nucleic acid molecule capable of reducing the expression of mRNA encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 by co-suppression; and (d) a low molecular weight compound or a small molecule.

Aspect 10. The method of aspect 9, wherein said binding molecule is selected form the group consisting of antibodies, affybodies, trinectins, anticalins, aptamers, PNA, DNA or RNA.

Aspect 11. The method of any one of aspects 1 to 6, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, wherein said agonist or antagonist is a molecule selected from the group consisting of:

(A) a binding molecule that binds to/interacts with OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 or binds to/interacts with a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1;

(B) a nucleic acid molecule capable of introducing an insertion of a heterologous sequence or a mutation into a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 via in vivo mutagenesis;

(C) a nucleic acid molecule capable of reducing the expression of mRNA encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 by co-suppression; and (D) a low molecular weight compound or a small molecule, wherein said binding molecule is selected from the group consisting of:

(i) an antibody that binds to the polypeptide or the nucleic acid molecule selected from the group consisting of:
(a) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(b) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.

(c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(d) a polypeptide comprising an amino acid sequence having at least 50% sequence identity to the polypeptide of any one of (a) to (c);

(e) a polypeptide comprising an amino acid sequence encoded by a nucleic acid molecule having at least 50% sequence identity to the nucleic acid molecule as defined in any one of (b) to (c);

(f) a polypeptide comprising an amino acid sequence encoded by a nucleic acid molecule hybridizing under stringent conditions to the complement stand of a nucleic acid molecule as defined in any one of (b) to (c); and (g) fragment of a polypeptide of any one of (b) to (f).

or to ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1;

(ii) an antisense nucleotide sequence that hybridizes to the nucleic acid molecule as defined in (i);

(iii) a siRNA that interacts with the nucleic acid molecule as defined in (i);

(iv) an aptamer that binds to the polypeptide or the nucleic acid molecule as defined in (i) or to ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1; and (v) ribozyme that interacts with the nucleic acid molecule as defined in (i).

Aspect 12. The method of any one of aspects 1 to 6, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, wherein said agonist or antagonist is a molecule selected from the group consisting of:

(A) a polypeptide as defined in (a)-(g) or a nucleotide sequence comprising a nucleic acid molecule as defined in (a)-(g);

(a) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(b) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.

(c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(d) a polypeptide comprising an amino acid sequence having at least 50% sequence identity to the polypeptide of any one of (a) to (c);

(e) a polypeptide comprising an amino acid sequence encoded by a nucleic acid molecule having at least 50% sequence identity to the nucleic acid molecule as defined in any one of (b) to (c);

(f) a polypeptide comprising an amino acid sequence encoded by a nucleic acid molecule hybridizing under stringent conditions to the complement stand of a nucleic acid molecule as defined in any one of (b) to (c); and (g) fragment of a polypeptide of any one of (a) to (f), (B) a binding molecule as defined in any one of claims 9, 10, and 11 (a) and (d) being an agonistic binding molecule; and (C) a low molecular weight compound or a small molecule.

Aspect 13. The method of any one of aspects 1 to 6, wherein said compound is selected from thiorphan, phenanthroline, ARP100, glucosamine, micro-RNA miR-203. SB2K763, cuytokine CXCL4, and isoflurane.

Aspect 14. The method of aspects 1 to 6, wherein said compound is SB-3CT.

Aspect 15. The method of any one of aspects 1 to 14, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a protease activity.

Aspect 16. The method of any one of aspects 1 to 14, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is an AAA protease activity.

Aspect 17. The method of any one of aspects 1 to 14, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is proteolytic cleavage of OPA1.

Aspect 18. The method of aspect 17, wherein said proteolytic cleavage of OPA1 leads to OPA1 processing.

Aspect 19. The method of any one of aspects 1 to 18, wherein said altered OPA1 processing is characterized by an altered (decrease of a) certain amount of at least one large isoform of OPA1, an altered (increase of a) certain amount of at least one small isoform of OPA1 and/or an altered (decrease of a) certain ratio of at least one large versus at least one small isoform of OPA1 compared to a control/standard.

Aspect 20. The method of aspect 19, wherein said at least one small isoform of OPA1 is OPA1-S3, OPA1-S4 and/or OPA1-S5.

Aspect 21. The method of any one of aspect 201 to 18, wherein said disorder or disease is selected from the group consisting of premature ageing, cardiomyopathy, a respiratory chain disorder, mtDNA depletion syndrome, myoclonus epilepsy, ragged-red fibers syndrome (MERRF), myopathy encephalopathy lactic acidosis, stroke-like episodes (MELAS) and optic atrophy, glaucoma, optic neuropathy, Parkinson's Disease, Alzheimer's Disease or any other form of neurodegenerative disease or aging-related disease, such as cancer or diseases related to ischemia.

Aspect 22. A method of screening for a compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof comprising the steps of (a) contacting OPA1 with said OMA1 and/or oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof in the presence of said compound to be screened for under conditions allowing OPA1 processing to occur; and (b) evaluating whether OPA1 processing is altered compared to a control, where OPA1 and OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof are contacted in the absence of said compound to be screened for under conditions allowing OPA1 processing to occur.

Aspect 23. The method of aspect 22, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof comprises a polypeptide selected from the group consisting of:

(a) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.

(b) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(d) a polypeptide comprising an amino acid sequence having at least 50% sequence identity to the polypeptide of any one of (a) to (c);

(e) a polypeptide comprising an amino acid sequence encoded by a nucleic acid molecule having at least 50% sequence identity to the nucleic acid molecule as defined in any one of (a) to (c);

(f) a polypeptide comprising an amino acid sequence encoded by a nucleic acid molecule hybridizing under stringent conditions to the complement stand of a nucleic acid molecule as defined in any one of (a) to (c); and (g) fragment of a polypeptide of any one of (a) to (f).

Aspect 24. The method of aspect 22, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a homo-oligomeric complex or a hetero-oligomeric complex.

Aspect 25. The method of aspect 22, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof comprises a polypeptide selected from the group consisting of:

(a) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.

(b) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(d) a polypeptide comprising an amino acid sequence having at least 50% sequence identity to the polypeptide of any one of (a) to (c);

(e) a polypeptide comprising an amino acid sequence encoded by a nucleic acid molecule having at least 50% sequence identity to the nucleic acid molecule as defined in any one of (a) to (c);

(f) a polypeptide comprising an amino acid sequence encoded by a nucleic acid molecule hybridizing under stringent conditions to the complement stand of a nucleic acid molecule as defined in any one of (a) to (c); and (g) fragment of a polypeptide of any one of (a) to (f).

Aspect 26. The method of aspect 22, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a homo-oligomeric complex or a hetero-oligomeric complex.

Aspect 27. The method of aspect 26, wherein said hetero-oligomeric complex comprises AFG3l1 and/or AFG3l2 and/or paraplegin and/or HIGD1a and/or OPA1 and/or BNIP3 and/or YME1L1 and/or PHB and/or PHB2 or a variant thereof.

Aspect 28. The method of any one of aspects 22 to 27, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a compound obtained by a method comprising the steps of:

(a) contacting OPA1 with OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof in the presence of said compound to be screened for under conditions allowing OPA1 processing to occur; and (b) evaluating whether OPA1 processing is altered compared to a control, where OPA1 and OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof are contacted in the absence of said compound to be screened for under conditions allowing OPA1 processing to occur.

Aspect 29. The method of any one of aspects 22 to 27, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

Aspect 30. The method of any one of aspects 20 to 25, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, wherein said agonist or antagonist is a molecule selected from the group consisting of:

(a) a binding molecule that binds to/interacts with OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 or binds to/interacts with a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1;

(b) a nucleic acid molecule capable of introducing an insertion of a heterologous sequence or a mutation into a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 via in vivo mutagenesis;

(c) a nucleic acid molecule capable of reducing the expression of mRNA encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 by co-suppression; and (d) a low molecular weight compound or a small molecule.

Aspect 31. The method of aspect 30, wherein said binding molecule is selected form the group consisting of antibodies, affybodies, trinectins, anticalins, aptamers, PNA, DNA or RNA.

Aspect 32. The method of any one of aspects 20 to 25, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, wherein said agonist or antagonist is a molecule selected from the group consisting of:

(A) a binding molecule that binds to/interacts with OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 or binds to/interacts with a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1;

(B) a nucleic acid molecule capable of introducing an insertion of a heterologous sequence or a mutation into a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 via in vivo mutagenesis;

(C) a nucleic acid molecule capable of reducing the expression of mRNA encoding ((a) subunit(s) of) OMA1 and/or the oligomeric complex comprising OMA1 and/or HIGD1A and/or OPAL and/or BNIP3 and/or YME1L1 and/or PHB and/or PHB2 and/or SAMM50 and/or IMMT or (a) variant(s) thereof as defined in claim 1 by co-suppression; and (D) a low molecular weight compound or a small molecule, wherein said binding molecule is selected from the group consisting of:

(i) an antibody that binds to the polypeptide or the nucleic acid molecule selected from the group consisting of:
  (a) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.
  (b) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.
  (c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.
  (d) a polypeptide comprising an amino acid sequence having at least 50% sequence identity to the polypeptide of any one of (a) to (c);
  (e) a polypeptide comprising an amino acid sequence encoded by a nucleic acid molecule having at least 50% sequence identity to the nucleic acid molecule as defined in any one of (b) to (c);
  (f) a polypeptide comprising an amino acid sequence encoded by a nucleic acid molecule hybridizing under stringent conditions to the complement stand of a nucleic acid molecule as defined in any one of (b) to (c); and
  (g) fragment of a polypeptide of any one of (b) to (f).
  or to ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1;
(ii) an antisense nucleotide sequence that hybridizes to the nucleic acid molecule as defined in (i);
(iii) a siRNA that interacts with the nucleic acid molecule as defined in (i);
(iv) an aptamer that binds to the polypeptide or the nucleic acid molecule as defined in (i) or to ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1; and
(v) ribozyme that interacts with the nucleic acid molecule as defined in (i).

Aspect 33. The method of any one of aspects 22 to 27, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, wherein said agonist or antagonist is a molecule selected from the group consisting of:

(A) a polypeptide as defined in (a)-(g) or a nucleotide sequence comprising a nucleic acid molecule as defined in (a)-(g);
  (a) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.
  (b) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.
  (c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.
  (d) a polypeptide comprising an amino acid sequence having at least 50% sequence identity to the polypeptide of any one of (a) to (c);
  (e) a polypeptide comprising an amino acid sequence encoded by a nucleic acid molecule having at least 50% sequence identity to the nucleic acid molecule as defined in any one of (b) to (c);
  (f) a polypeptide comprising an amino acid sequence encoded by a nucleic acid molecule hybridizing under stringent conditions to the complement stand of a nucleic acid molecule as defined in any one of (b) to (c); and
  (g) fragment of a polypeptide of any one of (a) to (f), (B) a binding molecule as defined in any one of claims 9, 10, and 11 (a) and (d) being an agonistic binding molecule; and (C) a low molecular weight compound or a small molecule.

Aspect 34. The method of any one of aspects 22 to 33, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a protease activity.

Aspect 35. The method of any one of aspects 22 to 33, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is an AAA protease activity.

Aspect 36. The method of any one of aspects 22 to 33, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is proteolytic cleavage of OPA1.

Aspect 37. The method of claim 36, wherein said proteolytic cleavage of OPA1 leads to OPA1 processing.

Aspect 38. The method of any one of aspects 22 to 37, wherein said OPA1 processing is characterized by (a decrease of) a certain amount of at least one large isoform of OPA1, (an increase of) a certain amount of at least one small isoform of OPA1 and/or (a decrease of) a certain ratio of at least one large versus at least one small isoform of OPA1 (compared to a control/standard).

Aspect 39. The method of aspect 38, whereby a large isoform of OPA1 has an apparent molecular weight of more than about 91 kD and whereby a small isoform of OPA1 has an apparent molecular weight of less than about 91 kD, said molecular weights being determined by SDS-PAGE analysis; and/or whereby a large isoform of OPA1 has an apparent molecular weight of more than about 95 kD and whereby a small isoform of OPA1 has an apparent molecular weight of less than about 95 kD, said molecular weights being determined by mass spectrometry.

Aspect 40. The method of aspect 39, wherein said SDS-PAGE is a 10% SDS-PAGE.

Aspect 41. The method of any one of aspects 39 to 40, wherein said mass spectrometry is MALDI-MS or LC-MS/MS.

Aspect 42. The method of any one of aspects 39 to 41, wherein said at least one large isoform of OPA1 is OPA1-L1 and/or OPA1-L2.

Aspect 43. The method of aspect 38, wherein said at least one large isoform of OPA1 comprises two isoforms (OPA1-L1 and OPA1-L2) and/or wherein said at least one small isoform of OPA1 comprises three isoforms (OPA1-S3, OPA1-S4 and OPA1-S5).

Aspect 44. The method of aspect 43, wherein said at least one large isoform of OPA1 comprises an isoform having an apparent molecular weight of about 97 kD (OPA1-L1) or an isoform having an apparent molecular weight of about 92 kD (OPA1-L2), said molecular weights being determined by SDS-PAGE analysis.

Aspect 45. The method of aspect 43, wherein said at least one small isoform of OPA1 comprises an isoform having an apparent molecular weight of about 88 kD (OPA1-S3), an isoform having an apparent molecular weight of about 84 kD (OPA1-S4) or an isoform having an apparent molecular weight of about 81 kD (OPA1-S5), said molecular weights being determined by SDS-PAGE analysis.

Aspect 46. The method of aspect 43, wherein said at least one large isoform of OPA1 comprises an isoform having an apparent molecular weight of about 104 kD (OPA1-L1) or an isoform having an apparent molecular weight of about 99 kD (OPA1-L2), said molecular weights being determined by mass spectrometry.

Aspect 47. The method of aspect 43, wherein said at least one small isoform of OPA1 comprises an isoform having an apparent molecular weight of about 92 kD (OPA1-S3), an isoform having an apparent molecular weight of about 89 kD (OPA1-S4) or an isoform having an apparent molecular weight of about 87 kD (OPA1-S5), said molecular weights being determined by mass spectrometry.

Aspect 48. The method of aspect 43, wherein,
  said OPA1-L1 has an apparent molecular weight of about 97 kD,
  said OPA1-L2 has an apparent molecular weight of about 92 kD,
  said OPA1-S3 has an apparent molecular weight of about 88 kD,
  said OPA1-S4 has an apparent molecular weight of about 84 kD, and/or
  said OPA1-S5 has an apparent molecular weight of about 81 kD,
  said molecular weights being determined by SDS-PAGE analysis; or wherein
  said OPA1-L1 has an apparent molecular weight of about 104 kD,
  said OPA1-L2 has an apparent molecular weight of about 99 kD,
  said OPA1-S3 has an apparent molecular weight of about 92 kD,
  said OPA1-S4 has an apparent molecular weight of about 89 kD, and/or
  said OPA1-S5 has an apparent molecular weight of about 87 kD, said molecular weights being determined by mass spectrometry.

Aspect 49. The method of aspect 43, wherein, (a) OPA1-L1 and OPA1-L2 are characterized by comprising amino acid stretches or amino acid peptides comprising one or more of the following sequences:
YLILGSAVGGGYTAK; (SEQ ID NO: 47)
TFDQWK; (SEQ ID NO: 48)
DMIPDLSEYK; (SEQ ID NO: 49)
WIVPDIVWEIDEYIDFEK; (SEQ ID NO: 50)
LAPDFDK; (SEQ ID NO: 51)
IVESLSLLK; (SEQ ID NO: 52)
ALPNSEDLVK; (SEQ ID NO: 53)
DFFTSGSPEETAFR; (SEQ ID NO: 54)
TRLLKLRYLILGS; (SEQ ID NO: 55) and
FWPARLATRLLKLRYLILGS; (SEQ ID NO: 56)
or derivatives thereof;

(b) OPA1-S3 is characterized by comprising amino acid stretches or amino acid peptides comprising one or more of the following sequences:
IVESLSLLK; (SEQ ID NO: 52)
DFFTSGSPEETAFR; (SEQ ID NO: 54)
GLLGELILLQQQIQEHEEEAR; (SEQ ID NO: 57)
AAGQYSTSYAQQK; (SEQ ID NO: 58) and
IDQLQEELLHTQLK; (SEQ ID NO: 59)
or derivatives thereof;

(c) OPA1-S4 is characterized by comprising amino acid stretches or amino acid peptides comprising one or more of the following sequences:
GLLGELILLQQQIQEHEEEAR; (SEQ ID NO: 57)
AAGQYSTSYAQQK; (SEQ ID NO: 58) and
IDQLQEELLHTQLK; (SEQ ID NO: 59)
or derivatives thereof; and/or (d) OPA1-S5 is characterized by comprising amino acid stretches or amino acid peptides comprising the following sequence:
IDQLQEELLHTQLK; (SEQ ID NO: 59)
or derivatives thereof.

Aspect 50. The method of aspect 43, wherein (a) OPA1-L2 is characterized by not comprising amino acid stretches or amino acid peptides comprising one or more of the following sequences:
GLLGELILLQQQIQEHEEEAR; (SEQ ID NO: 57) and
AAGQYSTSYAQQK; (SEQ ID NO: 58)
or derivatives thereof; and/or (b) OPA1-S3 is characterized by not comprising amino acid stretches or amino acid peptides comprising one or more of the following sequences:
YLILGSAVGGGYTAK; (SEQ ID NO: 47)
TFDQWK; (SEQ ID NO: 48)
DMIPDLSEYK; (SEQ ID NO: 49)
WIVPDIVWEIDEYIDFEK; (SEQ ID NO: 50)
LAPDFDK; (SEQ ID NO: 51)
IVESLSLLK; (SEQ ID NO: 52)
ALPNSEDLVK; (SEQ ID NO: 53)
TRLLKLRYLILGS; (SEQ ID NO: 55) and
FWPARLATRLLKLRYLILGS; (SEQ ID NO: 56)
or derivatives thereof;

(c) OPA1-S4 is characterized by not comprising amino acid stretches or amino acid peptides comprising one or more of the following sequences:
YLILGSAVGGGYTAK; (SEQ ID NO: 47)
TFDQWK; (SEQ ID NO: 48)
DMIPDLSEYK; (SEQ ID NO: 49)
WIVPDIVWEIDEYIDFEK; (SEQ ID NO: 50)
LAPDFDK; (SEQ ID NO: 51)
IVESLSLLK; (SEQ ID NO: 52)
ALPNSEDLVK; (SEQ ID NO: 53)
DFFTSGSPEETAFR; (SEQ ID NO: 54)
TRLLKLRYLILGS; (SEQ ID NO: 55) and
FWPARLATRLLKLRYLILGS; (SEQ ID NO: 56)
or derivatives thereof; and/or (d) OPA1-S5 is characterized by not comprising amino acid stretches or amino acid peptides comprising one or more of the following sequences:
YLILGSAVGGGYTAK; (SEQ ID NO: 47)
TFDQWK; (SEQ ID NO: 48)
DMIPDLSEYK; (SEQ ID NO: 49)
WIVPDIVWEIDEYIDFEK; (SEQ ID NO: 50)
LAPDFDK; (SEQ ID NO: 51)
IVESLSLLK; (SEQ ID NO: 52)
ALPNSEDLVK; (SEQ ID NO: 53)
DFFTSGSPEETAFR; (SEQ ID NO: 54)
TRLLKLRYLILGS; (SEQ ID NO: 55) and
GLLGELILLQQQIQEHEEEAR; (SEQ ID NO: 57) and
AAGQYSTSYAQQK; (SEQ ID NO: 58)
or derivatives thereof.

Aspect 51. A method for determining the susceptibility for, predisposition for or the presence of (i) a disorder or disease correlated with mitochondrial dysfunction or a mitochondrial disorder or disease; or (ii) a disorder or disease characterized by OPA1 alterations, wherein said method comprises the steps of (a) obtaining a sample from the subject and measuring the activity of OMA1 and/or YME1L1 or (a) combination(s) thereof in the sample, and/or measuring the gene expression levels of OMA1, HIGD1A, OPA1, BNIP3, YME1L1, PHB, SAMM50, IMMT and/or PHB2 or (a) combination(s) thereof in the sample, and/or measuring the protein levels of OMA1, HIGD1A, OPA1, BNIP3, YME1L1, PHB, SAMM50, IMMT and/or PHB2 or (a) combination(s) thereof in the sample;

(b) comparing the increase and/or decrease of measured activity and/or gene expression levels and/or protein levels of OMA1 and/or HIGD1A and/or OPA1 and/or BNIP3 and/or YME1L1 and/or PHB and/or SAMM50 and/or IMMT and/or PHB2 or (a) combination(s) thereof in the sample compared to a reference;

(c) integrating the results of these measurements through combination of 3 or more genes selected from the group of OMA1, HIGD1A, OPA1, BNIP3, YME1L1, PHB, SAMM50, IMMT and PHB2.

Aspect 52. The method of aspect 50, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a protease activity.

Aspect 53. The method of aspect 50, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is an AAA protease activity.

Aspect 54. The method of aspect 50, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is proteolytic cleavage of OPA1

Aspect 55. The method of aspect 54, wherein said proteolytic cleavage of OPA1 leads to OPA1 processing.

Aspect 56. The method of any one of aspects 50 to 55, wherein said altered OPA1 processing is characterized by an altered (decrease of a) certain amount of at least one large isoform of OPA1, an altered (increase of a) certain amount of at least one small isoform of OPA1 and/or an altered (decrease of a) certain ratio of at least one large versus at least one small isoform of OPA1 compared to a control/standard.

Aspect 57. The method of aspect 56, wherein said at least one small isoform of OPA1 is OPA1-S3, OPA1-S4 and/or OPA1-S5.

Aspect 58. The method of any one of aspects 50 to 57, wherein said disorder or disease is selected from the group consisting of premature ageing, cardiomyopathy, a respiratory chain disorder, mtDNA depletion syndrome, myoclonus epilepsy, ragged-red fibers syndrome (MERRF), myopathy encephalopathy lactic acidosis, stroke-like episodes (MELAS) and optic atrophy, glaucoma, optic neuropathy, Parkinson's Disease, Alzheimer's Disease or any other form of neurodegenerative disease or aging-related disease, such as cancer or diseases related to ischemia.

Aspect 59. The method of any one of aspects 50 to 58, wherein said method is utilized for determining whether a patient in need for medical intervention will benefit from administration of a pharmaceutically active amount of a compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

Aspect 60. The method of any one of aspects 50 to 59, wherein said method is a biomarker for the predisposition of a disorder or disease, a biomarker for a disorder or disease or a biomarker for evaluating efficacy of a method for treatment, prevention and/or amelioration of a disorder or disease.

Aspect 61. The method of aspect 60, wherein said biomarker is informative for selecting medical interventions and/or therapies, monitoring medical interventions and/or therapies or predicting outcomes of medical interventions and/or therapies.

Aspect 62. The method of any one of aspects 50 to 61, wherein said method compromises the use of a kit comprising reagents for the quantification of the expression levels of OMA1 and/or HIGD1A and/or OPA1 and/or BNIP3 and/or YME1L1 and/or PHB and/or SAMM50 and/or IMMT and/or PHB2 or (a) functionally equivalent variant(s) thereof or of any combination of these molecules.

Aspect 63. The method of any one of aspects 50 to 61, wherein said method compromises the use of a kit comprising reagents for the quantification of the levels of OMA1 and/or HIGD1A and/or OPA1 and/or BNIP3 and/or YME1L1 and/or PHB and/or SAMM50 and/or IMMT and/or PHB2 or (a) functionally equivalent variant(s) thereof or of any combination of these molecules, wherein such quantification is performed by means of Western blot, immunohistochemistry or ELISA.

Aspect 64. A compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof for the treatment, prevention and/or amelioration of
(i) a disorder or disease correlated with mitochondrial dysfunction or a mitochondrial disorder or disease; or
(ii) a disorder or disease characterized by OPA1 alterations,
wherein the compound is capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, and
wherein said altered OPA1 processing is characterized by an altered (decrease of a) certain amount of at least one large isoform of OPA1, an altered (increase of a) certain amount of at least one small isoform of OPA1 and/or an altered (decrease of a) certain ratio of at least one large versus at least one small isoform of OPA1 compared to a control/standard, Aspect 65. A method of treating a disease or disorder in a patient comprising administering to a patient in need of such treatment a therapeutically effective amount of the compound of aspect 65.

Aspect 66. A pharmaceutical composition comprising the compound of aspect 65 and a pharmaceutically acceptable excipient.

Aspect 67. A method of treating a disease or disorder in a patient comprising administering to a patient in need of such treatment a therapeutically effective amount of the pharmaceutical composition of aspect 66.

Aspect 68. A combination of two or more methods according to aspects 1, 22, and 51 that result in a medical intervention individualized for one or more patients and that may be referred to as personalized medicine and/or precision medicine.

It should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

REFERENCES

Akhtar, M. W., S. Sanz-Blasco, N. Dolatabadi, J. Parker, K. Chon, M. S. Lee, W. Soussou, S. R. McKercher, R. Ambasudhan, T. Nakamura and S. A. Lipton (2016). "Elevated glucose and oligomeric beta-amyloid disrupt synapses via a common pathway of aberrant protein S-nitrosylation." *Nat Commun* 7: 10242.

Alavi, M. V., S. Bette, S. Schimpf, F. Schuettauf, U. Schraermeyer, H. F. Wehrl, L. Ruttiger, S. C. Beck, F. Tonagel, B. J. Pichler, M. Knipper, T. Peters, J. Laufs and B. Wissinger (2007). "A splice site mutation in the murine Opa1 gene features pathology of autosomal dominant optic atrophy." *Brain* 130(Pt 4): 1029-1042.

Alavi, M. V. and N. Fuhrmann (2013). "Dominant optic atrophy, OPA1, and mitochondrial quality control: understanding mitochondrial network dynamics" *Mol Neurodegener* 8(1): 32.

Alexander, C., M. Votruba, U. E. Pesch, D. L. Thiselton, S. Mayer, A. Moore, M. Rodriguez, U. Kellner, B. Leo-Kottler, G. Auburger, S. S. Bhattacharya and B. Wissinger (2000). "OPA1, encoding a dynamin-related GTPase, is mutated in autosomal dominant optic atrophy linked to chromosome 3q28." *Nat Genet* 26(2): 211-215.

Aliev, G., D. Seyidova, B. T. Lamb, M. E. Obrenovich, S. L. Siedlak, H. V. Vinters, R. P. Friedland, J. C. LaManna, M. A. Smith and G. Perry (2003). "Mitochondria and vascular lesions as a central target for the development of Alzheimer's disease and Alzheimer disease-like pathology in transgenic mice." *Neurol Res* 25(6): 665-674.

Alirol, E. and J. C. Martinou (2006). "Mitochondria and cancer: is there a morphological connection?" *Oncogene* 25(34): 4706-4716.

Ameri, K., A. Jahangiri, A. M. Rajah, K. V. Tormos, R. Nagarajan, M. Pekmezci, V. Nguyen, M. L. Wheeler, M.

P. Murphy, T. A. Sanders, S. S. Jeffrey, Y. Yeghiazarians, P. F. Rinaudo, J. F. Costello, M. K. Aghi and E. Maltepe (2015). "HIGD1A Regulates Oxygen Consumption, ROS Production, and AMPK Activity during Glucose Deprivation to Modulate Cell Survival and Tumor Growth." *Cell Rep*.

Ameri, K. and E. Maltepe (2015). "HIGD1A-mediated dormancy and tumor survival." *Mol Cell Oncol* 2(4): e1030537.

Ameri, K., A. M. Rajah, V. Nguyen, T. A. Sanders, A. Jahangiri, M. Delay, M. Donne, H. J. Choi, K. V. Tormos, Y. Yeghiazarians, S. S. Jeffrey, P. F. Rinaudo, D. H. Rowitch, M. Aghi and E. Maltepe (2013). "Nuclear localization of the mitochondrial factor HIGD1A during metabolic stress." *PLoS One* 8(4): e62758.

An, H. J., G. Cho, J. O. Lee, S. G. Paik, Y. S. Kim and H. Lee (2013). "Higd-1a interacts with Opa1 and is required for the morphological and functional integrity of mitochondria." *Proc Natl Acad Sci USA* 110(32): 13014-13019.

An, H. J., H. Shin, S. G. Jo, Y. J. Kim, J. O. Lee, S. G. Paik and H. Lee (2011). "The survival effect of mitochondrial Higd-1a is associated with suppression of cytochrome C release and prevention of caspase activation." *Biochim Biophys Acta* 1813(12): 2088-2098.

Baek, S. H., S. J. Park, J. I. Jeong, S. H. Kim, J. Han, J. W. Kyung, S. H. Baik, Y. Choi, B. Y. Choi, J. S. Park, G. Bahn, J. H. Shin, D. S. Jo, J. Y. Lee, C. G. Jang, T. V. Arumugam, J. Kim, J. W. Han, J. Y. Koh, D. H. Cho and D. G. Jo (2017). "Inhibition of Drp1 Ameliorates Synaptic Depression, Abeta Deposition, and Cognitive Impairment in an Alzheimer's Disease Model." *J Neurosci* 37(20): 5099-5110.

Barrera, M., S. Koob, D. Dikov, F. Vogel and A. S. Reichert (2016). "OPA1 functionally interacts with MIC60 but is dispensable for crista junction formation." *FEBS Lett* 590(19): 3309-3322.

Bohovych, I., S. Kastora, S. Christianson, D. Topil, H. Kim, T. Fangman, Y. J. Zhou, A. Barrientos, J. Lee, A. J. Brown and O. Khalimonchuk (2016). "Oma1 Links Mitochondrial Protein Quality Control and TOR Signaling To Modulate Physiological Plasticity and Cellular Stress Responses." *Mol Cell Biol* 36(17): 2300-2312.

Bond, M. R. and J. A. Hanover (2015). "A little sugar goes a long way: the cell biology of O-GlcNAc." *J Cell Biol* 208(7): 869-880.

Bose, A. and M. F. Beal (2016). "Mitochondrial dysfunction in Parkinson's disease." *J Neurochem* 139 Suppl 1: 216-231.

Burke, N., A. R. Hall and D. J. Hausenloy (2015). "OPA1 in Cardiovascular Health and Disease." *Curr Drug Targets* 16(8): 912-920.

Burte, F., V. Carelli, P. F. Chinnery and P. Yu-Wai-Man (2015). "Disturbed mitochondrial dynamics and neurodegenerative disorders." *Nat Rev Neurol* 11(1): 11-24.

Butterfield, D. A., J. Drake, C. Pocernich and A. Castegna (2001). "Evidence of oxidative damage in Alzheimer's disease brain: central role for amyloid beta-peptide." *Trends Mol Med* 7(12): 548-554.

Cardoso, S. M., I. Santana, R. H. Swerdlow and C. R. Oliveira (2004). "Mitochondria dysfunction of Alzheimer's disease cybrids enhances Abeta toxicity." *J Neurochem* 89(6): 1417-1426.

Carelli, V., F. N. Ross-Cisneros and A. A. Sadun (2002). "Optic nerve degeneration and mitochondrial dysfunction: genetic and acquired optic neuropathies." *Neurochem Int* 40(6): 573-584.

Carelli, V., F. N. Ross-Cisneros and A. A. Sadun (2004). "Mitochondrial dysfunction as a cause of optic neuropathies." *Prog Retin Eye Res* 23(1): 53-89.

Carvalho, A. S., H. Ribeiro, P. Voabil, D. Penque, O. N. Jensen, H. Molina and R. Matthiesen (2014). "Global mass spectrometry and transcriptomics array based drug profiling provides novel insight into glucosamine induced endoplasmic reticulum stress." *Mol Cell Proteomics* 13(12): 3294-3307.

Caspersen, C., N. Wang, J. Yao, A. Sosunov, X. Chen, J. W. Lustbader, H. W. Xu, D. Stern, G. McKhann and S. D. Yan (2005). "Mitochondrial Abeta: a potential focal point for neuronal metabolic dysfunction in Alzheimer's disease." *FASEB J* 19(14): 2040-2041.

Chen, L., Q. Gong, J. P. Stice and A. A. Knowlton (2009). "Mitochondrial OPA1, apoptosis, and heart failure." *Cardiovasc Res* 84(1): 91-99.

Chen, L., T. Liu, A. Tran, X. Lu, A. A. Tomilov, V. Davies, G. Cortopassi, N Chiamvimonvat, D. M. Bers, M. Votruba and A. A. Knowlton (2012). "OPA1 mutation and late-onset cardiomyopathy: mitochondrial dysfunction and mtDNA instability." *J Am Heart Assoc* 1(5): e003012.

Choubey, V., D. Safiulina, A. Vaarmann, M. Cagalinec, P. Wareski, M. Kuum, A. Zharkovsky and A. Kaasik (2011). "Mutant A53T alpha-synuclein induces neuronal death by increasing mitochondrial autophagy." *J Biol Chem* 286 (12): 10814-10824.

Chrysostomou, V., F. Rezania, I. A. Trounce and J. G. Crowston (2013). "Oxidative stress and mitochondrial dysfunction in glaucoma." *Curr Opin Pharmacol* 13(1): 12-15.

Cipolat, S., T. Rudka, D. Hartmann, V. Costa, L. Serneels, K. Craessaerts, K. Metzger, C. Frezza, W. Annaert, L. D'Adamio, C. Derks, T. Dejaegere, L. Pellegrini, R. D'Hooge, L. Scorrano and B. De Strooper (2006). "Mitochondrial rhomboid PARL regulates cytochrome c release during apoptosis via OPA1-dependent cristae remodeling." *Cell* 126(1): 163-175.

Cogliati, S., C. Frezza, M. E. Soriano, T. Varanita, R. Quintana-Cabrera, M. Corrado, S. Cipolat, V. Costa, A. Casarin, L. C. Gomes, E. Perales-Clemente, L. Salviati, P. Fernandez-Silva, J. A. Enriquez and L. Scorrano (2013). "Mitochondrial cristae shape determines respiratory chain supercomplexes assembly and respiratory efficiency." *Cell* 155(1): 160-171.

Coughlin, L., R. S. Morrison, P. J. Horner and D. M. Inman (2015). "Mitochondrial morphology differences and mitophagy deficit in murine glaucomatous optic nerve." *Invest Ophthalmol Vis Sci* 56(3): 1437-1446.

Daoud, H., P. N. Valdmanis, F. Gros-Louis, V. Belzil, D. Spiegelman, E. Henrion, O. Diallo, A. Desjarlais, J. Gauthier, W. Camu, P. A. Dion and G. A. Rouleau (2011). "Resequencing of 29 candidate genes in patients with familial and sporadic amyotrophic lateral sclerosis." *Arch Neurol* 68(5): 587-593.

Delettre, C., G. Lenaers, J. M. Griffoin, N. Gigarel, C. Lorenzo, P. Belenguer, L. Pelloquin, J. Grosgeorge, C. Turc-Carel, E. Perret, C. Astarie-Dequeker, L. Lasquellec, B. Arnaud, B. Ducommun, J. Kaplan and C. P. Hamel (2000). "Nuclear gene OPA1, encoding a mitochondrial dynamin-related protein, is mutated in dominant optic atrophy." *Nat Genet* 26(2): 207-210.

Devi, L., B. M. Prabhu, D. F. Galati, N. G. Avadhani and H. K. Anandatheerthavarada (2006). "Accumulation of amyloid precursor protein in the mitochondrial import channels of human Alzheimer's disease brain is associated with mitochondrial dysfunction." *J Neurosci* 26(35): 9057-9068.

Diana, A., G. Simic, E. Sinforiani, N. Orru, G. Pichiri and G. Bono (2008). "Mitochondria morphology and DNA content upon sublethal exposure to beta-amyloid(1-42) peptide." *Coll Antropol* 32 Suppl 1: 51-58.

Dolle, C., I. Flones, G. S. Nido, H. Miletic, N. Osuagwu, S. Kristoffersen, P. K. Lilleng, J. P. Larsen, O. B. Tysnes, K. Haugarvoll, L. A. Bindoff and C. Tzoulis (2016). "Defective mitochondrial DNA homeostasis in the substantia nigra in Parkinson disease." *Nat Commun* 7: 13548.

Dorn, G. W., 2nd (2013). "Mitochondrial dynamics in heart disease." *Biochim Biophys Acta* 1833(1): 233-241.

Duvezin-Caubet, S., R. Jagasia, J. Wagener, S. Hofmann, A Trifunovic, A. Hansson, A. Chomyn, M. F. Bauer, G. Attardi, N. G. Larsson, W. Neupert and A. S. Reichert (2006). "Proteolytic processing of OPA1 links mitochondrial dysfunction to alterations in mitochondrial morphology." *J Biol Chem* 281(49): 37972-37979.

Eberlin, M., T. Muck and M. C. Michel (2012). "A comprehensive review of the pharmacodynamics, pharmacokinetics, and clinical effects of the neutral endopeptidase inhibitor racecadotril." *Front Pharmacol* 3: 93.

Eckert, A., S. Hauptmann, I. Scherping, V. Rhein, F. Muller-Spahn, J. Gotz and W. E. Muller (2008). "Soluble beta-amyloid leads to mitochondrial defects in amyloid precursor protein and tau transgenic mice." *Neurodegener Dis* 5(3-4): 157-159.

Edgar, R., M. Domrachev and A. E. Lash (2002). "Gene Expression Omnibus: NCBI gene expression and hybridization array data repository." *Nucleic Acids Res* 30(1): 207-210.

Ehses, S., I. Raschke, G. Mancuso, A. Bernacchia, S. Geimer, D. Tondera, J. C. Martinou, B. Westermann, E. I. Rugarli and T. Langer (2009). "Regulation of OPA1 processing and mitochondrial fusion by m-AAA protease isoenzymes and OMA1." *J Cell Biol* 187(7): 1023-1036.

Faccenda, D., J. Nakamura, G. Gorini, G. K. Dhoot, M. Piacentini, M. Yoshida and M. Campanella (2017). "Control of Mitochondrial Remodeling by the ATPase Inhibitory Factor 1 Unveils a Pro-survival Relay via OPA1." *Cell Rep* 18(8): 1869-1883.

Frezza, C., S. Cipolat, O. Martins de Brito, M. Micaroni, V. Beznoussenko, T. Rudka, D. Bartoli, R. S. Polishuck, N. N. Danial, B. De Strooper and L. Scorrano (2006). "OPA1 controls apoptotic cristae remodeling independently from mitochondrial fusion." *Cell* 126(1): 177-189.

Frezza, C. and E. Gottlieb (2009). "Mitochondria in cancer: not just innocent bystanders." *Semin Cancer Biol* 19(1): 4-11.

Fuhrmann, N., S. Schimpf, Y. Kamenisch, B. Leo-Kottler, C. Alexander, G. Auburger, E. Zrenner, B. Wissinger and M. V. Alavi (2010). "Solving a 50 year mystery of a missing OPA1 mutation: more insights from the first family diagnosed with autosomal dominant optic atrophy." *Mol Neurodegener* 5(1): 25.

Ghio, S., F. Kamp, R. Cauchi, A. Giese and N. Vassallo (2016). "Interaction of alpha-synuclein with biomembranes in Parkinson's disease-role of cardiolipin." *Prog Lipid Res* 61: 73-82.

Gibson, G. E., K. F. Sheu and J. P. Blass (1998). "Abnormalities of mitochondrial enzymes in Alzheimer disease." *J Neural Transm (Vienna)* 105(8-9): 855-870.

Gleissner, C. A., I. Shaked, K. M. Little and K. Ley (2010). "CXC chemokine ligand 4 induces a unique transcriptome in monocyte-derived macrophages." *J Immunol* 184(9): 4810-4818.

Glytsou, C., E. Calvo, S. Cogliati, A. Mehrotra, I. Anastasia, G. Rigoni, A. Raimondi, N. Shintani, M. Loureiro, J. Vazquez, L. Pellegrini, J. A. Enriquez, L. Scorrano and M. E. Soriano (2016). "Optic Atrophy 1 Is Epistatic to the Core MICOS Component MIC60 in Mitochondrial Cristae Shape Control." *Cell Rep* 17(11): 3024-3034.

Griparic, L., T. Kanazawa and A. M. van der Bliek (2007). "Regulation of the mitochondrial dynamin-like protein Opa1 by proteolytic cleavage." *J Cell Biol* 178(5): 757-764.

Guardia-Laguarta, C., E. Area-Gomez, C. Rub, Y. Liu, J. Magrane, D. Becker, W. Voos, E. A. Schon and S. Przedborski (2014). "alpha-Synuclein is localized to mitochondria-associated ER membranes." *J Neurosci* 34(1): 249-259.

Guo, Y., X. Chen, H. Zhang, N. Li, X. Yang, W. Cheng and K. Zhao (2012). "Association of OPA1 polymorphisms with NTG and HTG: a meta-analysis." *PLoS One* 7(8): e42387.

Hackenbrock, C. R. (1966). "Ultrastructural bases for metabolically linked mechanical activity in mitochondria. I. Reversible ultrastructural changes with change in metabolic steady state in isolated liver mitochondria." *J Cell Biol* 30(2): 269-297.

Hanahan, D. and R. A. Weinberg (2011). "Hallmarks of cancer: the next generation." *Cell* 144(5): 646-674.

Head, B., L. Griparic, M. Amiri, S. Gandre-Babbe and A. M. van der Bliek (2009). "Inducible proteolytic inactivation of OPA1 mediated by the OMA1 protease in mammalian cells." *J Cell Biol* 187(7): 959-966.

Hessenberger, M., R. M. Zerbes, H. Rampelt, S. Kunz, A. H. Xavier, B. Purfurst, H. Lilie, N. Pfanner, M. van der Laan and O. Daumke (2017). "Regulated membrane remodeling by Mic60 controls formation of mitochondrial crista junctions." *Nat Commun* 8: 15258.

Hokama, M., S. Oka, J. Leon, T. Ninomiya, H. Honda, K. Sasaki, T. Iwaki, T. Ohara, T. Sasaki, F. M. LaFerla, Y. Kiyohara and Y. Nakabeppu (2014). "Altered expression of diabetes-related genes in Alzheimer's disease brains: the Hisayama study." *Cereb Cortex* 24(9): 2476-2488.

Imaizumi, Y., Y. Okada, W. Akamatsu, M. Koike, N. Kuzumaki, H. Hayakawa, T. Nihira, T. Kobayashi, M. Ohyama, S. Sato, M. Takanashi, M. Funayama, A. Hirayama, T. Soga, T. Hishiki, M. Suematsu, T. Yagi, D. Ito, A. Kosakai, K. Hayashi, M. Shouji, A. Nakanishi, N. Suzuki, Y. Mizuno, N. Mizushima, M. Amagai, Y. Uchiyama, H. Mochizuki, N. Hattori and H. Okano (2012). "Mitochondrial dysfunction associated with increased oxidative stress and alpha-synuclein accumulation in PARK2 iPSC-derived neurons and postmortem brain tissue." *Mol Brain* 5: 35.

Ishihara, N., Y. Fujita, T. Oka and K. Mihara (2006). "Regulation of mitochondrial morphology through proteolytic cleavage of OPA1." *EMBO J* 25(13): 2966-2977.

Jakobs, S., N. Martini, A. C. Schauss, A. Egner, B. Westermann and S. W. Hell (2003). "Spatial and temporal dynamics of budding yeast mitochondria lacking the division component Fis1p." *J Cell Sci* 116(Pt 10): 2005-2014.

Jiang, X., H. Jiang, Z. Shen and X. Wang (2014). "Activation of mitochondrial protease OMA1 by Bax and Bak promotes cytochrome c release during apoptosis." *Proc Natl Acad Sci USA*.

Ju, W. K., K. Y. Kim, J. D. Lindsey, M. Angert, K. X. Duong-Polk, R. T. Scott, J. J. Kim, I. Kukhmazov, M. H. Ellisman, G. A. Perkins and R. N. Weinreb (2008). "Intraocular pressure elevation induces mitochondrial fission and triggers OPA1 release in glaucomatous optic nerve." Invest Ophthalmol Vis Sci 49(11): 4903-4911.

Kandimalla, R., M. Manczak, D Fry, Y. Suneetha, H. Sesaki and P. H. Reddy (2016). "Reduced dynamin-related protein 1 protects against phosphorylated Tau-induced mitochondrial dysfunction and synaptic damage in Alzheimer's disease." Hum Mol Genet 25(22): 4881-4897.

Kaser, M., M. Kambacheld, B. Kisters-Woike and T. Langer (2003). "Oma1, a novel membrane-bound metallopeptidase in mitochondria with activities overlapping with the m-AAA protease." J Biol Chem 278(47): 46414-46423.

Keeney, P. M., J. Xie, R. A. Capaldi and J. P. Bennett, Jr. (2006). "Parkinson's disease brain mitochondrial complex I has oxidatively damaged subunits and is functionally impaired and misassembled." J Neurosci 26(19): 5256-5264.

Kim, K. Y., G. A. Perkins, M. S. Shim, E. Bushong, N. Alcasid, S. Ju, M. H. Ellisman, R. N. Weinreb and W. K. Ju (2015). "DRP1 inhibition rescues retinal ganglion cells and their axons by preserving mitochondrial integrity in a mouse model of glaucoma." Cell Death Dis 6: e1839.

Kong, B., H. Tsuyoshi, M. Orisaka, D. B. Shieh, Y. Yoshida and B. K. Tsang (2015). "Mitochondrial dynamics regulating chemoresistance in gynecological cancers." Ann N Y Acad Sci 1350: 1-16.

Kong, B., Q. Wang, E. Fung, K. Xue and B. K. Tsang (2014). "p53 is required for cisplatin-induced processing of the mitochondrial fusion protein L-Opa1 that is mediated by the mitochondrial metallopeptidase Oma1 in gynecologic cancers." J Biol Chem 289(39): 27134-27145.

Kong, G. Y., N. J. Van Bergen, I. A. Trounce and J. G. Crowston (2009). "Mitochondrial dysfunction and glaucoma." J Glaucoma 18(2): 93-100.

Koob, S., M. Barrera, R. Anand and A. S. Reichert (2015). "The non-glycosylated isoform of MIC26 is a constituent of the mammalian MICOS complex and promotes formation of crista junctions." Biochim Biophys Acta 1853(7): 1551-1563.

Korwitz, A., C. Merkwirth, R. Richter-Dennerlein, S. E. Troder, H. G. Sprenger, P. M. Quiros, C. Lopez-Otin, E. I. Rugarli and T. Langer (2016). "Loss of OMA1 delays neurodegeneration by preventing stress-induced OPA1 processing in mitochondria." J Cell Biol 212(2): 157-166.

Landes, T., L. J. Emorine, D. Courilleau, M. Rojo, P. Belenguer and L. Arnaune-Pelloquin (2010). "The BH3-only Bnip3 binds to the dynamin Opa1 to promote mitochondrial fragmentation and apoptosis by distinct mechanisms." EMBO Rep 11(6): 459-465.

Le Page, S., M. Niro, J. Fauconnier, L. Cellier, S. Tamareille, A. Gharib, A. Chevrollier, L. Loufrani, C. Grenier, R. Kamel, E. Sarzi, A. Lacampagne, M. Ovize, D. Henrion, P. Reynier, G. Lenaers, D. Mirebeau-Prunier and F. Prunier (2016). "Increase in Cardiac Ischemia-Reperfusion Injuries in Opa1+/−Mouse Model." PLoS One 11(10): e0164066.

Lee, S., N. J. Van Bergen, G. Y. Kong, V. Chrysostomou, H. S. Waugh, E. C. O'Neill, J. G. Crowston and I. A. Trounce (2011). "Mitochondrial dysfunction in glaucoma and emerging bioenergetic therapies." Exp Eye Res 93(2): 204-212.

Lenaers, G., P. Reynier, G. Elachouri, C. Soukkarieh, A. Olichon, P. Belenguer, L. Baricault, B. Ducommun, C. Hamel and C. Delettre (2009). "OPA1 functions in mitochondria and dysfunctions in optic nerve." Int J Biochem Cell Biol 41(10): 1866-1874.

Lesnick, T. G., S. Papapetropoulos, D. C. Mash, J. Ffrench-Mullen, L. Shehadeh, M. de Andrade, J. R. Henley, W. A. Rocca, J. E. Ahlskog and D. M. Maraganore (2007). "A genomic pathway approach to a complex disease: axon guidance and Parkinson disease." PLoS Genet 3(6): e98.

Li, F., N. Y. Calingasan, F. Yu, W. M. Mauck, M. Toidze, C. G. Almeida, R. H. Takahashi, G. A. Carlson, M. Flint Beal, M. T. Lin and G. K. Gouras (2004). "Increased plaque burden in brains of APP mutant MnSOD heterozygous knockout mice." J Neurochem 89(5): 1308-1312.

Lustbader, J. W., M. Cirilli, C. Lin, H. W. Xu, K. Takuma, N. Wang, C. Caspersen, X. Chen, S. Pollak, M. Chaney, F. Trinchese, S. Liu, F. Gunn-Moore, L. F. Lue, D. G. Walker, P. Kuppusamy, Z. L. Zewier, O. Arancio, D. Stern, S. S. Yan and H. Wu (2004). "ABAD directly links Abeta to mitochondrial toxicity in Alzheimer's disease." Science 304(5669): 448-452.

Lutz, A. K., N. Exner, M. E. Fett, J. S. Schlehe, K. Kloos, K. Lammermann, B. Brunner, A. Kurz-Drexler, F. Vogel, A. S. Reichert, L. Bouman, D Vogt-Weisenhorn, W. Wurst, J. Tatzelt, C. Haass and K. F. Winklhofer (2009). "Loss of parkin or PINK1 function increases Drp1-dependent mitochondrial fragmentation." J Biol Chem 284 (34): 22938-22951.

Manczak, M., T. S. Anekonda, E. Henson, B. S. Park, J. Quinn and P. H. Reddy (2006). "Mitochondria are a direct site of A beta accumulation in Alzheimer's disease neurons: implications for free radical generation and oxidative damage in disease progression." Hum Mol Genet 15(9): 1437-1449.

Manczak, M., M. J. Calkins and P. H. Reddy (2011). "Impaired mitochondrial dynamics and abnormal interaction of amyloid beta with mitochondrial protein Drp1 in neurons from patients with Alzheimer's disease: implications for neuronal damage." Hum Mol Genet 20(13): 2495-2509.

Manczak, M., R. Kandimalla, D. Fry, H. Sesaki and P. H. Reddy (2016). "Protective effects of reduced dynamin-related protein 1 against amyloid beta-induced mitochondrial dysfunction and synaptic damage in Alzheimer's disease." Hum Mol Genet 25(23): 5148-5166.

Manczak, M. and P. H. Reddy (2012). "Abnormal interaction between the mitochondrial fission protein Drp1 and hyperphosphorylated tau in Alzheimer's disease neurons: implications for mitochondrial dysfunction and neuronal damage." Hum Mol Genet 21(11): 2538-2547.

Maraganore, D. M., M. de Andrade, T. G. Lesnick, K. J. Strain, M. J. Farrer, W. A. Rocca, P. V. Pant, K. A. Frazer, D. R. Cox and D. G. Ballinger (2005). "High-resolution whole-genome association study of Parkinson disease." Am J Hum Genet 77(5): 685-693.

Maresca, A., C. la Morgia, L. Caporali, M. L. Valentino and V. Carelli (2013). "The optic nerve: a "mito-window" on mitochondrial neurodegeneration." Mol Cell Neurosci 55: 62-76.

Marin-Garcia, J. and A. T. Akhmedov (2016). "Mitochondrial dynamics and cell death in heart failure." Heart Fail Rev 21(2): 123-136.

Maurer, I., S. Zierz and H. J. Moller (2000). "A selective defect of cytochrome c oxidase is present in brain of Alzheimer disease patients." Neurobiol Aging 21(3): 455-462.

Medja, F., V. Lelievre, R. H. Fontaine, F. Lebas, P. Leroux, T. Ouimet, A. Saria, C. Rougeot, P. Dournaud and P. Gressens (2006). "Thiorphan, a neutral endopeptidase inhibitor used for diarrhoea, is neuroprotective in newborn mice." *Brain* 129(Pt 12): 3209-3223.

Merkwirth, C., S. Dargazanli, T. Tatsuta, S. Geimer, B. Lower, F. T. Wunderlich, J. C. von Kleist-Retzow, A. Waisman, B. Westermann and T. Langer (2008). "Prohibitins control cell proliferation and apoptosis by regulating OPA1-dependent cristae morphogenesis in mitochondria." *Genes Dev* 22(4): 476-488.

Miller, J. A., R. L. Woltjer, J. M. Goodenbour, S. Horvath and D. H. Geschwind (2013). "Genes and pathways underlying regional and cell type changes in Alzheimer's disease." *Genome Med* 5(5): 48.

Mukherjee, U. A., S. B. Ong, S. G. Ong and D. J. Hausenloy (2015). "Parkinson's disease proteins: Novel mitochondrial targets for cardioprotection." *Pharmacol Ther* 156: 34-43.

Nakamura, K. (2013). "alpha-Synuclein and mitochondria: partners in crime?" *Neurotherapeutics* 10(3): 391-399.

Nakamura, K., V. M. Nemani, F. Azarbal, G. Skibinski, J. M. Levy, K. Egami, L. Munishkina, J. Zhang, B. Gardner, J. Wakabayashi, H. Sesaki, Y. Cheng, S. Finkbeiner, R. L. Nussbaum, E. Masliah and R. H. Edwards (2011). "Direct membrane association drives mitochondrial fission by the Parkinson disease-associated protein alpha-synuclein." *J Biol Chem* 286(23): 20710-20726.

Niemann, A., M. Ruegg, V. La Padula, A. Schenone and U. Suter (2005). "Ganglioside-induced differentiation associated protein 1 is a regulator of the mitochondrial network: new implications for Charcot-Marie-Tooth disease." *J Cell Biol* 170(7): 1067-1078.

Olichon, A., L. Baricault, N. Gas, E. Guillou, A. Valette, P. Belenguer and G. Lenaers (2003). "Loss of OPA1 perturbates the mitochondrial inner membrane structure and integrity, leading to cytochrome c release and apoptosis." *J Biol Chem* 278(10): 7743-7746.

Ong, S. B., S. B. Kalkhoran, S. Hernandez-Resendiz, P. Samangouei, S. G. Ong and D. J. Hausenloy (2017). "Mitochondrial-Shaping Proteins in Cardiac Health and Disease—the Long and the Short of It!" *Cardiovasc Drugs Ther* 31(1): 87-107.

Osborne, N. N. (2010). "Mitochondria: Their role in ganglion cell death and survival in primary open angle glaucoma." *Exp Eye Res* 90(6): 750-757.

Ott, C., E. Dorsch, M. Fraunholz, S. Straub and V. Kozjak-Pavlovic (2015). "Detailed analysis of the human mitochondrial contact site complex indicate a hierarchy of subunits." *PLoS One* 10(3): e0120213.

Pan, J. Z., H. Wei, J. G. Hecker, J. W. Tobias, R. G. Eckenhoff and M. F. Eckenhoff (2006). "Rat brain DNA transcript profile of halothane and isoflurane exposure." *Pharmacogenet Genomics* 16(3): 171-182.

Parker, W. D., Jr., C. M. Filley and J. K. Parks (1990). "Cytochrome oxidase deficiency in Alzheimer's disease." *Neurology* 40(8): 1302-1303.

Parker, W. D., Jr., J. K. Parks and R. H. Swerdlow (2008). "Complex I deficiency in Parkinson's disease frontal cortex." *Brain Res* 1189: 215-218.

Philibert, R. A., G. Y. Ryu, J. G. Yoon, H. Sandhu, N. Hollenbeck, T. Gunter, A. Barkhurst, W. Adams and A. Madan (2007). "Transcriptional profiling of subjects from the Iowa adoption studies." *Am J Med Genet B Neuropsychiatr Genet* 144B(5): 683-690.

Piquereau, J., F. Caffin, M. Novotova, C. Lemaire, V. Veksler, A. Garnier, R. Ventura-Clapier and F. Joubert (2013). "Mitochondrial dynamics in the adult cardiomyocytes: which roles for a highly specialized cell?" *Front Physiol* 4: 102.

Piquereau, J., F. Caffin, M. Novotova, A. Prola, A. Garnier, P. Mateo, D. Fortin, H. Huynh le, V. Nicolas, M. V. Alavi, C. Brenner, R. Ventura-Clapier, V. Veksler and F. Joubert (2012). "Downregulation of OPA1 alters mouse mitochondrial morphology, PTP function, and cardiac adaptation to pressure overload." *Cardiovasc Res* 94(3): 408-417.

Rainbolt, T. K., J. Lebeau, C. Puchades and R. L. Wiseman (2016). "Reciprocal Degradation of YME1L and OMA1 Adapts Mitochondrial Proteolytic Activity during Stress." *Cell Rep* 14(9): 2041-2049.

Rappold, P. M., M. Cui, J. C. Grima, R. Z. Fan, K. L. de Mesy-Bentley, L. Chen, X. Zhuang, W. J. Bowers and K. Tieu (2014). "Drp1 inhibition attenuates neurotoxicity and dopamine release deficits in vivo." *Nat Commun* 5: 5244.

Reddy, P. H., M. Manczak and X. Yin (2017). "Mitochondria-Division Inhibitor 1 Protects Against Amyloid-beta induced Mitochondrial Fragmentation and Synaptic Damage in Alzheimer's Disease." *J Alzheimers Dis* 58(1): 147-162.

Reddy, P. H., S. McWeeney, B. S. Park, M. Manczak, R. V. Gutala, D. Partovi, Y. Jung, V. Yau, R. Searles, M. Mori and J. Quinn (2004). "Gene expression profiles of transcripts in amyloid precursor protein transgenic mice: up-regulation of mitochondrial metabolism and apoptotic genes is an early cellular change in Alzheimer's disease." *Hum Mol Genet* 13(12): 1225-1240.

Richter, U., T. Lahtinen, P. Marttinen, F. Suomi and B. J. Battersby (2015). "Quality control of mitochondrial protein synthesis is required for membrane integrity and cell fitness." *J Cell Biol* 211(2): 373-389.

Rossello, A., E. Nuti, E. Orlandini, P. Carelli, S. Rapposelli, M. Macchia, F. Minutolo, L. Carbonaro, A. Albini, R. Benelli, G. Cercignani, G. Murphy and A. Balsamo (2004). "New N-arylsulfonyl-N-alkoxyaminoacetohydroxamic acids as selective inhibitors of gelatinase A (MMP-2)." *Bioorg Med Chem* 12(9): 2441-2450.

Sadun, A. A. (2002). "Mitochondrial optic neuropathies." *J Neurol Neurosurg Psychiatry* 72(4): 423-425.

Salminen, A., A. Haapasalo, A. Kauppinen, K. Kaarniranta, H. Soininen and M. Hiltunen (2015). "Impaired mitochondrial energy metabolism in Alzheimer's disease: Impact on pathogenesis via disturbed epigenetic regulation of chromatin landscape." *Prog Neurobiol* 131: 1-20.

Santos, D., A. R. Esteves, D. F. Silva, C. Januario and S. M. Cardoso (2015). "The Impact of Mitochondrial Fusion and Fission Modulation in Sporadic Parkinson's Disease." *Mol Neurobiol* 52(1): 573-586.

Schapira, A. H., J. M. Cooper, D. Dexter, J. B. Clark, P. Jenner and C. D. Marsden (1990). "Mitochondrial complex I deficiency in Parkinson's disease." *J Neurochem* 54(3): 823-827.

Schmidt, C., E. Lepsverdize, S. L. Chi, A. M. Das, S. V. Pizzo, A. Dityatev and M. Schachner (2008). "Amyloid precursor protein and amyloid beta-peptide bind to ATP synthase and regulate its activity at the surface of neural cells." *Mol Psychiatry* 13(10): 953-969.

Shields, L. Y., H. Kim, L. Zhu, D. Haddad, A. Berthet, D. Pathak, M. Lam, R. Ponnusamy, L. G. Diaz-Ramirez, T. M. Gill, H. Sesaki, L. Mucke and K. Nakamura (2015). "Dynamin-related protein 1 is required for normal mitochondrial bioenergetic and synaptic function in CA1 hippocampal neurons." *Cell Death Dis* 6: e1725.

Sit, A. J. (2014). "Intraocular pressure variations: causes and clinical significance." *Can J Ophthalmol* 49(6): 484-488.

Smith, M. A., G. Perry, P. L. Richey, L. M. Sayre, V. E. Anderson, M. F. Beal and N. Kowall (1996). "Oxidative damage in Alzheimer's." *Nature* 382(6587): 120-121.

Song, Z., H. Chen, M. Fiket, C. Alexander and D. C. Chan (2007). "OPA1 processing controls mitochondrial fusion and is regulated by mRNA splicing, membrane potential, and Yme1L." *J Cell Biol* 178(5): 749-755.

Stafa, K., E. Tsika, R. Moser, A. Musso, L. Glauser, A. Jones, S. Biskup, Y. Xiong, R. Bandopadhyay, V. L. Dawson, T. M. Dawson and D. J. Moore (2014). "Functional interaction of Parkinson's disease-associated LRRK2 with members of the dynamin GTPase superfamily." *Hum Mol Genet* 23(8): 2055-2077.

Takihara, Y., M. Inatani, K. Eto, T. Inoue, A. Kreymerman, S. Miyake, S. Ueno, M. Nagaya, A. Nakanishi, K. Iwao, Y. Takamura, H. Sakamoto, K. Satoh, M. Kondo, T. Sakamoto, J. L. Goldberg, J. Nabekura and H. Tanihara (2015). "In vivo imaging of axonal transport of mitochondria in the diseased and aged mammalian CNS." *Proc Natl Acad Sci USA* 112(33): 10515-10520.

Tan, E. P., S. R. McGreal, S. Graw, R. Tessman, S. J. Koppel, P. Dhakal, Z. Zhang, M. Machacek, N. E. Zachara, D. C. Koestler, K. R. Peterson, J. P. Thyfault, R. H. Swerdlow, P. Krishnamurthy, L. DiTacchio, U. Apte and C. Slawson (2017). "Sustained O-GlcNAcylation reprograms mitochondrial function to regulate energy metabolism." *J Biol Chem* 292(36): 14940-14962.

Taube, J. H., G. G. Malouf, E. Lu, N. Sphyris, V. Vijay, P. P. Ramachandran, K. R. Ueno, S. Gaur, M. S. Nicoloso, S. Rossi, J. I. Herschkowitz, J. M. Rosen, J. P. Issa, G. A. Calin, J. T. Chang and S. A. Mani (2013). "Epigenetic silencing of microRNA-203 is required for EMT and cancer stem cell properties." *Sci Rep* 3: 2687.

Taylor, J. P., J. Hardy and K. H. Fischbeck (2002). "Toxic proteins in neurodegenerative disease." *Science* 296 (5575): 1991-1995.

Thomas, E., J. J. Feld, Q. Li, Z. Hu, M. W. Fried and T. J. Liang (2011). "Ribavirin potentiates interferon action by augmenting interferon-stimulated gene induction in hepatitis C virus cell culture models." *Hepatology* 53(1): 32-41.

Tuccinardi, T., A. Martinelli, E. Nuti, P. Carelli, F. Balzano, G. Uccello-Barretta, G. Murphy and A. Rossello (2006). "Amber force field implementation, molecular modelling study, synthesis and MMP-1/MMP-2 inhibition profile of (R)- and (S)—N-hydroxy-2-(N-isopropoxybiphenyl-4-ylsulfonamido)-3-methylbutanamides." *Bioorg Med Chem* 14(12): 4260-4276.

Voigt, A., L. A. Berlemann and K. F. Winklhofer (2016). "The mitochondrial kinase PINK1: functions beyond mitophagy." *J Neurochem* 139 Suppl 1: 232-239.

Vyas, S., E. Zaganjor and M. C. Haigis (2016). "Mitochondria and Cancer." *Cell* 166(3): 555-566.

Wai, T., J. Garcia-Prieto, M. J. Baker, C. Merkwirth, P. Benit, P. Rustin, F. J. Ruperez, C. Barbas, B. Ibanez and T. Langer (2015). "Imbalanced OPA1 processing and mitochondrial fragmentation cause heart failure in mice." *Science* 350(6265): aad0116.

Wai, T., S. Saita, H. Nolte, S. Muller, T. Konig, R. Richter-Dennerlein, H. G. Sprenger, J. Madrenas, M. Muhlmeister, U. Brandt, M. Kruger and T. Langer (2016). "The membrane scaffold SLP2 anchors a proteolytic hub in mitochondria containing PARL and the i-AAA protease YME1L." *EMBO Rep* 17(12): 1844-1856.

Wallace, D. C. (2012). "Mitochondria and cancer." *Nat Rev Cancer* 12(10): 685-698.

Wang, H., P. Song, L. Du, W. Tian, W. Yue, M. Liu, D. Li, B. Wang, Y. Zhu, C. Cao, J. Zhou and Q. Chen (2011). "Parkin ubiquitinates Drp1 for proteasome-dependent degradation: implication of dysregulated mitochondrial dynamics in Parkinson disease." *J Biol Chem* 286(13): 11649-11658.

Wang, X., B. Su, S. L. Siedlak, P. I. Moreira, H. Fujioka, Y. Wang, G. Casadesus and X. Zhu (2008). "Amyloid-beta overproduction causes abnormal mitochondrial dynamics via differential modulation of mitochondrial fission/fusion proteins." *Proc Natl Acad Sci USA* 105(49): 19318-19323.

Wang, Z., M. Iwasaki, F. Ficara, C. Lin, C. Matheny, S. H. Wong, K. S. Smith and M. L. Cleary (2010). "GSK-3 promotes conditional association of CREB and its coactivators with MEIS1 to facilitate HOX-mediated transcription and oncogenesis." *Cancer Cell* 17(6): 597-608.

Warburg, O. (1956). "On the origin of cancer cells." *Science* 123(3191): 309-314.

Xiao, X., Y. Hu, P. M. Quiros, Q. Wei, C. Lopez-Otin and Z. Dong (2014). "OMA1 mediates OPA1 proteolysis and mitochondrial fragmentation in experimental models of ischemic kidney injury." *Am J Physiol Renal Physiol* 306(11): F1318-1326.

Yan, J., X. H. Liu, M. Z. Han, Y. M. Wang, X. L. Sun, N. Yu, T. Li, B. Su and Z. Y. Chen (2015). "Blockage of GSK3beta-mediated Drp1 phosphorylation provides neuroprotection in neuronal and mouse models of Alzheimer's disease." *Neurobiol Aging* 36(1): 211-227.

Yang, X., Q. Shi, J. Sun, Y. Lv, Y. Ma, C. Chen, K. Xiao, W. Zhou and X. P. Dong (2017). "Aberrant Alterations of Mitochondrial Factors Drp1 and Opa1 in the Brains of Scrapie Experiment Rodents." *J Mol Neurosci* 61(3): 368-378.

Yang, Y., Y. Ouyang, L. Yang, M. F. Beal, A. McQuibban, H. Vogel and B. Lu (2008). "Pink1 regulates mitochondrial dynamics through interaction with the fission/fusion machinery." *Proc Natl Acad Sci USA* 105(19): 7070-7075.

Yao, J., R. W. Irwin, L. Zhao, J. Nilsen, R. T. Hamilton and R. D. Brinton (2009). "Mitochondrial bioenergetic deficit precedes Alzheimer's pathology in female mouse model of Alzheimer's disease." *Proc Natl Acad Sci USA* 106 (34): 14670-14675.

Zhang, T., L. Xue, L. Li, C. Tang, Z. Wan, R. Wang, J. Tan, Y. Tan, H. Han, R. Tian, T. R. Billiar, W. A. Tao and Z. Zhang (2016). "BNIP3 Protein Suppresses PINK1 Kinase Proteolytic Cleavage to Promote Mitophagy." *J Biol Chem* 291(41): 21616-21629.

Zhang, Y., M. James, F. A. Middleton and R. L. Davis (2005). "Transcriptional analysis of multiple brain regions in Parkinson's disease supports the involvement of specific protein processing, energy metabolism, and signaling pathways, and suggests novel disease mechanisms." *Am J Med Genet B Neuropsychiatr Genet* 137B (1): 5-16.

Zhao, X., C. Tian, W. M. Puszyk, O. O. Ogunwobi, M. Cao, T. Wang, R. Cabrera, D. R. Nelson and C. Liu (2013). "OPA1 downregulation is involved in sorafenib-induced apoptosis in hepatocellular carcinoma." *Lab Invest* 93(1): 8-19.

Zuchner, S., I. V. Mersiyanova, M. Muglia, N. Bissar-Tadmouri, J. Rochelle, E. L. Dadali, M. Zappia, E. Nelis, A. Patitucci, J. Senderek, Y. Parman, O. Evgrafov, P. D. Jonghe, Y. Takahashi, S. Tsuji, M. A. Pericak-Vance, A. Quattrone, E. Battaloglu, A. V. Polyakov, V. Timmerman, J. M. Schroder and J. M. Vance (2004). "Mutations in the mitochondrial GTPase mitofusin 2 cause Charcot-Marie-Tooth neuropathy type 2A." *Nat Genet* 36(5): 449-451.

What is claimed is:

1. A method of selectively treating a subject with abnormally high OMA1 gene expression levels or activity and in need of medical intervention comprising:
   (a) means for assessing OMA1 or an oligomeric complex comprising OMA1 in said subject, and
   (b) selectively administering to said subject a pharmaceutically effective amount of ribavirin or an analog thereof, wherein the effective amount is selected to effectively reduce OMA1 gene expression levels, and whereby said method is useful for treating said subject according to the OMA1 gene expression levels or activity.

2. The method of claim 1, wherein said means for assessing OMA1 or the oligomeric complex comprising OMA1 comprises an apparatus for gene expression analysis.

3. The method of claim 1, wherein said pharmaceutically effective amount of ribavirin or analog thereof is administered by an apparatus so that the subject can inhale the ribavirin or the analog.

4. A method of selectively treating a subject with abnormally high OMA1 gene expression levels or activity and in need of medical intervention comprising:
   (a) obtaining a sample from said subject;
   (b) performing a reaction to detect an activity or a level of OMA1 or an oligomeric complex comprising OMA1 in said sample; and
   (c) selectively administering to said subject a pharmaceutically effective amount of ribavirin or an analog thereof, wherein the effective amount is selected to effectively reduce OMA1 gene expression levels.

5. The method of claim 4, wherein said pharmaceutically effective amount of ribavirin or analog thereof is administered by an apparatus so that the subject can inhale the ribavirin or the analog.

6. A method of selectively treating a subject with abnormally high OMA1 gene expression levels or activity and in need of medical intervention comprising administering to the subject a therapeutically effective amount of a pharmaceutical composition comprising ribavirin or an analog thereof, wherein the effective amount is selected to effectively reduce OMA1 gene expression levels.

7. The method of claim 6, wherein said composition comprises ribavirin and pharmaceutical acceptable excipient(s).

8. The method of claim 1, wherein the pharmaceutically effective amount of ribavirin or the analog thereof is administered in a composition further comprising a pharmaceutical acceptable excipient(s).

9. The method of claim 4, wherein the pharmaceutically effective amount of ribavirin or the analog thereof is administered in a composition further comprising a pharmaceutical acceptable excipient(s).

10. The method of claim 4, wherein said reaction is performed with an apparatus for gene expression analysis.

11. The method of claim 6, further comprising analyzing OMA1 gene expression levels in the subject before the administering step.

12. The method of claim 6, wherein said pharmaceutical composition is administered by an apparatus so that the subject can inhale the ribavirin or the analog thereof.

13. The method of claim 6, wherein said analog comprises a compound of the structure:

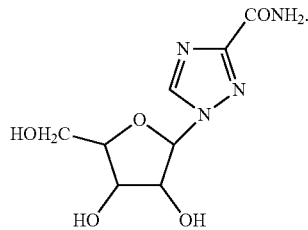 [SMILES: NC(=O)c1ncn(C2OC(CO)C(O)C2O)n1]

14. A method of treating a subject with abnormally high OMA1 gene expression levels, comprising administering a pharmaceutically effective amount of ribavirin or an analog thereof to said subject, wherein the effective amount is selected to effectively reduce OMA1 gene expression levels.

15. The method of claim 14, wherein the pharmaceutically effective amount of ribavirin or the analog thereof is administered in a composition further comprising a pharmaceutical acceptable excipient(s).

16. The method of claim 14, wherein said pharmaceutically effective amount of ribavirin is administered by an apparatus so that the subject can inhale the ribavirin or the analog thereof.

17. The method of claim 14, further comprising analyzing OMA1 gene expression levels in the subject before the administering step.

* * * * *